US007919519B2

(12) United States Patent
Burli et al.

(10) Patent No.: US 7,919,519 B2
(45) Date of Patent: *Apr. 5, 2011

(54) S1P RECEPTOR MODULATING COMPOUNDS AND USE THEREOF

(75) Inventors: Roland Burli, Pasadena, CA (US); Victor J. Cee, Thousand Oaks, CA (US); Jennifer Golden, Simi Valley, CA (US); Brian Alan Lanman, Oak Park, CA (US); Susana Neira, Thousand Oaks, CA (US); Ashis Saha, Stow, MA (US); Nili Schutz, Tel-Aviv (IL); Xiang Yu, Acton, MA (US); Dilara McCauley, Cambridge, MA (US); Mercedes Lobera, Bolton, MA (US); Yael Marantz, Kadima (IL); Jian Lin, Walpole, MA (US); Srinivasa R. Cheruku, Lexington, MA (US); Pini Orbach, Needham, MA (US); Anurag Sharadendu, Washington, DC (US); Robert C. Penland, Watertown, MA (US); Kimberley Gannon, Watertown, MA (US); Sharon Shacham, Newton, MA (US); Silvia Noiman, Herzliyya (IL); Oren Becker, Mevaseret Zion (IL); Zhaoda Zhang, Andover, MA (US)

(73) Assignee: Epix Pharmaceuticals Inc., Lexington, MA (US)

( * ) Notice: Subject to any disclaimer, the term of this patent is extended or adjusted under 35 U.S.C. 154(b) by 477 days.

This patent is subject to a terminal disclaimer.

(21) Appl. No.: 11/726,351

(22) Filed: Mar. 21, 2007

(65) Prior Publication Data
US 2008/0027036 A1 Jan. 31, 2008

Related U.S. Application Data

(63) Continuation-in-part of application No. 11/491,766, filed on Jul. 24, 2006.

(60) Provisional application No. 60/739,466, filed on Nov. 23, 2005, provisional application No. 60/753,806, filed on Dec. 22, 2005, provisional application No. 60/784,549, filed on Mar. 21, 2006.

(51) Int. Cl.
*A61K 31/404* (2006.01)
*A61K 31/381* (2006.01)
*A61K 31/343* (2006.01)
*C07D 209/12* (2006.01)
*C07D 333/56* (2006.01)
*C07D 307/80* (2006.01)

(52) U.S. Cl. ........ 514/419; 514/443; 514/469; 548/494; 549/58; 549/469

(58) Field of Classification Search .................. 514/419, 514/443, 469; 548/494; 549/58, 469
See application file for complete search history.

(56) References Cited

U.S. PATENT DOCUMENTS

| 3,329,781 | A | 7/1967 | Wiser |
|---|---|---|---|
| 4,304,785 | A | 12/1981 | Griengl et al. |
| 4,767,896 | A | 8/1988 | Nigg et al. |
| 5,145,865 | A | 9/1992 | Fujii et al. |
| 5,614,531 | A | 3/1997 | Juraszyk et al. |
| 5,880,284 | A | 3/1999 | Himmelsbach et al. |
| 6,384,061 | B1 | 5/2002 | Lee et al. |
| 6,411,326 | B1 | 6/2002 | Tabata |
| 2002/0156074 | A1 | 10/2002 | Barvian et al. |
| 2002/0183519 | A1 | 12/2002 | Nar et al. |
| 2005/0014725 | A1 | 1/2005 | Mi et al. |
| 2005/0113283 | A1 | 5/2005 | Solow-Cordero et al. |
| 2006/0135786 | A1 | 6/2006 | Saha et al. |
| 2007/0173487 | A1* | 7/2007 | Saha et al. ............... 514/210.19 |
| 2008/0015177 | A1 | 1/2008 | Saha et al. |
| 2008/0027036 | A1 | 1/2008 | Burli et al. |
| 2008/0064677 | A9 | 3/2008 | Saha et al. |

FOREIGN PATENT DOCUMENTS

| EP | 1 553 075 A1 | 7/2005 |
|---|---|---|
| JP | 10-204059 A * | 8/1998 |
| WO | WO 02/064616 A2 | 8/2002 |
| WO | WO 2005/020882 A3 | 3/2003 |
| WO | WO 03/061567 A2 | 7/2003 |
| WO | WO 03/062252 A1 | 7/2003 |
| WO | 03105771 A2 | 12/2003 |
| WO | WO 2004/048383 A1 | 6/2004 |
| WO | WO 2004/062663 A1 | 7/2004 |
| WO | WO 2004/113330 A1 | 12/2004 |

(Continued)

OTHER PUBLICATIONS

Pan et al., 2006, "A monoselective sphingosine-1-phosphate receptor-1 agonist prevents allograft rejection in a stringent rat heart transplantation model," *Chemistry & Biology*, vol. 13:1227-1234.

Traynor et al., 1995, "Modulation by μ-opioid agonists of guanosine-5'-O-(3-[$^{35}$S]thio)triphosphate binding to membranes from human neuroblastoma SH-SY5Y cells," *Molecular Pharmacology*, vol. 47:848-854.

Zemann et al., 2006, "Sphingosine kinase type 2 is essential for lymphopenia induced by the immunomodulatory drug FTY720," *Blood*, 107(4):1454-1458.

(Continued)

*Primary Examiner* — Joseph R Kosack
(74) *Attorney, Agent, or Firm* — McDonnell Boehnen Hulbert & Berghoff LLP

(57) ABSTRACT

The present invention relates to compounds of the general formula (I) that have activity as S1P receptor modulating agents and the use of such compounds to treat diseases associated with inappropriate S1P receptor activity. The compounds may be used as immunomodulators, e.g., for treating or preventing diseases such as autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behçet's disease, glomerulonephritis, chronic thrombocytopenic purpura, hemolytic anemia, hepatitis and Wegner's granuloma; and for treating other conditions.

8 Claims, No Drawings

FOREIGN PATENT DOCUMENTS

| WO | WO 2005/020882 A3 | 3/2005 |
|----|-------------------|--------|
| WO | 2006064757 A1 | 6/2006 |
| WO | WO 2007/061458 A2 | 5/2007 |
| WO | WO 2007/109330 A3 | 9/2007 |
| WO | WO 2007/109334 A2 | 9/2007 |
| WO | WO 2009/038759 A3 | 3/2009 |

OTHER PUBLICATIONS

PCT International Search Report dated Sep. 20, 2007, for International Application No. PCT/US2006/028657, filed Jul. 24, 2006.

PCT Written Opinion of the International Searching Authority dated Sep. 20, 2007, for International Application No. PCT/US2006/028657, filed Jul. 24, 2006.

PCT International Preliminary Report on Patentability dated May 27, 2008, for International Application No. PCT/US2006/028657, filed Jul. 24, 2006.

PCT International Search Report dated Nov. 12, 2007, for International Application No. PCT/US2006/007044, filed Mar. 21, 2007.

PCT Written Opinion of the International Searching Authority dated Nov. 12, 2007, for International Application No. PCT/US2006/007044, filed Mar. 21, 2007.

U.S. Patent and Trademark Office Non-Final Office Action dated Feb. 25, 2009, for U.S. Appl. No. 11/491,766, filed Jul. 24, 2006.

Abdel-Rahman, T.M., 1998, "Synthesis And Antimicrobial Activity of Some new Thiophene-2-Sulphonyl, Amino Acids and their Peptide Derivatives," Mans.Sci.Bull. (A Chem.) vol. 25 (1), Jun. 1998.

M.T. Shamin, D. Ukena, W.L. Padgett, O. Hong, J.W. Daley: "8-Zryl- and 8-Cycloalkyl-1,3-dipropylxanthines: Further Potent and Selective Antagonists for A1-Adenosine Receptors,"J. Med. Chem. vol. 31, No. 3, (1988) pp. 613-617.

\* cited by examiner

S1P RECEPTOR MODULATING COMPOUNDS AND USE THEREOF

RELATED APPLICATIONS

This application is a continuation-in-part of U.S. Ser. No. 11/491,766, filed Jul. 24, 2006, which claims priority to U.S. Ser. No. 60/739,466 filed Nov. 23, 2005, U.S. Ser. No. 60/753,806 filed Dec. 22, 2005 and U.S. Ser. No. 60/784,549 filed Mar. 21, 2006, and this application also claims the benefit of priority under 35 U.S.C. 119(e) to U.S. Provisional Application No. 60/784,549, filed on Mar. 21, 2006, the entire contents of which is incorporated herein by reference.

Amgen Inc., at One Amgen Center Drive, Thousand Oaks, Calif. 91320-1799 and Predix Pharmaceuticals Holdings, Inc., ("Predix") at 4 Maguire Road, Lexington, Mass. 02421, entered into a joint research agreement on Jul. 31, 2006. Predix merged into EPIX Delaware, Inc., a subsidiary of EPIX Pharmaceuticals, Inc. The field of the claimed invention is the design, discovery and development of S1P1 receptor modulators based on the scaffolds identified in patent applications 60/784549 (filed Mar. 21, 2006), 11/491766 (filed Jul. 24, 2006), and PCT/US2006/068657 (filed Jul. 24, 2006).

FIELD OF THE INVENTION

The present invention relates to compounds that have activity as S1P receptor modulating agents and the use of such compounds to treat diseases associated with inappropriate S1P receptor activity.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell chemotaxis and endothelial cell in vitro angiogenesis. S1P receptors are therefore good targets for therapeutic applications such as wound healing and tumor growth inhibition. S1P signals cells in part via a set of G protein-coupled receptors named S1P1, S1P2, S1P3, S1P4, and S1P5 (formerly called EDG-1, EDG-5, EDG-3, EDG-6, and EDG-8, respectively). These receptors share 50-55% amino acid and cluster identity with three other receptors (LPA1, LPA2, and LPA3 (formerly EDG-2, EDG-4 and EDG-7)) for the structurally-related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit, and each subunit can then associate with effector proteins, which activate second messengers leading to a cellular response. Eventually the GTP on the G-proteins is hydrolyzed to GDP, and the subunits of the G-proteins re-associate with each other and then with the receptor. Amplification plays a major role in the general GPCR pathway. The binding of one ligand to one receptor leads to the activation of many G-proteins, each capable of associating with many effector proteins, leading to an amplified cellular response.

S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other things. For example, the response specificity of the S1P receptors could allow for an S1P mimetic that initiates platelet aggregation without affecting cell morphology.

S1P is formed as a metabolite of sphingosine in its reaction with sphingosine kinase, and is abundantly stored in platelet aggregates where high levels of sphingosine kinase exist and sphingosine lyase is lacking. S1P is released during platelet aggregation, accumulates in serum and is also found in malignant ascites. S1P biodegradation most likely proceeds via hydrolysis by ectophosphohydrolases, specifically the sphingosine 1-phosphate phosphohydrolases.

SUMMARY OF THE INVENTION

The present invention relates to the use of new compositions which include S1P modulators, e.g., agonists, partial agonists, inverse agonists and antagonists, and their use in treating, preventing or curing various S1P receptor-related conditions. The invention features compounds which are S1P receptor modulators; in an embodiment, such compounds include those having the formula

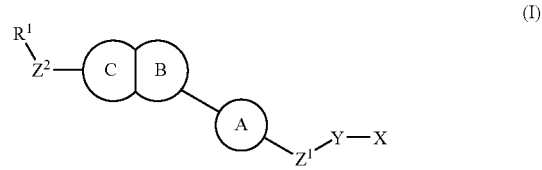

and pharmaceutically acceptable salts thereof, wherein $R^1$, $Z^2$, C, B, A, $Z^1$, Y and X are defined herein.

DETAILED DESCRIPTION OF THE INVENTION

In one embodiment, the present invention relates to compounds of formula I.

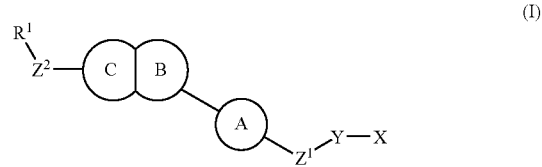

In formula I, A may be an aryl or heteroaryl group, optionally substituted with one, two or three substituents which may include halogen, hydroxyl, $SR^2$, $S(O)_2R^2$, $S(O)_2NR^2$, $NHS(O)_2R^2$, $COR^2$, $CO_2R^2$, cyano, amino, $C_{1-5}$ alkylamino/arylamino/heteroarylamino, alkyl, $C_{1-5}$ alkylthio, $C_{1-5}$ alkoxy, halogen-substituted $C_{1-6}$ alkyl, and halogen-substituted $C_{1-5}$ alkoxy. Optionally two adjacent substituents of A may, taken with $Z^1$ and the ring A to which they are attached, form a fused ring that may optionally contain one or more hetero atoms. $R^2$ may be selected independently from hydrogen, hydroxyl, amino, alkylamino/arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; or aryl/heteroaryl. A may desirably be a $C_{5-6}$ cyclic ring (alicyclic or aromatic) optionally having one or more heteroatoms.

B and C are an at least partially aromatic bicyclic ring system, e.g., bicycloaryl, bicycloheteroaryl, dihydrobicyclic or tetrahydrobicyclic aryl and heteroaryl. The bicyclic ring system may be substituted with 1 to 5 substituents, e.g., $C_{1-6}$ alkyl, $C_{1-5}$ alkylthio, $C_{1-5}$ alkoxy, halogen, hydroxyl, cyano, halogen-substituted $C_{1-6}$alkyl and halogen-substituted $C_{1-5}$ alkoxy.

$Z^1$ and $Z^2$ may be independently selected from O, $NR^3$, S, $S(O)$, $S(O)_2$, $S(O)_2NR^3$, $(CR^4R^5)_n$, $C=O$, $C=S$, $C=N-R^3$, or a direct bond. $R^3$ may be hydrogen, hydroxyl, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl. $R^4$ and $R^5$ may independently be hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl or together form "$C=O$"; n may be 0, 1, 2 or 3. In an embodiment where $Z^2$ is a direct bond, $R_3$ may be a $C_3$-$C_6$ ring optionally containing a heteroatom.

$R^1$ may be $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl. $R^1$ may optionally be substituted with, e.g., hydroxyl, halogen, cyano, amino, alkylamino, arylamino, heteroarylamino groups, and the aryl and heteroaryl groups may optionally be substituted with 1-5 substituents, e.g., hydroxyl, halogen, cyano, $C_{1-6}$ alkyl, $C_{1-5}$ alkylthio, $C_{1-5}$ alkoxy, $C_{3-6}$ cycloalkyl.

X may be $WC(O)OR^{6a}$, $WP(O)R^{6b}R^{6c}$, $WS(O)_2OH$, $WCONHSO_3H$ or 1H-tetrazol-5-yl. W may be a direct bond, oxygen or $C_{1-4}$ alkyl with substituents independently selected from the group consisting of: halogen, hydroxyl, cyano, amino, alkylamino, arylamino, heteroarylamino groups, $C_{1-4}$ alkoxy and; $R^{6a}$ may be hydrogen or $C_{1-4}$alkyl; $R^{6b}$ and $R^{6c}$ may be hydrogen, hydroxyl, $C_{1-4}$alkyl or halogen substituted $C_{1-4}$alkyl.

Y may be a residue of formula (a) where the left and right asterisks indicate the point of attachment:

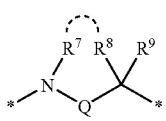

(a)

wherein Q may be a direct bond, $C=O$, $C=S$, $SO_2$, $C=ONR$ or $(CR^{10}R^{11})_m$; m may be 0, 1, 2 or 3; $R^7$ and $R^8$ may be independently hydrogen, halogen, amino, $C_{1-5}$ alkylamino, hydroxyl, cyano, $C_{1-6}$ alkyl, $C_{1-6}$ hydroxyalkyl (e.g., hydroxy-terminated alkyl), $C_{1-5}$ alkylthio, $C_{1-5}$ alkoxy, halogen-substituted $C_{1-6}$ alkyl and halogen-substituted $C_{1-5}$ alkoxy; or $R^7$ and $R^8$ may be joined together with the atoms to which they are attached to form a 4 to 7-membered ring, optionally having a hetero atom. $R^9$ may be hydrogen, halogen, hydroxyl, cyano, $C_{1-6}$ alkyl, $C_{1-5}$ alkylthio, $C_{1-5}$ alkoxy, halogen-substituted $C_{1-6}$ alkyl or halogen-substituted $C_{1-5}$ alkoxy; $R^{10}$ and $R^{11}$ may individually be hydrogen, halogen, hydroxyl, cyano, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy.

In another embodiment, the invention includes compounds having the formula

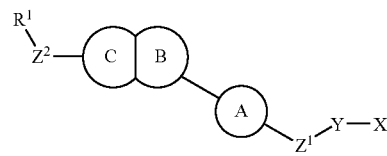

and pharmaceutically acceptable salts thereof. In formula I, A may be a $C_{1-6}$ cyclic ring (alicyclic or aromatic) that may have one or more heteroatoms. Where A is an aryl or heteroaryl group, A may be optionally substituted with one, two or three substituents which may include halogen, hydroxyl, S, $S(O)_2R^2$, $S(O)_2NR^2$, $NHS(O)_2R^2$, $COR^2$, $CO_2R^2$, cyano, amino, $C_{1-5}$ alkylamino/arylamino/heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy. Optionally two adjacent substituents may, taken with $Z^1$ and the ring to which they are attached, form an alicyclic or heterocyclic ring, e.g. piperidinyl. $R^2$ may be hydrogen, hydroxyl, amino, alkylamino/arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; or aryl/heteroaryl.

B and C are an at least partially aromatic bicyclic ring system, e.g., bicycloaryl, bicycloheteroaryl, dihydrobicyclic or tetrahydrobicyclic aryl and heteroaryl. The bicyclic ring system may be substituted with 1 to 5 substituents, e.g., $C_{1-6}$ alkyl, $C_{1-5}$ alkylthio, $C_{1-5}$ alkoxy, halogen, hydroxyl, cyano, halogen-substituted $C_{1-6}$alkyl and halogen-substituted $C_{1-5}$ alkoxy; $Z^1$ and $Z^2$ may be independently selected from O, $NR^3$, S, $S(O)$, $S(O)_2$, $S(O)_2NR^3$, $(CR^4R^5)_n$, $C=O$, $C=S$, $C=N-R^3$, or a direct bond. $R^3$ may be hydrogen, hydroxyl, $S(O)_2$, $C=O$, $C=S$, $C=NH$, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl. $R^4$ and $R^5$ may independently be hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl or together form "$C=O$"; n may be 0, 1, 2 or 3. $R^1$ may be $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl. $R_1$ may optionally be substituted with, e.g., hydroxyl, halogen, cyano, amino, alkylamino, arylamino, heteroarylamino groups, and the aryl and heteroaryl groups may optionally be substituted with 1-5 substituents, e.g., hydroxyl, halogen, cyano, $C_{1-6}$ alkyl, $C_{1-5}$ alkylthio, $C_{1-5}$ alkoxy, $C_{3-6}$ cycloalkyl.

X may be $WC(O)OR^{6a}$, $WP(O)R^{6b}R^{6c}$, $WS(O)_2OH$, $WCONHSO_3H$ or 1H-tetrazol-5-yl. W may be a direct bond, oxygen or $C_{1-4}$ alkyl with substituents independently selected from the group consisting of: halogen, hydroxyl, cyano, amino, alkylamino, arylamino, heteroarylamino groups, $C_{1-4}$ alkoxy and $COO_2H$; $R^{4a}$ may be hydrogen or $C_{1-4}$alkyl; $R^{6b}$ and $R^{6c}$ may be hydrogen, hydroxyl, $C_{1-4}$alkyl or halogen substituted $C_{1-4}$alkyl. Y has the formula:

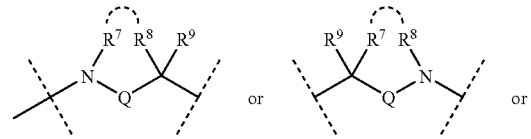

or

-continued

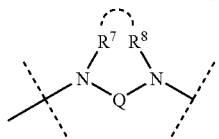

wherein Q may be a direct bond, C=O, C=S, SO$_2$, C=ONR or $(CR^{10}R^{11})_m$; m may be 0, 1, 2 or 3, and $R_7$-$R_8$ may be hydrogen, halogen, amino, $C_{1-5}$ alkylamino, hydroxyl, cyano, $C_{1-6}$ alkyl, $C_{1-5}$ alkylthio, $C_{1-5}$ alkoxy, halogen-substituted $C_{1-6}$ alkyl and halogen-substituted $C_{1-5}$ alkoxy; or $R^7$ and $R^8$ may be joined together with the atoms to which they are attached to form a 4 to 7 member ring. $R^9$ may be hydrogen, halogen, hydroxyl, cyano, $C_{1-6}$ alkyl, $C_{1-5}$ alkylthio, $C_{1-5}$ alkoxy, halogen-substituted $C_{1-6}$ alkyl or halogen-substituted $C_{1-5}$ alkoxy; $R^{10}$ and $R^{11}$ may individually be hydrogen, halogen, hydroxyl, cyano, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy.

In another embodiment, the present invention relates to a compound having the formula

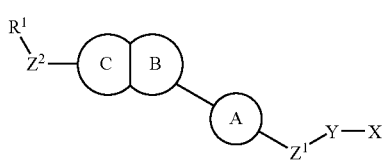

(I)

wherein
A is an optionally substituted aryl or heteroaryl group;
B and C are an at least partially aromatic bicyclic ring system;
X is selected from the group consisting of WC(O)OR$^{6a}$, WP(O)R$^{6b}$R$^{6c}$, WS(O)$_2$OH, WCONHSO$_3$H or 1H-tetrazol-5-yl; where W is a direct bond, oxygen or $C_{1-4}$ alkyl having one or more substituents independently selected from the group consisting of halogen, hydroxyl, cyano, amino, alkylamino, arylamino, heteroarylamino groups, $C_{1-4}$ alkoxy and COOH$_2$H; R$^{6a}$ is hydrogen or $C_{1-4}$alkyl; and R$^{6b}$ and R$^{6c}$ are independently hydrogen, hydroxyl, $C_{1-4}$alkyl or halogen substituted $C_{1-4}$alkyl;
Y is residue of formula (a) where the left and right asterisks indicate the point of attachment

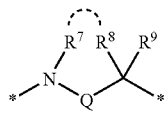

(a)

wherein
Q is selected from C=O, C=S, SO$_2$, C=ONR and $(CR^{10}R^{11})_m$;
m is 0, 1, 2 or 3;
R$^7$ and R$^8$ are independently selected from the group consisting of hydrogen, halogen, amino, $C_{1-5}$ alkylamino, hydroxyl, cyano, $C_{1-6}$ alkyl, $C_{1-6}$ hydroxyalkyl (e.g., hydroxy-terminated alkyl), $C_{1-5}$ alkylthio, $C_{1-5}$ alkoxy, halogen-substituted $C_{1-6}$ alkyl and halogen-substituted $C_{1-5}$ alkoxy; or R$^7$ and R$^8$ may be joined together with the atoms to which they are attached to form a 4 or 5-membered ring; and R$^9$ is selected from the group consisting of hydrogen, halogen, hydroxyl, cyano, $C_{1-6}$ alkyl, $C_{1-5}$ alkylthio, $C_{1-5}$ alkoxy, halogen-substituted $C_{1-6}$ alkyl or halogen-substituted $C_{1-5}$ alkoxy;
R$^{10}$ and R$^{11}$ are independently selected from the group consisting of hydrogen, halogen, hydroxyl, cyano, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy and
Z$^1$ is selected from O, NR$^3$, S, S(O), S(O)$_2$, S(O)$_2$NR$^3$, $(CR^4R^5)_n$, C=O, C=S and C=N—R$^3$; and Z$^2$ is selected from O, NR$^3$, S, S(O), S(O)$_2$, S(O)$_2$NR$^3$, $(CR^4R^5)_n$, C=O, C=S and C=N—R$^3$; wherein
R$^3$ is selected from the group consisting of hydrogen, hydroxyl, SO$_2$, C=O, C=S, C=NH, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl, or when Z$^2$ is a direct bond, R$_3$ is a $C_3$-$C_6$ ring optionally containing a heteroatom;
R$^4$ and R$^5$ are independently selected from the group consisting of hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl or together form C=O; and
n is 0, 1, 2 or 3; and
R$^1$ is selected from the group consisting of $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl.

In another embodiment, the invention includes compounds of formula (II):

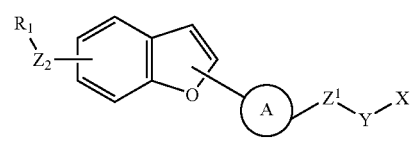

(II)

wherein A may be an aryl or heteroaryl group; X is —C(O)OR$^{6a}$, where R$^{6a}$ is hydrogen or $C_{1-4}$alkyl; Y is a residue of formula (a)

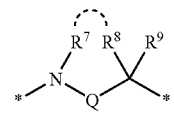

(a)

wherein Q is $(CR^{10}R^{11})_m$; m is 0, 1, 2, 3 or 4; R$^7$ and R$^8$ may independently be hydrogen, hydroxyl, lower alkyl; or R$^7$ and R$^8$, taken with the atoms to which they are attached, form a ring; R$^9$ is selected from, e.g., hydrogen, halogen, hydroxyl, or cyano; and Z$^1$ and Z$^2$ are independently O or $(CR^4R^5)_n$, where R$^4$ and R$^5$ are independently hydrogen, halogen, hydroxyl, cyano, $C_{1-6}$ alkyl, $C_{1-5}$ alkoxy; n is 0, 1, 2 or 3; and R$^1$ is selected from, e.g., $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl; or a pharmaceutically acceptable salts thereof.

The aryl or heteroaryl group may be substituted with one, two or three substituents such as halogen, hydroxyl, S, S(O)$_2$R$^2$, S(O)$_2$NR$^2$, NHS(O)$_2$R$^2$, COR$^2$, CO$_2$R$^2$, cyano, amino, $C_{1-5}$ alkylamino/arylamino/heteroarylamino, $C_{1-6}$ alkyl, $C_{1-5}$ alkylthio, $C_{1-5}$ alkoxy, halogen-substituted $C_{1-6}$ alkyl, or halogen-substituted $C_{1-5}$ alkoxy (where R$^2$ is, e.g., of hydrogen, hydroxyl, amino, alkylamino/arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; or aryl/heteroaryl; or optionally, two adjacent substituents on A may, taken with $Z^1$ and the ring to which they are attached, form an alicyclic or heterocyclic ring. $R^2$ may be selected from hydrogen, hydroxyl, amino, alkylamino/arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; or aryl/heteroaryl.

The benzofuranyl ring may be substituted with 1 to 5 substituents, e.g., of $C_{1-6}$ alkyl, $C_{1-5}$ alkylthio, $C_{1-5}$ alkoxy, halogen, hydroxyl, cyano, halogen-substituted $C_{1-6}$alkyl or halogen-substituted $C_{1-5}$ alkoxy. $R^1$ may be $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl; $R_1$ may optionally substituted with, e.g., hydroxyl, halogen, cyano, amino, alkylamino, arylamino, or heteroarylamino groups. (The aryl and heteroaryl groups may be substituted with one to five substituents such as hydroxyl, halogen, cyano, $C_{1-6}$ alkyl, $C_{1-5}$ alkylthio, $C_{1-5}$ alkoxy, and $C_{3-6}$ cycloalkyl.

The present invention relates, in one embodiment, to compounds according to Formula I. Preferably A is a substituted or unsubstituted aryl or heteroaryl group, which may be one illustrated below, where $R^{12}$ is hydrogen or $C_{1-6}$alkyl; and the left and right asterisks indicate the point of attachment in formula (I);

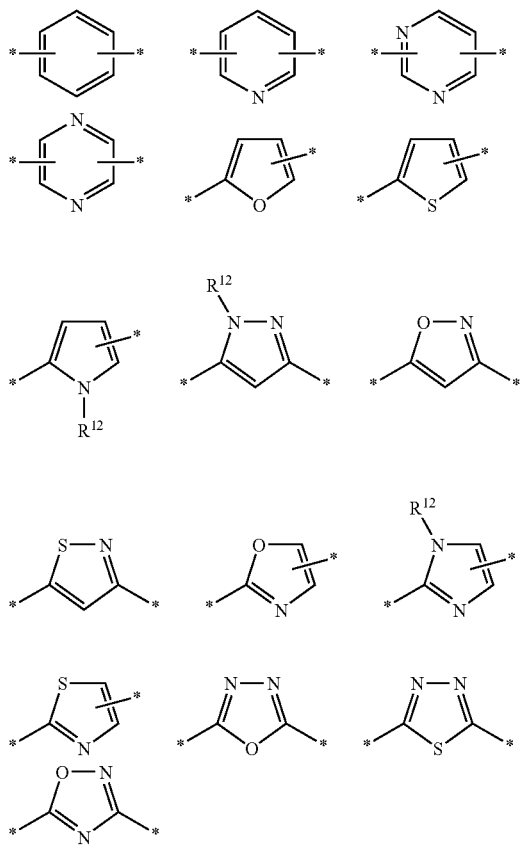

$R^{12}$ may be hydrogen, hydroxyl, amino, alkylamino or arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl; more preferably hydrogen.

B and C preferably are substituted or unsubstituted aryl or heteroaryl, e.g.,

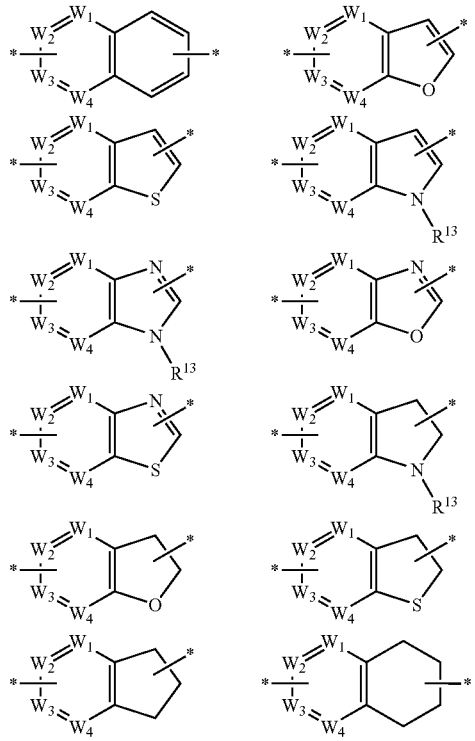

In the groups shown in the two tables directly above, the asterisks indicate that the group depicted may be attached to the molecule as shown, or "inverted". The groups depicted immediately above this text may desirably be present in the molecule in the orientation illustrated.

wherein $R^{12}$ is hydrogen or $C_{1-6}$ alkyl; and the left and right asterisks indicate the point of attachment in formula (I); $W_1$, $W_2$, $W_3$ or $W_4$ may be C, N, C—OH, C—$OR^{13}$ or C—$R^{13}$; $R^{13}$ is hydrogen or $C_{1-6}$alkyl, $C_{1-5}$alkylthio, $C_{1-5}$alkoxy, halogen, hydroxyl, cyano, halogen-substituted $C_{1-6}$alkyl and halogen-substituted $C_{1-5}$alkoxy.

$Z^1$ and $Z^2$ are preferably $CH_2$, O, S or a direct bond. $R^3$ is preferably methyl. $R^4$ and $R^5$ are preferably hydrogen or methyl. n is preferably 1 or 2. X may be combined with Y, e.g.,

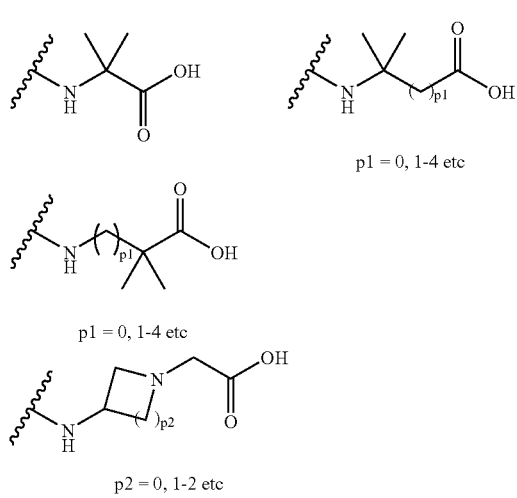

p1 = 0, 1-4 etc p1 = 0, 1-4 etc p2 = 0, 1-2 etc

-continued

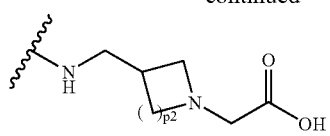

p2 = 0, 1-2 etc

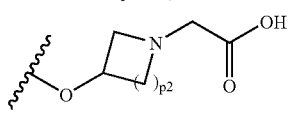

p2 = 0, 1-2 etc

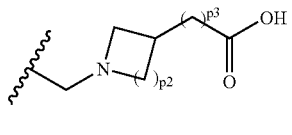

p2 = 0, 1-2 etc
p3 = 0, 1-4

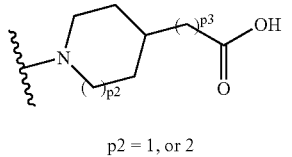

p2 = 1, or 2
p3 = 0, 1-4

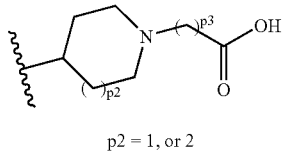

p2 = 1, or 2
p3 = 0, 1-4

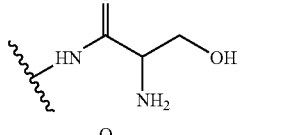

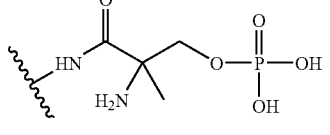

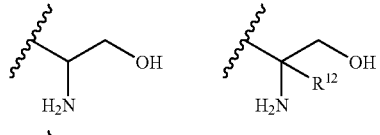

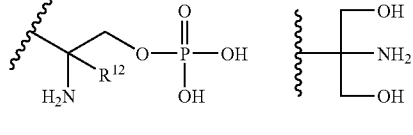

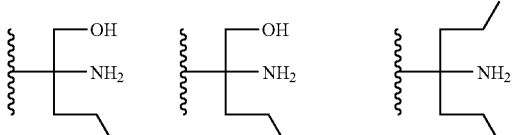

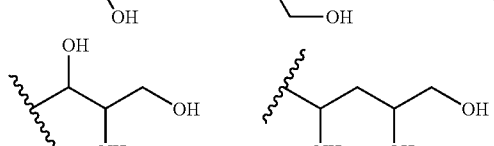

-continued

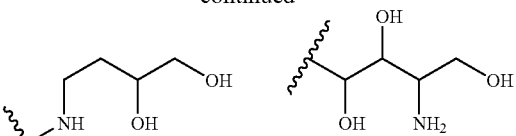

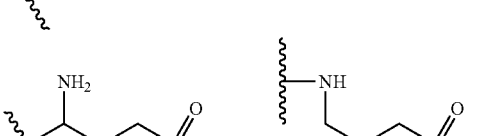

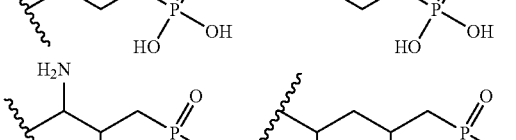

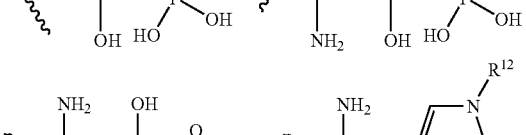

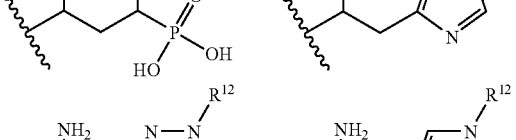

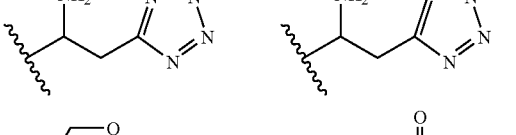

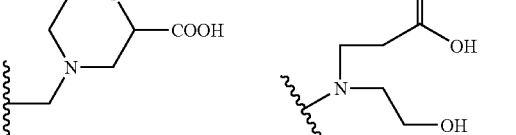

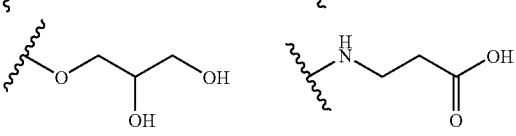

Optionally, two adjacent substituents on the ring A with $Z^1$ to form a fused ring, that may contain one or more hetero atoms, and wherein X may be combined with Y, e.g.,

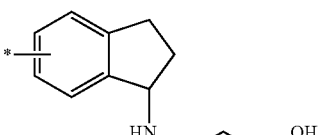

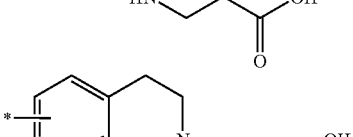

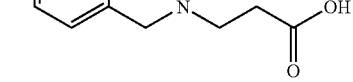

In another embodiment of the invention, in conjunction with the above and below embodiments, A is an aryl or heteroaryl group, optionally substituted with one, two or three substituents selected from halogen, hydroxyl, $SR^2$, S(O)₂R², S(O)₂NR², NHS(O)₂R², COR², CO₂R², cyano, amino, $C_{1-5}$ alkylamino, arylamino, heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy; wherein R² is selected independently, in each instance, from hydrogen, hydroxyl, amino, alkylamino, arylamino, $C_{1-6}$ alkyl, $C_{1-5}$ alkoxy, $C_{1-5}$ alkylthio, halogen-substituted $C_{1-6}$ alkyl, halogen-substituted $C_{1-5}$ alkoxy, aryl and heteroaryl.

In another embodiment of the invention, in conjunction with the above and below embodiments, A is 1,4-disubstituted phenyl, additionally optionally substituted with one, two or three substituents selected from halogen, hydroxyl, SR², S(O)₂R², S(O)₂NR², NHS(O)₂R², COR², CO₂R², cyano, amino, $C_{1-5}$ alkylamino, arylamino, heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy; wherein R² is selected independently, in each instance, from hydrogen, hydroxyl, amino, alkylamino, arylamino, $C_{1-6}$ alkyl, $C_{1-5}$ alkoxy, $C_{1-5}$ alkylthio, halogen-substituted $C_{1-6}$ alkyl, halogen-substituted $C_{1-5}$ alkoxy, aryl and heteroaryl.

In another embodiment of the invention, in conjunction with the above and below embodiments, A is an aryl or heteroaryl group, optionally substituted with one, two or three halogen atoms.

In another embodiment of the invention, in conjunction with the above and below embodiments, A is an phenyl, optionally substituted with one, two or three halogen atoms.

In another embodiment of the invention, in conjunction with the above and below embodiments, A is an phenyl, optionally substituted with one, two or three fluorine atoms.

In another embodiment of the invention, in conjunction with the above and below embodiments, A is fluorophenyl.

In another embodiment of the invention, in conjunction with the above and below embodiments, A is

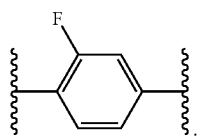

In another embodiment of the invention, in conjunction with the above and below embodiments, A is a heteroaryl group, optionally substituted with one, two or three halogen atoms.

In another embodiment of the invention, in conjunction with the above and below embodiments, A is a heteroaryl group.

In another embodiment of the invention, in conjunction with the above and below embodiments, B and C together are bicycloheteroaryl optionally substituted with 1 to 5 substituents selected from $C_{1-6}$ alkyl, $C_{1-5}$ alkylthio, $C_{1-5}$ alkoxy, halogen, hydroxyl, cyano, halogen-substituted $C_{1-6}$ alkyl and halogen-substituted $C_{1-5}$ alkoxy.

In another embodiment of the invention, in conjunction with the above and below embodiments, B and C together are a bicycloheteroaryl selected from:

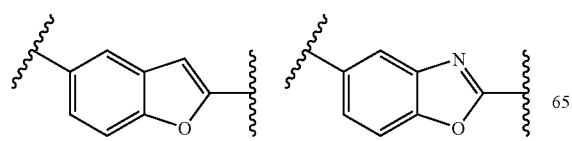

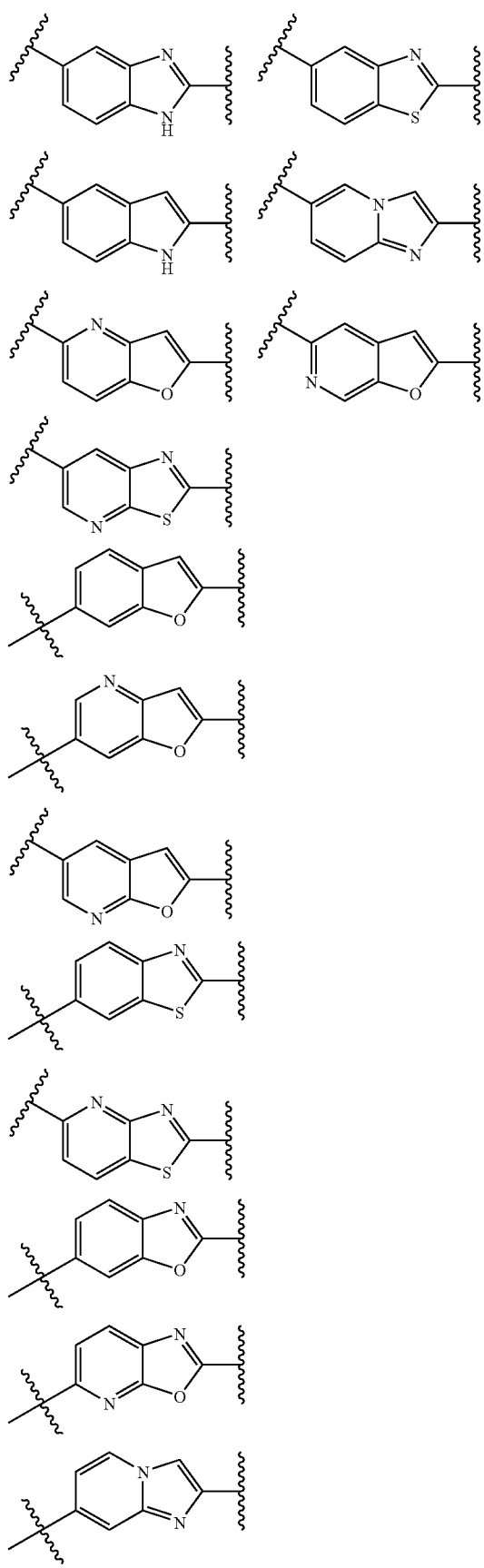

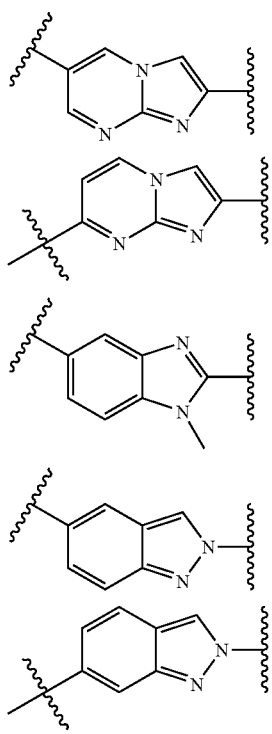
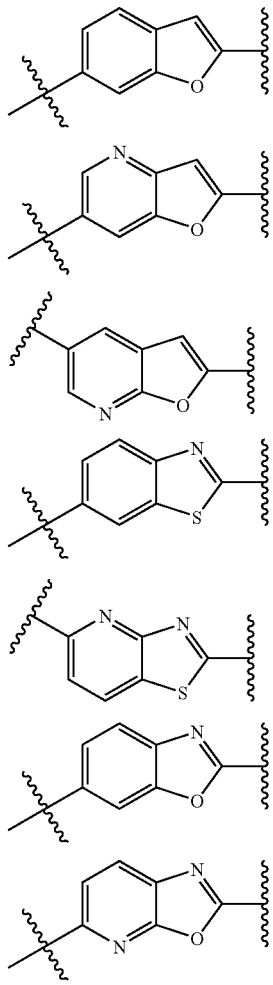
any of which are optionally substituted with 1 to 5 substituents selected from $C_{1-6}$ alkyl, $C_{1-5}$ alkylthio, $C_{1-5}$ alkoxy, halogen, hydroxyl, cyano, halogen-substituted $C_{1-6}$alkyl and halogen-substituted $C_{1-5}$ alkoxy.
In another embodiment of the invention, in conjunction with the above and below embodiments, B and C together are a bicycloheteroaryl selected from:
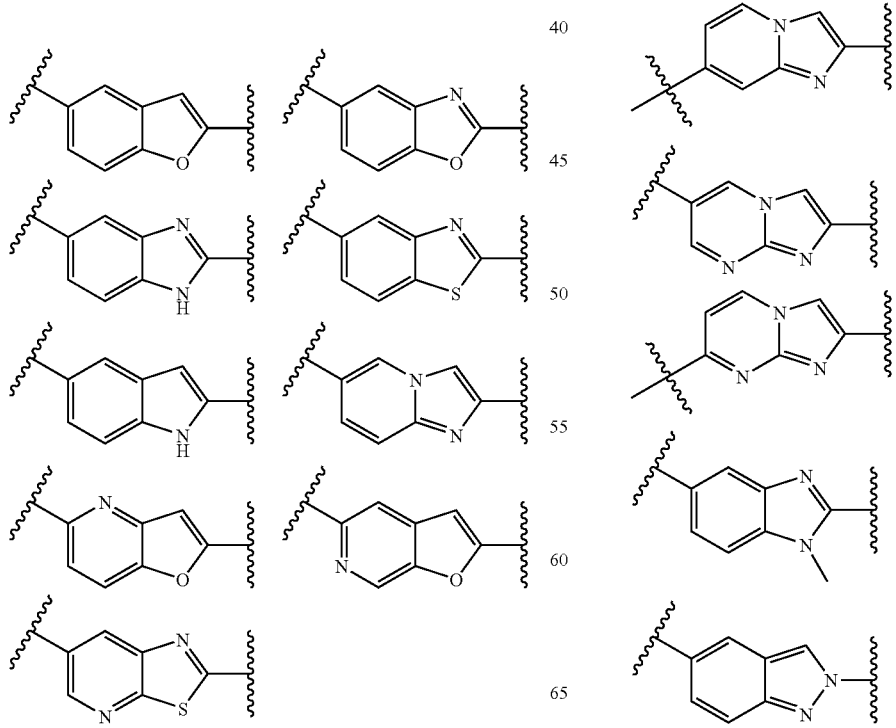

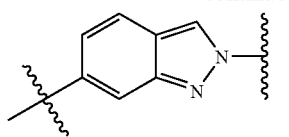

any of which are substituted with 1 to 5 substituents selected from $C_{1-6}$ alkyl, halogen, and halogen-substituted $C_{1-6}$alkyl.

In another embodiment of the invention, in conjunction with the above and below embodiments, B and C together are a bicycloheteroaryl selected from:

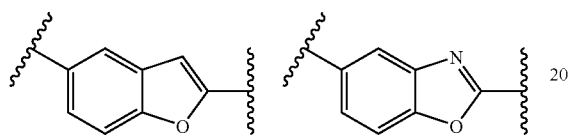
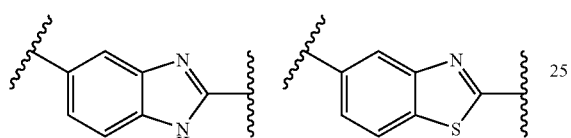
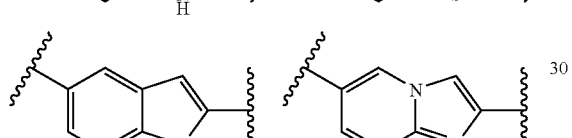
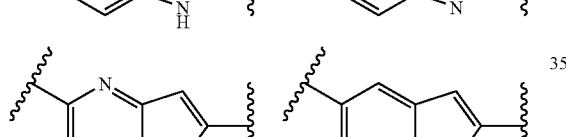
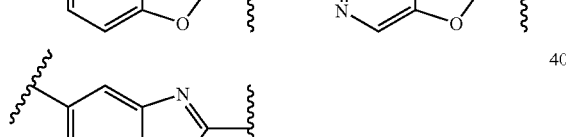
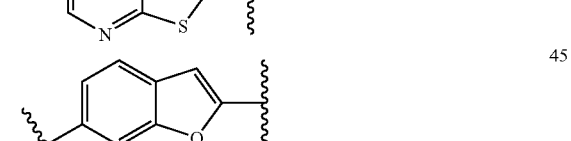
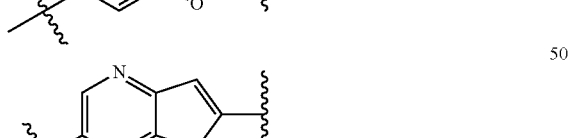
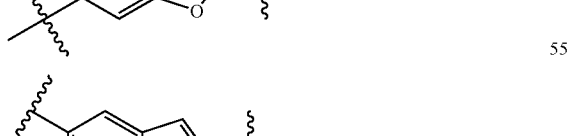
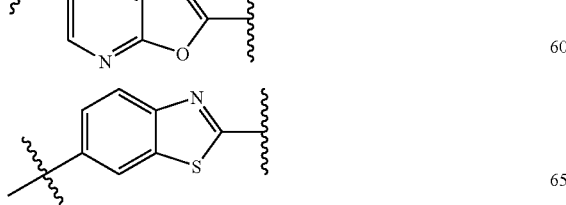

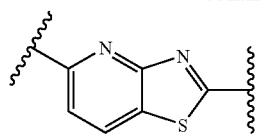
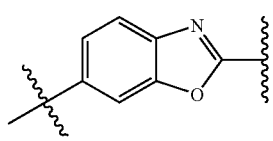
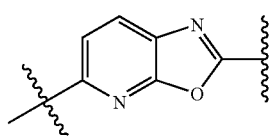
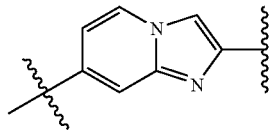
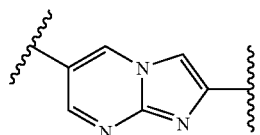
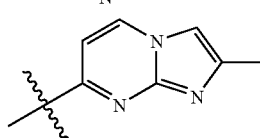
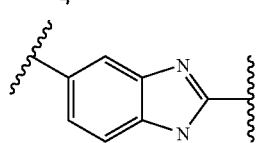
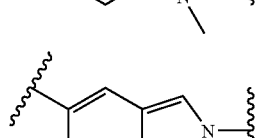
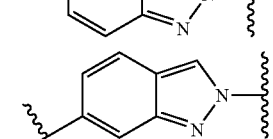
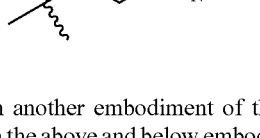
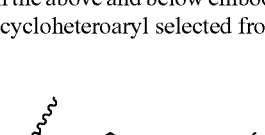 and
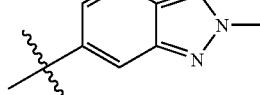

In another embodiment of the invention, in conjunction with the above and below embodiments, B and C together are a bicycloheteroaryl selected from:

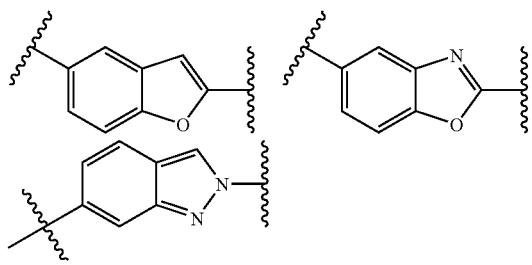

-continued

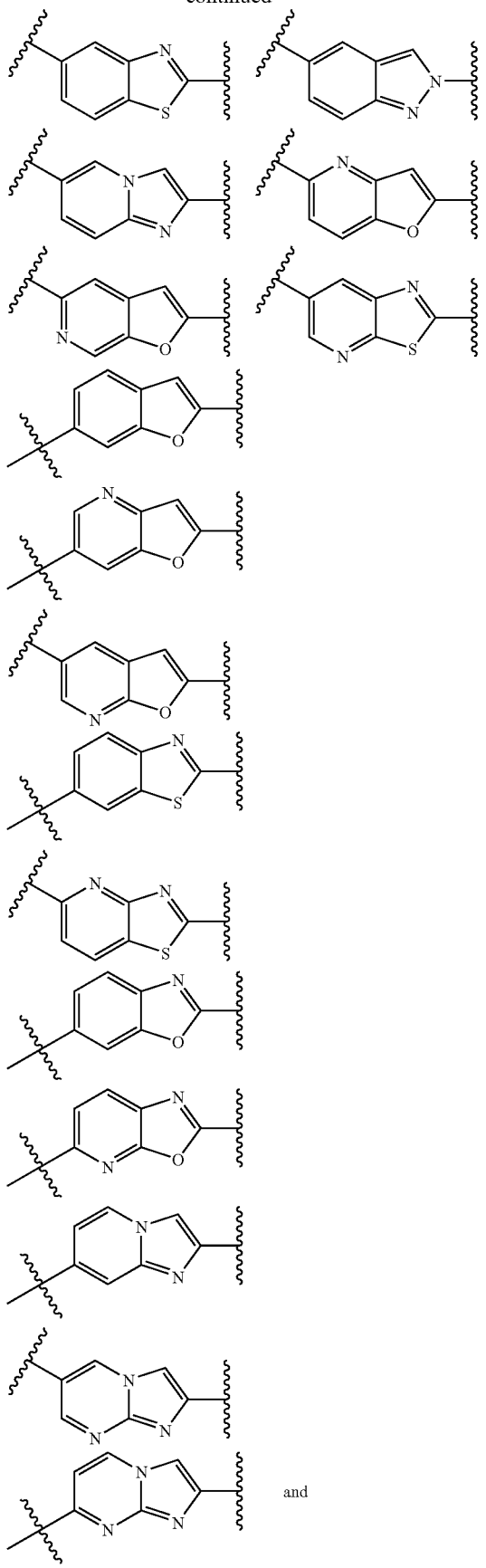

-continued

In another embodiment of the invention, in conjunction with the above and below embodiments, $R^1$ is selected from $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl and heteroaryl; any of which are optionally substituted with hydroxyl, halogen, cyano, amino, alkylamino, arylamino or heteroarylamino, wherein the aryl and heteroaryl groups may optionally be substituted with 1-5 substituents independently selected from hydroxyl, halogen, cyano, $C_{1-6}$ alkyl, $C_{1-5}$ alkylthio, $C_{1-5}$ alkoxy and $C_{3-6}$ cycloalkyl.

In another embodiment of the invention, in conjunction with the above and below embodiments, $R^1$ is selected from phenyl and heteroaryl; both of which are optionally substituted with halogen.

In another embodiment of the invention, in conjunction with the above and below embodiments, $R^1$ is phenyl optionally substituted with halogen.

In another embodiment of the invention, in conjunction with the above and below embodiments, $R^1$ is heteroaryl optionally substituted with halogen.

In another embodiment of the invention, in conjunction with the above and below embodiments, $R^1$ is phenyl.

In another embodiment of the invention, in conjunction with the above and below embodiments, $R^1$ is heteroaryl.

In another embodiment of the invention, in conjunction with the above and below embodiments, $R^1$ is 5- or 6-membered unsaturated ring including one atom selected from N, O and S, and 0, 1, 2 or 3 additional N atoms.

In another embodiment of the invention, in conjunction with the above and below embodiments, $R^1$ is selected from pyridinyl, pyrimidine, thiazolyl, oxazolyl, furanyl and thiophenyl.

In another embodiment of the invention, in conjunction with the above and below embodiments, X is $WC(O)OR^{6a}$, $WP(O)R^{6b}R^{6c}$, $WS(O)_2OH$, $WCONHSO_3H$ or 1H-tetrazol-5-yl. W is a direct bond, oxygen or $C_{1-4}$ alkyl with substituents independently selected from halogen, hydroxyl, cyano, amino, alkylamino, arylamino, heteroarylamino and $C_{1-4}$ alkoxy; and $R^{6a}$ is hydrogen or $C_{1-4}$ alkyl; $R^{6b}$ and $R^{6c}$ are independently selected from hydrogen, hydroxyl, $C_{1-4}$ alkyl and halogen substituted $C_{1-4}$ alkyl.

In another embodiment of the invention, in conjunction with the above and below embodiments, X is $CO_2H$.

In another embodiment of the invention, in conjunction with the above and below embodiments, Y is

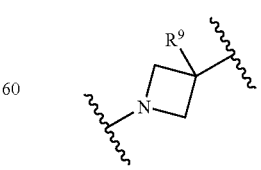

wherein $R^9$ is selected from hydrogen, halogen, hydroxyl, cyano, $C_{1-6}$ alkyl, $C_{1-5}$ alkylthio, $C_{1-5}$ alkoxy, halogen-substituted $C_{1-6}$ alkyl and halogen-substituted $C_{1-5}$ alkoxy.

In another embodiment of the invention, in conjunction with the above and below embodiments, Y is

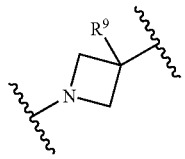

wherein $R^9$ is selected from hydrogen, halogen and hydroxyl.

In another embodiment of the invention, in conjunction with the above and below embodiments, $R^9$ is hydrogen.

In another embodiment of the invention, in conjunction with the above and below embodiments, $R^9$ is hydroxyl.

In another embodiment of the invention, in conjunction with the above and below embodiments, $Z^1$ is $CR^4R^5$; wherein $R^4$ and $R^5$ are independently hydrogen, halogen, hydroxyl, cyano, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy.

In another embodiment of the invention, in conjunction with the above and below embodiments, $Z^1$ is $CR^4R^5$; wherein $R^4$ and $R^5$ are independently hydrogen, halogen, $C_{1-6}$ alkyl or halogen-substituted $C_{1-6}$ alkyl.

In another embodiment of the invention, in conjunction with the above and below embodiments, $Z^1$ is $CH_2$.

In another embodiment of the invention, in conjunction with the above and below embodiments, $Z^2$ is selected from O, $NR^3$, S, S(O), $S(O)_2$, $S(O)_2NR^3$, $(CR^4R^5)_n$, C=O, C=S, and C=N—$R^3$;

$R^3$ is hydrogen, hydroxyl, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy;

$R^4$ and $R^5$ are independently selected from hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy, or together form "C=O"; and n is 1, 2 or 3.

In another embodiment of the invention, in conjunction with the above and below embodiments, $Z^2$ is selected from O, $NR^3$, S, S(O), $S(O)_2$, $S(O)_2NR^3$, $CR^4R^5$, C=O, C=S, and C=N—$R^3$;

$R^3$ is hydrogen, hydroxyl, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy; and $R^4$ and $R^5$ are independently selected from hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy.

In another embodiment of the invention, in conjunction with the above and below embodiments $Z^2$ is selected from O, $NR^3$, S, $CR^4R^5$, C=O, C=S, and C=N—$R^3$;

$R^3$ is hydrogen, hydroxyl, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy; and $R^4$ and $R^5$ are independently selected from hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy.

In another embodiment of the invention, in conjunction with the above and below embodiments $Z^2$ is selected from O, S, $CH_2$, C=O, C=S and C=N—OH.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

In one aspect, the present invention provides methods for modulating S1P-1 receptor mediated biological activity. The present invention also provides methods for using S1P-1 modulators (i.e., agonists or antagonists) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostate cancer; acute lung diseases, adult respiratory distress syndrome ("ARDS"), acute inflammatory exacerbation of chronic lung diseases such as asthma, surface epithelial cell injury such as transcorneal freezing or cutaneous burns, and cardiovascular diseases such as ischemia in a subject in need of such treatment or prevention.

In another aspect, the invention provides methods for using S1P-1 modulators in treating or preventing disorders such as, but not limited to, vasoconstriction in cerebral arteries, autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behçet's disease, glomerulonephritis, chronic thrombocytopenic purpura, hemolytic anemia, hepatitis and Wegner's granuloma.

In still another aspect, the invention provides methods for using S1P-1 modulators to treat or prevent a disease or disorder in a subject, comprising administering to a subject in need of such treatment or prevention a therapeutically effective amount of an S1P-1 modulator, e.g., an agonist, that stimulates the immune system. In certain embodiments, the subject is afflicted by an infectious agent. In other embodiments, the subject is immunocompromised.

In still another aspect, the present invention provides a method of modulating an S1P-1 receptor-mediated biological activity in a cell. A cell expressing the S1P-1 receptor is contacted with an amount of an S1P-1 receptor modulator sufficient to modulate the S1P-1 receptor mediated biological activity.

In yet another aspect, the present invention provides a method for modulating an S1P-1 receptor mediated biological activity in a subject. In such a method, an amount of a modulator of the S1P-1 receptor effective to modulate an S1P-1 receptor-mediated biological activity is administered to the subject.

In yet another aspect, the present invention provides a method for treating, preventing or ameliorating an S1P-1 receptor mediated condition in a subject. In such a method, an amount of a modulator of the S1P-1 receptor effective to modulate an S1P-1 receptor-mediated biological activity is administered to the subject. The S1P-1 receptor mediated condition may be, e.g., transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

The features and other details of the invention will now be more particularly described. It will be understood that particular embodiments described herein are shown by way of illustration and not as limitations of the invention. The principal features of this invention can be employed in various embodiments without departing from the scope of the invention. All parts and percentages are by weight unless otherwise specified.

DEFINITIONS

For convenience, certain terms used in the specification and examples are collected here.

"Treating", includes any effect, e.g., lessening, reducing, modulating, or eliminating, that results in the improvement of the condition, disease, disorder, etc.

"Alkyl" includes saturated aliphatic groups, e.g., straight-chain alkyl groups such as methyl, ethyl, propyl, butyl, pentyl, hexyl, heptyl, octyl, nonyl, and decyl; branched-chain alkyl groups (e.g., isopropyl, tert-butyl, and isobutyl); cycloalkyl (alicyclic) groups like cyclopropyl, cyclopentyl, cyclohexyl, cycloheptyl, and cyclooctyl); alkyl-substituted cycloalkyl groups; and cycloalkyl-substituted alkyl groups.

"Alkyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkyl groups may have six or fewer carbon atoms in their backbone (e.g., $C_1$-$C_6$ for straight chain, $C_3$-$C_6$ for branched chain), and more preferably four or fewer. Preferred cycloalkyl groups have from three to eight carbon atoms in their ring structure, and more preferably five or six carbons in the ring structure. "$C_1$-$C_6$" includes alkyl groups containing one to six carbon atoms.

"Substituted alkyls" refers to alkyl moieties having substituents replacing a hydrogen on one or more carbons of the hydrocarbon backbone. Such substituents can include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, thiocarboxylate, sulfates, alkylsulfinyl, sulfonato, sulfamoyl, sulfonamido, nitro, trifluoromethyl, cyano, azido, or heterocyclyl.

"Aryl" includes groups with aromaticity, including 5- and 6-membered unconjugated (i.e., single-ring) aromatic groups that may include from zero to four heteroatoms, as well as conjugated (i.e., multicyclic) systems having at least one ring that is aromatic. Examples of aryl groups include benzene, phenyl, tolyl and the like. Multicyclic aryl groups include tricyclic and bicyclic systems, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indolizine, tetralin, and methylenedioxyphenyl.

Aryl groups having heteroatoms in the ring structure may also be referred to as "aryl heterocycles", "heterocycles," "heteroaryls" or "heteroaromatics"; e.g., pyrrole, furan, thiophene, thiazole, isothiazole, imidazole, triazole, tetrazole, pyrazole, oxazole, isooxazole, pyridine, pyrazine, pyridazine, and pyrimidine. The aromatic ring can be substituted at one or more ring positions with, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "alkylaryl" or an "aralkyl" moiety is an alkyl substituted with an aryl group (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, and decenyl), branched-chain alkenyl groups, cycloalkenyl groups such as cyclopropenyl, cyclopentenyl, cyclohexenyl, cycloheptenyl, and cyclooctenyl; alkyl or alkenyl-substituted cycloalkenyl groups, and cycloalkyl or cycloalkenyl-substituted alkenyl groups.

"Alkenyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkenyl groups may have six or fewer carbon atoms in their backbone (e.g., $C_2$-$C_6$ for straight chain, $C_3$-$C_6$ for branched chain.) Preferred cycloalkenyl groups have from three to eight carbon atoms in their ring structure, and more preferably have five or six carbons in the ring structure. The term "$C_2$-$C_6$" includes alkenyl groups containing two to six carbon atoms.

"Substituted alkenyls" refers to alkenyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups.

"Alkynyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound Straight or branched chain alkynyls group may have six or fewer carbon atoms in their backbone (e.g., $C_2$-$C_6$ for straight chain, $C_3$-$C_6$ for branched chain). The term "$C_2$-$C_6$" includes alkynyl groups containing two to six carbon atoms.

"Substituted alkynyls" refers to alkynyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups. "Alkylamino" includes moieties wherein an alkyl moiety is bonded to an amino group; "dialkylamino", "arylamino", "diarylamino", and "alkylarylamino" are analogously named. In some embodiments, "amino" may include acylamino and/or alkylamino groups.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

"Alkoxy" includes alkyl, alkenyl, and alkynyl groups covalently linked to an oxygen atom. Examples of alkoxy groups include methoxy, ethoxy, isopropyloxy, propoxy, butoxy, and pentoxy groups. Examples of "substituted alkoxy" groups include halogenated alkoxy groups. Substituted alkoxy groups can include alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl substituents. Examples of halogen-substituted alkoxy groups include fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like.

Heterocyclic rings may be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

"At least partially aromatic bicyclic ring system", means a bicyclic ring system where either or both of the rings forming the bicycle are aromatic.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Combination therapy" (or "co-therapy") includes the administration of a S1P receptor modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp. 19-23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

An "S1P-modulating agent" includes compound or compositions capable of inducing a detectable change in S1P receptor activity in vivo or in vitro, e.g., at least 10% increase or decrease in S1P activity as measured by a given assay such as the bioassay described hereinbelow.

"$EC_{50}$ of an agent" included that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% activation is set at the amount of activity in the assay in the absence of added ligand/agonist.

"Purified" and like terms relate to the isolation of a molecule or compound in a form that is substantially free of contaminants normally associated with the molecule or compound in a native or natural environment.

An "effective amount" includes an amount sufficient to produce a selected effect. For example, an effective amount of an S1P receptor antagonist is an amount that decreases the cell signaling activity of the S1P receptor.

"Immunomodulation" includes effects on the functioning of the immune system, and includes both the enhancement of an immune response as well as suppression of the immune response.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention are high affinity agonists (or antagonists) at various S1P receptors. The compounds of the invention are also expected to evoke lymphopenia when introduced into rodents, non human primate or humans. Thus the compounds of the invention can be used as immune modulators, and are useful in treating or preventing pathologies mediated by lymphocyte actions, including acute or chronic rejection of tissue grafts such as organ transplants, and autoimmune diseases. Autoimmune diseases that may be treated with compounds of the invention include: systemic lupus erythematosus, multiple sclerosis, Behçet's disease, glomerulonephritis, rheumatoid arthritis, inflammatory bowel diseases such as Crohn's disease and ulcerative colitis, type I diabetes, uveitis, psoriasis, myasthenia gravis, Hashimoto's thyroiditis, autoimmune hemolytic anemia, autoimmune thrombocytopenic purpura, hepatitis and Wegner's granuloma.

The compounds of the invention are useful also in treating inflammatory disorders, including atopic asthma, inflammatory glomerular injury and ischemia-reperfusion injury.

Lysophospholipids, S1P and lysophosphatidic acid (LPA), stimulate cellular proliferation and affect numerous cellular functions by signaling through G protein-coupled endothelial differentiation gene-encoded (S1P) receptors. Accordingly, the S1P receptor modulators of the invention are anticipated to have utility in immunomodulation, e.g., in anti-angiogenesis therapy, such as in neoplastic disease treatment.

In one embodiment of the invention, a pharmaceutical composition comprising one or more of the S1P receptor agonists of the present invention is administered to a mammalian species, including humans, to enhance wound repair, improve neuronal function or enhance an immune response of that species. It has also been reported that S1P inhibits fibrosis in various organs. Accordingly, the S1P receptor agonists of the invention can be used to prevent/treat diseases associated with organ fibrosis, such as pulmonary fibrosis, interstitial pneumonia, chronic hepatitis, hepatic cirrhosis, chronic renal insufficiency or kidney glomerular sclerosis. In one embodiment, a composition comprising an S1P receptor agonist of the present invention is used to treat wounds, including burns, cuts, lacerations, surgical incisions, bed sores, and slow-healing ulcers such as those seen in diabetics.

In addition, S1P modulating compounds of the invention are believed to mobilize lymphocytes and increase their homing to secondary lymphoid tissues. Thus the present compounds can be used to direct lymphocytes away from transplanted organs, e.g., allografts, or healthy cells, e.g., pancreatic islets as in type I diabetes, myelin sheathing (multiple sclerosis), or other tissues that may be subjected to an undesirable immunoresponse, and thus decrease damage to such tissues from the immune system.

In another embodiment, the S1P receptor-modulating compounds of the invention are administered to a subject to treat or prevent a disorder of abnormal cell growth and differentiation. These disorders include Alzheimer's disease, aberrant corpus luteum formation, osteoporosis, anovulation, Parkinson's disease, and cancer. In one embodiment, an S1P antagonist is administered to a patient to treat a disease associated with abnormal growth.

In one embodiment, the compounds of the invention are used as immunomodulators to alter immune system activities and prevent damage to healthy tissue that would otherwise occur in autoimmune diseases and in organ transplantation. In particular, the compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, rapamycin, azathioprine, cyclophosphamide, methotrexate and corticosteroids such as cortisone, des-oxymetasone, betametasone, desametasone, flunisolide, prednisolone, prednisone, amcinomide, desonide, methylprednisolone, triamcinolone, and alclometasone.

S1P also acts as a survival factor in many cell types. In particular, compounds of the invention having S1P antagonistic activity are anticipated to be useful in protecting cells and tissues from hypoxic conditions. In accordance with one embodiment, compounds of the invention are administered to a patient judged to be or actually in need of treatment, to treat cells and tissues exposed to hypoxic conditions, including injury sustained as a result of ischemia. In accordance with one embodiment, compounds of the invention that show S1P receptor antagonist activity can be used to treat ischemia reperfusion type injury. Interference with the supply of oxygenated blood to tissues is defined as ischemia. The effects of ischemia are known to be progressive, so that over time cellular vitality continues to deteriorate and tissues become necrotic. Total persistent ischemia, with limited oxygen perfusion of tissues, results in cell death and eventually in coagulation-induced necrosis despite reperfusion with arterial blood. Evidence indicates that a significant proportion of the injury associated with ischemia is a consequence of the events associated with reperfusion of ischemic tissues, hence the term reperfusion injury.

Pharmaceutical compositions comprising the compounds of the invention may be administered to an individual in need by any number of routes, including topical, oral, intravenous, intramuscular, intra-arterial, intramedullary, intrathecal, intraventricular, transdermal, subcutaneous, intraperitoneal, intranasal, enteral, topical, sublingual, or rectal means. The oral route is typically employed for most conditions requiring the compounds of the invention. Preference is given to intravenous injection or infusion for the acute treatments. For maintenance regimens the oral or parenteral, e.g., intramuscular or subcutaneous, route is preferred. In accordance with one embodiment a composition is provided that comprises a compound of invention and albumin, e.g., a compound of the present invention, a pharmaceutically acceptable carrier and 0.1-1.0% albumin. Albumin functions as a buffer and improves the solubility of the compounds.

The invention also provides a pharmaceutical pack or kit comprising one or more containers filled with one or more of the ingredients of the pharmaceutical compositions of the invention. In accordance with one embodiment, a kit is provided for treating a patient in need of immunomodulation, including instructions for use of the kit. In this embodiment the kit comprises one or more of the S1P modulators of the invention, and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

The activity of compounds of the invention may be determined by using an assay for detecting S1P receptor activity (such as the [$\gamma$-35 S] GTP binding assay) and assaying for activity in the presence of S1P and the test compound. More particularly, in the method described by Traynor et al., 1995, *Mol. Pharmacol.* 47: 848-854, incorporated herein by reference, G-protein coupling to membranes can be evaluated by measuring the binding of labeled GTP.

For example, samples comprising membranes isolated from cells expressing an S1P polypeptide can be incubated in a buffer promoting binding of the polypeptide to ligand (i.e. S1P), in the presence of radiolabeled GTP and unlabeled GDP (e.g., in 20 mM HEPES, pH 7.4, 100 mM NaCl, and 10 mM $MgCl_2$, 80 pM $^{35}$S-GTP$_\gamma$S and 3 µM GDP), with and without a candidate modulator. The assay mixture is incubated for a suitable period of time to permit binding to and activation of the receptor (e.g., 60 minutes at 30° C.), after which time unbound labeled GTP is removed (e.g., by filtration onto GF/B filters). Bound, labeled GTP can be measured by liquid scintillation counting. A decrease of 10% or more in labeled GTP binding as measured by scintillation counting in a sample containing a candidate modulator, relative to a sample without the modulator, indicates that the candidate modulator is an inhibitor of S1P receptor activity.

A similar GTP-binding assay can be performed without the presence of the ligand (S1P) to identify agents that act as agonists. In this case, ligand-stimulated GTP binding is used as a standard. An agent is considered an agonist if it induces at least 50% of the level of GTP binding induced by S1P when the agent is present at 10 µm or less, and preferably will induce a level which is the same as or higher than that induced by the ligand.

GTPase activity can be measured by incubating cell membrane extracts containing an S1P receptor with $\gamma^{32}$P-GTP. Active GTPase will release the label as inorganic phosphate, which can be detected by separation of free inorganic phosphate in a 5% suspension of activated charcoal in 20 mM $H_3PO_4$, followed by scintillation counting. Controls would include assays using membrane extracts isolated from cells not expressing an S1P receptor (e.g., mock-transfected cells), in order to exclude possible non-specific effects of the candidate modulator. In order to assay for the effect of a candidate modulator on S1P-regulated GTPase activity, cell membrane samples can be incubated with the ligand (S1P), with and without the modulator, and a GTPase assay can be performed as described above. A change (increase or decrease) of 10% or more in the level of GTP binding or GTPase activity relative to samples without modulator is indicative of S1P modulation by a candidate modulator.

S1P receptor activity may also be measured by an S1P receptor (e.g., hS1P1, hS1P3, rS1P1, rS1P3 and parental cell) $Ca^{2+}$ Flux protocol as described below:
1. Material
   a. FLIPR buffer: 1×HBSS; 10 mM HEPES
   b. Cell growth media:
      i. human and rat S1P1 and S1P3: F12-Ham's media; 10% FBS (qualified); 1× Pen/Strep/Glu; 300 ug/mL Hygromycin; 400 ug/mL Geneticin
      ii. Parental cell: human and rat S1P1 and S1P3: F12-Ham's media; 10% FBS (qualified); 1× Pen/Strep/Glu; 300 ug/mL Hygromycin;
   c. Cell seeding media; F12-Ham's media; 10% FBS (Charcoal/dextran stripped); 1× Pen/Strep/Glu;
   d. Cell dissociation buffer: Versene from Invitrogen
   e. Agonist (S1P) dissolving buffer: 0.4% (w/v) fatty-acid free BSA (Sigma #A8806) in FLIPR buffer f. FLIPR dye: BD PBX Calcium assay kit; Cat#641077 is composed of Calcium indicator (Cat#850000) and 100× PBX signal enhancer (cat#850001). The 100×PBX signal enhancer is diluted into FLIPR buffer 1:100 and the calcium indicator is then added at 1:1000 ratio.
g. Cell plates (96-well): Greiner Cat#655090
h. Compound plates (96-well): Costar #3365
i. S1P stock solution preparation: S1P is purchased from CalBioChem (Catalog #970471; 1 mg vial; custom prep using methanol, & nitrogen gas drying inside glass vial; Storage @ −20° C.). Dissolve 1 vial of S1P into 26.4 ml of agonist dissolving buffer in a 50 ml centrifuge tube; Remove label from bottle of S1P, open and drop entire bottle into tube. Sonicate at 37° for ½ hour. Clear solution of 100 μM will result. This stock solution is aliquoted and stored at −80 C 2. Cell line maintenance
a. V5 tags were added at the N-terminus of hS1P1, hS1P3, rS1P1 and rS1P3. All four genes were transfected into CHO K1 cells which stably express Gqi5.
b. hS1P1 and hS1P3 were established as stable clones and rS1P1 and rS1P3 were sorted by anti V5 tag and established as stable pools after sorting.
c. Parental cell line CHO/K1 Gqi5 is used as the control.
d. All the cells are maintained in cell growth media and splitted twice a week using Versene.
e. All the cell lines are used under passage 30.

3. Assay protocol
a. Cell seeding: Cells are lifted from the flask by Versene and seeded in cell plates at 50K/well in cell seeding media. Cells are grown overnight at 37 degree.
b. Cell loading: Cell seeding media is discarded. Cells are loaded with 50 ul of FLIPR dye at RT for 90 min. Signal is stable for up to 5 h after dye loading.
c. Agonist (S1P) preparation: Frozen stock of S1P is thawed out and sonicated at 37 c for 30 minutes every time before use. The stock is then diluted into FLIPR buffer at proper concentration.
d. Compound preparation: Compounds are dissolved in DMSO. A 3×, 10 point dilution of the compounds are carried out in DMSO. Then the compounds are diluted into assay buffer 133× so that the DMSO concentration is 0.75%.
e. Activity measurement: The fluorescence signal change of the cells upon compound addition is monitored in FLIPRtetra. 25 ul of compound is transferred into the cell plates (50 ul of FLIPR dye; DMSO concentration: 0.25%). Signal is recorded for 90 sec after compound addition. Then 50 ul of 500 nM S1P is added in the cell plate, and signal is recorded for 90 seconds upon addition.

4. Data analysis
a. Peak value is calculated for each compound/S1P addition
b. The peak value of S1P at 200 nM is used as high control (100%), and the peak value of buffer only is used as low control (0%).
c. Data is normalized against high and low controls using the following equation:

$POC\_S=100*(RAW-LO)/(HI-LO)$ d. Peak value is plotted against the concentration of compound.
e. Curve is fitted using the 4 parameter fit:

$Y=(A+(B/(1+((x/C)\char`\^D))))$ where:
Y is POC_S (or POC)
X is compound concentration
A is the minimum (EC50min or IC50min)
B is the maximum (EC50max or IC50max)
C is the inflection point (EC50IP or IC50IP)
D is the hill slope (EC50 slope or IC50 slope).

Identified S1P receptor agonists and antagonists can be used to treat a variety of human diseases and disorders, including, but not limited to the treatment of infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergy; benign prostatic hypertrophy; migraine; vomiting; psychotic and neurological disorders, including anxiety, schizophrenia, manic depression, depression, delirium, dementia, and severe mental retardation.

Pain is a complex subjective sensation reflecting real or potential tissue damage and the affective response to it. Acute pain is a physiological signal indicating a potential or actual injury. Chronic pain can either be somatogenetic (organic) or psychogenic. Chronic pain is frequently accompanied or followed by vegetative signs, which often result in depression.

Somatogenetic pain may be of nociceptive origin, inflammatory or neuropathic. Nociceptive pain is judged to be commensurate with ongoing activation of somatic or visceral pain-sensitive nerve fibers. Neuropathic pain results from dysfunction in the nervous system; it is believed to be sustained by aberrant somatosensory processes in the peripheral nervous system, the CNS, or both. Chronic pain results in individual suffering and social economic costs of tremendous extent. Existing pharmacological pain therapies are widely unsatisfying both in terms of efficacy and of safety.

In one embodiment, S1P modulators of the present invention are used as immunomodulators to suppress the immune system and prevent damage to healthy tissue that would otherwise occur in autoimmune diseases and in organ transplantation. The compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, azatioprine, desoxymetasone, cyclophosphamide, cortisone, betametasone, FK 506 (a fungal macrolide immunosuppressant), desametasone, flunisolide, prednisolone, prednisone, amcinomide desonide, methylprednisolone, triamcinolone, alclometasone and methotrexate.

The dosage to be used is, of course, dependent on the specific disorder to be treated, as well as additional factors including the age, weight, general state of health, severity of the symptoms, frequency of the treatment and whether additional pharmaceuticals accompany the treatment. The dosages are in general administered several times per day and preferably one to three times per day. The amounts of the individual active compounds are easily determined by routine procedures known to those of ordinary skill in the art S1P also acts as a survival factor in many cell types. S1P receptor modulators are anticipated to have activity in protecting cells and tissues from hypoxic conditions. In accordance with one embodiment compounds of the invention are administered to treat cells and tissues exposed to hypoxic conditions, including injury sustained as a result of ischemia. In accordance with one embodiment, the S1P modulators having antagonistic activity can be used to treat ischemia reperfusion type injury. Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermolysis fluid or injected at the proposed site of infusion, (see for example, *Remington's Pharmaceutical Sciences,* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives, and internal salts such as N-oxides.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The following examples are given for the purpose of illustrating the invention, but not for limiting the scope or spirit of the invention.
Compounds of the invention may be prepared as described in the following schemes.
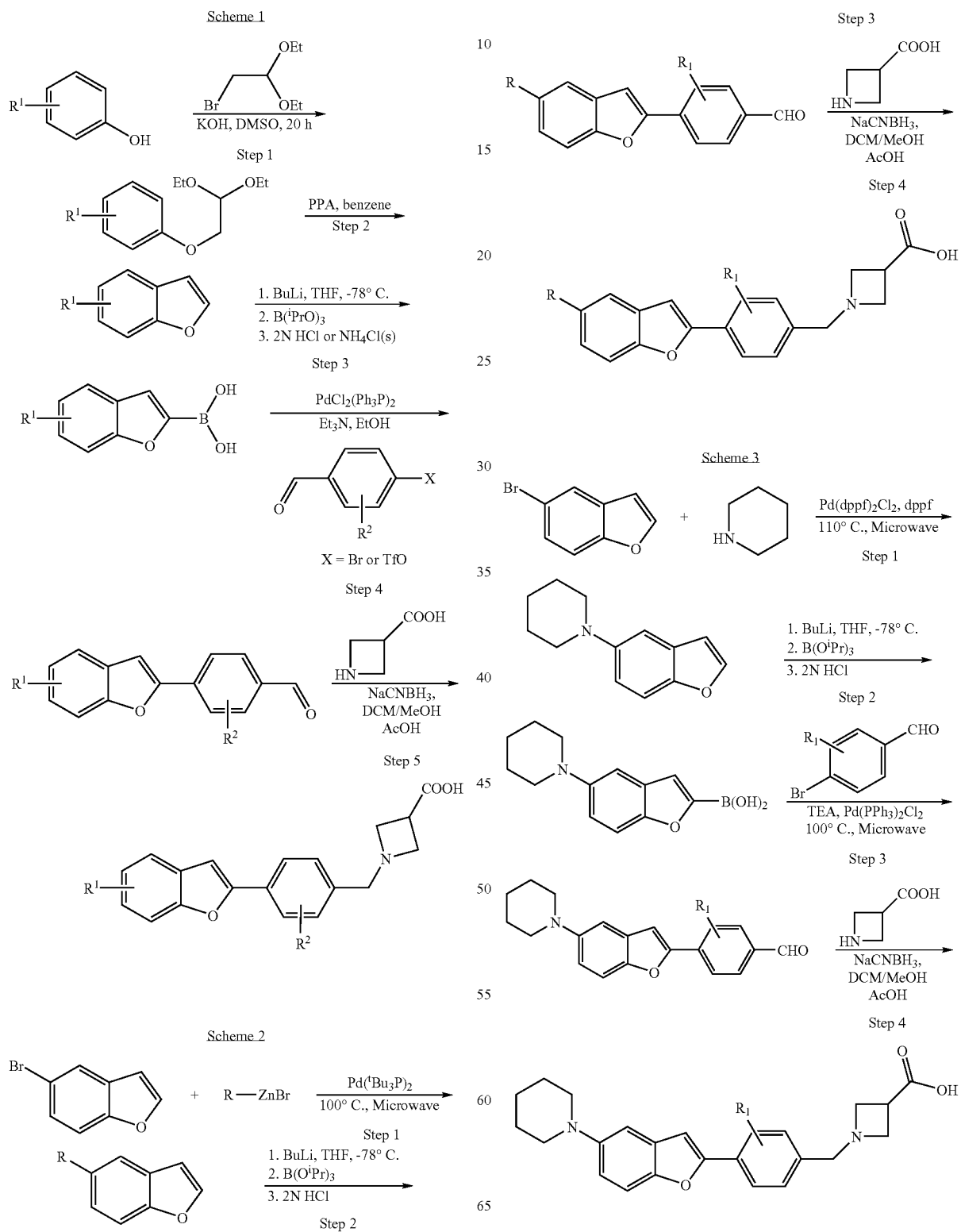

Scheme 4
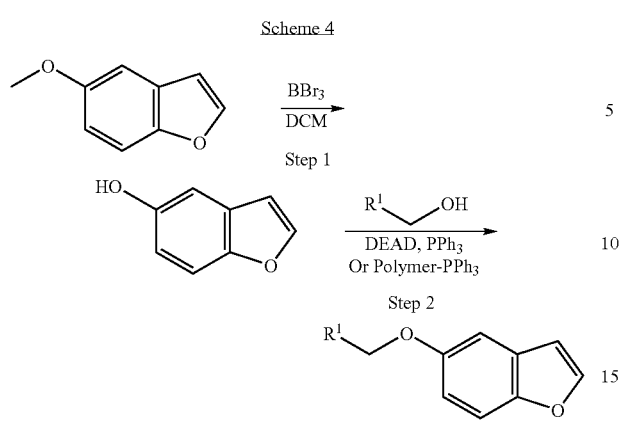
Scheme 5
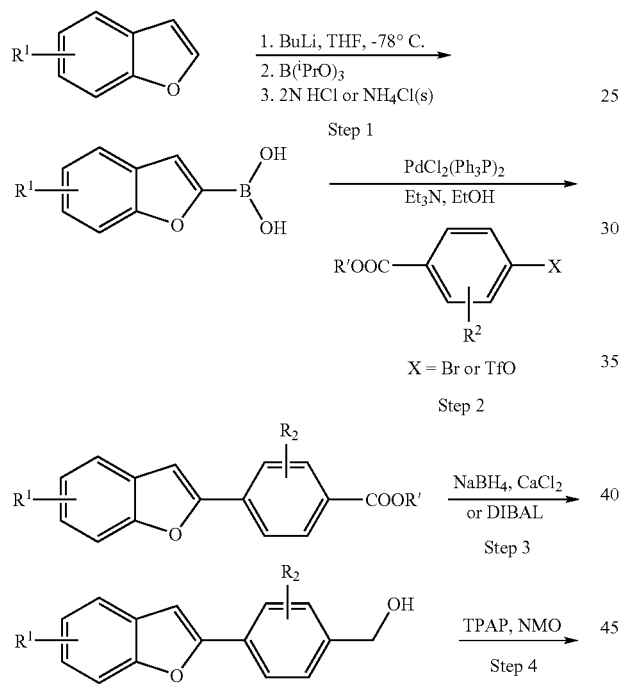
-continued
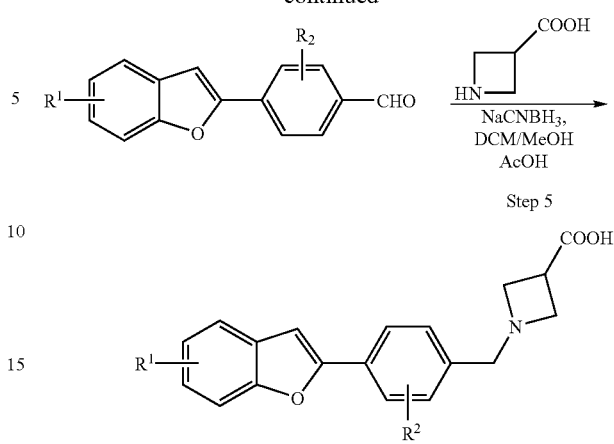
Scheme 6
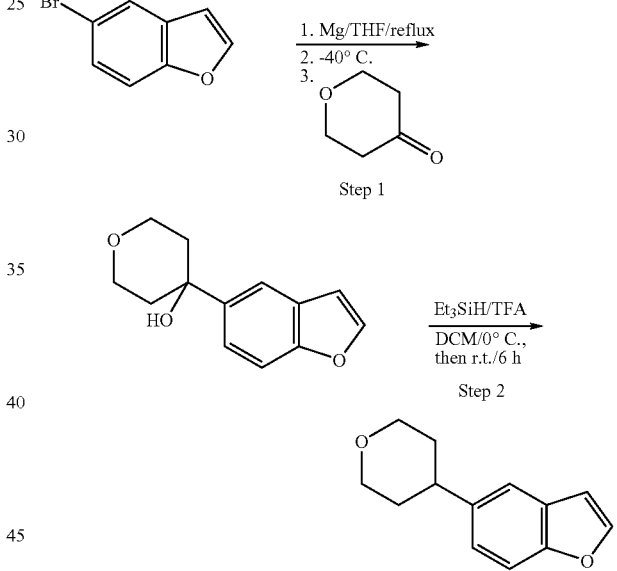
Scheme 7
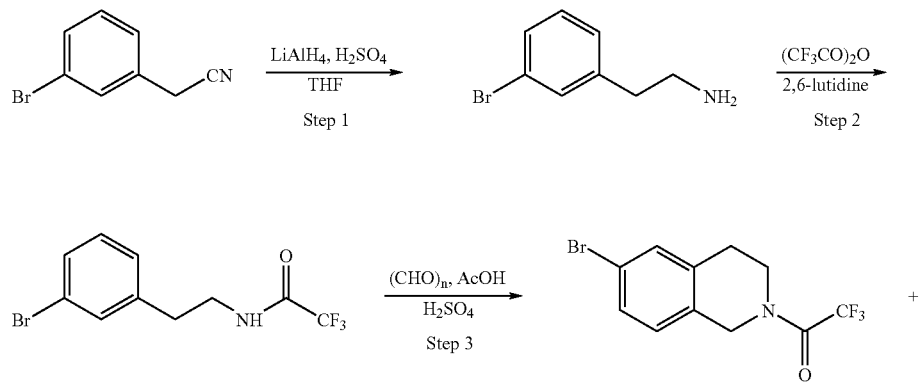

-continued
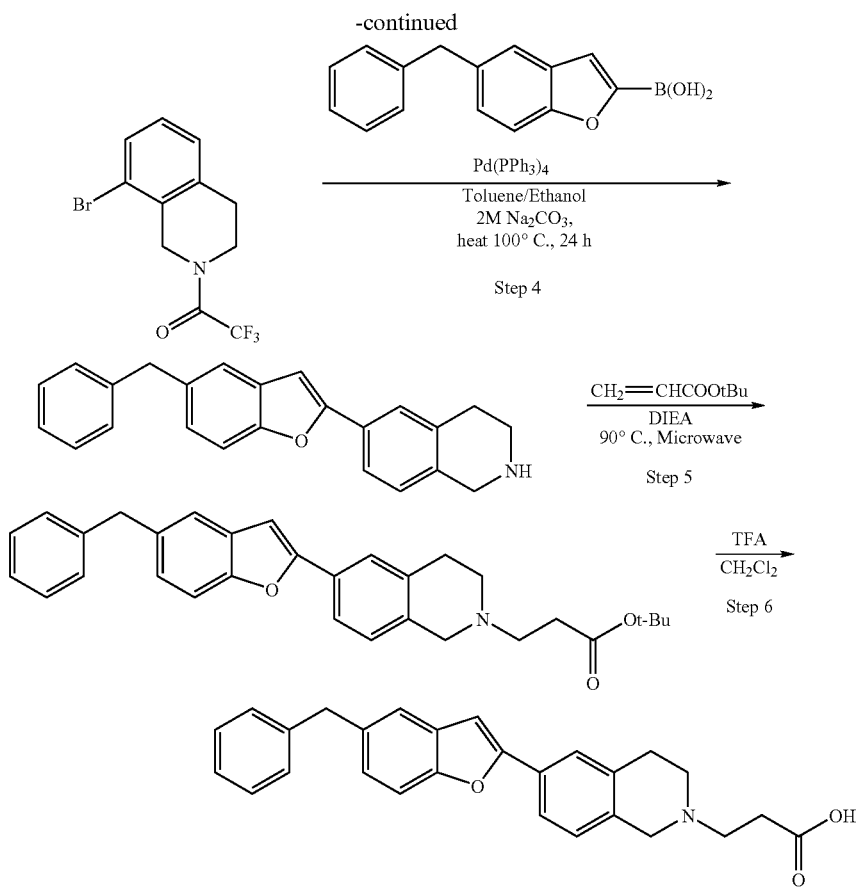
Scheme 8
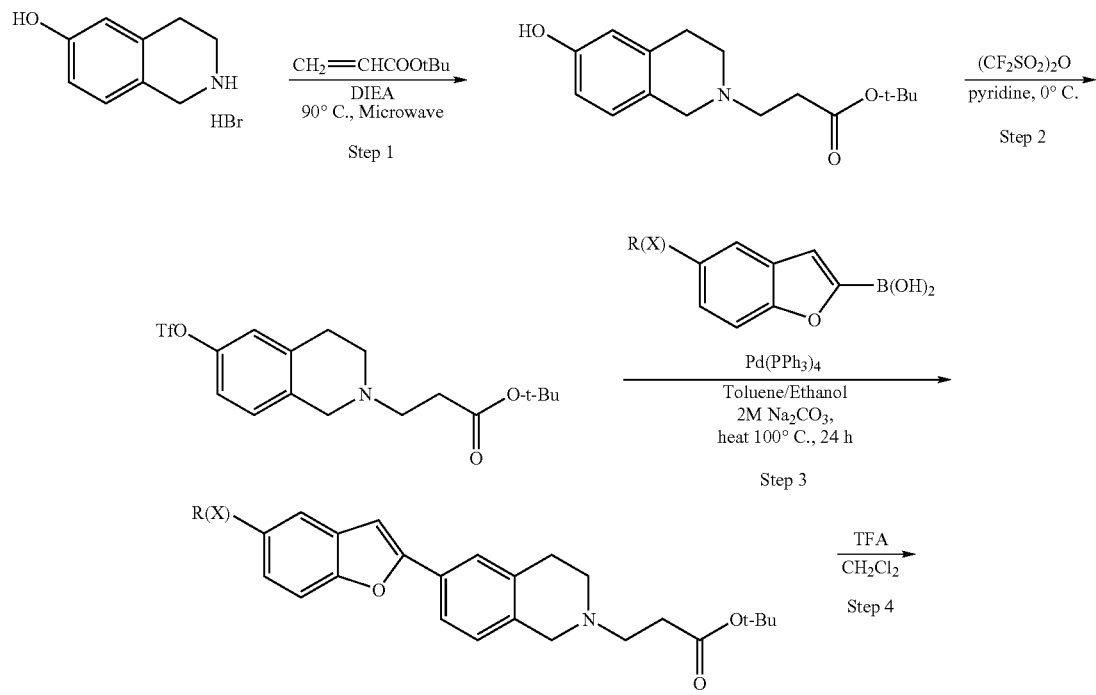

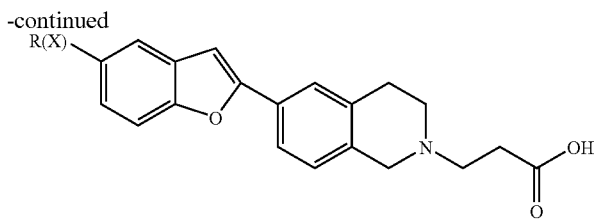

Scheme 9

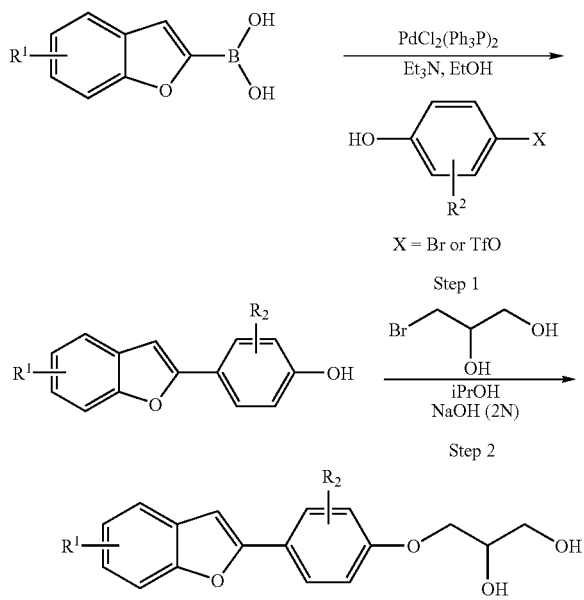

EXAMPLES

Compounds were prepared using the general procedures as described below:

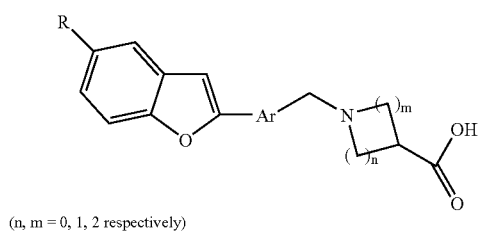

(n, m = 0, 1, 2 respectively)

A: General Procedure for C—C Bond Coupling with Rieke Reagents 5-bromobenzofuran (1.0 mmol) was dissolved in a THF solution of Rieke reagent (0.5M, 2.9 mmol) in a microwave reaction tube. Pd(PtBu$_3$)$_2$ (0.05 mmol) was added to this solution. The mixture was purged with N$_2$ gas for 3-5 min and heated at 100° C. for 30 min under microwave irradiation (Personal Chemistry Emrys™ Optimizer microwave reactor). Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system) to give a pure product.

B: General Procedure for N—C Bond Coupling Reaction

5-Bromobenzofuran (1.0 mmol), piperidine (1.2 mmol), Pd(dppf)Cl$_2$ (0.03 mmol), dppf (0.045 mmol) and sodium tert-butoxide (1.5 mmol) was mixed in toluene (2 mL). The mixture was purged with N$_2$ gas for 3-5 min and heated at 120° C. for 30 min under microwave irradiation (Personal Chemistry Emrys™ Optimizer microwave reactor). Upon completion of the reaction, the reaction mixture was directly loaded on silica gel column and purified on ISCO system (5% EtOAc in hexanes) to give a pure product.

C: General Preparative Procedure for Formation of Benzofuran Boronic Acids

A solution of n-BuLi (1.2 mmol, 2.5M solution in hexanes) was added dropwise to a solution of benzofuran compounds (1.0 mmol) in anhydrous THF (20 mL) at −78° C. The resulting mixture was stirred at −78° C. for 20 min, and treated with B($^i$PrO)$_3$ (1.5 mmol). The reaction mixture was allowed to warm up slowly to room temperature and stirred for 1 h. The reaction was cooled in ice-bath and quenched with 2N HCl or saturate NH$_4$Cl and extracted with Et$_2$O. The combined organic extracts were washed with brine, dried and concentrated under reduced pressure to yield a desired benzofuran boronic acid without further purification for next step.

D: General Procedure of Coupling Boronic Acids with Aryl Halides

A mixture of benzofuran boronic acid (1.1 mmol), aryl halide (1.0 mmol), triethylamine (20 mmol) and bis(triphenylphosphine)palladium(II) chloride (0.05 mmol) in ethanol (30 mL) was irradiated in a microwave instrument at 100° C. for 20 min. The reaction mixture was cooled, and the solvent was removed. The residue was treated with water and extracted with ethyl acetate. The organic layer was dried and concentrated in vacuo (the aqueous work-up is optional). Purification by silica gel chromatography gave the desired product.

E: General Procedure of Reductive Amination

A mixture of aldehyde (1.0 mmol), acetic acid (1.5 mmol) and azetidine-3-carboxylic acid or piperidine-4-carboxylic acid (1.2-1.5 mmol) in DCM/MeOH (1:1, 10 mL) was stirred at room temperature for 1 h. Sodium cyanoborohydride (0.5 mmol) was added and the reaction mixture was stirred for 2-3 h at room temperature. After concentration of solvent under reduced pressure, the resulting residue was dissolved in DMSO, filtered and purified by reverse phase preparative HPLC (Phenomenex reverse phase Luna 5μ C18(2) column, 60×21.2 mm ID, mobile phase: A=0.05% TFA in water; B=0.05% TFA in acetonitrile. The flow rate was 10-12 mL/min) to yield the desired final product with purity greater than 95%. All final products were obtained as the TFA salts except for Compound 59. Alternatively, the crude mixture of reductive amination can be purified by trituration with MeOH and water.

Compound 1

1-(4-(5-Phenylbenzofuran-2-yl)benzyl)azetidine-3-carboxylic acid 1-(2,2-Diethoxyethoxy)-4-phenylbenzene (step 1 in Scheme 1)

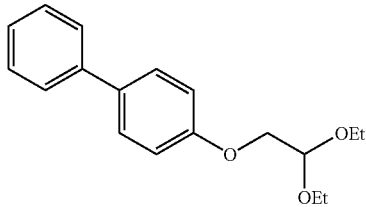

A mixture of 4-phenylphenol (5 g, 29.4 mmol), bromoacetaldehyde diethyl acetal (4.56 mL, 29.4 mmol) and KOH (1.94 g, 29.4 mmol) in DMSO (15 mL) was stirred at reflux for 6 h. The reaction mixture was allowed to cool down to room temperature and poured over ice containing 0.60 g of KOH and diluted to 100 mL with water. The solution was extracted with $Et_2O$ (20 mL×3); the combined extracts were washed with 1N NaOH solution, water and brine, dried, and concentrated under reduced pressure to yield 7.97 g (94%) of a yellow oil that was used without further purification: $^1$H NMR (400 MHz, $CDCl_3$) δ 7.56-7.50 (m, 4H), 7.41 (t, 2H), 7.30 (t, 1H), 7.00 (dt, 2H), 4.86 (t, 1H), 4.05 (d, 2H), 3.82-3.74 (m, 2H), 3.69-3.62 (m, 2H).

5-Phenylbenzofuran (step 2 in Scheme 1)

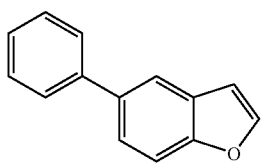

A mixture of 1-(2,2-diethoxyethoxy)-4-phenylbenzene (3.52 g, 12.3 mmol) and polyphosphoric acid (2.95 g, 29.4 mmol) in benzene (60 mL) was stirred at reflux for 2 h. The reaction mixture was cooled to room temperature, decanted from the PPA and filtered through a plug of silica gel, which was washed with hexanes. The filtrate and the wash were combined anc concentrated under reduced pressure to yield 2.00 g of the crude benzofuran: $^1$H NMR (400 MHz, $CD_3OD$) δ 7.79 (dd, 1H), 7.66 (d, 1H), 7.63-7.60 (m, 2H), 7.58-7.51 (m, 2H), 7.45 (t, 2H), 7.36-7.33 (m, 1H), 6.82 (dd, 1H).

5-Phenylbenzofuran-2-yl-2-boronic acid (step 3 in Scheme 1)

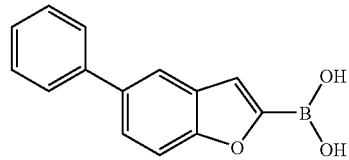

A solution of n-BuLi (2.0 mL, 2.5M solution in hexanes) was added dropwise to a solution of 5-phenylbenzofuran (816 mg, 4.21 mmol) in anhydrous THF (20 mL) at −78° C. The resulting mixture was stirred at −78° C. for 20 min, and treated with B($^i$PrO)$_3$ (1.46 mL, 6.31 mmol). The reaction mixture was allowed to warm up slowly to room temperature and stirred for 1 h. The reaction was quenched with 2N HCl and extracted with $Et_2O$. The combined extracts were washed with brine, dried and concentrated under reduced pressure to yield 1.2 g of crude boronic acid, that was used without further purification: $^1$H NMR (400 MHz, $CD_3OD$) δ 7.83 (dd, 1H), 7.64-7.55 (m, 4H), 7.48-7.42 (m, 3H), 7.38-7.32 (m 1H).

4-(5-Phenylbenzofuran-2-yl)benzaldehyde (step 4 in Scheme 1)

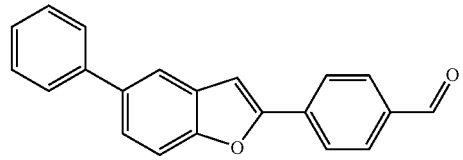

A solution of 5-phenylbenzofuran-2-yl-2-boronic acid (527 mg, 2.22 mmol), 4-bromobenzaldehyde (315 mg, 1.70 mmol), palladiumdichlorobis(triphenylphosphine) (60 mg, 0.085 mmol) and triethylamine (4.74 mL, 34 mmol) in EtOH was irradiated in the microwave at 100° C. for 1200 s. The precipitated that formed was filtered and rinsed with ethanol to yield 217 mg of desired benzaldehyde: $^1$H NMR (400 MHz, $CD_3OD$) δ 10.06 (s, 1H), 8.05 (d, 2H), 7.98 (d, 2H), 7.82 (br s, 1H), 7.65-7.52 (m, 4H), 7.48 (dd, 2H), 7.37 (t, 1H). MS (ESI) m/z: Calculated: 298.10; Observed: 299.1 (M$^+$+1).

1-(4-(5-Phenylbenzofuran-2-yl)benzyl)azetidine-3-carboxylic acid (step 5 in Scheme 1)

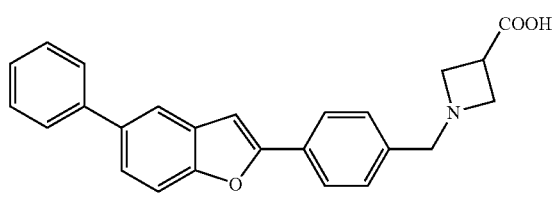

A mixture of 4-(5-phenylbenzofuran-2-yl)benzaldehyde (49 mg, 0.14 mmol) and azetidine-3-carboxylic acid (30 mg, 0.28 mmol) in MeOH (1 mL) was stirred at room temperature for 1 h. Sodium cyanoborohydride (60 mg, 0.28 mmol) was added in two portions and the reaction mixture was stirred for 16 h. Concentration of the solvent under reduced pressure yielded a yellow solid that was dissolved in DMSO (3 mL) and filtered to give a yellow solution that was purified by HPLC to yield 3 mg of desired product [hS1P1 $EC_{50}$=1200 nM]: $^1$H NMR (400 MHz, $CD_3OD$) δ 8.03 (d, 2H), 7.84 (br s, 1H), 7.66-7.58 (m, 6H), 7.45 (t, 2H), 7.36-7.32 (m, 2H), 4.47 (s, 2H), 4.40-4.32 (m, 4H), 3.72 (m, 1H). MS (ESI) m/z: Calculated: 383.15; Observed: 383.9 ($M^+$+1).

Compound 2

1-((4-(5-Butylbenzofuran-2-yl)phenyl)methyl)azetidine-3-carboxylic acid 1-(2,2-Diethoxyethoxy)-4-butylbenzene

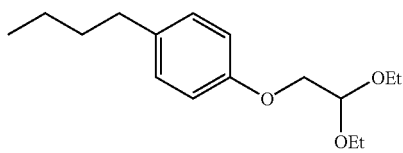

The title compound was prepared as Example Compound 1 (step 1 in Scheme 1) in the general method described above (90% yield): $^1$H NMR (400 MHz, $CDCl_3$) δ 7.07 (d, J=8.8, 2H), 6.83 (d, J=8.8, 2H), 4.83 (t, J=5.1, 1H), 3.98 (d, J=5.1, 2H), 3.80-3.72 (m, 2H), 3.67-3.59 (m, 2H), 2.54 (t, J=7.7, 2H), 1.59-1.51 (m, 2H), 1.36-1.30 (m, 2H), 1.24 (t, J=7.0, 6H), 0.91 (t, J=7.3, 3H).

5-Butylbenzofuran

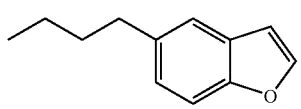

The title compound was prepared as Example Compound 1 (step 2 in Scheme 1) in the general method described above (91% yield): $^1$H NMR (400 MHz, $CDCl_3$) δ 7.58 (d, J=2.2, 1H), 7.41-7.36 (m, 2H), 7.11 (dd, J=8.5, 1.8, 1H), 6.70 (dd, J=2.2, 1.1, 1H), 2.70 (t, J=7.7, 2H), 1.67-1.60 (m, 2H), 1.42-1.32 (m, 2H), 0.93 (t, J=7.3, 3H).

5-Butylbenzofuran-2-yl-2-boronic acid

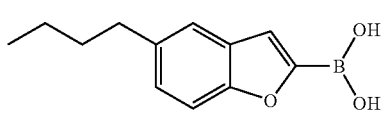

The title compound was prepared as Example Compound 1 (step 3 in Scheme 1) in the general method described above (67% yield): $^1$H NMR (400 MHz, $CDCl_3$) δ 7.43-7.31 (m, 2H), 7.22-7.14 (m, 2H), 2.70 (t, J=7.7, 2H), 1.67-1.59 (m, 2H), 1.41-1.32 (m, 2H), 0.93 (t, J=7.3, 3H).

4-(5-Butylbenzofuran-2-yl)benzaldehyde

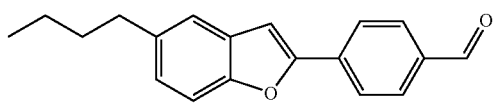

The title compound was prepared as Example Compound 1 (step 4 in Scheme 1) in the general method described above (72% yield): $^1$H NMR (400 MHz, $CDCl_3$) δ 10.03 (s, 1H), 8.00 (d, J=8.4, 2H), 7.94 (d, J=8.4, 2H), 7.45-7.41 (m, 2H), 7.17-7.15 (m, 2H), 2.71 (t, J=7.7, 2H), 1.68-1.61 (m, 2H), 1.41-1.33 (m, 2H), 0.94 (t, J=7.3, 3H).

1-((4-(5-Butylbenzofuran-2-yl)phenyl)methyl)azetidine-3-carboxylic acid

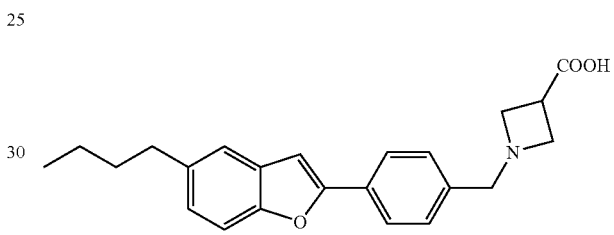

The title compound was prepared as Example Compound 1 (step 5 in Scheme 1) in the general method described above (42% yield) [hS1P1 $EC_{50}$=200 nM, 510 nM, 867 nM]: $^1$H NMR (400 MHz, $CD_3OD$) δ 7.98 (d, J=8.4, 2H), 7.55 (d, J=8.4, 2H), 7.43-7.41 (m, 2H), 7.23 (s, 1H), 7.15 (d, J=8.8, 1H), 4.40 (s, 2H), 4.25-4.23 (m, 4H), 3.52-3.46 (m, 1H), 2.71 (t, J=7.7, 2H), 1.67-1.61 (m, 2H), 1.41-1.33 (m, 2H), 0.95 (t, J=7.3, 3H). MS (ESI) m/z: Calculated: 363.18; Observed: 364.0 ($M^+$+1).

Compound 3

1-(4-(5-Butoxybenzofuran-2-yl)phenyl)methyl)azetidine-3-carboxylic acid 1-(2,2-Diethoxyethoxy)-4-butoxybenzene

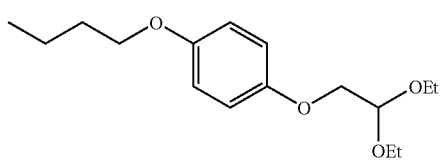

The title compound was prepared as Example Compound 1 (step 1 in Scheme 1) in the general method described above (84% yield): $^1$H NMR (400 MHz, $CDCl_3$) δ 6.86-6.80 (m, 4H), 4.81 (t, J=5.1, 1H), 3.96 (d, J=5.1, 2H), 3.90 (t, J=6.6, 2H), 3.79-3.72 (m, 2H), 3.67-3.59 (m, 2H), 1.77-1.70 (m, 2H), 1.52-1.43 (m, 2H), 1.24 (t, J=7.0, 6H), 0.96 (t, J=7.4, 3H).

5-Butoxybenzofuran

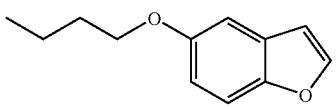

The title compound was prepared as Example Compound 1 (step 2 in Scheme 1) in the general method described above (81% yield): $^1$H NMR (400 MHz, CDCl$_3$) δ 7.58 (d, J=2.2, 1H), 7.38 (d, J=9.2, 1H), 7.05 (d, J=2.5, 1H), 6.90 (dd, J=2.5, 8.8, 1H), 6.69 (br d, J=2.2, 1H), 3.99 (t, J=6.6, 2H), 1.82-1.75 (m, 2H), 1.56-1.47 (m, 2H), 0.99 (t, J=7.3, 3H).

5-Phenylbenzofuran-2-yl-2-boronic acid (step 3 in Scheme 1)

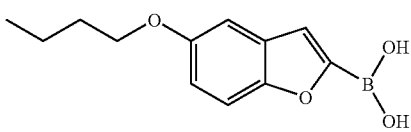

A solution of n-BuLi (2.5 mL, 2.5M solution in hexanes) was added dropwise to a solution of 5-butoxybenzofuran (1.0 g, 5.21 mmol) in anhydrous THF (20 mL) at −78° C. The resulting mixture was stirred at −78° C. for 20 min, and treated with B($^i$PrO)$_3$ (1.80 mL, 7.8 mmol). The reaction mixture was allowed to warm up slowly to room temperature and stirred for 1 h. The reaction was quenched with 2N HCl and extracted with Et$_2$O. The combined extracts were washed with brine, dried and concentrated under reduced pressure to yield 1.2 g of crude boronic acid, that was used without further purification: (98% yield): $^1$H NMR (400 MHz, CDCl$_3$) δ 7.37 (d, 1H), 7.30 (d, 1H), 7.06 (s, 1H), 6.98 (d, 1H), 4.44 (s, 2H), 1.81-1.71 (m, 2H), 1.58-1.50 (m, 2H), 1.00 (t, 3H).

4-(5-Butoxybenzofuran-2-yl)benzaldehyde (step 4 in Scheme 1)

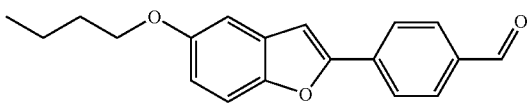

A solution of 5-phenylbenzofuran-2-yl-2-boronic acid (702 mg, 3.0 mmol), 4-bromobenzaldehyde (427 mg, 2.30 mmol), palladiumdichlorobis(triphenylphosphine) (80 mg, 0.11 mmol) and triethylamine (6.5 mL, 45 mmol) in EtOH (2 mL) was irradiated in the microwave at 100° C. for 1200 s. The precipitate that formed was filtered and rinsed with ethanol to yield 620 mg of crude product, which upon column chromatography afforded 375 mg of the desired compound (43%): $^1$H NMR (400 MHz, CDCl$_3$) δ 10.03 (s, 1H), 8.05 (d, 2H), 7.98 (d, 2H), 7.82 (d, 1H), 7.18 (d, 1H), 7.16 (d, 1H), 6.94 (s, 1H), 4.44 (s, 2H), 1.81-1.71 (m, 2H), 1.58-1.50 (m, 2H), 1.00 (t, 3H). MS (ESI) m/z: Calculated: 294.34; Observed: 295.2 (M$^+$+1).

1-(4-(5-Butoxybenzofuran-2-yl)phenyl)methyl)azetidine-3-carboxylic acid (step 5 in Scheme 1)

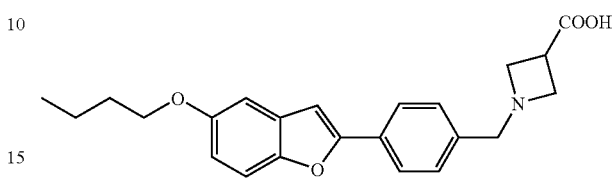

A mixture of 4-(5-butoxybenzofuran-2-yl)benzaldehyde (70 mg, 0.30 mmol), azetidine-3-carboxylic acid (46 mg, 0.45 mmol) and acetic acid (0.50 mmol) in MeOH-DCM (3:1; 2 mL) was stirred at room temperature for 1 h. Sodium triacetoxyborohydride (211 mg, 1.00 mmol) was added and the reaction mixture was stirred for 16 h. Concentration of the solvent under reduced pressure yielded a yellow solid that was dissolved in DMSO (3 mL) and filtered to give a yellow solution that was purified by HPLC to afford 6 mg of desired product (5% yield) [hS1P1 EC$_{50}$=520 nM]: $^1$H NMR (400 MHz, CD$_3$OD) δ 7.97 (d, 2H), 7.55 (d, 2H), 7.40 (d, 1H), 7.21 (s, 1H), 7.10 (d, 1H), 6.92-6.89 (dd, 1H), 4.44 (s, 2H), 4.37 (q, 4H), 4.00 (t, 2H), 3.72-3.64 (m, 1H), 1.81-1.71 (m, 2H), 1.58-1.50 (m, 2H), 1.00 (t, 3H). MS (ESI) m/z: Calculated: 379.45; Observed: 380.3 (M$^+$+1).

Compound 4

1-((4-(5-Benzylbenzofuran-2-yl)phenyl)methyl)azetidine-3-carboxylic acid

1-(4-(2,2-Diethoxyethoxy)benzyl)benzene

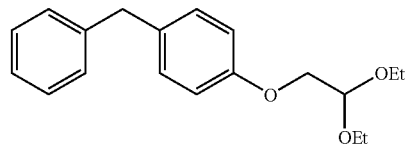

The title compound was prepared as Example Compound 1 (step 1 in Scheme 1) in the general method described above (84% yield): $^1$H NMR (400 MHz, CDCl$_3$) δ 7.30-7.25 (m, 2H), 7.20-7.15 (m, 3H), 7.09 (d, J=8.8, 2H), 6.84 (d, J=8.8, 2H), 4.82 (t, J=5.5, 1H), 3.98 (d, J=5.5, 2H), 3.92 (s, 2H), 3.79-3.72 (m, 2H), 3.66-3.59 (m, 2H), 1.24 (t, 7.1, 3H).

5-Benzylbenzofuran

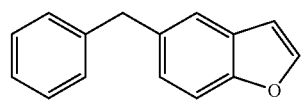

The title compound was prepared as Example Compound 1 (step 2 in Scheme 1) in the general method described above (89% yield): ¹H NMR (400 MHz, CDCl₃) δ 7.58 (d, J=2.2, 1H), 7.42-7.40 (m, 2H), 7.31-7.7.26 (m, 3H), 7.25-7.12 (m, 3H), 6.70 (m, 1H), 4.08 (s, 2H).

5-Benzylbenzofuran-2-yl-2-boronic acid

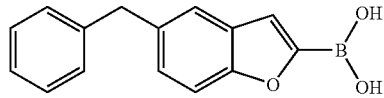

The title compound was prepared as Example Compound 1 (step 3 in Scheme 1) in the general method described above (66% yield): ¹H NMR (400 MHz, CDCl₃) δ 7.44 (m, 1H), 7.42 (d, J=8.4, 1H), 7.32-7.26 (m, 4H), 7.25-7.19 (m, 3H), 4.81 (s, 2H), 4.08 (s, 2H).

4-(5-Benzylbenzofuran-2-yl)benzaldehyde

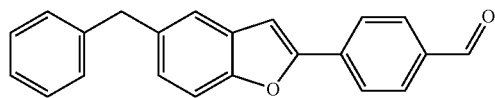

The title compound was prepared as Example Compound 1 (step 4 in Scheme 1) in the general method described above (76% yield): ¹H NMR (400 MHz, CDCl₃) δ 10.03 (s, 1H), 7.99 (d, J=8.4, 2H), 7.94 (d, J=8.4, 2H), 7.46-7.41 (m, 2H), 7.32-7.17 (m, 6H), 7.13 (br s, 1H), 4.08 (s, 2H).

1-((4-(5-Benzylbenzofuran-2-yl)phenyl)methyl)azetidine-3-carboxylic acid

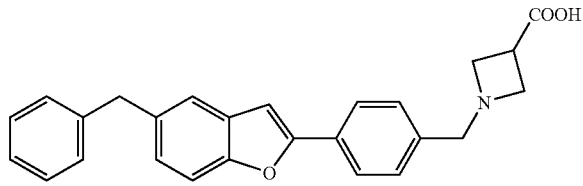

The title compound was prepared as Example Compound 1 (step 5 in Scheme 1) in the general method described above (62% yield) [hS1P1 EC₅₀=400 nM, 460 nM, 420 nM, 107 nM]: ¹H NMR (400 MHz, CD₃OD) δ 7.98 (d, J=8.4, 2H), 7.55 (d, J=8.4, 2H), 7.45-7.42 (m, 2H), 7.28-7.15 (m, 7H), 4.44 (s, 2H), 4.37-4.22 (m, 4H), 4.06 (s, 2H), 3.72-3.64 (m, 1H). MS (ESI) m/z: Calculated: 397.17; Observed: 398.0 (M⁺+1).

Compound 5

1-((4-(7-Benzylbenzofuran-2-yl)phenyl)methyl)azetidine-3-carboxylic acid 1-(2-(2,2-Diethoxyethoxy)benzyl)benzene

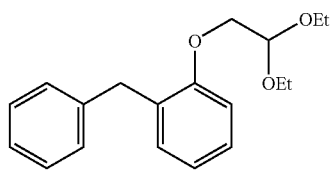

The title compound was prepared as Example Compound 1 (step 1 in Scheme 1) in the general method described above (99% yield): ¹H NMR (400 MHz, CDCl₃) δ 7.27-7.21 (m, 4H), 7.19-7.15 (m, 2H), 7.08 (br d, J=5.9, 1H), 6.90-6.83 (m, 2H), 4.78 (t, J=5.1, 1H), 4.00-3.98 (m, 4H), 3.76-3.69 (m, 2H), 3.63-3.56 (m, 2H), 1.22 (t, J=7.0, 6H).

7-Benzylbenzofuran

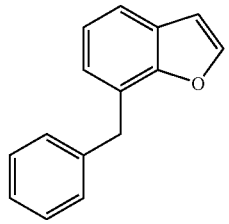

The title compound was prepared as Example Compound 1 (step 2 in Scheme 1) in the general method described above (84% yield): ¹H NMR (400 MHz, CDCl₃) δ 7.62 (d, J=2.2, 1H), 7.45 (d, J=7.7, 1H), 7.36 (s, 1H), 7.29-7.26 (m, 3), 7.25-7.13 (m, 2), 7.05 (d, J=7.4, 1H), 6.76 (d, J=2.2, 1H), 4.27 (s, 2H).

7-Benzylbenzofuran-2-yl-2-boronic acid

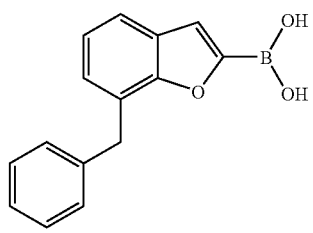

The title compound was prepared as Example Compound 1 (step 3 in Scheme 1) in the general method described above (67% yield): ¹H NMR (400 MHz, CDCl₃) δ 7.50 (dd, J=7.7, 1H), 7.36 (s, 1H), 7.29-7.25 (m, 4H), 7.18-7.09 (m, 3H), 4.29 (s, 2H).

4-(7-Benzylbenzofuran-2-yl)benzaldehyde

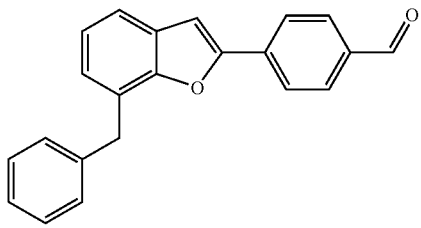

The title compound was prepared as Example Compound 1 (step 4 in Scheme 1) in the general method described above (72% yield): $^1$H NMR (400 MHz, CDCl$_3$) δ 10.04 (s, 1H), 8.00-7.94 (m, 4H), 7.50 (d, J=9.9, 1H), 7.47-7.27 (m, 4H), 7.24-7.17 (m, 3H), 7.11 (d, J=7.3, 1H), 4.33 (s, 2H).

1-((4-(7-Benzylbenzofuran-2-yl)phenyl)methyl)azetidine-3-carboxylic acid

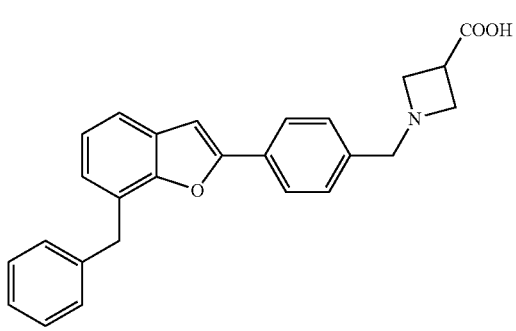

The title compound was prepared as Example Compound 1 (step 5 in Scheme 1) in the general method described above (81% yield) [hS1P1 EC$_{50}$>1 nM]: $^1$H NMR (400 MHz, CD$_3$OD) δ 7.97 (d, J=8.0, 2H), 7.56 (d, J=8.0, 2H), 7.48 (d, J=7.7, 1H), 7.34-7.24 (m, 5H), 7.19-7.10 (m, 3H), 4.44 (s, 2H), 4.32-4.25 (m, 6H), 3.66-3.56 (m, 1H). MS (ESI) m/z: Calculated: 397.17; Observed: 397.9 (M$^+$+1).

Compound 6

1-(4-(5-cyclohexylbenzofuran-2-yl)benzyl)azetidine-3-carboxylic acid

5-cyclohexylbenzofuran (step 1 in Scheme 2)

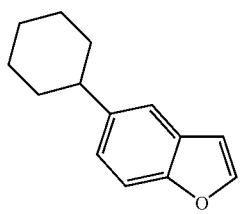

5-bromobenzofuran (500 mg, 2.55 mmol) was dissolved in a THF solution of cyclohexyl zinc(II) bromide (0.5M, 15 mL, 7.40 mmol) in a microwave reaction tube. Pd(P$^t$Bu$_3$)$_2$ (65 mg, 0.128 mmol, 0.05 eqv.) was added to this solution. The mixture was purged with N$_2$ gas for 3-5 min and heated at 100° C. for 30 min under microwave irradiation. Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system, 5% EtOAc in hexanes) to give 0.217 g desired product (43% yield): $^1$H NMR (400 MHz, CDCl$_3$) δ 7.57 (d, 1H), 7.41 (d, 2H), 7.15 (d, 1H), 6.72 (d, 1H), 2.58 (m, 1H), 1.92-1.74 (m, 4H), 1.51-1.35 (m, 4H), 1.31-1.25 (m, 2H).

5-cyclohexylbenzofuran-2-ylboronic acid (step 2 in Scheme 2)

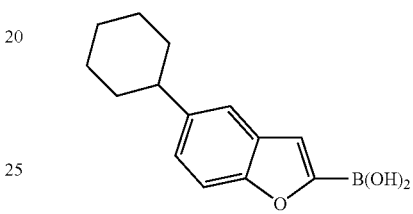

A solution of n-BuLi (360 µL, 0.9 mmol, 2.5M solution in hexanes) was added dropwise to a solution of 5-cyclohexylbenzofuran (150 mg, 0.75 mmol) in anhydrous THF (5 mL) at −78° C. The resulting mixture was stirred at −78° C. for 40 min, and treated with B($^i$PrO)$_3$ (260 µL, 1.13 mmol). The reaction mixture was allowed to warm up slowly to room temperature and stirred for 1 h. TLC indicated the completion of reaction. The reaction was cooled in ice-bath and quenched with 2N HCl (3 mL) and extracted with Et$_2$O. The combined organic extracts were washed with brine, dried and concentrated under reduced pressure to yield a desired boronic acid (0.156 g, 85% yield) without further purification for next step. $^1$H NMR (400 MHz, CDCl$_3$) δ 7.46 (s, 1H), 7.43 (d, 1H), 7.32 (s, 1H), 7.25 (d, 1H), 2.62 (m, 1H), 1.93-1.85 (m, 4H), 1.78-1.75 (m, 4H), 1.34-1.22 (m, 2H).

4-(5-cyclohexylbenzofuran-2-yl)benzaldehyde (step 3 in Scheme 2)

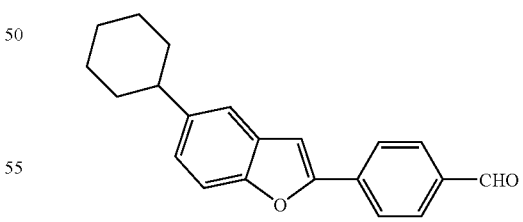

A mixture of 5-cyclohexylbenzofuran-2-ylboronic acid (75 mg, 0.37 mmol), 4-bromobenzaldehyde (62 mg, 0.34 mmol), triethylamine (1.1 mL, 7.5 mmol) and bis(triphenylphosphine)palladium(II) chloride (13 mg, 0.05 mmol) in ethanol (11 mL) was irradiated in a microwave instrument at 100° C. for 20 min. The reaction mixture was cooled, and the solvent was removed. The residue was purification by silica gel chromatography on ISCO system gave the title compound (52 mg, 46% yield): >95% purity by LCMS, ESI-MS: 305.2

(M+H⁺). ¹H NMR (400 MHz, CDCl₃) δ 10.03 (s, 1H), 8.00 (d, 2H), 7.95 (d, 2H), 7.46 (d, 2H), 7.19 (d, 1H), 7.16 (s, 1H), 2.63-2.58 (m, 1H), 1.94-1.76 (m, 4H), 1.53-1.42 (m, 4H), 1.38-1.25 (m, 2H). MS (ESI) m/z: Calculated: 304.38; Observed: 305.2 (M⁺+1).

1-(4-(5-cyclohexylbenzofuran-2-yl)benzyl)azetidine-3-carboxylic acid (step 4 of Scheme 2)

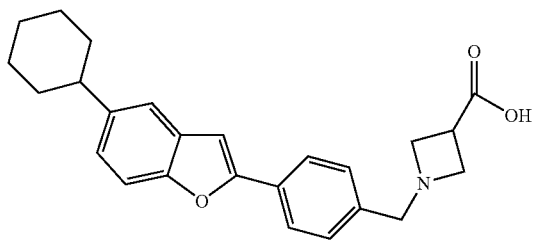

A mixture of 4-(5-cyclohexylbenzofuran-2-yl)benzaldehyde (30 mg, 0.1 mmol), acetic acid (9 μL, 0.15 mmol) and azetidine-3-carboxylic acid (15 mg, 0.15 mmol) in DCM/MeOH (1:1, 2 mL) was stirred at room temperature for 1 h. Sodium cyanoborohydride (3.1 mg, 0.05 mmol) was added and the reaction mixture was stirred for 3 h at room temperature. After concentration of solvent under reduced pressure, the resulting residue was dissolved in hot MeOH and filtered. The filtrate and the white solid, which was redissolved in hot DMSO, were both purified by reverse phase preparative HPLC (Phenomenex reverse phase Luna 5μ C18(2) column, 60×21.2 mm ID) to yield the desired final product (16 mg, 42% yield) as a white powder [hS1P1 EC₅₀=970 nM, 400 nM, 440 nM, 421 nM]: >95% purity by LCMS, ESI-MS: 459.1 (M+H)⁺, ¹H NMR (400 MHz, CD₃OD) δ 7.95 (d, 2H), 7.56 (d, 2H), 7.45 (d, 1H), 7.42 (d, 1H), 7.24 (s, 1H), 7.19 (dd, 1H), 4.45 (s, 2H), 4.34 (dd, 4H), 3.69 (m, 1H), 2.64-2.57 (d, 1H), 1.89 (t, 4H), 1.58-1.40 (m, 4H), 1.38-1.26 (m, 2H).

Compound 7

1-(4-(5-cyclohexylbenzofuran-2-yl)benzyl)piperidine-4-carboxylic acid

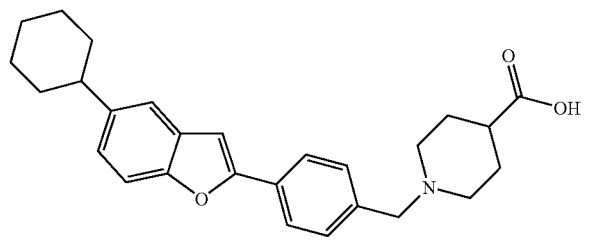

A mixture of 4-(5-cyclohexylbenzofuran-2-yl)benzaldehyde (22 mg, 0.07 mmol), acetic acid (7 μL, 0.11 mmol) and piperidine-4-carboxylic acid (14 mg, 0.11 mmol) in DCM/MeOH (1:1, 1.6 mL) was stirred at room temperature for 1 h. Sodium cyanoborohydride (2.3 mg, 0.05 mmol) was added and the reaction mixture was stirred for 4 h at room temperature. After concentration of solvent under reduced pressure, the resulting residue was dissolved in DMSO, filtered and purified by reverse phase preparative HPLC (Phenomenex reverse phase Luna 5μ C18(2) column, 60×21.2 mm ID) to yield the desired final product (15.4 mg, 51%) [hS1P1 EC₅₀=1600 nM, >25000 nM]: >95% purity by LCMS, ESI-MS: 418.1 (M+H)⁺, ¹H NMR (400 MHz, CD₃OD) δ 8.00 (d, J=8.0 Hz, 2H), 7.59 (d, J=8.0 Hz, 2H), 7.45 (d, J=1.6 Hz, 1H), 7.43 (d, J=8.4 Hz, 1H), 7.26 (s, 1H), 7.21 (dd, J=8.4 Hz, J=1.6 Hz), 4.35 (s, 2H), 3.57 (d, J=11.6 Hz, 2H), 3.07 (t, J=12 Hz, 2H), 2.64-2.53 (m, 2H), 2.24 (d, 2H), 1.19-1.86 (m, 4H), 1.79 (t, 2H), 1.58-1.42 (m, 4H), 1.38-1.26 (m, 2H).

Compound 8

1-((4-(5-Butylbenzofuran-2-yl)phenyl)methyl)piperidine-4-carboxylic acid

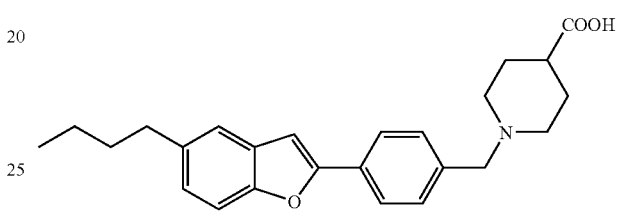

The title compound was prepared as Example Compound 1 (step 5 in Scheme 1) in the general method described above except using piperidine-4-carboxylic acid (57% yield) [hS1P1 EC₅₀=3100 nM, >25000 nM]: ¹H NMR (400 MHz, CD₃OD) δ 8.00 (d, J=8.1, 2H), 7.59 (d, J=8.1, 2H), 7.43-7.41 (m, 2H), 7.25 (s, 1H), 7.15 (d, J=8.8, 1H), 4.35 (s, 2H), 3.57 (br d, J=11.7, 2H), 3.07 (br t, J=12.5, 2H), 2.71 (t, J=7.7, 2H), 2.70-2.59 (m, 1H), 2.25 (br d, J=14.6, 2H), 1.93-1.79 (m, 2H), 1.67-1.61 (m, 2H), 1.43-1.33 (m, 2H), 0.95 (t, J=7.3, 3H). MS (ESI) m/z: Calculated: 391.21; Observed: 392.0 (M⁺+1).

Compound 9

1-((4-(5-Benzylbenzofuran-2-yl)phenyl)methyl)piperidine-4-carboxylic acid

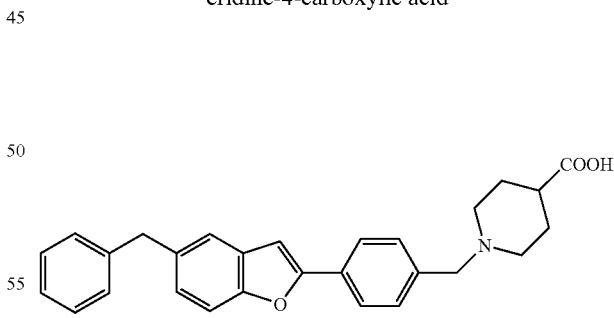

The title compound was prepared as Example Compound 1 (step 5 in Scheme 1) in the general method described above except using piperidine-4-carboxylic acid [hS1P1 EC₅₀=4800 nM, 25000 nM]: ¹H NMR (400 MHz, CD₃OD) δ 7.99 (br d, J=8.0, 2H), 7.58 (br d, J=8.0, 2H), 7.44-7.42 (m, 2H), 7.28-7.16 (m, 7H), 4.34 (br s, 2H), 4.05 (br s, 2H), 3.57 (br d, J=11.7, 2H), 3.05 (br t, J=12.4, 2H), 2.65-2.62 (m, 1H), 2.23 (br d, J=13.5, 2H), 1.89-1.80 (m, 2H). MS (ESI) m/z: Calculated: 425.20; Observed: 426.0 (M++1).

Compound 10

1-((4-(5-isobutylbenzofuran-2-yl)phenyl)methyl)azetidine-3-carboxylic acid (Scheme 2)

5-isobutylbenzofuran (step 1 in Scheme 2)

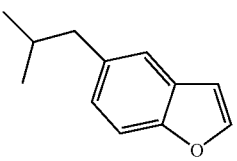

5-bromobenzofuran (500 mg, 2.56 mmol) was dissolved in THF solution of isobutylzinc(II) bromide (0.5M, 15 mL, 7.40 mmol) in a microwave reaction tube. Pd(P$^t$Bu$_3$)$_2$ (65 mg, 0.128 mmol, 0.05 eqv.) was added to this solution. The mixture was purged with N$_2$ gas for 3-5 min and heated at 100° C. for 30 min under microwave irradiation. Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system, 5% EtOAc in hexanes) to give 0.331 g desired product (74% yield): $^1$H NMR (400 MHz, CDCl$_3$) δ 7.59 (s, 1H), 7.35 (d, 1H), 7.07 (d, 1H), 6.70 (s, 1H), 2.59 (d, 2H), 1.9 (m, 1H), 0.9 (d, 6H).

5-isobutylbenzofuran-2-ylboronic acid (step 2 in Scheme 2)

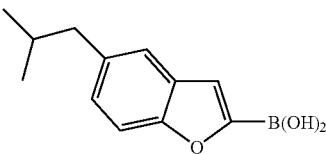

A solution of n-BuLi (912 μL, 2.28 mmol, 2.5M solution in hexanes) was added dropwise to a solution of 5-isobutylbenzofuran (331 mg, 1.9 mmol) in anhydrous THF (12 mL) at −78° C. The resulting mixture was stirred at −78° C. for 40 min, and treated with B($^i$PrO)$_3$ (658 μL, 2.85 mmol). The reaction mixture was allowed to warm up slowly to room temperature and stirred for 1 h. TLC indicated the completion of reaction. The reaction was cooled in ice-bath and quenched with 2N HCl (6 mL) and extracted with Et$_2$O. The combined organic extracts were washed with brine, dried and concentrated under reduced pressure to yield a crude benzofuran boronic acid (0.76 g) without further purification for next step.

4-(5-isobutylbenzofuran-2-yl)benzaldehyde (step 3 in Scheme 2)

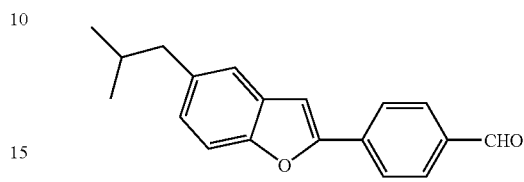

A mixture of 5-isobutylbenzofuran-2-ylboronic acid (70 mg, 0.33 mmol), 4-bromobenzaldehyde (61 mg, 0.33 mmol), triethylamine (1.7 mL, 12.6 mmol) and bis(triphenylphosphine)palladium(II) chloride (12 mg, 0.017 mmol) in ethanol (10 mL) was irradiated in a microwave instrument at 100° C. for 20 min. The reaction mixture was cooled, and the solvent was removed. The residue was treated with water and extracted with ethyl acetate. The organic layer was dried and concentrated in vacuo (the aqueous work-up is optional). Purification by silica gel chromatography on ISCO system gave the title compound (59 mg, 65% yield): >99% purity by LCMS, ESI-MS: 279.2 (M+H)$^+$.

1-((4-(5-isobutylbenzofuran-2-yl)phenyl)methyl)azetidine-3-carboxylic acid (step 4 in Scheme 2)

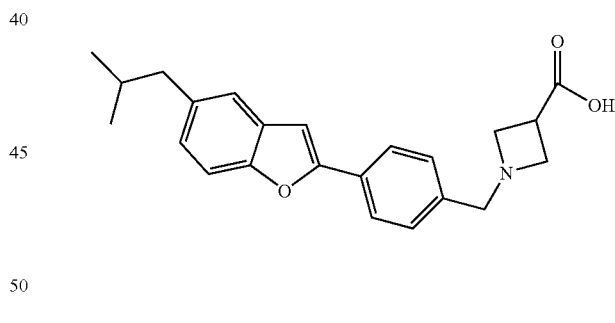

A mixture of 4-(5-isobutylbenzofuran-2-yl)benzaldehyde (30 mg, 0.11 mmol), acetic acid (10 μL, 0.15 mmol) and azetidine-3-carboxylic acid (16 mg, 0.16 mmol) in DCM/MeOH (1:1, 2 mL) was stirred at room temperature for 1 h. Sodium cyanoborohydride (3.4 mg, 0.054 mmol) was added and the reaction mixture was stirred for 3 h at room temperature. After concentration of solvent under reduced pressure, the resulting residue was dissolved in an aliquot of DMSO and purified by reverse phase preparative HPLC (Phenomenex reverse phase Luna 5μ C18(2) column, 60×21.2 mm ID) to yield the desired final product (25.6 mg, 65% yield) as a colorless film [hS1P1 EC$_{50}$=270 nM, 490 nM, 383 nM]: >95% purity by LCMS, ESI-MS: 364.0 (M+H)$^+$, $^1$H NMR (400 MHz, CD$_3$OD) δ 7.99 (d, 2H), 7.55 (d, 2H), 7.42 (d, 1H), 7.39 (s, 1H), 7.24 (s, 1H), 7.12 (dd, 1H), 4.44 (s, 2H), 4.33 (d, 4H), 3.68 (m, 1H), 2.57 (d, 2H), 1.90 (m, 1H), 0.92 (d, 6H).

Compound 11

1-((4-(5-phenethylbenzofuran-2-yl)phenyl)methyl)azetidine-3-carboxylic acid

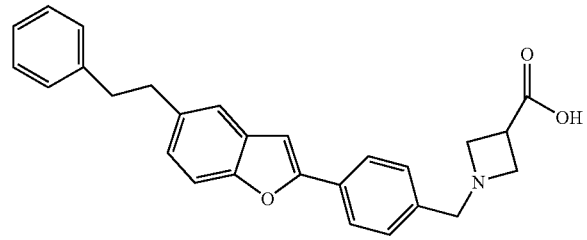

The title compound was prepared in the same manner as Example Compound 6 [hS1P1 EC$_{50}$=580 nM, 25000 nM]: >95% purity by LCMS, ESI-MS: 411.9 (M+H)$^+$, $^1$H NMR (400 MHz, CD$_3$OD) δ 7.99 (d, 2H), 7.55 (d, 2H), 7.41 (d, 1H), 7.38 (s, 1H), 7.24-7.21 (m, 3H), 7.17-7.14 (m, 4H), 4.44 (s, 2H), 4.34 (d, 4H), 3.70 (m, 1H), 3.01-2.90 (m, 4H).

Compound 12

1-(4-(5-(pyridin-3-yl)benzofuran-2-yl)benzyl)azetidine-3-carboxylic acid 3-(benzofuran-5-yl)pyridine (step 1 in Scheme 2 except using Suzuki coupling)

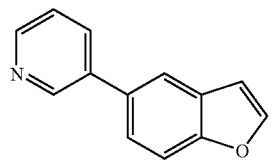

A solution of 5 pyridin-3-ylboronic acid (390 mg, 3.18 mmol), 5-bromobenzofuran (500 mg, 2.54 mmol), palladiumdichlorobis(triphenylphosphine) (111 mg, 0.16 mmol) and triethylamine (8.8 mL, 63.5 mmol) in EtOH was irradiated in the microwave at 100° C. for 1200 s. Removal of the solvents followed by dissolving in CH$_2$Cl$_2$ and filtering gave the residue after concentration of the solvent under reduced pressure. The compound was purifided on ISCO to afford 316 mg of the title compound as a light yellow solid: $^1$H NMR (400 MHz, CDCl$_3$) δ 8.89 (s, 1H), 8.60 (d, 1H), 7.90 (d, 1H), 7.80 (s, 1H), 7.69 (s, 1H), 7.55 (d, 1H), 7.50 (d, 1H) 7.38 (dd, 1H), 6.85 (dd, 1H). MS (ESI) m/z: Calculated: 195.07; Observed: 196.30 (M$^+$+1).

5-(pyridin-3-yl)benzofuran-2-ylboronic acid (step 2 in Scheme 2)

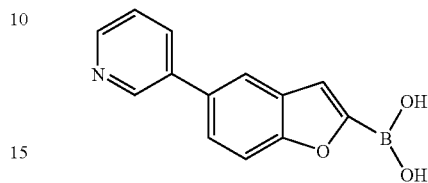

A solution of n-BuLi (0.76 mL, 2.5M solution in hexanes) was added dropwise to a solution of 3-(benzofuran-5-yl)pyridine (310 mg, 1.59 mmol) in anhydrous THF (10 mL) at −78° C. The resulting mixture was stirred at −78° C. for 30 min, and treated with B($^i$PrO)$_3$ (0.55 mL, 2.39 mmol). The reaction mixture was allowed to warm up slowly to room temperature and stirred for 1 h. The reaction was quenched with 2N HCl and extracted with Et$_2$O. The aqueous layer was neutralized with 5N NaOH (PH=6) followed by extraction with THF:ether (1:1) three times. The combined extracts were washed with brine, dried and concentrated under reduced pressure to yield 241 mg of the crude boronic acid, which was used without further purification.

4-(5-(pyridin-3-yl)benzofuran-2-yl)benzaldehyde (step 3 in Scheme 2)

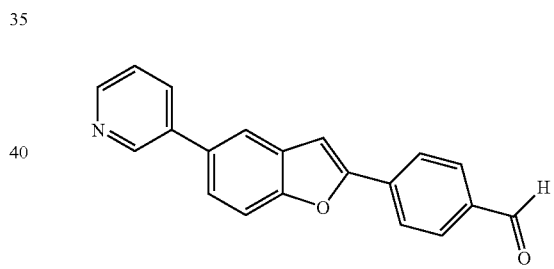

The title compound was prepared as Example Compound 6 in the general method described above (44% yield): $^1$H NMR (400 MHz, CDCl$_3$) δ 10.06 (s, 1H), 8.91 (br s, 1H), 8.61 (br s, 1H), 8.07 (d, 2H), 7.98 (d, 2H), 7.93 (d, 1H), 7.65 (d, 1H), 7.55 (d, 1H), 7.82 (m, 1H), 7.39 (m, 1H), 7.27 (m, 1H). MS (ESI) m/z: Calculated: 299.09; Observed: 300.30 (M$^+$+1).

1-(4-(5-(pyridin-3-yl)benzofuran-2-yl)benzyl)azetidine-3-carboxylic acid (step 4 in Scheme 2)

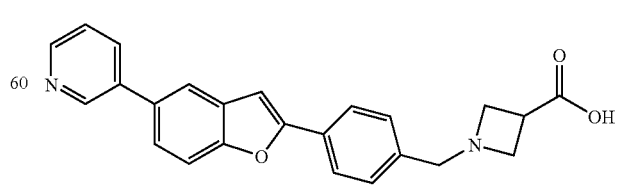

The title compound was prepared as Example Compound 6 in the general method described above (22% yield) [hS1P1

EC$_{50}$=3600, >1 nM]: $^1$H NMR (400 MHz, CD$_3$OD) δ 9.11 (br s, 1H), 8.70 (m, 2H), 8.06 (m, 3H), 7.98 (m, 1H), 7.74 (m, 2H), 7.60 (d, 2H), 7.44 (s, 1H), 4.47 (s, 2H), 4.40-4.38 (m, 4H), 3.72 (m, 1H). MS (ESI) m/z: Calculated: 384.20; Observed: 385.00 (M$^+$+1).

Compound 13

1-(4-(5-isobutylbenzofuran-2-yl)benzyl)piperidine-4-carboxylic acid

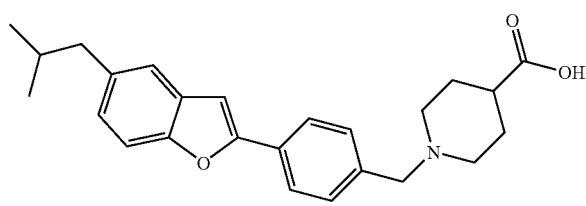

A mixture of 4-(5-isobutylbenzofuran-2-yl)benzaldehyde (22 mg, 0.08 mmol), acetic acid (7 μL, 0.12 mmol) and piperidine-4-carboxylic acid (15 mg, 0.12 mmol) in DCM/MeOH (1:1, 1.4 mL) was stirred at room temperature for 1 h. Sodium cyanoborohydride (2.5 mg, 0.04 mmol) was added and the reaction mixture was stirred for 4 h at room temperature. After concentration of solvent under reduced pressure, the resulting residue was dissolved in an aliquot of DMSO and purified by reverse phase preparative HPLC (Phenomenex reverse phase Luna 5μ C18(2) column, 60×21.2 mm ID) to yield the desired final product (16.9 mg, 55%) [hS1P1 EC$_{50}$=1700 nM, >25000]: >95% purity by LCMS, ESI-MS: 392.0 (M+H)$^+$, $^1$H NMR (400 MHz, CD$_3$OD) δ 8.01 (d, 2H), 7.59 (d, 2H), 7.43 (d, 1H), 7.39 (s, 1H), 7.26 (s, 1H), 7.13 (dd, 1H), 4.36 (s, 2H), 3.58 (m, 2H), 3.10 (m, 2H), 2.65 (m, 1H), 2.57 (d, 2H), 1.90 (m, 1H), 0.92 (d, 6H).

Compound 14

1-((4-(5-Benzylbenzofuran-2-yl)2-fluorophenyl)methyl)azetidine-3-carboxylic acid 4-(5-Benzylbenzofuran-2-yl)2-fluorobenzaldehyde

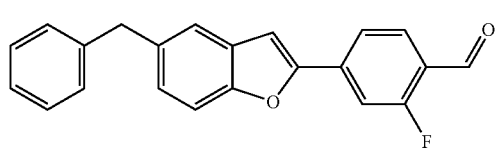

The title compound was prepared as Example Compound 1 (step 4 in Scheme 1) in the general method described above (67% yield): $^1$H NMR (400 MHz, CDCl$_3$) δ 10.35 (s, 1H), 7.92 (dd, J=8.1, 7.0, 2H), 7.69 (d, J=8.5, 1H), 7.63 (d, J=11.4, 1H), 7.46-7.42 (m, 2H), 7.33-7.19 (m, 6H), 7.13 (s, 1H), 4.09 (s, 2H).

1-((4-(5-Benzylbenzofuran-2-yl)2-fluorophenyl)methyl)azetidine-3-carboxylic acid

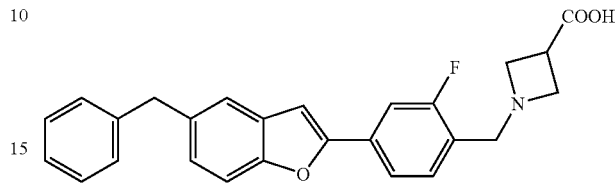

The title compound was prepared as Example Compound 1 (step 5 Scheme 1) in the general method described above (54% yield) [hS1P1 EC$_{50}$=620 nM, 334 nM]: $^1$H NMR (400 MHz, CD$_3$OD) δ 7.78 (d, J=8.1, 1H), 7.73 (d, J=9.9, 1H), 7.58 (t, J=7.7, 1H), 7.46-7.44 (m, 2H), 7.29-7.16 (m, 7H), 4.39 (s, 2H), 4.17-4.15 (m, 4H), 4.06 (s, 2H), 3.72-3.64 (m, 1H). MS (ESI) m/z: Calculated: 415.16; Observed: 416.0 (M$^+$+1).

Compound 15

1-((4-(5-Benzylbenzofuran-2-yl)-3-fluorophenyl)methyl)azetidine-3-carboxylic acid 4-(5-Benzylbenzofuran-2-yl)-3-fluorobenzaldehyde

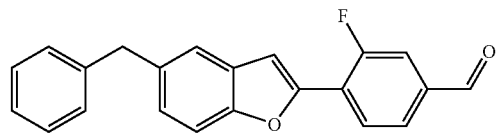

The title compound was prepared as Example Compound 1 (step 4 Scheme 1) in the general method described above (65% yield): $^1$H NMR (400 MHz, CDCl$_3$) δ 10.01 (s, 1H), 8.20 (t, J=7.7, 1H), 7.77 (d, J=8.0, 1H), 7.68 (d, J=11.3, 1H), 7.47-7.45 (m, 2H), 7.37-7.20 (m, 7H), 4.10 (s, 2H).

1-((4-(5-Benzylbenzofuran-2-yl)-3-fluorophenyl)methyl)azetidine-3-carboxylic acid

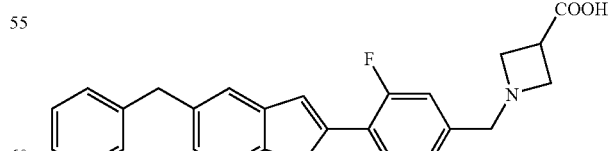

The title compound was prepared as Example Compound 1 (step 5 Scheme 1) in the general method described above (56% yield) [hS1P1 EC$_{50}$=160 nM, 38 nM]: $^1$H NMR (400 MHz, CD$_3$OD) δ 8.09 (t, J=7.9, 1H), 7.47-7.45 (m, 2H), 7.40-7.37 (m, 2H), 7.28-7.16 (m, 7H), 4.34 (s, 2H), 4.17-4.15

(m, 4H), 4.07 (s, 2H), 3.53-3.45 (m, 1H). MS (ESI) m/z: Calculated: 415.16; Observed: 415.9 (M⁺+1).

Compound 16

1-(4-(5-Butoxybenzofuran-2-yl)phenyl)methyl)piperidine-4-carboxylic acid

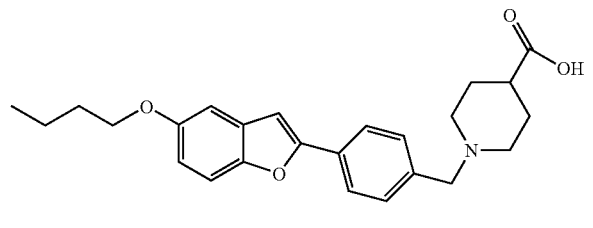

A mixture of 4-(5-butoxybenzofuran-2-yl)benzaldehyde (50 mg, 0.20 mmol), piperidine-4-carboxylic acid (41 mg, 0.31 mmol) and acetic acid (0.50 mmol) in MeOH-DCM (3:1; 2 mL) was stirred at room temperature for 1 h. Sodium triacetoxyborohydride (135 mg, 0.64 mmol) was added and the reaction mixture was stirred for 16 h. Concentration of the solvent under reduced pressure yielded a yellow solid that was dissolved in DMSO (3 mL) and filtered to give a yellow solution that was purified by HPLC to afford the desired product [hS1P1 EC$_{50}$=17000 nM]: ¹H NMR (400 MHz, CD$_3$OD) δ 7.98 (d, 1H), 7.97 (d, 1H), 7.58 (d, 2H), 7.40 (d, 1H), 7.24 (s, 1H), 7.11 (d, 1H), 6.90 (dd, 1H), 4.35 (s, 2H), 4.00 (dd, 2H), 3.55 (m, 2H), 3.3 (m, 1H), 3.10 (m, 2H), 2.2 (m, 2H), 1.8 (m, 2H), 1.52 (m, 2H), 1.28 (m, 2H), 1.00 (dd, 3H). MS (ESI) m/z: Calculated: 407.21; Observed: 407.90 (M⁺+1).

Compound 17

1-((6-(5-cyclohexylbenzofuran-2-yl)pyridin-3-yl)methyl)azetidine-3-carboxylic acid

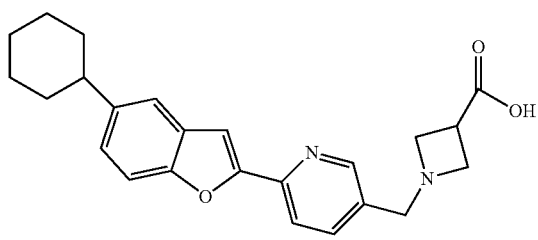

The title compound was prepared in the same manner as Example Compound 6 except using 6-bromo-3-pyridinecarboxaldehyde in step-3 (Scheme 2) [hS1P1 EC$_{50}$=720 nM, 302 nM]: >95% purity by LCMS, ESI-MS: 391.1 (M+H)⁺, ¹H NMR (400 MHz, CD$_3$OD) δ 8.81 (d, 1H), 7.94 (d, 1H), 7.65 (d, 1H), 7.59 (s, 1H), 7.50 (m, 2H), 7.35 (m, 1H), 4.44 (s, 2H), 4.45 (s, 2H), 4.34 (dd, 4H), 3.69 (m, 1H), 2.64-2.57 (d, 1H), 1.89 (t, 4H), 1.58-1.41 (m, 4H), 1.38-1.26 (m, 2H).

Compound 18

1-(4-(5-(6-methylpyridin-2-yl)benzofuran-2-yl)benzyl)azetidine-3-carboxylic acid (Scheme 2)

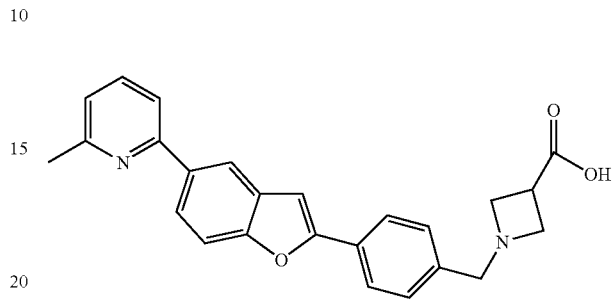

The title compound was prepared in the same manner as Example Compound 6 except using (6-methylpyridin-2-yl) zinc (II) bromide in step-1 (Scheme 2) [hS1P1 EC$_{50}$=2900 nM]: >95% purity by LCMS, ESI-MS: 391.1 (M+H)⁺, ¹H NMR (400 MHz, CD$_3$OD) δ 8.42 (t, 1H), 8.22 (d, 1H), 8.07-8.10 (m, 3H), 7.77-7.88 (m, 3H), 7.62 (d, 2H), 7.50 (dd, 1H), 4.48 (s, 2H), 4.36 (d, 4H), 3.71 (m, 1H), 2.85 (s, 3H).

Compound 19

1-(4-(5-phenoxybenzofuran-2-yl)benzyl)azetidine-3-carboxylic acid 1-(2,2-Diethoxy-ethoxy)-4-phenoxy-benzene

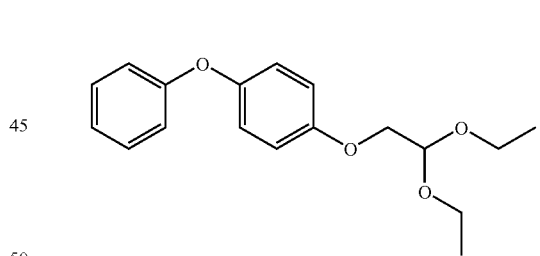

The title compound was prepared as Example Compound 1 (step 1 Scheme 1) in the general method described above.

5-Phenoxy-benzofuran

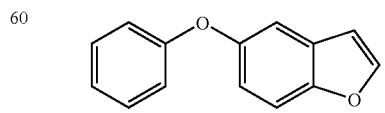

The title compound was prepared as Example Compound 1 (step 2 Scheme 1) in the general method described above (65% yield): $^1$H NMR (400 MHz, CDCl$_3$) δ 7.63 (d, 1H), 7.45 (d, 1H), 7.29 (m, 2H), 7.22 (d, 1H), 7.00-7.08 (m, 4H), 6.71 (m 1H).

5-phenoxybenzofuran-2-ylboronic acid

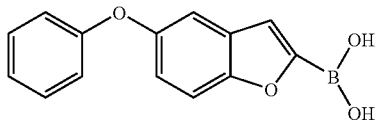

The title compound was prepared as Example Compound 1 (step 3 Scheme 1) in the general method described above (74% yield).

4-(5-phenoxybenzofuran-2-yl)benzaldehyde

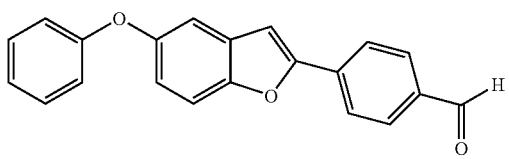

The title compound was prepared as Example Compound 1 (step 4 Scheme 1) in the general method described above (65% yield): $^1$H NMR (400 MHz, DMSO-d$_6$) δ 10.05 (s, 1H), 8.13 (d, 2H), 8.03 (d, 2H), 7.70 (d, 1H), 7.66 (br s, 1H), 7.39 (m, 4H), 7.10 (m, 2H), 7.00 (dd, 1H). MS (ESI) m/z: Calculated: 314.10; Observed: 315.10 (M$^+$+1).

1-(4-(5-phenoxybenzofuran-2-yl)benzyl)azetidine-3-carboxylic acid

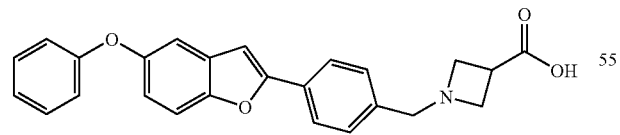

The title compound was prepared as Example Compound 1 (step 5 Scheme 1) in the general method described above (7% yield) [hS1P1 EC$_{50}$=510 nM, 92 nM]: $^1$H NMR (400 MHz, CD$_3$OD) δ 7.90 (d, 2H), 7.55 (m, 3H), 7.32 (m, 2H), 7.27 (s, 1H), 7.22 (d, 1H), 7.03 (m, 4H), 4.47 (s, 2H), 4.34 (m, 4H), 3.62 (m, 1H). MS (ESI) m/z: Calculated: 399.20; Observed: 399.90 (M$^+$+1).

Compound 20

1-((4-(5-Isopentylbenzofuran-2-yl)phenyl)methyl) azetidine-3-carboxylic acid

5-Isopentylbenzofuran

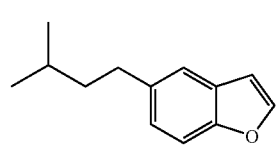

The title compound was prepared as Example Compound 6 (step 1 in Scheme 2) in the general method described above (75% yield): $^1$H NMR (400 MHz, CDCl$_3$) δ 7.58 (d, J=2.0, 1H), 7.41-7.39 (m, 2H), 7.11 (dd, J=8.2, 2.0, 1H), 6.70 (br s, 1H), 2.72-2.68 (m, 2H), 1.62-1.51 (m, 3), 0.94 (d, J=6.6, 6H).

5-Isopentylbenzofuran-2-yl-2-boronic acid

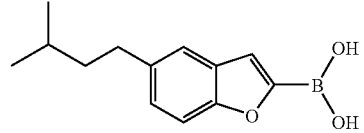

The title compound was prepared as Example Compound 6 (step 2 in Scheme 2) in the general method described above (53% yield): $^1$H NMR (400 MHz, CDCl$_3$) δ 7.43-7.38 (m, 2H), 7.30 (s, 1H), 7.18 (d, J=8.5, 1H), 2.72-2.68 (m, 2H), 1.60-1.50 (m, 3), 0.94 (d, J=6.6, 6H).

4-(5-Isopentylbenzofuran-2-yl)benzaldehyde

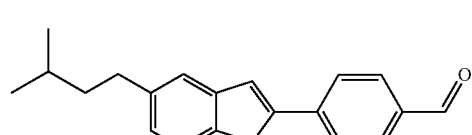

The title compound was prepared as Example Compound 6 (step 3 in Scheme 2) in the general method described above (79% yield): $^1$H NMR (400 MHz, CDCl$_3$) δ 10.03 (s, 1H), 8.00 (d, J=8.5, 2H), 7.95 (d, J=8.5, 2H), 7.46-7.42 (m, 2H), 7.18-7.15 (m, 2H), 2.73-2.69 (m, 2H), 1.62-1.54 (m, 3), 0.95 (d, J=6.2, 6H).

1-((4-(5-Isopentylbenzofuran-2-yl)phenyl)methyl) azetidine-3-carboxylic acid

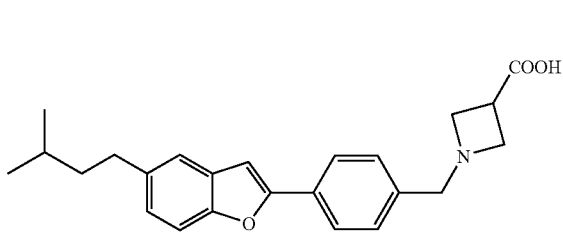

The title compound was prepared as Example Compound 6 (step 4 in Scheme 2) in the general method described above (63% yield) [hS1P1 EC$_{50}$=630 nM]: $^1$H NMR (400 MHz, CD$_3$OD) δ 7.98 (d, J=8.3, 2H), 7.55 (d, J=8.3, 2H), 7.43-7.41 (m, 2H), 7.23 (s, 1H), 7.15 (d, J=8.8, 1H), 4.44 (s, 2H), 4.38-4.30 (m, 4H), 3.73-3.65 (m, 1H), 2.73-2.69 (m, 2H), 1.62-1.52 (m, 3), 0.96 (d, J=7.6, 6H). MS (ESI) m/z: Calculated: 377.2; Observed: 377.9 (M$^+$+1).

Compound 21

1-((4-(6-Butoxybenzofuran-2-yl)phenyl)methyl) azetidine-3-carboxylic acid 1-(2,2-Diethoxyethoxy)-3-butoxybenzene

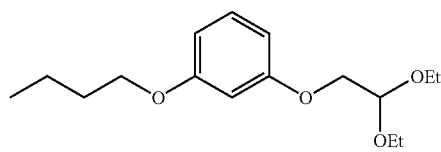

The title compound was prepared as Example Compound 1 (step 1 in Scheme 1) in the general method described above (86% yield): $^1$H NMR (400 MHz, CDCl$_3$) δ 7.15 (t, J=7.4), 6.52-6.49 (m, 3H), 4.83 (t, J=5.1, 1H), 3.99 (d, J=5.1, 2H), 3.93 (t, J=6.6, 2H), 3.80-3.72 (m, 2H), 3.67-3.60 (m, 2H), 1.79-1.72 (m, 2H), 1.53-1.43 (m, 2H), 1.25 (t, J=7.3, 6H), 0.97 (t, J=7.3, 3H).

6-Butoxybenzofuran

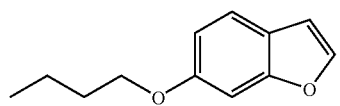

The title compound was prepared as Example Compound 1 (step 2 in Scheme 1) in the general method described above (83% yield): $^1$H NMR (400 MHz, CDCl$_3$) δ 7.52 (d, J=2.2, 1H), 7.44 (d, J=8.5, 1H), 7.03 (d, J=2.2, 1H), 6.87 (dd, J=8.8, 2.5, 1H), 6.69-6.68 (m, 1H), 4.00 (t, J=6.6, 2H), 1.83-1.76 (m, 2H), 1.56-1.47 (m, 2H), 0.99 (t, J=7.4, 3H).

6-Butoxybenzofuran-2-yl-2-boronic acid

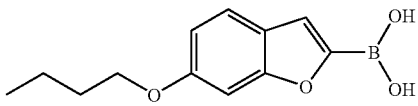

The title compound was prepared as Example Compound 1 (step 3 in Scheme 1) in the general method described above (76% yield): $^1$H NMR (400 MHz, CDCl$_3$) δ 7.52-7.42 (m, 2H), 7.00 (br s, 1H), 6.90-6.85 (m, 1H), 4.00 (t, J=6.6, 2H), 1.82-1.78 (m, 2H), 1.56-1.48 (m, 2H), 0.98 (t, J=7.3, 3H).

4-(6-Butoxybenzofuran-2-yl)benzaldehyde

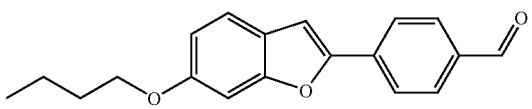

The title compound was prepared as Example Compound 1 (step 4 in Scheme 1) in the general method described above (62% yield): $^1$H NMR (400 MHz, CDCl$_3$) δ 9.94 (s, 1H), 7.94-7.89 (m, 4H), 7.45 (d, J=8.5, 2H), 7.10 (s, 10H), 7.05 (br d, J=2.2, 1H), 6.89 (dd, J=8.5, 2.2, 1H), 4.02 (t, J=6.2), 1.85-1.78 (m, 2H), 1.57-1.52 (m, 2H), 1.00 (t, J=7.3, 3H).

1-((4-(6-Butoxybenzofuran-2-yl)phenyl)methyl) azetidine-3-carboxylic acid

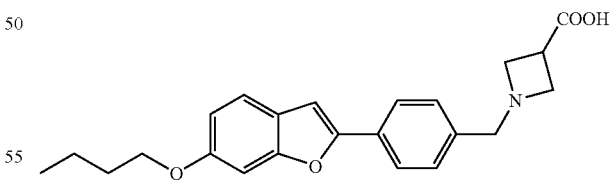

The title compound was prepared as Example Compound 1 (step 5 in Scheme 1) in the general method described above (46% yield) [hS1P1 EC$_{50}$=200 nM]: $^1$H NMR (400 MHz, CD$_3$OD) δ 7.94 (d, J=8.4, 2H), 7.53 (d, J=8.4, 2H), 7.47 (d, J=8.5, 1H), 7.21 (s, 1H), 7.11 (br d, J=2.2, 1H), 6.88 (dd, J=8.5, 2.2), 4.43 (s, 2H), 4.34-4.32 (m, 4H), 4.04 (t, J=6.2), 3.71-3.63 (m, 1H), 1.81-1.76 (m, 2H), 1.57-1.52 (m, 2H), 1.01 (t, J=7.3, 3H). MS (ESI) m/z: Calculated: 379.18; Observed: 379.8 (M⁺+1).

Compound 22

1-((2-(5-butoxybenzofuran-2-yl)thiazol-5-yl)methyl)azetidine-3-carboxylic acid 2-(5-butoxybenzofuran-2-yl)thiazole-5-carbaldehyde

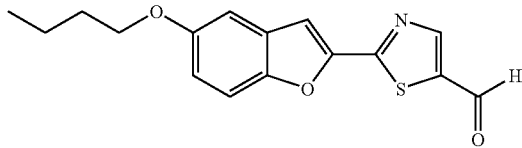

The title compound was prepared as Example Compound 1 (step 4 in Scheme 1) in the general method described above except using 2-bromothiazole-5-carbaldehyde (29% yield): ¹H NMR (400 MHz, CDCl₃) δ 10.07 (s, 1H), 8.46 (dd, 1H), 7.45 (dd, 2H), 7.03 (dd, 2H), 4.01 (dd, 2H), 1.74 (m, 2H), 1.54 (m, 2H), 1.01 (t, 3H). MS (ESI) m/z: Calculated: 301.10; Observed: 302.10 (M⁺+1).

1-((2-(5-butoxybenzofuran-2-yl)thiazol-5-yl)methyl)azetidine-3-carboxylic acid

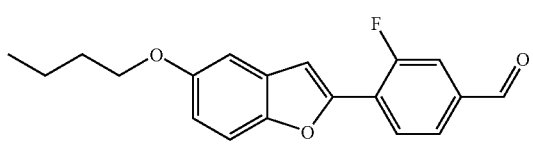

The title compound was prepared as Example Compound 1 (step 5 in Scheme 1) in the general method described above (36% yield) [hS1P1 EC₅₀=3200 nM, 1100 nM]: ¹H NMR (400 MHz, CD₃OD) δ 8.06 (br s, 1H), 7.344 (m, 2H), 7.18 (m, 1H), 7.01 (ddd, 1H), 4.79 (s, 2H), 4.36 (m, 4H), 3.98 (m, 2H), 3.69 (m, 1H), 1.75 (m, 2H), 1.50 (m, 2H), 1.00 (t, 3H). MS (ESI) m/z: Calculated: 386.13; Observed: 386.90 (M⁺+1).

Compound 23

1-((4-(5-Butoxybenzofuran-2-yl)3-fluorophenyl)methyl)azetidine-3-carboxylic acid (4-(5-Butoxybenzofuran-2-yl)3-fluorobenzaldehyde

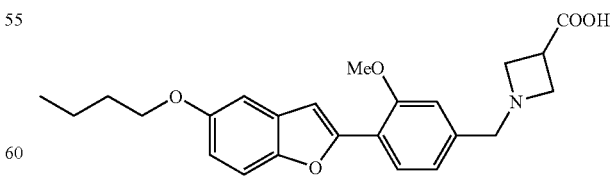

The title compound was prepared as Example Compound 1 (step 4 in Scheme 1) in the general method described above (36% yield): ¹H NMR (400 MHz, CDCl₃) δ 10.02 (s, 1H), 8.18 (t, J=7.7, 1H), 7.73 (d, J=8.0, 1H), 7.66 (d, J=11.2, 1H), 7.44-7.39 (m, 2H), 7.09 (d, J=2.4, 1H), 6.92 (dd, J=2.4, 8.8, 1H), 4.01 (t, J=6.2), 1.81-1.76 (m, 2H), 1.57-1.51 (m, 2H), 1.01 (t, J=7.2, 3H).

1((4-(5-Butoxybenzofuran-2-yl)-3-fluorophenyl)methyl)azetidine-3-carboxylic acid

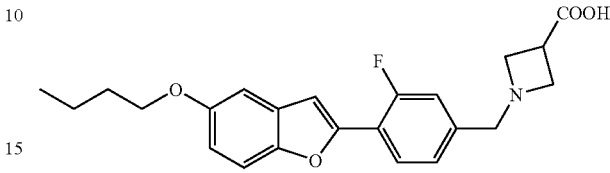

The title compound was prepared as Example Compound 1 (step 5 in Scheme 1) in the general method described above (51% yield) [hS1P1 EC₅₀=520 nM]: ¹H NMR (400 MHz, CD₃OD) δ 8.08 (t, J=7.7, 1H), 7.44-7.37 (m, 3H), 7.25 (d, J=3.7, 1H), 7.14 (d, J=2.2, 1H), 6.94 (dd, J=8.8, 2.2), 4.35 (s, 2H), 4.18-4.15 (m, 4H), 4.01 (t, J=6.2), 3.45-3.37 (m, 1H), 1.82-1.75 (m, 2H), 1.57-1.49 (m, 2H), 1.00 (t, J=7.2, 3H). MS (ESI) m/z: Calculated: 397.17; Observed: 397.9 (M⁺+1).

Compound 24

1-((4-(5-Butoxybenzofuran-2-yl)-3-methoxyphenyl)methyl)azetidine-3-carboxylic acid 4-(5-butoxybenzofuran-2-yl)-3-methoxybenzaldehyde

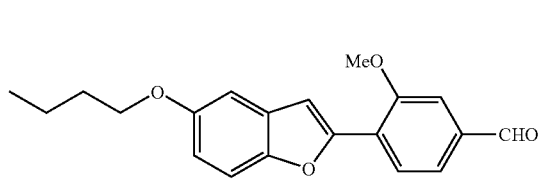

The title compound was prepared as Example Compound 1 (step 4 in Scheme 1) in the general method described above (65% yield): ¹H NMR (400 MHz, CD₃Cl) δ 10.03 (s, 1H), 8.22 (d, 1H), 7.59 (s, 1H), 7.50 (s, 1H), 7.45 (d, 1H), 7.41 (s, 1H), 7.08 (d, 1H), 6.93 (d, 1H), 4.16 (s, 3H), 4.05 (t, 2H), 1.84 (m, 2H), 1.61 (m, 2H), 1.04 (t, 3H). MS (ESI) m/z: Calculated: 324.14; Observed: 324.9 (M⁺+1).

1-((4-(5-Butoxybenzofuran-2-yl)-3-methoxyphenyl)methyl)azetidine-3-carboxylic acid

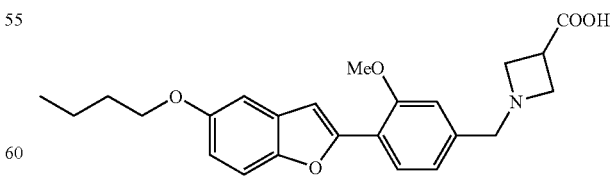

The title compound was prepared as Example Compound 1 (step 5 in Scheme 1) in the general method described above (36% yield) [hS1P1 EC₅₀=420 nM, 700 nM]: ¹H NMR (400 MHz, CD₃OD) δ 8.04 (d, 1H), 7.39 (s, 1H), 7.38 (s, 1H), 7.21 (s, 1H), 7.15 (d, 1H), 7.08 (s, 1H), 6.83 (d, 1H), 4.44 (s, 2H), 4.38 (m, 7H), 4.02 (m, 2H), 3.62 (m, 1H), 1.82 (m, 2H), 1.63 (m, 2H), 1.01 (t, 3H). MS (ESI) m/z: Calculated: 409.19; Observed: 409.9 (M⁺+1).

Compound 25

1-((5-(5-butoxybenzofuran-2-yl)thiophen-2-yl)methyl)azetidine-3-carboxylic acid 5-(5-butoxybenzofuran-2-yl)thiophene-2-carbaldehyde

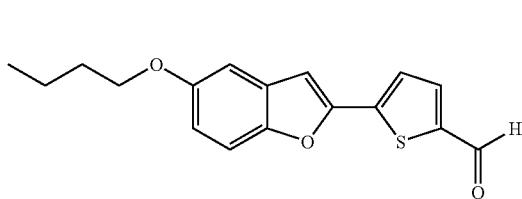

The title compound was prepared as Example Compound 1 (step 4 in Scheme 1) in the general method described above except using 5-bromothiophene-2-carbaldehyde (32% yield): $^1$H NMR (400 MHz, CDCl$_3$) δ 9.92 (s, 1H), 7.73 (d, 1H), 7.51 (dd, 1H), 7.39 (d, 1H), 7.96 (m, 2H), 6.94 (dd, 1H), 3.98 (dd, 2H), 1.80 (m, 2H), 1.70 (m, 2H), 1.01 (t, 3H).

1-((5-(5-butoxybenzofuran-2-yl)thiophen-2-yl)methyl)azetidine-3-carboxylic acid

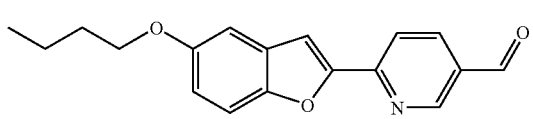

The title compound was prepared as Example Compound 1 (step 5 in Scheme 1) in the general method described above (27% yield) [hS1P1 EC$_{50}$=1600 nM]: $^1$H NMR (400 MHz, CD$_3$OD) δ 7.49 (br s, 1H), 7.35 (m, 2H), 7.03 (d, 2H), 6.89 (dd, 1H), 4.67 (s, 2H), 4.35 (m, 4H), 3.98 (m, 2H), 3.67 (m, 1H), 1.73 (m, 2H), 1.51 (m, 2H), 0.99 (t, 3H). MS (ESI) m/z: Calculated: 385.13; Observed: 385.70 (M⁺+1).

Compound 26

1-((6-(5-Butoxylbenzofuran-2-yl)pyridin-3-yl)methyl)azetidine-3-carboxylic acid 4-(5-Butoxybenzofuran-2-yl)pyridine-3-carboxaldehyde

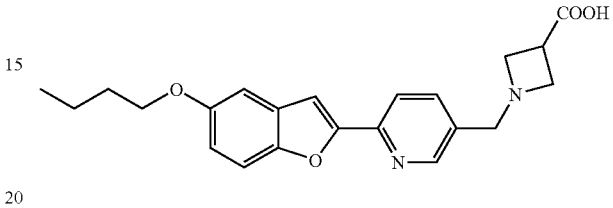

The title compound was prepared in the same manner as described in step 4 (Scheme 1) by using 6-bromo-3-pyridinecarboxaldehyde (48%): $^1$H NMR (400 MHz, CDCl$_3$) δ 10.10 (s, 1H), 9.08 (s, 1H), 8.24 (d, 1H), 8.01 (d, 1H), 7.56 (s, 1H), 7.47 (d, 1H), 7.02 (s, 1H), 6.99 (d, 1H), 4.03 (q, 4H), 1.84-1.77 (m, 2H), 1.50-1.48 (m, 2H), 1.00 (t, 3H). MS (ESI) m/z: Calculated: 295.33; Observed: 296.2 (M⁺+1).

1-((6-(5-Butoxylbenzofuran-2-yl)pyridin-3-yl)methyl)azetidine-3-carboxylic acid

The title compound was prepared as in step 5 (Scheme 1) of the general method described earlier (68% yield) [hS1P1 EC$_{50}$=2600 nM, 201 nM]: $^1$H NMR (400 MHz, CDCl$_3$) δ 8.86 (s, 1H), 8.19 (d, 1H), 7.90 (d, 1H), 7.49 (s, 1H), 7.47 (d, 1H), 7.23 (d, 1H), 6.86 (s, 1H), 3.80 (q, 2H), 4.52-4.40 (m, 4H), 3.80 (t, 2H), 3.52-3.47 (m, 1H), 1.68-1.66 (m, 2H), 1.44-1.37 (m, 2H), 0.94 (t, 3H). MS (ESI) m/z: Calculated: 380.44; Observed: 381.0 (M⁺+1).

Compound 27

1-(4-(5-cyclohexylbenzofuran-2-yl)3-fluorophenyl)methyl)azetidine-3-carboxylic acid 5-cyclohexylbenzofuran (step 1 in Scheme 2)

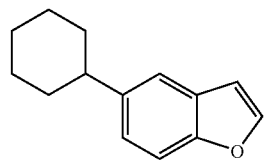

5-bromobenzofuran (500 mg, 2.55 mmol) was dissolved in a THF solution of cyclohexyl zinc(II) bromide (0.5M, 15 mL, 7.40 mmol) in a microwave reaction tube. Pd(P$^t$Bu$_3$)$_2$ (65 mg, 0.128 mmol, 0.05 eq.) was added to this solution. The mixture was purged with N$_2$ gas for 3-5 min and heated at 100° C. for 30 min under microwave irradiation. Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system, 5% EtOAc in hexanes) to give 0.217 g desired product (43% yield): $^1$H NMR (400 MHz, CDCl$_3$) δ

7.57 (d, 1H), 7.41 (d, 2H), 7.15 (d, 1H), 6.72 (d, 1H), 2.58 (m, 1H), 1.92-1.74 (m, 4H), 1.51-1.35 (m, 4H), 1.31-1.25 (m, 2H).

5-cyclohexylbenzofuran-2-ylboronic acid (step 2 in Scheme 2)

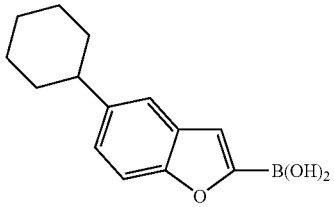

A solution of n-BuLi (360 µL, 0.9 mmol, 2.5M solution in hexanes) was added dropwise to a solution of 5-cyclohexylbenzofuran (150 mg, 0.75 mmol) in anhydrous THF (5 mL) at −78° C. The resulting mixture was stirred at −78° C. for 40 min, and treated with B($^{i}$PrO)$_3$ (260 µL, 1.13 mmol). The reaction mixture was allowed to warm up slowly to room temperature and stirred for 1 h. TLC indicated the completion of reaction. The reaction was cooled in ice-bath and quenched with 2N HCl (3 mL) and extracted with Et$_2$O. The combined organic extracts were washed with brine, dried and concentrated under reduced pressure to yield a desired boronic acid (0.156 g, 85% yield) without further purification for next step. $^{1}$H NMR (400 MHz, CDCl$_3$) δ 7.46 (s, 1H), 7.43 (d, 1H), 7.32 (s, 1H), 7.25 (d, 1H), 2.62 (m, 1H), 1.93-1.85 (m, 4H), 1.78-1.75 (m, 4H), 1.34-1.22 (m, 2H).

4-(5-cyclohexylbenzofuran-2-yl)2-fluorobenzaldehyde (step 3 in Scheme 2)

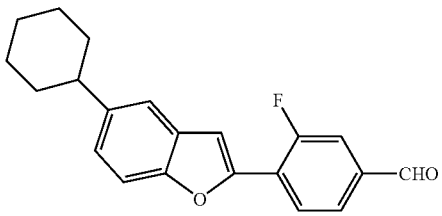

A mixture of 5-cyclohexylbenzofuran-2-ylboronic acid (75 mg, 0.30 mmol), 4-bromo-2-fluorobenzaldehyde (48 mg, 0.24 mmol), triethylamine (1.1 mL, 7.5 mmol) and bis(triphenylphosphine)palladium(II) chloride (12 mg, 0.05 mmol) in ethanol (11 mL) was irradiated in a microwave instrument at 100° C. for 20 min. The reaction mixture was cooled, and the solvent was removed. The residue was treated with water and extracted with ethyl acetate. The organic layer was dried and concentrated in vacuo (the aqueous work-up is optional). Purification by silica gel chromatography on ISCO system gave the title compound (51 mg, 49% yield). $^{1}$H NMR (400 MHz, CDCl$_3$) δ 10.04 (s, 1H), 8.00-7.97 (m, 2H), 7.46 (s, 1H), 7.43 (d, 2H), 7.32 (s, 1H), 7.25 (d, 1H), 2.62 (m, 1H), 1.95-1.77 (m, 4H), 1.58-1.56 (m, 4H), 1.46-1.44 (m, 2H). MS (ESI) m/z: Calculated: 322.27; Observed: 323.2 (M$^{+}$+1).

1-(4-(5-cyclohexylbenzofuran-2-yl)3-fluorophenyl)methyl)azetidine-3-carboxylic acid (step 4 in Scheme 2)

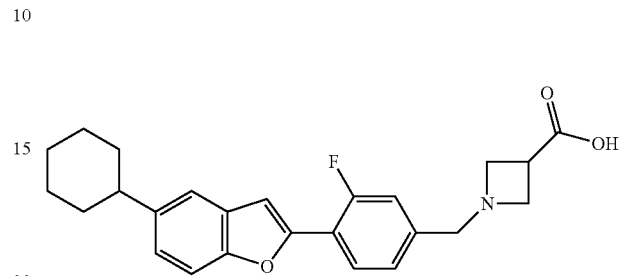

A mixture of 4-(5-cyclohexylbenzofuran-2-yl)3-fluorobenzaldehyde (40 mg, 0.12 mmol), acetic acid (10 µL, 0.15 mmol) and azetidine-3-carboxylic acid (15 mg, 0.15 mmol) in DCM/MeOH (1:1, 2 mL) was stirred at room temperature for 1 h. Sodium cyanoborohydride (3.0 mg, 0.05 mmol) was added and the reaction mixture was stirred for 3 h at room temperature. After concentration of solvent under reduced pressure, the resulting residue was dissolved in hot MeOH and filtered. The filtrate and the white solid, which was redissolved in hot DMSO, were both purified by reverse phase preparative HPLC (Phenomenex reverse phase Luna 5µ C18 (2) column, 60×21.2 mm ID) to yield the desired final product (12 mg, 42% yield) as a white powder [hS1P1 EC$_{50}$=160 nM, 361 nM]: >95% purity by LCMS, $^{1}$H NMR (400 MHz, CD$_3$OD) δ 8.12 (d, 1H), 7.47-7.38 (m, 4H), 7.28-7.20 (m, 2H), 4.66 (s, 2H), 4.34 (m, 4H), 3.72 (m, 1H), 2.61 (m, 1H), 1.95-1.82 (m, 4H), 1.60-1.56 (m, 4H), 1.42-1.40 (m, 2H). MS (ESI) m/z: Calculated: 407.48; Observed: 408.2 (M$^{+}$+1).

Compound 28

1-((4-(5-(thiophen-2-yl)benzofuran-2-yl)phenyl)methyl)azetidine-3-carboxylic acid

5-(Thiophen-2-yl)benzofuran

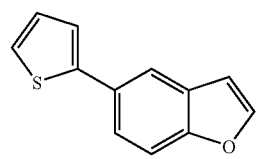

The title compound was prepared as Example Compound 6 (step 1 in Scheme 2) in the general method described above except using thiophen-2-ylboronic acid (55% yield). $^1$H NMR (400 MHz, CD$_3$Cl) δ 7.82 (s, 1H), 7.62 (s, 1H), 7.55-7.03 (m, 5H), 6.79 (d, 1H).

5-(Thiophen-2-yl)benzofuran-2-yl-boronic acid

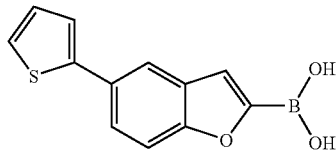

The title compound was prepared as Example Compound 6 (step 2 in Scheme 2) in the general method described above (77% yield). $^1$H NMR (400 MHz, CD$_3$Cl) δ 7.92 (s, 1H), 7.88 (s, 1H), 7.66-7.34 (m, 4H), 7.08 (d, 1H).

4-(5-(thiophen-2-yl)benzofuran-2-yl)benzaldehyde

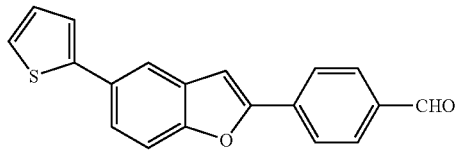

The title compound was prepared as Example Compound 6 (step 3 in Scheme 2) in the general method described above (61% yield): $^1$H NMR (400 MHz, CD$_3$Cl) δ 10.01 (s, 1H), 8.19 (d, 1H), 8.01 (d, 1H), 7.82 (s, 1H), 7.62-7.24 (m, 7H), 7.16 (dd, 1H). MS (ESI) m/z: Calculated: 304.06; Observed: 304.9 (M$^+$+1).

1-((4-(5-(thiophen-2-yl)benzofuran-2-yl)phenyl)methyl)azetidine-3-carboxylic acid

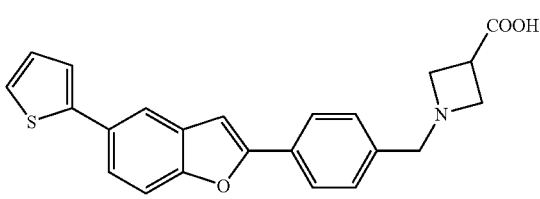

The title compound was prepared as Example Compound 6 (step 4 in Scheme 2) in the general method described above (31% yield) [hS1P1 EC$_{50}$=1800 nM, 25000 nM]: $^1$H NMR (400 MHz, DMSO-d$_6$) δ 8.01 (d, 2H), 7.87 (s, 1H), 7.64-7.44 (m, 7H), 7.19 (dd, 1H), 4.25 (m, 2H), 3.55 (m, 5H). MS (ESI) m/z: Calculated: 389.11; Observed: 389.9 (M$^+$+1).

Compound 29

3-(6-(5-benzylbenzofuran-2-yl)-3,4-dihydroisoquinolin-2(1H)-yl)propanoic acid 2-(3-bromophenyl)ethanamine (step 1 in Scheme 7)

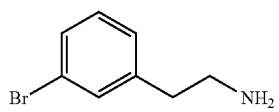

A suspension of LiAlH$_4$ (3.04 g, 80 mmole) in dry THF (100 mL) was cooled to −5° C. Concentrated H$_2$SO$_4$ (3.9 g, 40 mmole) was added dropwise, and the resulting mixture was stirred at −5° C. for 1 hour. A solution of 3-bromo-benzenacetonitrile (9.80 g, 50 mmole) in THF (5 mL) was added dropwise, and the reaction was allowed to warm to room temperature when the addition was complete. The reaction was stirred at room temperature for 1 hour, and then cooled back to 0° C. and quenched by the addition of a 1:1 THF: H$_2$O mixture (12.4 mL). Et$_2$O was added (50 mL), followed by a 3.6 M solution of NaOH (24.4 mL). The mixture was filtered through Celite, and the solids were washed well with additional Et$_2$O. The organic phase was dried over Na$_2$SO$_4$, filtered, and concentrated in vacuo to provide the title compound (9.7 g, 97%). The crude compound was used in subsequent steps. $^1$H NMR (400 MHz, CDCl$_3$) δ 7.38-7.30 (m, 2H), 7.20-7.10 (m, 2H), 2.96 (t, 2H), 2.72 (t, 2H), 1.35 (br s, 2H). MS (ESI) m/z: Calculated: 199; Observed: 200/202 (M$^+$+1).

N-(3-bromophenethyl)-2,2,2-trifluoroacetamide (step 2 in Scheme 7)

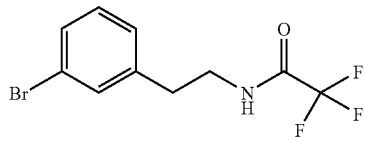

A mixture of 3-bromobenzeneethanamine (9.70 g, 48.5 mmole) and 2,6-lutidine (5.8 mL, 50.0 mmole) in dry CH$_2$Cl$_2$ (150 mL) was cooled to 0° C. Trifluoroacetic anhydride (5.6 mL, 40 mmole) was added dropwise; the reaction was then warmed to room temperature and allowed to stir for 24 hours. Water (120 mL) was added to the reaction, the phases were separated, and the aqueous layer was extracted with CH$_2$Cl$_2$ (2×100 mL). The combined organic phases were washed successively with 1N HCl (100 mL) and saturated NaHCO$_3$ (100 mL), and then dried over Na$_2$SO$_4$, filtered, and concentrated in vacuo to provide the tile compound (12.3 g, 86%). The crude compound was used in subsequent steps. $^1$H NMR (400 MHz, CDCl$_3$) δ 7.40 (d, J=8.0 Hz, 1H), 7.36 (s, 1H), 7.21 (t, J=7.6 Hz, 1H), 7.12 (t, J=7.6 Hz, 1H), 6.31 (br s, 1H), 3.59 (q, J=6.8 Hz, 2H), 2.87 (t, J=7.2 Hz, 2H).

1-(6-bromo-3,4-dihydroisoquinolin-2(1H)-yl)-2,2,2-trifluoroethanone and 1-(8-bromo-3,4-dihydroisoquinolin-2(1H)-yl)-2,2,2-trifluoroethanone (step 3 in Scheme 7)

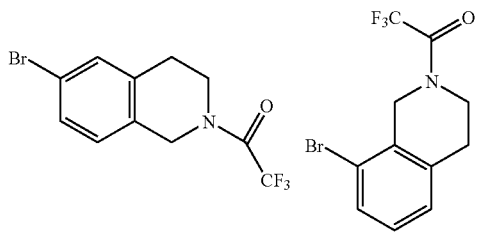

A mixture of glacial acetic acid (68 mL) and concentrated sulfuric acid (45 mL) was added to a mixture of N-(3-bromophenethyl)-2,2,2-trifluoroacetamide (12.3 g, 41.54 mmol) and paraformaldehyde (2.0 g). The reaction was stirred at room temperature for 24 hours, and then poured into 300 mL of cold water. The aqueous solution was extracted with EtOAc (3×150 mL). The combined organic phases were washed with saturated NaHCO$_3$ (200 mL) and water (2×200 mL). The organic phase was then dried over Na$_2$SO$_4$, filtered and concentrated in vacuo. The residue was purified on ISCO column (20% EtOAc/Hexane) to provide a mixture of the title compounds (9.6 g, 75%). $^1$H NMR (400 MHz, CDCl$_3$) δ 7.46 (dd, J=2.0 Hz, J=8.0 Hz, 0.33H), 7.38-7.31 (m, 1.33H), 7.15-7.09 (m, 0.67H), 7.05-6.98 (m, 0.67H), 4.75, 4.73, 4.69 (3×s, 2H), 3.90-3.80 (m, 2H), 3.00-2.90 (m, 2H). MS (ESI) m/z: Calculated: 306.98; Observed: 308/310 (M$^+$+1).

6-(5-benzylbenzofuran-2-yl)-1,2,3,4-tetrahydroisoquinoline (step 4 in Scheme 7)

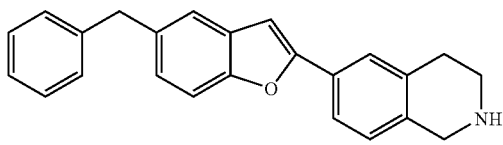

A solution of 5-benzylbenzofuran-2-ylboronic acid (252 mg, 1.0 mmole) in ethanol (3 mL) was added to a mixture of 1-(6-bromo-3,4-dihydroisoquinolin-2(1H)-yl)-2,2,2-trifluoroethanone and 1-(8-bromo-3,4-dihydroisoquinolin-2(1H)-yl)-2,2,2-trifluoroethanone (308 mg, 1.0 mmole), Pd(PPh$_3$)$_4$, toluene, and 2 M Na$_2$CO$_3$ (3.5 mL). The resulting mixture was heated at reflux overnight. The reaction was concentrated in vacuo, and the residue was diluted with water. The aqueous phase was extracted with EtOAc (3×50 mL). The combined organic phases were washed with brine, dried over Na$_2$SO$_4$, filtered and concentrated in vacuo. The residue was purified on ISCO column (5% to 10% MeOH/CH$_2$Cl$_2$) to provide the title compounds (189 mg, 56%). $^1$H NMR (400 MHz, CDCl$_3$) δ 7.60 (m, 2H), 7.39 (dd, 1H), 7.37 (s, 1H), 7.25 (m, 5H), 7.10 (dd, 2H), 6.90 (s, 1H), 4.10 (s, 2H), 3.40 (s, 2H), 3.18 (m, 2H), 2.94 (m, 2H). MS (ESI) m/z: Calculated: 339.16; Observed: 340.10 (M$^+$+1).

Tert-butyl 3-(6-(5-benzylbenzofuran-2-yl)-3,4-dihydroisoquinolin-2(1H)-yl)propanoate (step 5 in Scheme 6)

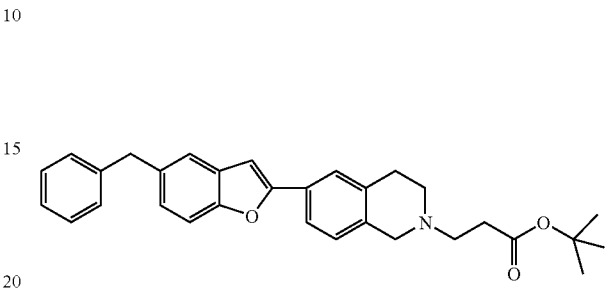

6-(5-benzylbenzofuran-2-yl)-1,2,3,4-tetrahydroisoquinoline (67 mg, 0.2 mmol) was dissolved in methanol (2 mL). DIEA (0.35 mL) and acrylic acid tert-butyl ester (51 mg, 0.4 mmol) were added. The mixture was headed to 90° C. for 30 minutes using microwave irradiation. All the solvents was evaporated and the crude product of tert-butyl 3-(6-(5-benzylbenzofuran-2-yl)-3,4-dihydroisoquinolin-2(1H)-yl)propanoate was used in the next step without further purification. MS (ESI) m/z: Calculated: 467.25; Observed: 468.30 (M$^+$+1).

3-(6-(5-benzylbenzofuran-2-yl)-3,4-dihydroisoquinolin-2(1H)-yl)propanoic acid (step 6 in Scheme 7)

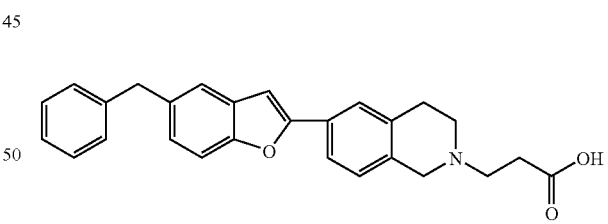

To a solution of tert-butyl 3-(6-(5-benzylbenzofuran-2-yl)-3,4-dihydroisoquinolin-2(1H)-yl)propanoate (40 mg, 0.086 mmole) in CH$_2$Cl$_2$ (1 mL) was added TFA (1 mL). The mixture was stirred at room temperature for 3 hours. All the solvents were evaporated. The mixture was purified by reverse phase preparative HPLC to give the title compound (14 mg, 40%) [hS1P1 EC$_{50}$=160 nM, 261 nM]. $^1$H NMR (400 MHz, CD$_3$OD) δ 7.77 (m, 2H), 7.42 (dd, 1H), 7.40 (s, 1H), 7.20-7.30 (m, 5H), 7.10 (m, 3H), 4.50 (s, 2H), 4.04 (s, 2H), 3.64 (dd, 2H), 3.55 (dd, 2H), 3.26 (dd, 2H), 2.90 (dd, 2H). MS (ESI) m/z: Calculated: 411.18; Observed: 412.10 (M$^+$+1).

Compound 30

1-(4-(5-cyclopentylbenzofuran-2-yl)benzyl)azetidine-3-carboxylic acid

5-Cyclopentylbenzofuran

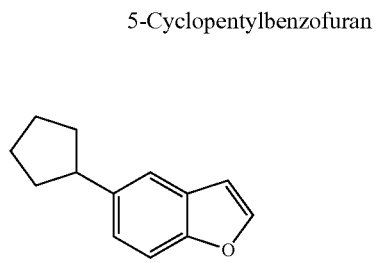

The title compound was prepared as Example Compound 6 (step 1 in Scheme 2) in the general method described above (67% yield): $^1$H NMR (400 MHz, CDCl$_3$) δ 7.58 (d, J=2.2, 1H), 7.45 (br d, J=1.8, 1H), 7.41 (d, J=8.8, 1H), 7.18 (dd, J=8.8, 1.8, 1H), 6.71 (dd, J=1.1, 2.2, 1H), 3.13-3.05 (m, 1H), 2.14-2.07 (m, 2H), 1.88-1.58 (m, 6H).

5-Cyclopentylbenzofuran-2-yl-2-boronic acid

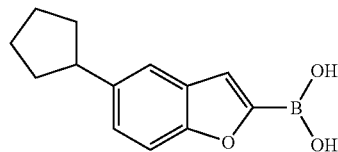

The title compound was prepared as Example Compound 6 (step 2 in Scheme 2) in the general method described above (yield): $^1$H NMR (400 MHz, CDCl$_3$) δ 7.50-7.45 (m, 2H), 7.43-7.39 (m, 1H), 7.31 (s, 1H), 3.12-3.05 (m, 1H), 2.14-2.06 (m, 2H), 1.80-1.60 (m, 6H).

4-(5-Cyclopentylbenzofuran-2-yl)benzaldehyde

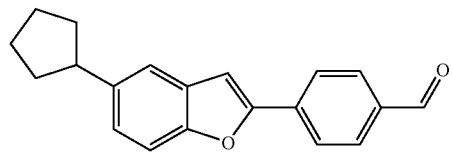

The title compound was prepared as Example Compound 6 (step 3 in Scheme 2) in the general method described above (95% yield): $^1$H NMR (400 MHz, CDCl$_3$) δ 10.03 (s, 1H), 8.00 (d, J=8.0, 2H), 7.94 (d, J=8.0, 2H), 7.51-7.44 (m, 3H), 7.15 (s, 1H), 3.14-3.06 (m, 1H), 2.20-2.10 (m, 2H), 1.88-1.62 (m, 6H).

1-(4-(5-cyclopentylbenzofuran-2-yl)benzyl)azetidine-3-carboxylic acid (step 4 in Scheme 2)

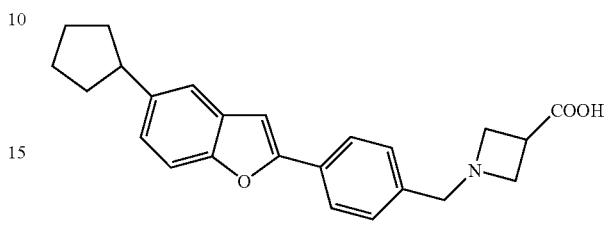

The title compound was prepared as Example Compound 6 (step 4 in Scheme 2) in the general method described earlier for reductive amination (71% yield) [hS1P1 EC$_{50}$=210 nM]. $^1$H NMR (400 MHz, CD$_3$OD) δ 8.02 (d, 2H), 7.57 (d, 2H), 7.49 (s, 1H), 7.44 (d, 1H), 7.25 (d, 2H), 4.56 (s, 2H), 4.30 (m, 4H), 3.62 (m, 1H), 3.11 (m, 1H), 2.25-2.12 (m, 2H), 1.90-1.66 (m, 6H). MS (ESI) m/z: Calculated: 375.46; Observed: 375.9 (M$^+$+1).

Compound 31

1-(3-fluoro-4-(5-(piperidin-1-yl)benzofuran-2-yl)benzyl)azetidine-3-carboxylic acid 1-(benzofuran-5-yl)piperidine (step 1 of Scheme 3)

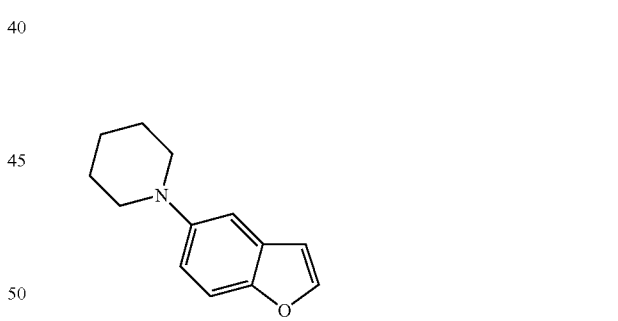

5-bromobenzofuran (2 g, 10 mmol), piperidine (1.2 mL, 12 mmol), Pd(dppf)Cl$_2$ (245 mg, 0.3 mmol), dppf (250 mg, 0.45 mmol) and sodium tert-butoxide (1.44 g, 15 mmol) was mixed in toluene (10 mL). The mixture was purged with N$_2$ gas for 3-5 min and heated at 120° C. for 30 min under microwave irradiation (Personal Chemistry Emrys™ Optimizer microwave reactor). Upon completion of the reaction, the reaction mixture was directly loaded on silica gel column and purified on ISCO system (<2% EtOAc in hexanes) to give 0.539 g desired product (27% yield): ESI-MS: 202.3 (M+H)$^+$, $^1$H NMR (400 MHz, CDCl$_3$) δ 7.58 (s, 1H), 7.40 (d, 1H), 7.15 (s, 1H), 7.00 (d, 1H), 6.65 (s, 1H), 3.10 (m, 4H), 1.70 (m, 4H), 1.48 (m, 2H). Note: the title compound appeared to be very volatile. The evaporation of solvent should be carried out very carefully.

5-(piperidin-1-yl)benzofuran-2-ylboronic acid (step 2 of Scheme 3)

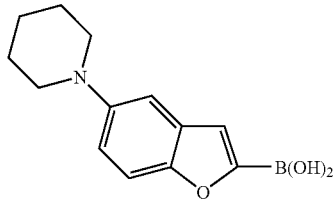

A solution of n-BuLi (334 µL, 0.83 mmol, 2.5 M solution in hexanes) was added dropwise to a solution of 1-(benzofuran-5-yl)piperidine (140 mg, 0.70 mmol) in anhydrous THF (5 mL) at −78° C. The resulting mixture was stirred at −78° C. for 40 min, and treated with B($^i$PrO)$_3$ (241 µL, 1.04 mmol). The reaction mixture was allowed to warm up slowly to room temperature and stirred for 1 h. TLC indicated the completion of reaction. The reaction was cooled in ice-bath and quenched with saturated NH$_4$Cl (1.5 mL) and extracted with Et$_2$O. The separated aqueous layer was neutralized to pH~5. The solution turned cloudy, which was extracted with ethyl acetate (×3). The combined organic extracts were concentrated in vacuo yielding the desired boronic acid as brown solids (0.16 g, 94% yield) without further purification for next step. ESI-MS: 246.3 (M+H)$^+$.

3-fluoro-4-(5-(piperidin-1-yl)benzofuran-2-yl)benzaldehyde (step 3 of Scheme 3)

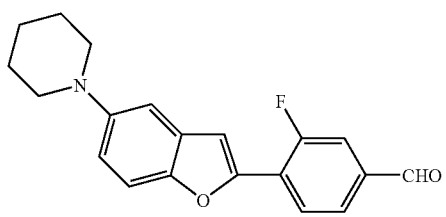

A mixture of 5-(piperidin-1-yl)benzofuran-2-ylboronic acid (50 mg, 0.204 mmol), 4-bromo-3-fluorobenzaldehyde (37 mg, 0.184 mmol), triethylamine (0.56 mL, 4.1 mmol) and bis(triphenylphosphine)palladium(II) chloride (14 mg, 0.02 mmol) in ethanol (5 mL) was irradiated in a microwave instrument at 100° C. for 20 min. The reaction mixture was cooled, and the solvent was removed. The residue was purification by silica gel chromatography on ISCO system yielding the title compound (15 mg, 15% yield). ESI-MS: 324.2 (M+H)$^+$, $^1$H NMR (400 MHz, CDCl$_3$) δ 10.00 (s, 1H), 8.19 (t, 1H), 7.75 (d, 1H), 7.67 (d, 1H), 7.43 (d, 1H), 7.35 (d, 1H), 7.14-7.11 (m, 2H), 3.13 (m, 4H), 1.77 (m, 4H), 1.59 (m, 2H).

1-(3-fluoro-4-(5-(piperidin-1-yl)benzofuran-2-yl) benzyl)azetidine-3-carboxylic acid trifluoroacetic acid salt (step 4 of Scheme 3)

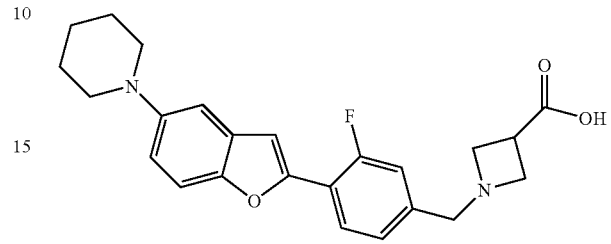

A mixture of 3-fluoro-4-(5-(piperidin-1-yl)benzofuran-2-yl)benzaldehyde (9 mg, 0.028 mmol), acetic acid (2.5 µL, 0.042 mmol) and azetidine-3-carboxylic acid (4.2 mg, 0.042 mmol) in DCM/MeOH (2:1, 0.9 mL) was stirred at room temperature for 1 h. Sodium cyanoborohydride (1.0 mg, 0.014 mmol) was added and the reaction mixture was stirred for 3 h at room temperature. After concentration of solvent under reduced pressure, the resulting residue was dissolved in DMSO, and purified by reverse phase preparative HPLC (Phenomenex reverse phase Luna 5µ C18 (2) column, 60×21.2 mm ID, mobil phase: A=0.05% TFA in water; B=0.05% TFA in acetonitrile. The flow rate was 12 mL/min. The gradient time was 2% B to 52% B over 25 min.) to yield the desired final product (10.3 mg, 70% yield) as a white powder (ditrifluoroacetic acid salt) [hS1P1 EC$_{50}$=860 nM, 307 nM]: >95% purity by LCMS, ESI-MS: 409.1 (M+H)$^+$, $^1$H NMR (400 MHz, CD$_3$OD) δ 8.17 (t, 1H), 8.02 (d, 1H), 7.81 (d, 1H), 7.66 (dd, 1H), 7.49-7.47 (m, 3H), 4.50 (s, 2H), 4.39 (dd, 4H), 3.72-3.70 (m, 5H), 2.08 (m, 4H), 1.84 (m, 2H).

Compound 32

1-((6-(5-benzylbenzofuran-2-yl)pyridin-3-yl)methyl) azetidine-3-carboxylic acid 6-(5-benzylbenzofuran-2-yl)nicotinaldehyde

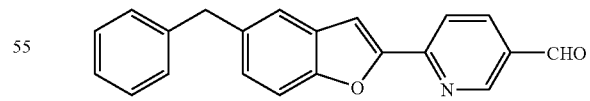

The title compound was prepared as the Example Compound 1 (step 4 in Scheme 1) in the general method described above except using 6-bromo-3-pyridinecarboxaldehyde (53% yield): $^1$H NMR (400 MHz, DMSO-d$_6$) δ 10.13 (s, 1H), 9.15 (s, 1H), 8.36 (d, 1H), 8.14 (m, 1H), 7.76 (d, 1H), 7.62 (m, 2H), 7.29 (m, 6H), 4.07 (s, 2H). MS (ESI) m/z: Calculated: 313.11; Observed: 314.20 (M⁺+1).

1-((6-(5-benzylbenzofuran-2-yl)pyridin-3-yl)methyl)azetidine-3-carboxylic acid

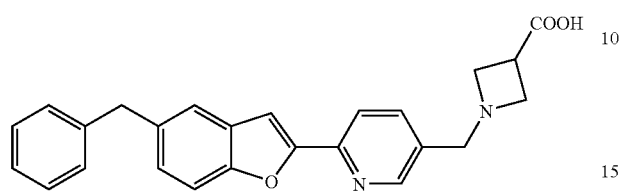

The title compound was prepared as Example Compound 1 (step 5 in Scheme 1) in the general method described above (33% yield) [hS1P1 $EC_{50}$=2600 nM, 516 nM]: $^1$H NMR (400 MHz, $CD_3OD$) δ 8.68 (s, 1H), 8.01 (br s, 2H), 7.45 (m, 3H), 7.16 (m, 6H), 4.50 (s, 2H), 4.35 (m, 4H), 4.04 (s, 2H), 3.70 (m, 1H). MS (ESI) m/z: Calculated: 398.16; Observed: 399.00 (M⁺+1).

Compound 33

1-((4-(5-benzylbenzofuran-2-yl)-3-methoxyphenyl)methyl)azetidine-3-carboxylic acid

4-(5-benzylbenzofuran-2-yl)-3-methoxybenzaldehyde

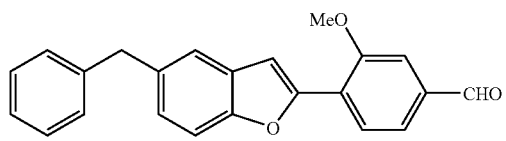

The title compound was prepared as Example Compound 1 (step 4 in Scheme 1) in the general method described above (60% yield): $^1$H NMR (400 MHz, $CDCl_3$) δ 10.03 (s, 1H), 8.22 (d, 1H), 7.64-7.44 (m, 11H), 4.16 (m, 5H). MS (ESI) m/z: Calculated: 342.13; Observed: 342.9 (M⁺+1).

1-((4-(5-benzylbenzofuran-2-yl)-3-methoxyphenyl)methyl)azetidine-3-carboxylic acid

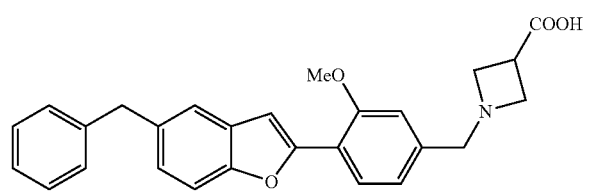

The title compound was prepared as Example Compound 1 (step 5 in Scheme 1) in the general method described above (50% yield) [hS1P1 $EC_{50}$=1000 nM, 1900 nM, 196 nM]: $^1$H NMR (400 MHz, DMSO-$d_6$) δ 7.98 (d, 1H), 7.42-7.07 (m, 11H), 4.18 (m, 2H), 3.82 (m, 5H), 3.57 (m, 1H), 3.14 (m, 4H). MS (ESI) m/z: Calculated: 427.18; Observed: 427.9 (M⁺+1).

Compound 34

1-(4-(5-(piperidin-1-yl)benzofuran-2-yl)benzyl)azetidine-3-carboxylic acid

4-(5-(piperidin-1-yl)benzofuran-2-yl)benzaldehyde (step 3 of Scheme 3)

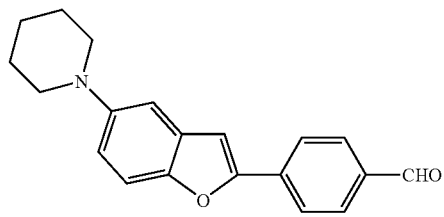

A mixture of 5-(piperidin-1-yl)benzofuran-2-ylboronic acid (90 mg, 0.367 mmol), 4-bromobenzaldehyde (62 mg, 0.330 mmol), triethylamine (1.0 mL, 7.3 mmol) and bis(triphenylphosphine)palladium(II) chloride (12.8 mg, 0.02 mmol) in ethanol (9 mL) was irradiated in a microwave instrument at 100° C. for 20 min. The reaction mixture was cooled, and the solvent was removed. The residue was purification by silica gel chromatography on ISCO system yielding the title compound (31 mg, 28% yield). ESI-MS: 306.4 (M+H)⁺, $^1$H NMR (400 MHz, $CDCl_3$) δ 10.02 (s, 1H), 7.95 (dd, 4H), 7.42 (d, 1H), 7.11 (m, 2H), 7.07 (dd, 1H), 3.13 (t, 4H), 1.78-1.74 (m, 4H), 1.62-1.56 (m, 2H).

1-(4-(5-(piperidin-1-yl)benzofuran-2-yl)benzyl)azetidine-3-carboxylic acid (step 4 of Scheme 3)

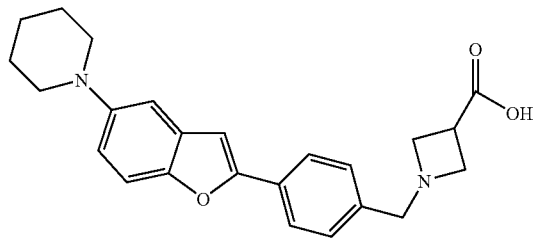

A mixture of 4-(5-(piperidin-1-yl)benzofuran-2-yl)benzaldehyde (31 mg, 0.102 mmol), acetic acid (9 μL, 0.15 mmol) and azetidine-3-carboxylic acid (12.3 mg, 0.122 mmol) in DCM/MeOH (2:1, 1.5 mL) was stirred at room temperature for 1 h. Sodium cyanoborohydride (3.2 mg, 0.051 mmol) was added and the reaction mixture was stirred for 3 h at room temperature. After concentration of solvent under reduced pressure, the resulting residue was dissolved in DMSO, and purified by reverse phase preparative HPLC (Phenomenex reverse phase Luna 5μ C18 (2) column, 60×21.2 mm ID, mobile phase: A=0.05% TFA in water; B=0.05% TFA in acetonitrile) to yield the desired final product (29.1 mg, 57% yield) as a white powder (ditrifluoroacetic acid salt) [hS1P1 $EC_{50}$=1500 nM]: >95% purity by LCMS, ESI-MS: 391.1 (M+H)⁺, $^1$H NMR (400 MHz, $CD_3OD$) δ 8.05

(t, 3H), 7.79 (d, 1H), 7.65-7.62 (m, 3H), 7.47 (s, 1H), 4.48 (m, 2H), 4.38-4.32 (m, 4H), 3.73-3.70 (m, 5H), 2.15 (m, 4H), 1.16 (m, 2H).

Compound 35

6-(5-benzylbenzofuran-2-yl)-2-(2-carboxyethyl)-3,4-dihydroisoquinolinium 2,2,2-trifluoroacetate (step 6 in Scheme 7)

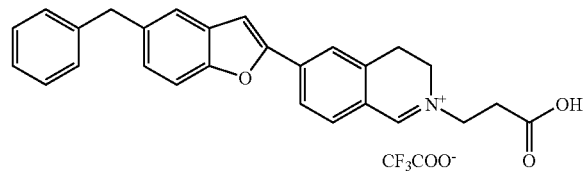

The title compound was isolated by reverse phase preparative HPLC during the purification of Compound 29. $^1$H NMR (400 MHz, CD$_3$OD) δ 9.17 (s, 1H), 8.04 (m, 2H), 7.90 (d, 1H), 7.50 (m, 3H), 7.23 (m, 6H), 4.28 (dd, 2H), 4.16 (dd, 2H), 4.08 (s, 2H), 3.34 (m, 2H), 3.03 (m, 2H). MS (ESI) m/z: Calculated: 410.18; Observed: 410.30 (M$^+$).

Compound 36

1-((4-(5-benzylbenzofuran-2-yl)-3-chlorophenyl)methyl)azetidine-3-carboxylic acid 4-(Ethoxycarbonyl)-2-chlorophenyl trifluoromethanesulfonate

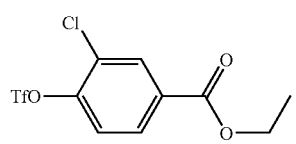

Trifluoroacetic anhydride (4.6 mL, 27.2 mmol) was added dropwise to a solution of ethyl 3-chloro-4-hydroxybenzoate (5.02 g, 25.0 mmol) and pyridine (2.2 mL, 27.5 mmol) in DCM (31 mL) at −10° C. The reaction mixture was stirred for 1 h at −10° C., allowed to warm up to rt and stirred for an additional 2 h. The reaction mixture was quenched with H$_2$O, and the resulting biphasic mixture was stirred for 15 min. The layers were separated and the organic layer was washed with 0.2 N HCl, water and brine. The final organic layer was dried (Na$_2$SO$_4$) and concentrated under reduced pressure to yield 6.8 g of a white solid, containing a mixture of triflate and remaining phenol. The mixture was redissolved in DCM and passed through a plug of silica gel to afford 3.8 g (45%) of pure triflate and 3 g of product impure with starting material. $^1$H NMR (400 MHz, CDCl$_3$) δ 8.21 (d, J=1.8, 1H), 8.03 (dd, J=8.5, 1.8, 1H), 7.43 (d, J=8.5, 1H), 4.42 (q, J=7.3, 2H), 1.41 (t, J=7.3, 3H).

Ethyl 4-(5-benzylbenzofuran-2-yl)-3-chlorobenzoate (step 2 in Scheme 5)

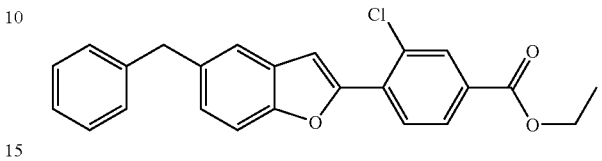

The title compound was prepared as Example Compound 40 (step 2 of Scheme 5) in the general method described above (94% yield): $^1$H NMR (400 MHz, CDCl$_3$) δ 8.15-8.12 (m, 2H), 8.00 (br d, J=8.4, 1H), 7.62 (s, 1H), 7.45-7.44 (m, 2H), 7.32-7.19 (m, 6H), 4.42 (q, J=7.3, 2H), 4.09 (s, 2H), 1.42 (t, J=7.3, 3H).

(4-(5-benzylbenzofuran-2-yl)-3-chlorophenyl)methanol (step 3 in Scheme 5)

The title compound was prepared as Example Compound 40 (step 3 of Scheme 5) in the general method described above (66 mg of a 1:1 mixture of primary alcohol and aldehyde that was used without further purification).

4-(5-Benzylbenzofuran-2-yl)-3-chlorobenzaldehyde (step 4 in Scheme 5)

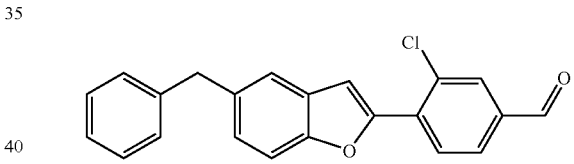

The title compound was prepared as Example Compound 40 (step 4 of scheme 5) in the general method described above (63% for the two steps): $^1$H NMR (400 MHz, CDCl$_3$) δ 10.00 (s, 1H), 8.24 (d, J=8.4, 1H), 7.99 (d, J=1.4, 1H), 7.86 (dd, J=8.0, 1.5), 7.69 (s, 1H), 7.47-7.45 (m, 2H), 7.32-7.19 (m, 6H), 4.10 (s, 2H).

1-(4-(5-Benzylbenzofuran-2-yl)-3-chlorobenzyl)azetidine-3-carboxylic acid (step 5 in Scheme 5)

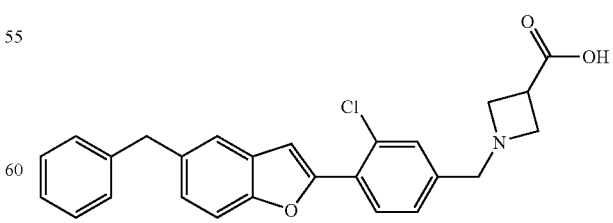

The title compound was prepared as Example Compound 40 (step 5 in Scheme 5) in the general method described above (42% yield) [hS1P1 EC$_{50}$=199 nM]: $^1$H NMR (400 MHz, DMSO-d$_6$) δ 8.05 (d, J=7.8, 1H), 7.76-7.72 (m, 1H), 7.59-

7.54 (m, 4H), 7.27-7.16 (m, 6H), 4.46-4.36 (m, 2H), 4.32-4.16 (m, 4H), 4.03 (s, 2H), 3.64-3.58 (m, 1H). MS (ESI) m/z: Calculated: 431.13; Observed: 431.9 (M++1).

Compound 37

3-(6-(5-cyclopentylbenzofuran-2-yl)-3,4-dihydroisoquinolin-2(1H)-yl)propanoic acid Tert-butyl 3-(6-hydroxy-3,4-dihydroisoquinolin-2(1H)-yl)propanoate (step 1 in Scheme 8)

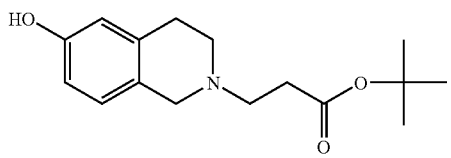

A solution of 1,2,3,4-tetrahydroisoquinolin-6-ol hydrobromide (345 mg, 1.5 mmol), tert-butyl acrylate (0.44 mL, 3.0 mmol) and N-ethyl-N-isopropylpropan-2-amine (2.6 mL, 15.0 mmol) in MeOH was irradiated in the microwave at 90° C. for 1800 s. Removal of the solvents gave the residue which was purified on ISCO column (2% to 5% MeOH/$CH_2Cl_2$) to provide the title compounds (332 mg, 80%). $^1$H NMR (400 MHz, $CD_3OD$) δ 6.85 (d, 1H), 6.55 (dd, 1H), 6.54 (s, 1H), 3.55 (s, 2H), 2.83 (m, 4H), 2.76 (m, 2H), 2.54 (dd, 2H), 1.45 (s, 9H). MS (ESI) m/z: Calculated: 277.17; Observed: 277.90 (M++1).

Tert-butyl 3-(6-(trifluoromethylsulfonyloxy)-3,4-dihydroisoquinolin-2(1H)-yl)propanoate (step 2 in Scheme 8)

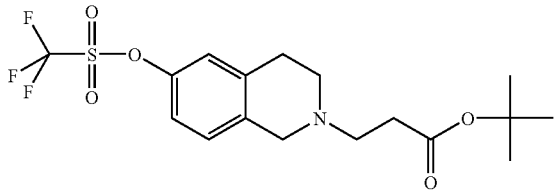

Trifluorosulfonic anhydride (87 µL, 0.52 mmol) was added to the solution of tert-butyl 3-(6-hydroxy-3,4-dihydroisoquinolin-2(1H)-yl)propanoate (111 mg, 0.4 mmol) in pyridine (5 mL) at 0° C. The reaction mixture was stirred for 1 hour at room temperature, concentrated, purified on ISCO column (2% to 5% MeOH/$CH_2Cl_2$) to provide the title compounds (93 mg, 57%). $^1$H NMR (400 MHz, $CD_3OD$) δ 7.20 (d, 1H), 7.12 (s, 1H), 7.10 (s, 1H), 3.68 (s, 2H), 2.94 (dd, 2H), 2.83 (dd, 2H), 2.78 (dd, 2H), 2.54 (dd, 2H), 1.44 (s, 9H). MS (ESI) m/z: Calculated: 409.12; Observed: 409.80 (M++1).

Tert-butyl 3-(6-(5-cyclopentylbenzofuran-2-yl)-3,4-dihydroisoquinolin-2(1H)-yl)propanoate (step 3 in Scheme 8)

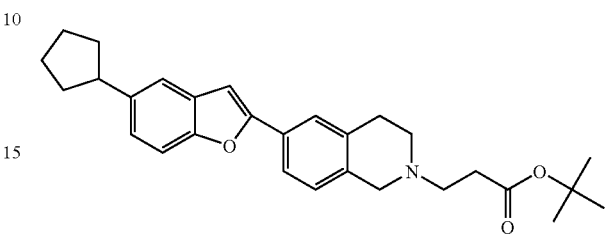

A mixture of 5-cyclopentylbenzofuran-2-ylboronic acid (78 mg, 0.34 mmol), tert-butyl 3-(6-(trifluoromethylsulfonyloxy)-3,4-dihydroisoquinolin-2(1H)-yl)propanoate (93 mg, 0.23 mmol), triethylamine (0.95 mL, 6.8 mmol) and bis(triphenylphosphine)palladium(II) chloride (16 mg, 0.02 mmol) in ethanol (5 mL) was irradiated in a microwave instrument at 100° C. for 20 min. The reaction mixture was cooled, and the solvent was removed. The residue was purification by silica gel chromatography on ISCO system yielding the title compound (34 mg, 34% yield). $^1$H NMR (400 MHz, $CDCl_3$) δ 7.59 (m, 2H), 7.40 (d, 2H), 7.15 (dd, 1H), 7.07 (d, 1H), 6.91 (s, 1H), 3.70 (s, 2H), 3.08 (m, 1H), 2.96 (dd, 2H), 2.85 (dd, 2H), 2.78 (dd, 2H), 2.54 (dd, 2H), 2.11 (m, 2H), 1.84 (m, 2H), 1.68 (m, 4H), 1.46 (s, 9H). MS (ESI) m/z: Calculated: 445.26; Observed: 446.00 (M++1).

3-(6-(5-cyclopentylbenzofuran-2-yl)-3,4-dihydroisoquinolin-2(1H)-yl)propanoic acid (step 4 in Scheme 8)

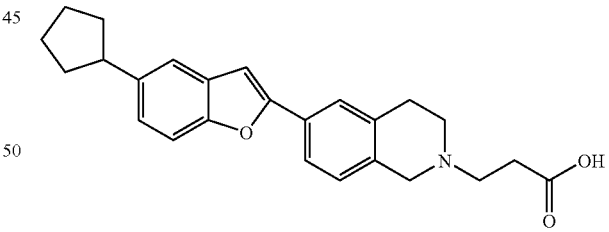

To a stirring solution of tert-butyl 3-(6-(5-cyclopentylbenzofuran-2-yl)-3,4-dihydroisoquinolin-2(1H)-yl)propanoate (25 mg, 0.056 mmole) in $CH_2Cl_2$ (0.5 mL) was added TFA (0.5 mL). The mixture was stirred at room temperature for 3 hours. Under reduced pressure, solvents and excess of TFA were removed affording a yellow oil which was rinsed with a mixture of $CH_2Cl_2$/Hexane (1:4) followed by ether. The solvents were removed under vacuum to give the title compound (19 mg, 90%) [hS1P1 $EC_{50}$=4170 nM]. $^1$H NMR (400 MHz, $CD_3OD$) δ 7.82 (m, 2H), 7.47 (s, 1H), 7.40 (d, 1H), 7.30 (d, 1H), 7.20 (d, 1H), 7.19 (s, 1H), 4.54 (br, 2H), 3.69 (br, 2H), 3.60 (dd, 2H), 3.28 (m, 2H), 3.10 (m, 1H), 2.96 (dd, 2H), 2.10

(m, 2H), 1.85 (m, 2H), 1.74 (m, 2H), 1.65 (m, 2H). MS (ESI) m/z: Calculated: 389.2; Observed: 390.20 (M++1).

Compound 38

1-(4-(5-(cyclopentylmethoxy)benzofuran-2-yl)-3-fluorobenzyl)azetidine-3-carboxylic acid 5-hydroxy benzofuran (step 1 of Scheme 4)

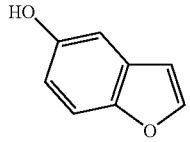

To an ice-cooled solution of 5-methylbenzofuran (0.5 g, 3.37 mmol) in DCM (7 mL) was added boron tribromide (3.4 mL, 3.37 mmol, 1M in DCM). The light brown solution was stirred at 0° C. for 1 h, another equivalent of boron tribromide (3.4 mL) was then added. The mixture was stirred at room temperature for 2 h. TLC analysis indicated the completion of the reaction. The mixture was poured into ice and the pH was adjusted to 7 with $Na_2CO_3$. The aqueous was extracted with DCM (×2). The combined organic layers were washed with brine, dried over $Na_2SO_4$ and concentrated. The resulting light brown sold gave the satisfactory purity without further purification for next step: 0.36 g (79.6% yield), $^1$H NMR (400 MHz, $CD_3OD$) δ 7.59 (d, J=2.0 Hz, 1H), 7.35 (d, J=9.2 Hz, 1H), 7.01 (d, J=2.4 Hz, 1H), 6.82 (dd, J=8.8 Hz, J=2.8 Hz, 1H), 6.67 (m, 1H), 4.73 (s, 1H).

5-(cyclopentylmethoxy)benzofuran (step 2 of Scheme 4)

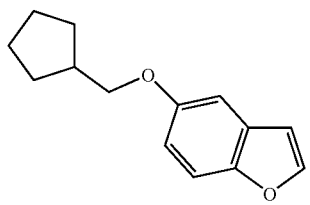

DEAD (362 mg, 2.09 mmol) was slowly added to a solution of 5-hydroxybenzofuran (200 mg, 1.49 mmol), triphenylphosphine (547 mg, 2.09 mmol) and cyclopentyl-methanol (203 mg, 2.0 2 mmol) in 3 mL of THF. The mixture was stirred at room temperature for 16 hours. The solvent was removed and the residue was purified by ISCO column chromatography using 0-5% AcOEt in Hexanes. The title compound was obtained as a white solid (0.208 g, 65% yield): 84% purity by HPLC; $^1$H NMR (400 MHz, $CD_3OD$) δ 7.58 (d, 1H), 7.38 (d, J=8.4 Hz, 1H), 7.06 (s, 1H), 6.91 (d, J=9.2 Hz, 1H), 6.69 (m, 1H), 3.82 (d, 2H), 2.39 (m, 1H), 1.85 (m, 2H), 1.63 (m, 4H), 1.39 (m, 2H).

5-(cyclopentylmethoxy)benzofuran-2-ylboronic acid (step 3 of Scheme 1)

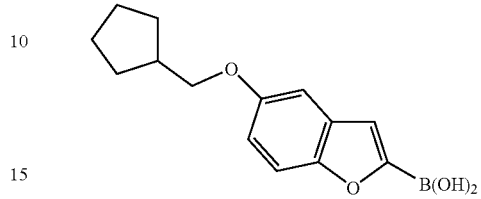

The title compound was prepared as Example Compound 1 (step 3 in Scheme 1) by the general method C described above (94.7% yield): $^1$H NMR (400 MHz, $CD_3OD$) δ 7.39 (d, J=9.2 Hz, 1H), 7.30 (s, 1H), 7.07 (d, 1H), 6.99 (dd, J=9.2 Hz, J=2.4 Hz, 1H), 3.82 (d, J=7.0 Hz, 2H), 2.39 (m, 1H), 1.86 (m, 2H), 1.63 (m, 4H), 1.39 (m, 2H).

4-(5-(cyclopentylmethoxy)benzofuran-2-yl)-3-fluorobenzaldehyde (step 4 of Scheme 1)

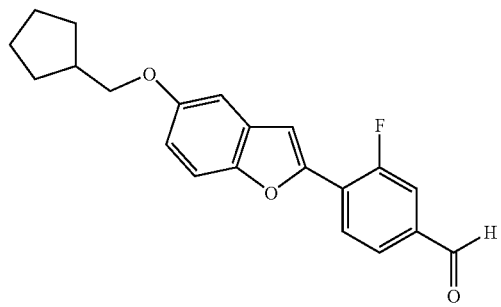

The title compound was prepared as Example Compound 1 (step 4 in Scheme 1) by the general method D described above (53% yield): ESI-MS: 339.3 (M+H)+, $^1$H NMR (400 MHz, $CD_3OD$) δ 10.0 (s, 1H), 8.20 (t, 1H), 7.30 (s, 1H), 7.77 (d, 1H), 7.68 (d, 1H), 7.43 (d, 1H), 7.36 (d, 1H), 7.09 (s, 1H), 6.99 (dd, 1H), 3.88 (d, J=7.0 Hz, 2H), 2.39 (m, 1H), 1.86 (m, 2H), 1.63 (m, 4H), 1.39 (m, 2H).

1-(4-(5-(cyclopentylmethoxy)benzofuran-2-yl)-3-fluorobenzyl)azetidine-3-carboxylic acid (step 5 of Scheme 1)

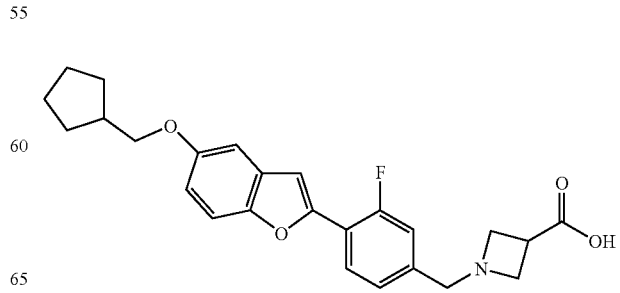

The title compound was prepared as Example Compound 1 (step 5 in Scheme 1) by the general method E described above (79% yield) [hS1P1 EC$_{50}$=803 nM]: ESI-MS: 423.9 (M+H)$^+$, $^1$H NMR (400 MHz, CD$_3$OD) δ 8.11 (t, 1H), 7.45-7.40 (m, 3H), 7.28 (d, 1H), 7.15 (d, 1H), 6.95 (dd, 1H), 4.46 (s, 2H), 4.36-4.34 (m, 4H), 3.88 (d, J=7.4 Hz, 2H), 3.68 (m, 1H), 2.38 (m, 1H), 1.85 (m, 2H), 1.65 (m, 4H), 1.43 (m, 2H).

Compound 39

1-(4-(5-(cyclopentylmethoxy)benzofuran-2-yl)benzyl)azetidine-3-carboxylic acid 4-(5-(cyclopentylmethoxy)benzofuran-2-yl)benzaldehyde (step 4 of Scheme 1)

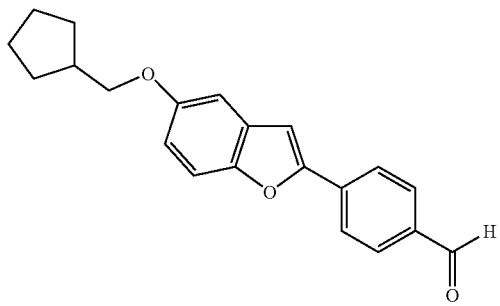

The title compound was prepared as Example Compound 1 (step 4 in Scheme 1) by the general method D described above (33% yield): ESI-MS: 321.2 (M+H)$^+$, $^1$H NMR (400 MHz, CD$_3$OD) δ 10.0 (s, 1H), 7.98 (dd, 4H), 7.43 (d, 1H), 7.14 (s, 1H), 7.07 (d, 1H), 6.96 (dd, 1H), 3.88 (d, J=7.0 Hz, 2H), 2.41 (m, 1H), 1.86 (m, 2H), 1.63 (m, 4H), 1.39 (m, 2H).

1-(4-(5-(cyclopentylmethoxy)benzofuran-2-yl)benzyl)azetidine-3-carboxylic acid (step 5 of Scheme 1)

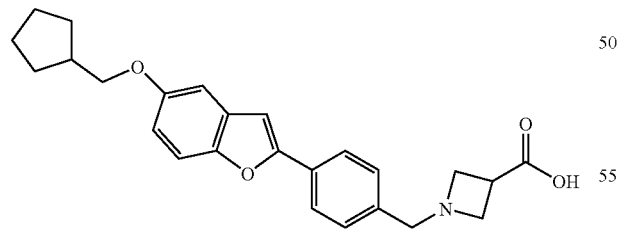

The title compound was prepared as Example Compound 1 (step 5 in Scheme 1) by the general method E described above (76% yield): ESI-MS: 405.9 (M+H)$^+$, $^1$H NMR (400 MHz, CD$_3$OD) δ 7.97 (d, 2H), 7.55 (d, 2H), 7.40 (d, 1H), 7.23 (s, 1H), 7.11 (d, 1H), 6.95 (dd, 1H), 4.44 (s, 2H), 4.35-4.33 (m, 4H), 3.88 (d, J=7.0 Hz, 2H), 3.69 (m, 1H), 2.38 (m, 1H), 1.87 (m, 2H), 1.65 (m, 4H), 1.43 (m, 2H).

Compound 40

1-((4-(5-Benzylbenzofuran-2-yl)-3-cyanophenyl)methyl)azetidine-3-carboxylic acid 4-(ethoxycarbonyl)-2-cyanophenyl trifluoromethanesulfonate

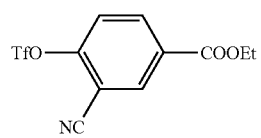

The title compound was prepared as Example Compound 36 in the general method described above (92% yield): $^1$H NMR (400 MHz, CDCl$_3$) δ 8.61 (s, 1H), 8.40 (d, 1H), 7.96 (d, 1H), 4.23 (q, 2H), 1.21 (t, 3H).

Ethyl-4-(5-benzylbenzofuran-2-yl)-3-cyanobenzoate (step 4, Scheme 1)

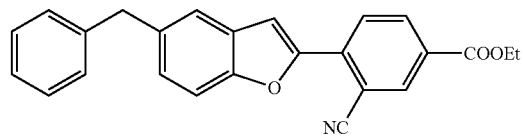

The title compound was prepared as Example Compound 1 (step 4, Scheme 1) in the general method described above (26% yield): $^1$H NMR (400 MHz, CDCl$_3$) δ 8.42 (s, 1H), 8.31 (d, 1H), 8.19 (d, 1H), 7.81 (s, 1H), 7.42 (d, 2H), 7.32-7.17 (m, 6H), 4.38 (q, 2H), 4.06 (s, 2H), 1.41 (t, 3H).

2-(5-Benzylbenzofuran-2-yl)-5-(hydroxymethyl)benzonitrile (step 3, scheme 5)

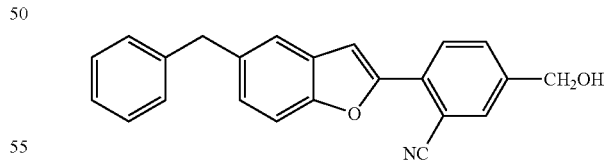

A solution of Ethyl-4-(5-benzylbenzofuran-2-yl)-3-cyanobenzoate (0.05 g, 0.13 mmol), sodium borohydride (0.01 g, 0.26 mmol) and calcium chloride (0.015 g, 0.13 mmol) in ethanol (2.5 mL) were stirred at room temperature for 1 hour. Water was added and the aqueous layer was extracted with ethyl acetate (×2, 10 mL). Organic layer was washed with water and brine and dried over sodium sulphate in 75% yield: $^1$H NMR (400 MHz, CDCl$_3$) δ 8.06 (d, 1H), 7.79 (s, 1H), 7.64 (d, 1H), 7.63 (s, 1H), 7.43-7.21 (m, 8H), 4.78 (s, 2H), 4.06 (s, 3H).

2-(5-Benzylbenzofuran-2-yl)-5-formylbenzonitrile (step 4, Scheme 5)

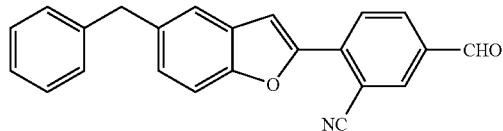

A suspension of 2-(5-Benzylbenzofuran-2-yl)-5-(hydroxymethyl)benzonitrile (0.03 g, 0.09 mmol), Molecular sieves 4A (0.2 g), TPAP (0.0016 mg, 0.004 mmol) and N-morpholino oxide (0.02 g, 0.18 mmol) in acetonitrile was stirred for 1 hour and then filtered through celite to obtain title compound in 93% yield (step 4, Scheme 5): $^1$H NMR (400 MHz, CDCl$_3$) δ 10.05 (s, 1H), 8.25 (s, 1H), 8.24 (d, 1H), 8.14 (d, 1H), 7.84 (s, 1H), 7.45 (m, 2H), 7.38-7.18 (m, 6H), 4.06 (s, 2H).

1-((4-(5-Benzylbenzofuran-2-yl)-3-cyanophenyl)methyl)azetidine-3-carboxylic acid (step 5, Scheme 1)

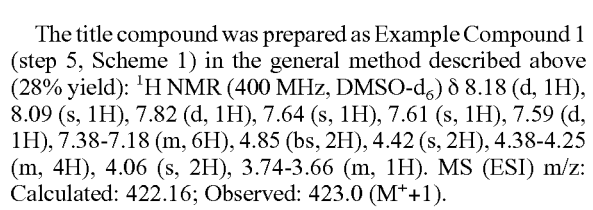

The title compound was prepared as Example Compound 1 (step 5, Scheme 1) in the general method described above (28% yield): $^1$H NMR (400 MHz, DMSO-d$_6$) δ 8.18 (d, 1H), 8.09 (s, 1H), 7.82 (d, 1H), 7.64 (s, 1H), 7.61 (s, 1H), 7.59 (d, 1H), 7.38-7.18 (m, 6H), 4.85 (bs, 2H), 4.42 (s, 2H), 4.38-4.25 (m, 4H), 4.06 (s, 2H), 3.74-3.66 (m, 1H). MS (ESI) m/z: Calculated: 422.16; Observed: 423.0 (M$^+$+1).

Compound 41

1-(4-(5-benzylbenzofuran-2-yl)-3-fluorophenyl)methyl)pyrrolidine-3-carboxylic acid

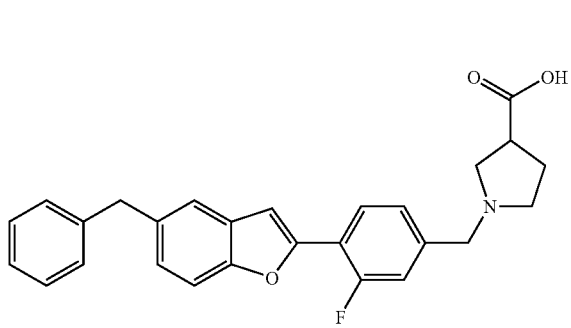

The title compound was prepared as racemic mixture according the reductive amination procedure as described in step 5 of Scheme-1 (60% yield) [hS1P1 EC$_{50}$=315 nM]. $^1$H NMR (400 MHz, CD$_3$OD) δ 8.11 (t, 1H), 7.47-7.44 (m, 4H), 7.27-7.19 (m, 7H), 4.45 (s, 2H), 4.05 (s, 2H), 3.73-3.52 (m, 2H), 3.48-3.34 (m, 3H), 251-2.38 (m, 2H). MS (ESI) m/z: Calculated: 429.48; Observed: 430.0 (M$^+$+1).

Compound 42

1-(4-(5-cyclopentylbenzofuran-2-yl)-3-fluorobenzyl) azetidine-3-carboxylic acid

4-(5-cyclopentylbenzofuran-2-yl)-3-fluorobenzaldehyde (step 3 in Scheme 2)

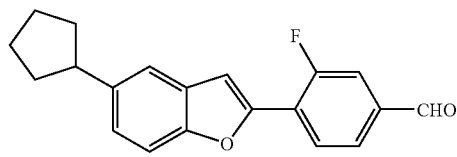

A solution of 5-cyclopentylbenzofuran-2-ylboronic acid (276 mg, 1.2 mmol), 4-bromobenzaldehyde (162 mg, 0.80 mmol), palladiumdichlorobis(triphenylphosphine) (56 mg, 0.08 mmol) and triethylamine (2.2 mL, 16 mmol) in EtOH (5 mL) was irradiated in the microwave at 100° C. for 20 min. The reaction mixture was cooled, and the solvent was removed. The residue was purification by silica gel chromatography on ISCO system yielding the title compound (34 mg, 34% yield). $^1$H NMR (400 MHz, CDCl$_3$) δ 10.0 (s, 1H), 8.21 (dd, 1H), 7.77 (d, 1H), 7.66 (d, 1H), 7.51 (s, 1H), 7.46 (d, 1H), 7.38 (d, 1H), 7.28 (d, 1H), 3.11 (m, 1H), 2.12 (m, 2H), 1.84 (m, 2H), 1.72 (m, 2H), 1.64 (m, 2H).

1-(4-(5-cyclopentylbenzofuran-2-yl)-3-fluorobenzyl) azetidine-3-carboxylic acid (step 5 in Scheme 1)

The title compound was prepared as Example Compound 1 (step 5 in Scheme 1) in the general method described above (20 mg, 18% yield): $^1$H NMR (400 MHz, CD$_3$OD) δ 8.09 (dd, 1H), 7.51 (s, 1H), 7.44 (d, 1H), 7.40 (s, 1H), 7.37 (d, 1H), 7.29 (m, 2H), 4.34 (s, 2H), 4.14 (m, 4H), 3.39 (m, 1H), 3.11 (m, 1H), 2.12 (m, 2H), 1.85 (m, 2H), 1.74 (m, 2H), 1.65 (m, 2H). MS (ESI) m/z: Calculated: 393.17; Observed: 393.90 (M⁺+1).

Compound 43

1-((4-(5-Benzylbenzofuran-2-yl)-3-methylphenyl) methyl)azetidine-3-carboxylic acid Methyl 4-(5-benzylbenzofuran-2-yl)-3-methylbenzoate (step 2 in Scheme 5)

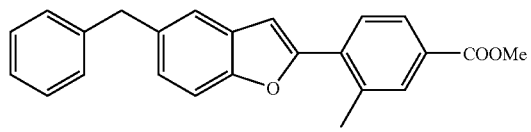

The title compound was prepared as Example Compound 40 (step 2, Scheme 5) in the general method described above (52% yield): ¹H NMR (400 MHz, CDCl₃) δ 7.89 (m, 2H), 7.61 (d, 1H), 7.42-7.17 (m, 8H), 6.95 (s, 1H), 4.06 (s, 2H), 3.82 (s, 3H), 2.61 (s, 3H).

(4-(5-Benzylbenzofuran-2-yl)-3-methylphenyl) methanol (step 3 in Scheme 5)

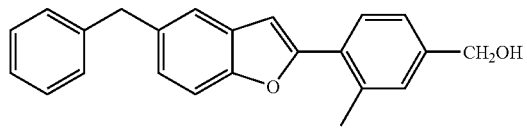

The title compound was prepared as Example Compound 40 (step 3, Scheme 5) in the general method described above (86% yield): ¹H NMR (400 MHz, CDCl₃) δ 7.94 (s, 1H), 7.82 (d, 1H), 7.48-7.07 (m, 9H), 6.85 (s, 1H), 4.67 (brs, 1H), 4.06 (s, 4H), 2.58 (s, 3H).

4-(5-Benzylbenzofuran-2-yl)-3-methylbenzaldehyde (step 4 in Scheme 5)

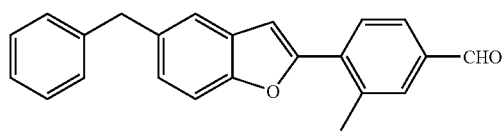

The title compound was prepared as Example Compound 40 (step 4, Scheme 5) in the general method described above (90% yield): ¹H NMR (400 MHz, CDCl₃) δ 10.03 (s, 1H), 8.07 (d, 1H), 7.81 (m, 2H), 7.46-7.17 (m, 8H), 7.01 (s, 1H), 4.08 (s, 2H), 2.63 (s, 3H).

1-((4-(5-Benzylbenzofuran-2-yl)-3-methylphenyl) methyl)azetidine-3-carboxylic acid (step 5 in Scheme 1)

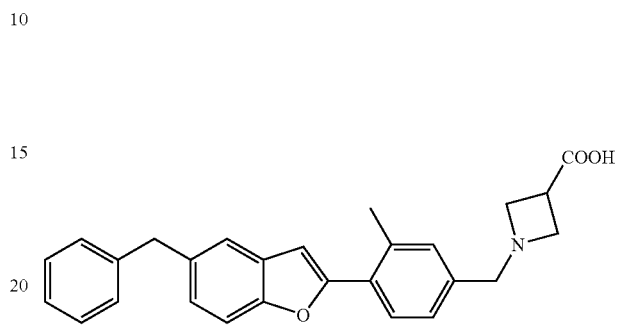

The title compound was prepared as Example Compound 1 (step 5, Scheme 1) in the general method described above (62% yield) [hS1P1 EC$_{50}$=241 nM]: ¹H NMR (400 MHz, CD₃OD) δ 7.92 (d, 1H), 7.51-7.17 (m, 10H), 7.03 (s, 1H), 4.84 (bs, 2H), 4.41 (s, 2H), 4.37-4.22 (m, 4H), 4.08 (s, 2H), 3.68-3.61 (m, 1H), 2.63 (s, 3H). MS (ESI) m/z: Calculated: 411.18; Observed: 411.9 (M⁺+1).

Compound 44

3-(6-(5-butoxybenzofuran-2-yl)-3,4-dihydroisoquinolin-2(1H)-yl)propanoic acid

Tert-butyl 3-(6-(5-butoxybenzofuran-2-yl)-3,4-dihydroisoquinolin-2(1H)-yl)propanoate (step 3 in Scheme 8)

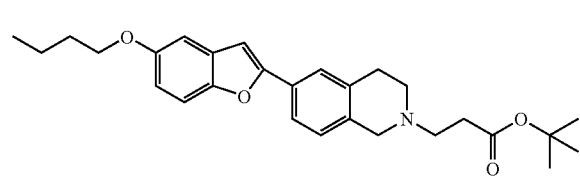

The title compound was prepared as Example Compound 37 (step 3 in Scheme 8) in the general method described above (57 mg, 50% yield): ¹H NMR (400 MHz, CDCl₃) δ 7.57 (m, 2H), 7.36 (d, 1H), 7.06 (d, 1H), 7.00 (d, 1H), 6.88 (s, 1H), 6.85 (d, 1H), 3.99 (dd, 2H), 3.68 (s, 2H), 2.96 (dd, 2H), 2.85 (dd, 2H), 2.78 (dd, 2H), 2.53 (dd, 2H), 1.80 (m, 2H), 1.56 (m, 2H), 1.45 (s, 9H), 1.00 (t, 3H). MS (ESI) m/z: Calculated: 449.26; Observed: 449.90 (M⁺+1).

3-(6-(5-butoxybenzofuran-2-yl)-3,4-dihydroisoquinolin-2(1H)-yl)propanoic acid (step 4 in Scheme 8)

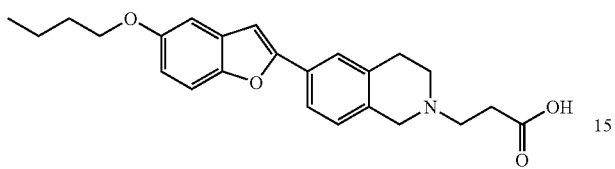

The title compound was prepared as Example Compound 37 (step 4 in Scheme 8) in the general method described above (25 mg, 75% yield) [hS1P1 EC$_{50}$=4440 nM]: $^1$H NMR (400 MHz, CD$_3$OD) δ 7.79 (m, 2H), 7.38 (d, 1H), 7.30 (d, 1H), 7.17 (s, 1H), 7.09 (d, 1H), 6.88 (dd, 1H), 4.54 (br s, 2H), 4.00 (dd, 2H), 3.68 (m, 2H), 3.60 (dd, 2H), 3.21 (m, 1H), 2.95 (dd, 2H), 1.78 (m, 2H), 1.53 (m, 2H), 1.00 (t, 2H). MS (ESI) m/z: Calculated: 393.19; Observed: 394.20 (M⁺+1).

Compound 45

3-(5-(5-benzylbenzofuran-2-yl)-2,3-dihydro-1H-inden-2-ylamino)-propanoic acid

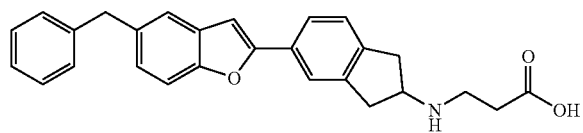

The title compound was prepared according the reductive amination procedure as described in step 5 of Scheme-1 (60% yield) [hS1P1 EC$_{50}$=807 nM]. $^1$H NMR (400 MHz, CD$_3$Cl$_3$) δ 7.80-7.74 (m, 2H), 7.54 (d, 1H), 7.40-7.22 (m, 7H), 7.18 (d, 1H), 6.92 (s, 1H), 4.79 (s, 1H), 4.02 (s, 2H), 3.28-2.92 (m, 4H), 2.73 (t, 2H), 2.48-2.30 (m, 2H). MS (ESI) m/z: Calculated: 411.49; Observed: 412.7 (M⁺+1).

Compound 46

3-((4-(5-Benzylbenzofuran-2-yl)-3-fluorophenyl)methylamino)-3-methylbutanoic acid

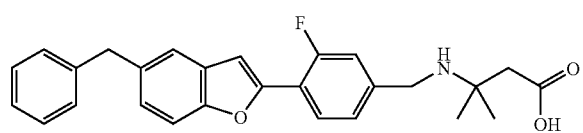

The title compound was prepared as Example Compound 1 (step 5, in Scheme 1) in the general method described above but using 3-amino-3-methylbutanoic acid instead of azetidine-3-carboxylic acid (46% yield) [hS1P1 EC$_{50}$>25000 nM]: $^1$H NMR (400 MHz, CD$_3$OD) δ 8.11 (t, J=7.8, 1H), 7.50-7.17 (m, 12H), 4.28 (s, 2H), 4.07 (s, 2H), 1.51 (s, 6H). MS (ESI) m/z: Calculated: 431.19; Observed: 432.0 (M⁺+1).

Compound 47

1-((4-(5-cyclopentylbenzofuran-2-yl)-3-methoxyphenyl)methyl)azetidine-3-carboxylic acid 4-(5-cyclopentylbenzofuran-2-yl)-3-methoxybenzaldehyde

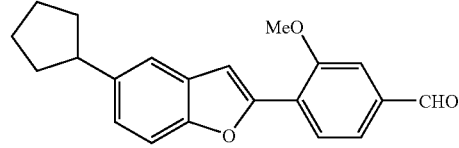

The title compound was prepared as Example Compound 1 (step 4 in Scheme 1) in the general method described above (56% yield): $^1$H NMR (400 MHz, CDCl$_3$) δ 10.04 (s, 1H), 8.21 (d, 1H), 7.77 (d, 1H), 7.59-7.19 (m, 5H), 4.04 (s, 3H), 3.11 (m, 1H), 2.15-1.77 (m, 4H), 1.58-1.56 (m, 4H).

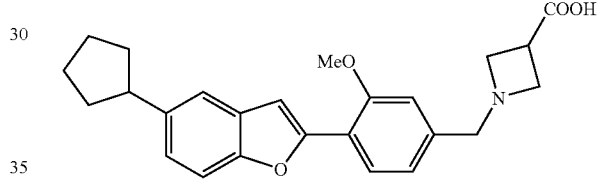

The title compound was prepared as Example Compound 1 (step 5, in Scheme 1) in the general method described earlier for reductive amination (71% yield) [hS1P1 EC$_{50}$=1070 nM]. $^1$H NMR (400 MHz, CD$_3$OD) δ 8.16 (d, 1H), 7.45 (s, 1H), 7.41-7.36 (m, 2H), 7.26-7.17 (m, 3H), 4.85 (bs, 2H), 4.41 (s, 2H), 4.32 (m, 4H), 4.04 (s, 3H), 3.62 (m, 1H), 3.11 (m, 1H), 2.25-2.12 (m, 2H), 1.90-1.66 (m, 6H). MS (ESI) m/z: Calculated: 405.19; Observed: 405.9 (M⁺+1).

Compound 48

1-((4-(5-Benzylbenzofuran-2-yl)-3,5-difluorophenyl)methyl)azetidine-3-carboxylic acid 4-(5-Benzylbenzofuran-2-yl)-3,5-difluorobenzaldehyde

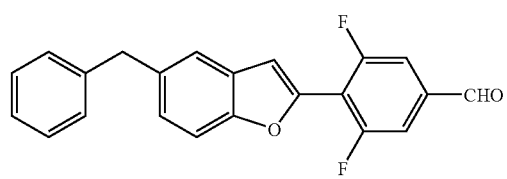

The title compound was prepared as Example Compound 1 (step 4, Scheme 1) in the general method described above (66% yield): $^1$H NMR (400 MHz, CDCl$_3$) δ 10.04 (s, 1H), 7.66 (s, 1H), 7.45 (d, 1H), 7.41-7.17 (m, 8H), 4.08 (s, 2H).

1-((4-(5-Benzylbenzofuran-2-yl)-3,5-difluorophenyl)methyl)azetidine-3-carboxylic acid

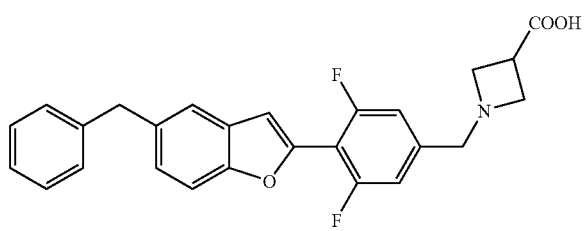

The title compound was prepared as Example Compound 1 (step 5, Scheme 1) in the general method described above (62% yield) [hS1P1 EC$_{50}$=89 nM]: $^1$H NMR (400 MHz, DMSO-d$_6$) δ 7.55 (s, 1H), 7.47 (d, 1H), 7.41-7.12 (m, 8H), 4.42 (s, 2H), 4.37-4.22 (m, 7H), 4.06 (s, 2H), 3.72-3.64 (m, 1H). MS (ESI) m/z: Calculated: 433.15; Observed: 433.9 (M$^+$+1).

Compound 49

1-(4-(5-(cyclopentylmethoxy)benzofuran-2-yl)-3-fluorobenzyl)azetidine-3-carboxylic acid 5-(cyclopropylmethoxy)benzofuran (step 2 of Scheme 4)

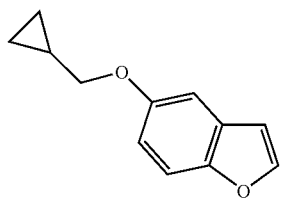

The title compound was prepared as Example Compound 38 (step 2 in Scheme 4) by the general method described above (49% yield): $^1$H NMR (400 MHz, CD$_3$OD) δ 7.60 (d, 1H), 7.38 (d, 1H), 7.05 (s, 1H), 6.94 (d, 1H), 6.69 (m, 1H), 3.84 (d, 2H), 1.31 (m, 1H), 0.66 (m, 2H), 0.37 (m, 2H).

5-(cyclopropylmethoxy)benzofuran-2-ylboronic acid (step 3 of Scheme 1)

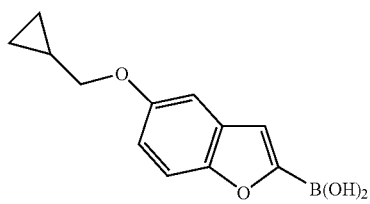

The title compound was prepared as Example Compound 1 (step 3 in Scheme 1) by the general method C described above (98% yield): $^1$H NMR (400 MHz, CD$_3$OD) δ 7.39 (d, 1H), 7.29 (s, 1H), 7.06 (d, 1H), 7.00 (dd, 1H), 3.83 (d, J=6.9 Hz, 2H), 1.30 (m, 1H), 0.66 (m, 2H), 0.38 (m, 2H).

4-(5-(cyclopropylmethoxy)benzofuran-2-yl)-3-fluorobenzaldehyde (step 4 of Scheme 1)

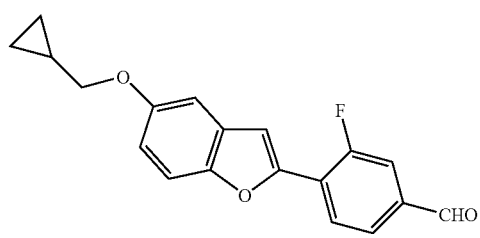

The title compound was prepared as Example Compound 1 (step 4 in Scheme 1) by the general method D described above (50% yield): ESI-MS: 311.2 (M+H)$^+$, $^1$H NMR (400 MHz, CD$_3$OD) δ 10.01 (s, 1H), 8.20 (t, 1H), 7.78 (d, 1H), 7.69 (d, 1H), 7.44 (d, 1H), 7.36 (d, 1H), 7.08 (s, 1H), 7.01 (d, 1H), 3.85 (d, J=7.1 Hz, 2H), 1.32 (m, 1H), 0.68 (m, 2H), 0.38 (m, 2H).

1-(4-(5-(cyclopentylmethoxy)benzofuran-2-yl)-3-fluorobenzyl)azetidine-3-carboxylic acid

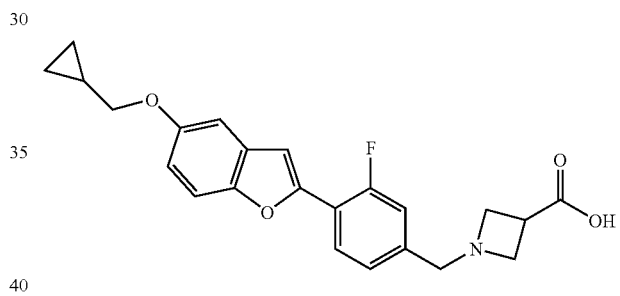

The title compound was prepared as Example Compound 1 (step 5 in Scheme 1) by the general method E described above (68% yield) [hS1P1 EC$_{50}$=109 nM]: ESI-MS: 395.9 (M+H)$^+$, $^1$H NMR (400 MHz, CD$_3$OD) δ 8.01 (t, 1H), 7.35-7.30 (m, 3H), 7.17 (d, 1H), 7.04 (d, 1H), 6.87 (dd, 1H), 4.37 (s, 2H), 4.28-4.25 (m, 4H), 3.76 (d, J=6.7 Hz, 2H), 3.60 (m, 1H), 1.18 (m, 2H), 0.54-0.51 (m, 2H), 0.28-0.26 (m, 2H).

Compound 50

1-((4-(5-Butoxybenzofuran-2-yl)-3-chlorophenyl)methyl)azetidine-3-carboxylic acid 2-Chloro-4-formylphenyl trifluoromethanesulfonate

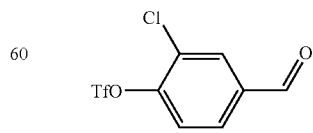

The title compound was prepared as Example Compound 36 in the general method described above but using 3-chloro-4-hydroxybenzaldehyde instead of ethyl 3-chloro-4-hydroxybenzoate (92% yield): ¹H NMR (400 MHz, CDCl₃) δ 10.00 (s, 1H), 8.06 (d, J=1.8, 1H), 7.88 (dd, J=8.4, 1.8, 1H), 7.55 (d, J=8.4, 1H).

4-(5-Butoxybenzofuran-2-yl)-3-chlorobenzaldehyde

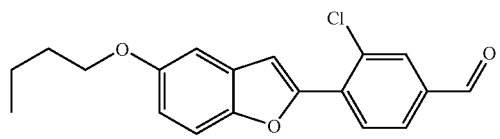

The title compound was prepared as Example Compound 1 (step 4 in Scheme 1) in the general method described above (72% yield): ¹H NMR (400 MHz, CDCl₃) δ 10.00 (s, 1H), 8.25 (d, J=8.0, 1H), 7.99 (d, J=1.4, 1H), 7.86 (dd, J=8.4, 1.5), 7.70 (s, 1H), 7.42 (d, J=8.8), 7.10 (d, J=2.6, 1H), 6.99 (dd, J=8.8, 2.5), 4.01 (t, J=6.5, 2H), 1.84-1.77 (m, 2H), 1.54-1.49 (m, 2H), 1.00 (t, J=7.3, 3H).

1-((4-(5-Butoxybenzofuran-2-yl)-3-chlorophenyl) methyl)azetidine-3-carboxylic acid

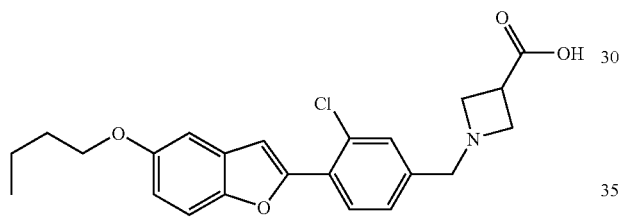

The title compound was prepared as Example Compound 1 (step 5 in Scheme 1) in the general method described above (66% yield) [hS1P1 EC₅₀=266 nM]: ¹H NMR (400 MHz, CD₃OD) δ 8.13 (d, J=8.4, 1H), 7.70 (d, J=1.8, 1H), 7.57 (s, 1H), 7.53 (dd, J=8.4, 1.8, 1H), 7.42 (d, J=9.1, 1H), 7.15 (d, J=2.5 1H), 6.95 (dd, J=9.1, 2.5), 4.45 (s, 2H), 4.40-4.32 (m, 4H), 4.00 (t, J=6.5, 2H), 3.74-3.66 (m, 1H), 1.81-1.74 (m, 2H), 1.58-1.49 (m, 2H), 1.00 (t, J=7.3, 3H). Calculated: 413.14; Observed: 413.9 (M⁺+1).

Compound 51

1-((3-chloro-4-(5-cyclopentylbenzofuran-2-yl)phe-nyl)methyl)azetidine-3-carboxylic acid Ethyl 3-chloro-4-(5-cyclopentylbenzofuran-2-yl)benzoate

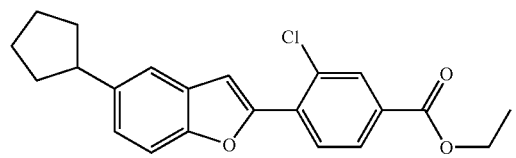

The title compound was prepared as Example Compound 40 (step 2 in Scheme 5) in the general method described above (73% yield): ¹H NMR (400 MHz, CDCl₃) δ 8.14 (d, J=7.8, 2H), 8.00 (d, J=8.1, 1H), 7.64 (s, 1H), 7.51-7.44 (m, 3H), 4.42 (q, J=7.0, 2H), 3.12-3.08 (m, 1H), 2.16-2.08 (m, 2H), 1.84-1.58 (m, 6H), 1.42 (t, J=7.3, 3H).

(3-Chloro-4-(5-cyclopentylbenzofuran-2-yl)phenyl) methanol

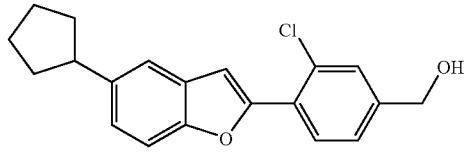

The title compound was prepared as Example Compound 40 (step 3 in Scheme 5) in the general method described above (142 mg of a 1:1 mixture of primary alcohol and aldehyde that was used without further purification).

3-Chloro-4-(5-cyclopentylbenzofuran-2-yl)benzalde-hyde

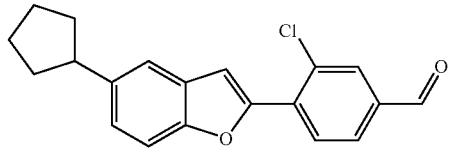

The title compound was prepared as Example Compound 40 (step 4 of Scheme 5) in the general method described above (61% for the two steps): ¹H NMR (400 MHz, CDCl₃) δ 10.00 (s, 1H), 8.25 (d, J=8.1, 1H), 7.99 (s, 1H), 7.86 (d, J=8.1), 7.71 (s, 1H), 7.52 (s, 1H), 7.47 (d, J=8.8, 1H), 7.27 (d, J=8.8, 1H), 3.16-3.06 (m, 1H), 2.18-2.06 (m, 2H), 1.88-1.60 (m, 6H).

1-((3-chloro-4-(5-cyclopentylbenzofuran-2-yl)phe-nyl)methyl)azetidine-3-carboxylic acid

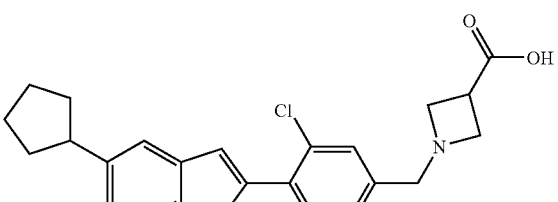

The title compound was prepared as Example Compound 40 (step 5 of Scheme 5) in the general method described above (60% yield) [hS1P1 EC₅₀=558 nM]: ¹H NMR (400 MHz, CD₃OD) δ 8.16 (d, J=8.1, 1H), 7.70 (d, J=1.5, 1H), 7.61 (s, 1H), 7.55-7.53 (m, 2H), 7.45 (d, J=8.8, 1H), 7.28 (dd, J=8.4, 1.5), 4.45 (s, 2H), 4.40-4.34 (m, 4H), 3.72-3.64 (m, 1H), 3.16-3.10 (m, 1H), 2.15-2.06 (m, 2H), 1.87-1.66 (m, 6H). Calculated: 409.14; Observed: 409.9 (M⁺+1).

Compound 52

3-(N-((4-(5-(cyclopentylmethoxy)benzofuran-2-yl)-3-fluorophenyl)methyl)-N-(2-hydroxyethyl)amino)propanoic acid

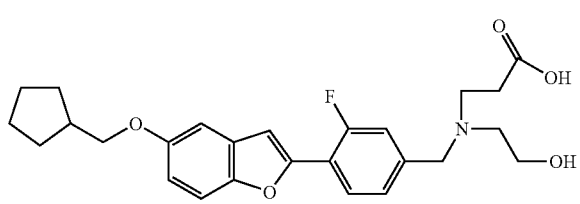

The title compound was prepared as Example Compound 1 (step 5, Scheme 1) in the general method described above except using 3-(2-hydroxyethylamino)propanoic acid (13% yield): ¹H NMR (400 MHz, DMSO-d₆) δ 7.57 (d, 1H), 7.55-7.47 (m, 2H), 7.26 (m, 2H), 7.22 (s, 1H), 6.96 (d, 1H), 4.82 (bs, 3H), 4.42 (s, 2H), 4.06 (s, 2H), 3.92-3.65 (m, 4H), 2.75-2.33 (m, 4H), 1.95-1.31 (m, 9H). MS (ESI) m/z: Calculated: 455.21; Observed: 455.9 (M⁺+1).

Compound 53

1-((3-fluoro-4-(5-morpholinobenzofuran-2-yl)phenyl)methyl)azetidine-3-carboxylic acid 4-(benzofuran-5-yl)morpholine

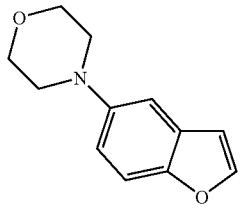

The title compound was prepared as Example Compound 31 (step 1 Scheme 3) in the general method described above (52% yield) [hS1P1 EC₅₀=2090 nM]: ¹H NMR (400 MHz, CDCl₃) δ 7.46 (s, 1H), 7.36 (d, 1H), 6.95 (s, 1H), 6.81 (d, 1H), 6.58 (s, 1H), 3.78 (m, 4H), 2.95 (m, 4H).

5-morpholinobenzofuran-2-yl-2-boronic acid

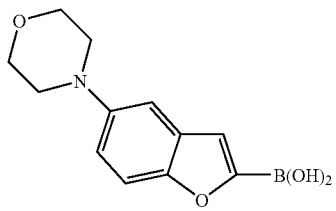

The title compound was prepared as Example Compound 31 (step 2 scheme 3) in the general method described above (72% yield): MS (ESI) m/z: Calculated: 247.1; Observed: 248.1 (M⁺+1).

3-fluoro-4-(5-morpholinobenzofuran-2-yl)benzaldehyde

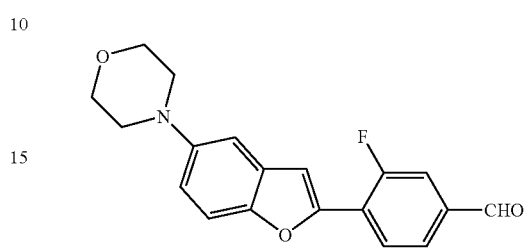

The title compound was prepared as Example Compound 31 (step 3 Scheme 3) in the general method described above (52% yield): ¹H NMR (400 MHz, CDCl₃) δ 10.01 (s, 1H), 7.76 (d, 1H), 7.61 (d, 1H), 7.55-7.06 (m, 5H), 3.86 (m, 4H), 3.15 (m, 4H).

1-((3-fluoro-4-(5-morpholinobenzofuran-2-yl)phenyl)methyl)azetidine-3-carboxylic acid

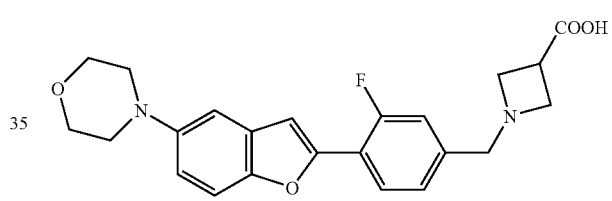

The title compound was prepared as Example Compound 1 (step 5 in Scheme 1) in the general method described above (28% yield): ¹H NMR (400 MHz, CD₃OD) δ 8.03 (t, 1H), 7.56 (d, 1H), 7.53 (d, 1H), 7.43 (d, 1H), 7.22 (d, 1H), 7.19 (d, 1H) 7.05 (dd, 1H), 4.50 (s, 2H), 4.39 (dd, 4H), 3.72-3.70 (m, 6H), 2.08 (m, 4H), 1.84 (m, 2H). MS (ESI) m/z: Calculated: 410.1; Observed: 411.1 (M⁺+1).

Compound 54

4-((4-(5-benzylbenzofuran-2-yl)-3-fluorophenyl)methyl)morpholine-2-carboxylic acid

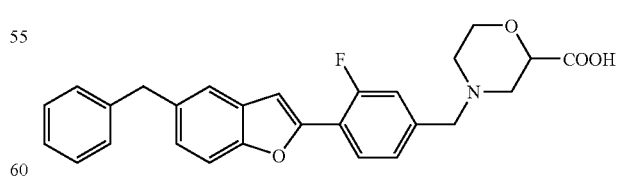

The title compound was prepared as Example Compound 1 (step 5 in Scheme 1) in the general method described above but using morpholine-2-carboxylic acid instead of azetidine-3-carboxylic acid (57% yield) [hS1P1 EC₅₀=1860 nM]: ¹H NMR (400 MHz, CD₃OD) δ 8.09 (t, J=7.8, 1H), 7.46-7.42 (m, 4H), 7.28-7.14 (m, 7H), 4.38 (br d, J=9.5, 1H), 4.30-4.21

(m, 2H), 4.13-4.04 (m, 1H), 4.06 (s, 2H), 3.83 (br t, J=10.6, 1H), 3.53 (br d, J=12.4, 1H), 3.30-3.22 (m, 1H), 3.13-3.00 (m, 2H). MS (ESI) m/z: Calculated: 445.17; Observed: 445.90 (M$^+$+1).

Compound 55

4-((4-(5-(cyclopentylmethoxy)benzofuran-2-yl)-3-fluorophenyl)methyl)morpholine-2-carboxylic acid

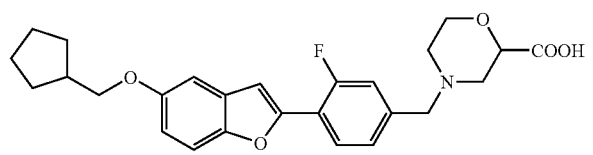

The title compound was prepared as Example Compound 1 (step 5 in Scheme 1) in the general method described above but using morpholine-2-carboxylic acid instead of azetidine-3-carboxylic acid (57% yield) [hS1P1 EC$_{50}$>25000 nM]: $^1$H NMR (400 MHz, CD$_3$OD) δ 8.06 (t, J=7.8, 1H), 7.44-7.42 (m, 3H), 7.24 (d, J=3.3, 1H), 7.13 (d, J=2.5, 1H), 6.95-6.92 (m, 1H), 4.38 (dd, J=9.5, 2.6, 1H), 4.21-4.09 (m, 3H), 3.88 (d, J=7.0, 2H), 3.81 (t, J=10.2, 1H), 3.45 (br d, J=11.4, 1H), 3.15 (br d, J=12.4, 1H), 3.03-2.91 (m, 2H), 2.41-2.34 (m, 1H), 1.90-1.83 (m, 2H), 1.71-1.57 (m, 4H), 1.46-1.37 (m, 2H). MS (ESI) m/z: Calculated: 453.20; Observed: 453.90 (M$^+$+1).

Compound 56

1-(5-(5-benzylbenzofuran-2-yl)-2,3-dihydro-1H-inden-2-yl azetidine-3-carboxylic acid

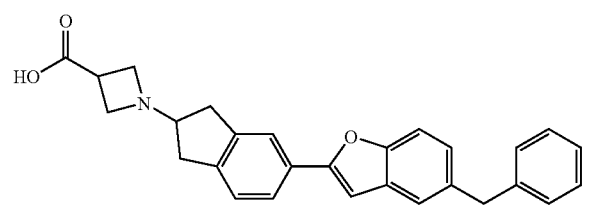

The title compound was prepared according the reductive amination procedure as described in step 5 of Scheme-1 (69% yield). $^1$H NMR (400 MHz, CD$_3$Cl$_3$) δ 7.78-7.68 (m, 2H), 7.45-7.22 (m, 8H), 7.22 (d, 1H), 6.94 (s, 1H), 4.73 (s, 1H), 4.05 (s, 2H), 3.52-3.20 (m, 2H), 3.29-2.62 (m, 7H), 2.48-2.31 (m, 2H). MS (ESI) m/z: Calculated: 423.5; Observed: 423.7 (M$^+$+1).

Compound 57

3-(6-(5-(cyclopentylmethoxy)benzofuran-2-yl)-3,4-dihydroisoquinolin-2(1H)-yl)propanoic acid Tert-butyl 3-(6-(5-(cyclopentylmethoxy)benzofuran-2-yl)-3,4-dihydroisoquinolin-2(1H)-yl)propanoate (step 3 in Scheme 8)

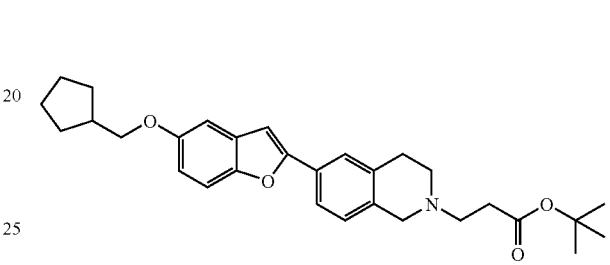

The title compound was prepared as Example Compound 37 (step 3 in Scheme 8) in the general method described above (73 mg, 40% yield) [hS1P1 EC$_{50}$=877 nM]: $^1$H NMR (400 MHz, CDCl$_3$) δ 7.57 (m, 2H), 7.36 (d, 1H), 7.06 (d, 1H), 7.01 (d, 1H), 6.85 (m, 2H), 3.85 (d, 2H), 3.69 (s, 2H), 2.96 (dd, 2H), 2.86 (dd, 2H), 2.79 (dd, 2H), 2.54 (dd, 2H), 2.38 (m, 1H), 1.66 (m, 2H), 1.59 (m, 4H), 1.45 (s, 9H), 1.39 (t, 2H). MS (ESI) m/z: Calculated: 475.27; Observed: 475.90 (M$^+$+1).

3-(6-(5-(cyclopentylmethoxy)benzofuran-2-yl)-3,4-dihydroisoquinolin-2(1H)-yl)propanoic acid (step 4 in Scheme 8)

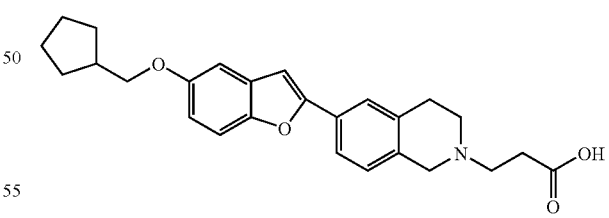

The title compound was prepared as Example Compound 37 (step 4 in Scheme 8) in the general method described above (19 mg, 72% yield): $^1$H NMR (400 MHz, CD$_3$OD) δ 7.78 (m, 2H), 7.38 (d, 1H), 7.30 (d, 1H), 7.17 (s, 1H), 7.09 (d, 1H), 6.88 (dd, 1H), 4.53 (s, 2H), 3.87 (d, 2H), 3.68 (m, 2H), 3.58 (dd, 2H), 3.27 (m, 1H), 2.93 (dd, 2H), 2.37 (m, 1H), 1.86 (m, 2H), 1.63 (m, 4H), 1.41 (m, 2H). MS (ESI) m/z: Calculated: 419.21; Observed: 420.2 (M$^+$+1).

Compound 58

3-(4-(5-cyclopentylbenzofuran-2-yl)-3-fluorobenzylamino)propanoic acid

Step 5 in Scheme 1

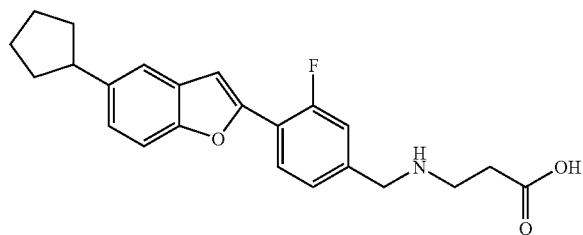

The title compound was prepared as Example Compound 1 (Step 5 in Scheme 1) in the general method described above (4.1 mg, 4.6% yield) [hS1P1 EC$_{50}$=1070 nM]: $^1$H NMR (400 MHz, CD$_3$OD) δ 8.10 (dd, 1H), 7.50 (s, 1H), 7.42 (m, 3H), 7.25 (m, 2H), 4.30 (s, 2H), 3.25 (m, 2H), 3.10 (m, 1H), 2.25 (dd, 2H), 2.18 (m, 2H), 1.84 (m, 2H), 1.65 (m, 4H). MS (ESI) m/z: Calculated: 381.17; Observed: 381.80 (M$^+$+1).

Compound 59

3-(4-(5-benzylbenzofuran-2-yl)-3-fluorophenoxy)propane-1,2-diol 4-(5-benzylbenzofuran-2-yl)-3-fluorophenol (step 4 in Scheme 1)

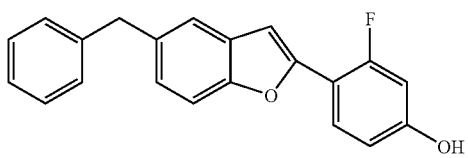

The title compound was prepared as the Example Compound 1 (step 4 in Scheme 1). in the general method described above except using 4-bromo-3-fluorophenol. The compound was used without further purification for the next step reaction.

3-(4-(5-benzylbenzofuran-2-yl)-3-fluorophenoxy)propane-1,2-diol (step 2 in Scheme 9)

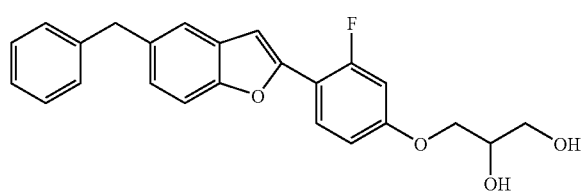

A mixture of 4-(5-benzylbenzofuran-2-yl)-3-fluorophenol (22 mg, 0.069 mmol), and 3-bromopropane-1,2-diol (48 mg, 0.31 mmol) and 2 N NaOH (200 µL) in i-PrOH (1 mL) was heated at 90° C. for overnight. After concentration of solvents under reduced pressure, the resulting residue was dissolved in DMSO and purified by reverse phase preparative HPLC (Phenomenex reverse phase Luna 5µ C18 (2) column, 60×21.2 mm ID, mobile phase: A=0.05% TFA in water; B=0.05% TFA in acetonitrile) to yield the desired final product (4.4 mg, 16% yield) as a white powder: $^1$H NMR (400 MHz, CD$_3$OD) δ 7.89 (m, 1H), 7.40 (m, 2H), 7.23 (m, 4H), 7.10 (m, 2H), 6.99 (m, 1H), 6.89 (m, 2H), 4.10 (m, 1H), 4.04 (s, 2H), 3.96 (m, 2H), 3.65 (m, 2H). MS (ESI) m/z: Calculated: 392.14; Observed: 393.20 (M$^+$+1).

Compound 60

1-((3-Fluoro-4-(5-(1-(methylsulfonyl)piperidine-4-yl)benzofuran-2-yl)phenyl)methyl)azetidine-3-carboxylic acid 4-(4-(2,2-Diethoxyethoxy)-1-(methylsulfonyl)piperidine

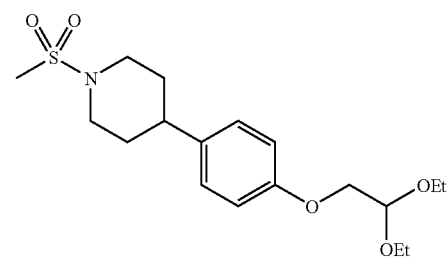

The title compound was prepared as Example Compound 1 (step 1 in Scheme 1) in the general method described above (70% yield): $^1$H NMR (400 MHz, CDCl$_3$) δ 7.07 (d, 2H), 6.82 (d, 2H), 4.81 (t, 1H), 3.96 (d, 4H), 3.90 (t, 2H), 3.79-3.72 (m, 2H), 3.67-3.59 (m, 2H), 2.81 (s, 3H), 2.77 (t, 2H), 2.61 (m, 1H), 1.77-1.70 (m, 2H), 1.21 (t, 6H).

4-(Benzofuran-5-yl)-1-(methylsulfonyl)piperidine

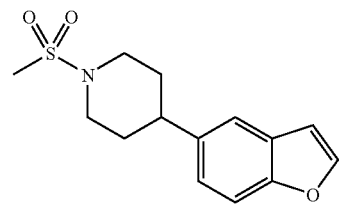

The title compound was prepared as Example Compound 1 (step 2 in Scheme 1) in the general method described above (20% yield): $^1$H NMR (400 MHz, CDCl$_3$) δ 7.45 (d, 1H), 7.42

(s, 1H), 7.13 (d, 1H), 6.62 (s, 1H), 4.03 (m, 4H), 2.83 (s, 3H), 2.78 (t, 1H), 1.82-1.75 (m, 4H).

5-(1-(Methylsulfonyl)piperidin-4-yl)benzofuran-2-yl-2-boronic acid

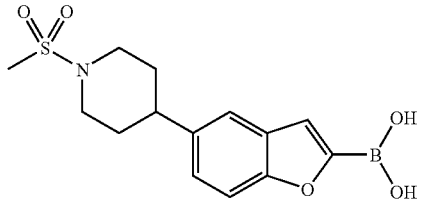

The title compound was prepared as Example Compound 1 (step 3 in Scheme 1) in the general method described above (84% yield): MS (ESI) m/z: Calculated: 323.1; Observed: 324.1 (M⁺+1).

3-Fluoro-4-(5-(1-(methylsulfonyl)piperidin-4-yl) benzofuran-2-yl)benzaldehyde

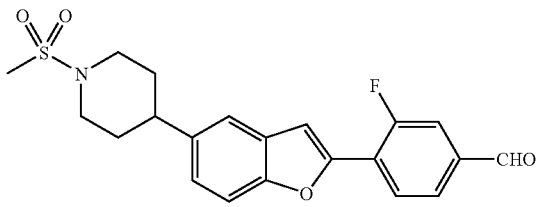

The title compound was prepared as Example Compound 1 (step 4 in Scheme 1) in the general method described above (62% yield): $^1$H NMR (400 MHz, CDCl$_3$) δ 10.03 (s, 1H), 8.21 (t, 1H), 7.79 (d, 1H), 7.72 (d, 1H), 7.51-7.21 (m, 4H), 3.98 (m, 4H), 2.84 (s, 3H), 2.76 (m, 1H), 2.05-1.81 (m, 4H).

1-((3-Fluoro-4-(5-(1-(methylsulfonyl)piperidine-4-yl)benzofuran-2-yl)phenyl)methyl)azetidine-3-carboxylic acid

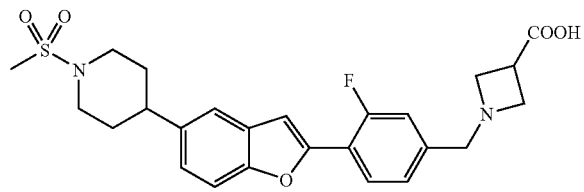

The title compound was prepared as Example Compound 1 (step 5 in Scheme 1) in the general method described above (70% yield): $^1$H NMR (400 MHz, DMSO-d$_6$) δ 8.21 (t, 1H), 7.84 (d, 1H), 7.77 (d, 1H), 7.51-7.21 (m, 4H), 4.85 (bs, 2H), 4.46 (s, 2H), 3.98 (m, 4H), 3.68 (m, 1H), 3.62 (m, 4H), 2.84 (s, 3H), 2.76 (m, 1H), 1.91-1.71 (m, 4H). MS (ESI) m/z: Calculated: 486.1; Observed: 486.9 (M⁺+1).

Compound 61

1-(3-fluoro-4-(5-(tetrahydro-2H-pyran-4-yl)benzofuran-2-yl)phenyl)methyl)azetidine-3-carboxylic acid 4-(benzofuran-5-yl)-tetrahydro-2H-pyran-4-ol (step 1 in Scheme 6)

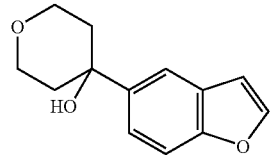

To a suspension of Mg (550 mg, 23.0 mmol) in dry THF (15 mL), under nitrogen atmosphere was added 5-bromobenzofuran (3.9 g, 20.0 mmol) in one portion. A crystal of iodine was added and then the contents were refluxed for 3 h. The reaction was then allowed to attain ambient temperature, and then cooled to −40° C. Pyran-4-one (3.0 g, 30.0 mmol) was added drop-wise and the resulting solution was allowed to reach room temperature. The reaction mixture was quenched by addition of 1N HCl (5 mL) and then was diluted with ether (30 mL). It was washed with water (2×15 mL) and the combined organic extract was washed with brine (15 mL), dried and concentrated under reduced pressure to give the crude carbinol as colorless oil. Purification by column chromatography using 5% EtOAc-hexanes afforded the desired product as white solid (41%). $^1$H NMR (400 MHz, CDCl$_3$) δ 7.74 (d, 1H), 7.64 (d, 1H), 7.51-7.44 (m, 2H), 6.78 (d, 1H), 4.00-3.88 (m, 4H), 2.25 (t, 2H), 1.78-1.74 (m, 2H).

5-(Tetrahydro-2H-pyran-4-yl)benzofuran (step 2 in Scheme 6)

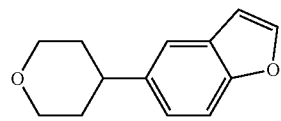

To a solution of 4-(benzofuran-5-yl)-tetrahydro-2H-pyran-4-ol (109 mg, 0.5 mmol) in DCM (5 mL) at 0° C. under nitrogen atmosphere was added triethylsilane (175 mg, 1.5 mmol) followed by TFA (570 mg, 5.0 mmol). After stirring for 15 min at the same temperature, the cooling bath was removed, and allowed the reaction mixture to reach room temperature. It was further stirred at room temperature for 6 h and then poured into crushed ice-water mixture (10 mL). It was extracted with DCM (3×10 mL), and the combined organic layer was washed with brine (10 mL), dried and evaporated. The crude compound was purified by column chromatography using 5% EtOAc-hexanes to afford the desired product (88%). $^1$H NMR (400 MHz, CDCl$_3$) δ 7.61

(d, 1H), 7.44 (d, 2H), 7.15 (d, 1H), 6.73 (d, 1H), 4.11 (dd, 2H), 3.56 (t, 2H), 2.89-2.81 (m, 1H), 1.93-1.79 (m, 4H).

5-(tetrahydro-2H-pyran-4-yl-benzofuran-2-yl-2-boronic acid (step 3 in Scheme 1)

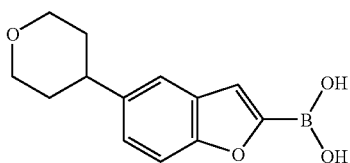

The title compound was prepared in the same manner as described in step 3 of Scheme 1 (86%): $^1$H NMR (400 MHz, CDCl$_3$) δ 7.48-7.41 (m, 2H), 7.28 (d, 1H), 7.20 (d, 1H), 4.10 (t, 2H), 3.60 (t, 2H), 2.98-2.94 (m, 1H), 1.97-1.80 (m, 4H). MS (ESI) m/z: Calculated: 324.35; Observed: 325.1 (M$^+$+1).

3-Fluoro-4-(5-(tetrahydro-2H-pyran-4-yl-benzofuran-2-yl)benzaldehyde (step 4 in Scheme 1)

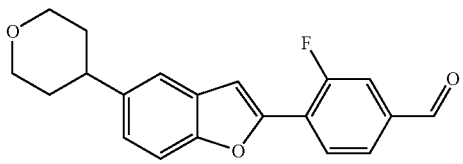

The title compound was prepared in the same manner as described in step 4 of Scheme 1 (68%): $^1$H NMR (400 MHz, CDCl$_3$) δ 10.01 (s, 1H), 8.04 (t, 1H), 7.80 (t, 1H), 7.74 (d, 1H), 7.52 (t, 2H), 7.40 (d, 1H), 7.22 (s, 1H), 4.10 (t, 2H), 3.60 (t, 2H), 2.98-2.94 (m, 1H), 1.97-1.80 (m, 4H). MS (ESI) m/z: Calculated: 324.35; Observed: 325.1 (M$^+$+1).

1-(3-fluoro-4-(5-(tetrahydro-2H-pyran-4-yl)benzofuran-2-yl)phenyl)methyl)azetidine-3-carboxylic acid (step 5 in Scheme 1)

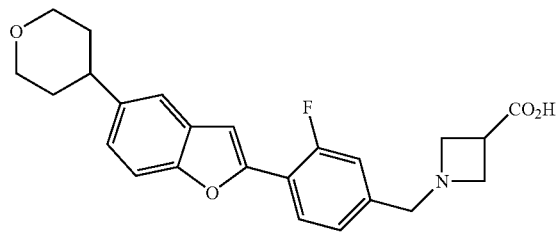

The title compound was prepared according the reductive amination procedure as described in step 5 of Scheme-1 (73% yield) [hS1P1 EC$_{50}$=207 nM]. $^1$H NMR (400 MHz, CD$_3$OD) δ 8.12 (t, 1H), 7.54 (s, 1H), 7.49 (d, 1H), 7.43 (s, 1H), 7.41 (d, 1H), 7.31-7.27 (m, 2H), 4.46 (s, 2H), 4.39-4.31 (m, 4H), 4.05 (d, 2H), 3.71-3.64 (m, 1H), 3.59 (t, 2H), 1.95-1.89 (m, 4H). MS (ESI) m/z: Calculated: 409.45; Observed: 410.0 (M$^+$+1).

The following examples are given for the purpose of illustrating the invention, but not for limiting the scope or spirit of the invention.

Compounds of the invention may be prepared as described in the following schemes.

Scheme A-2

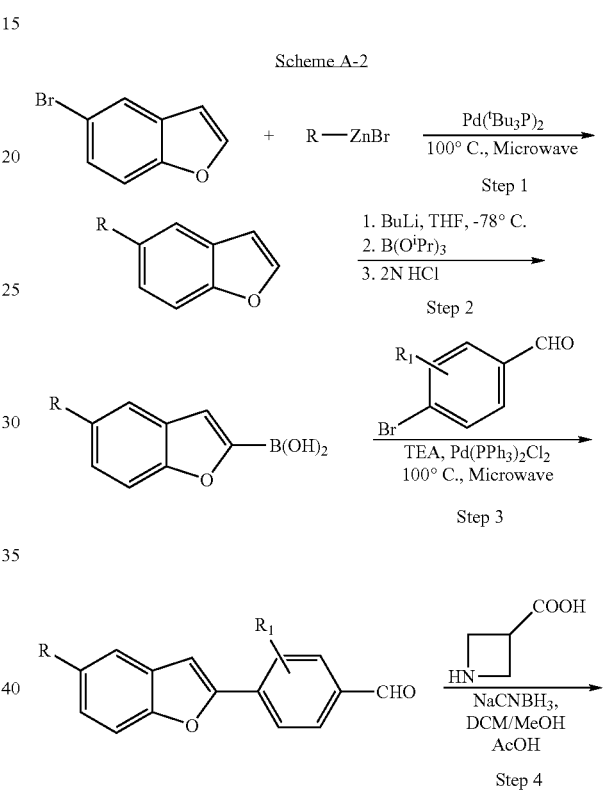

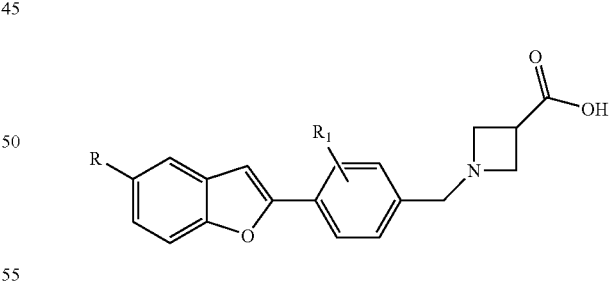

Scheme A-3-a

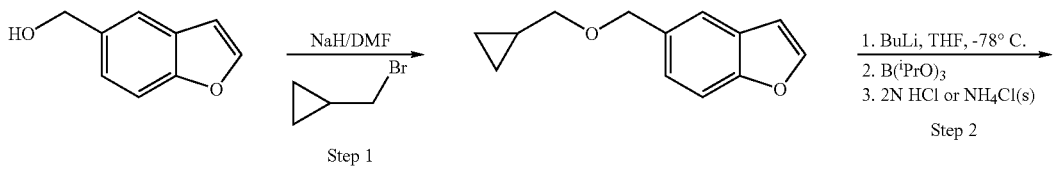

-continued
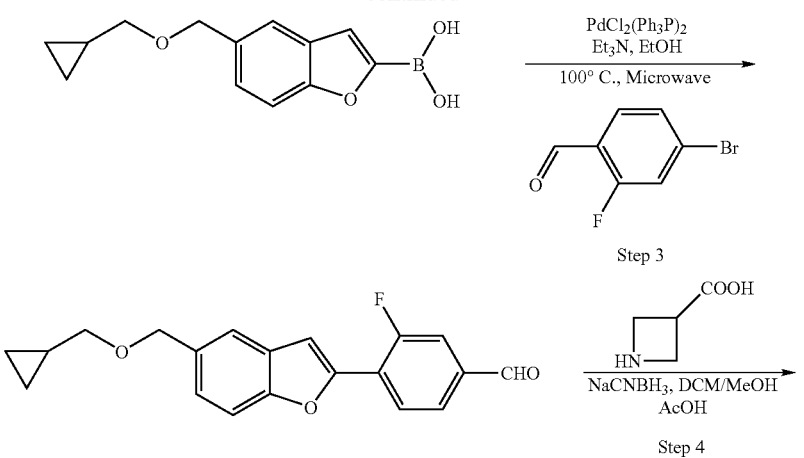
Step 3
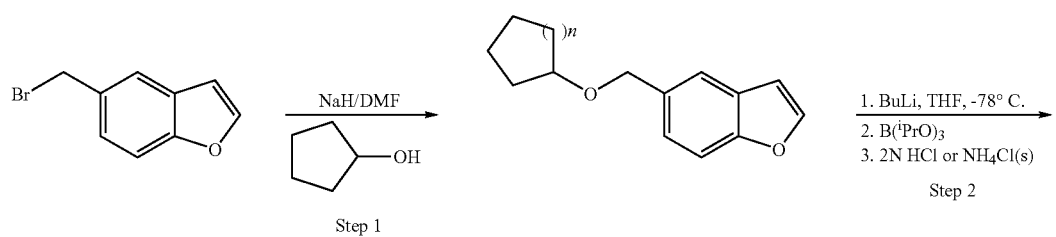
Step 4
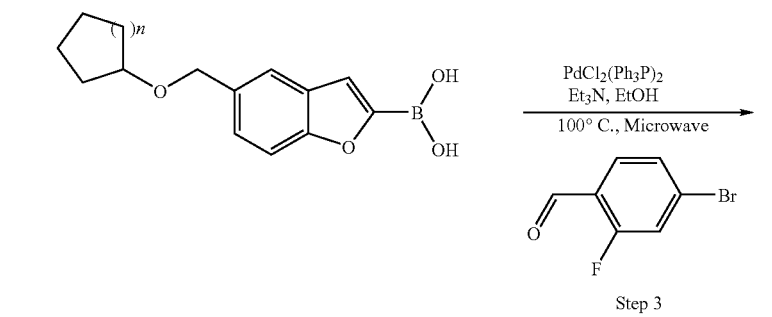
Scheme A-3-b
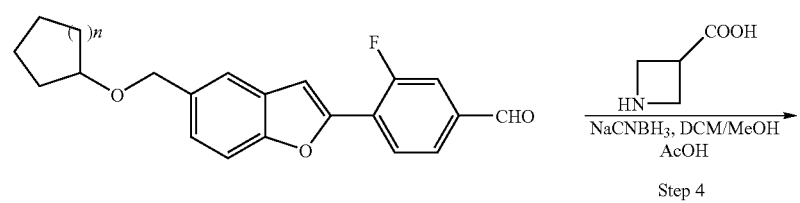

US 7,919,519 B2 n = 0, 1, 2

Scheme A-4

Step 1

Step 2

Step 3

Step 4

Step 5

Step 6

Step 7

Scheme A-5

Step 1

123                          124
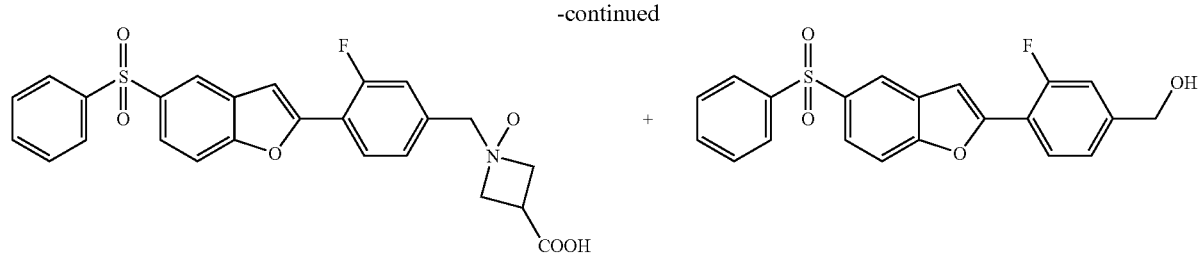
minor product                      major product
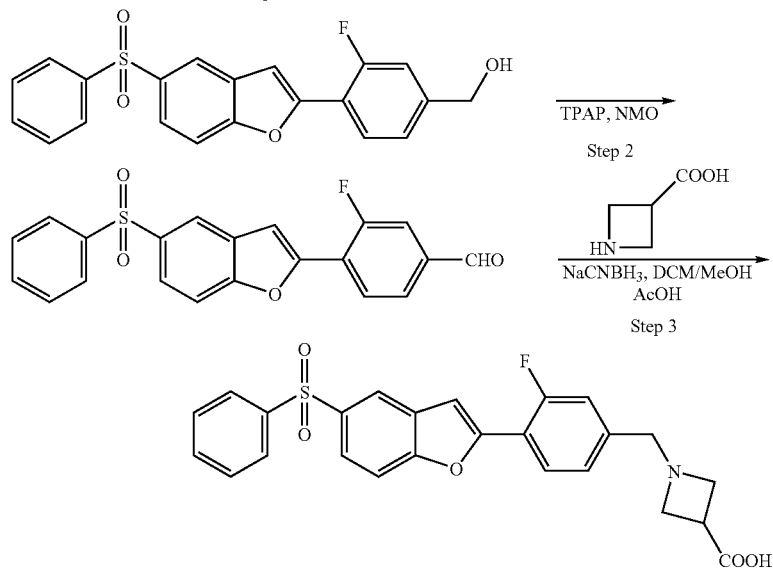
35
Scheme A-6
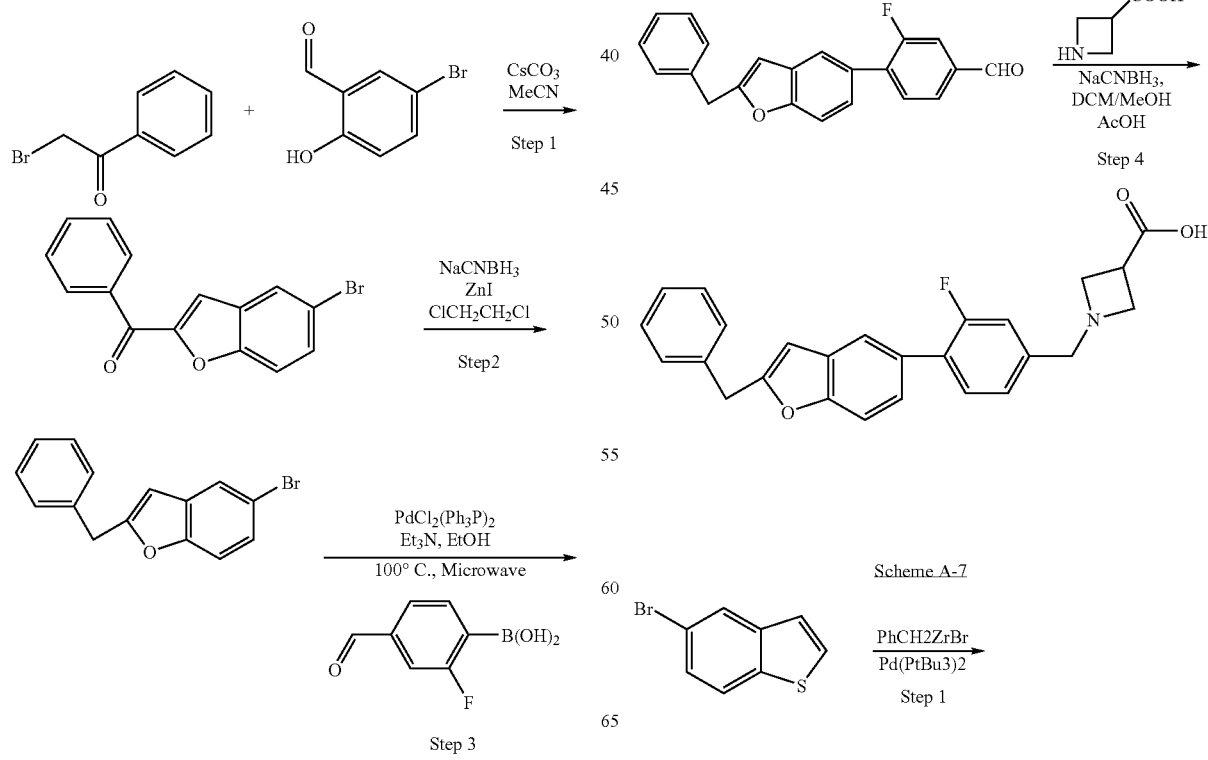
Scheme A-7

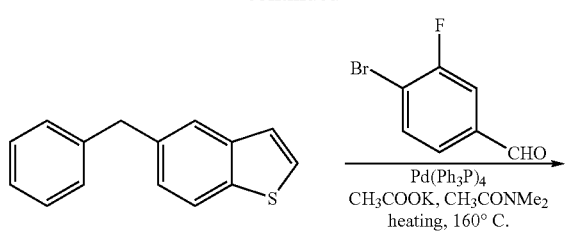
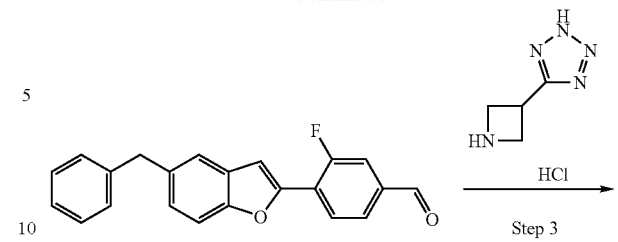
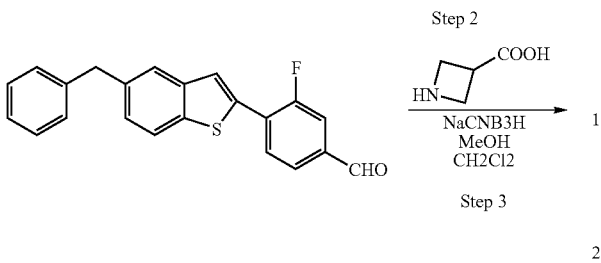
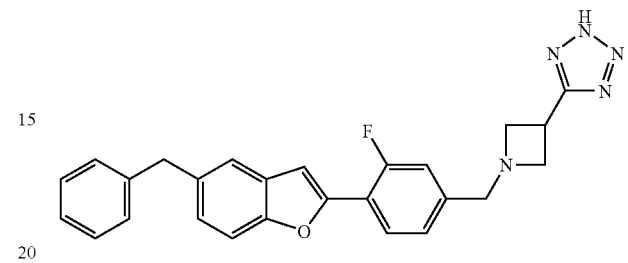
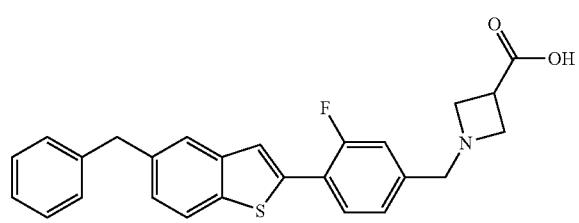
Scheme A-9
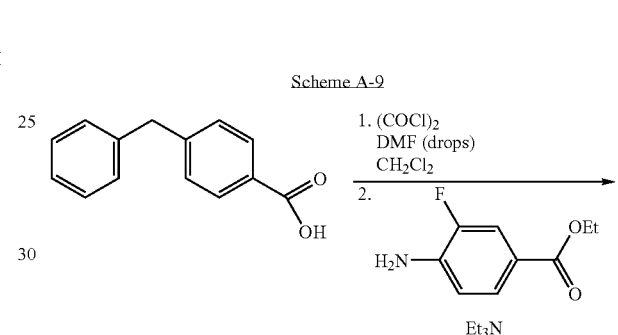
Scheme A-8
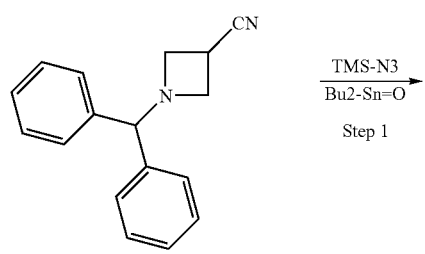
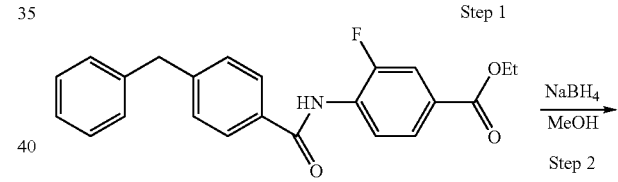
ethyl 4-(4-benzylbenzamido)-3-fluorobenzoate
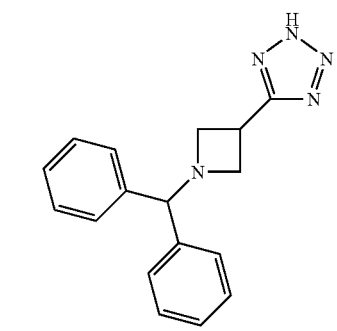
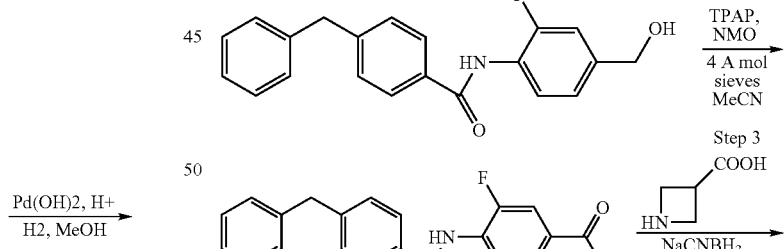
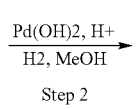
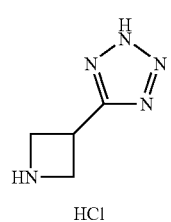
HCl
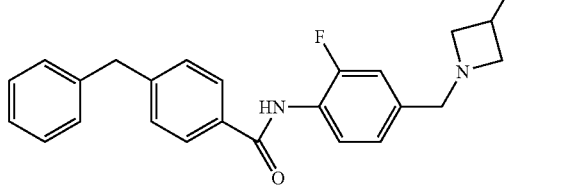

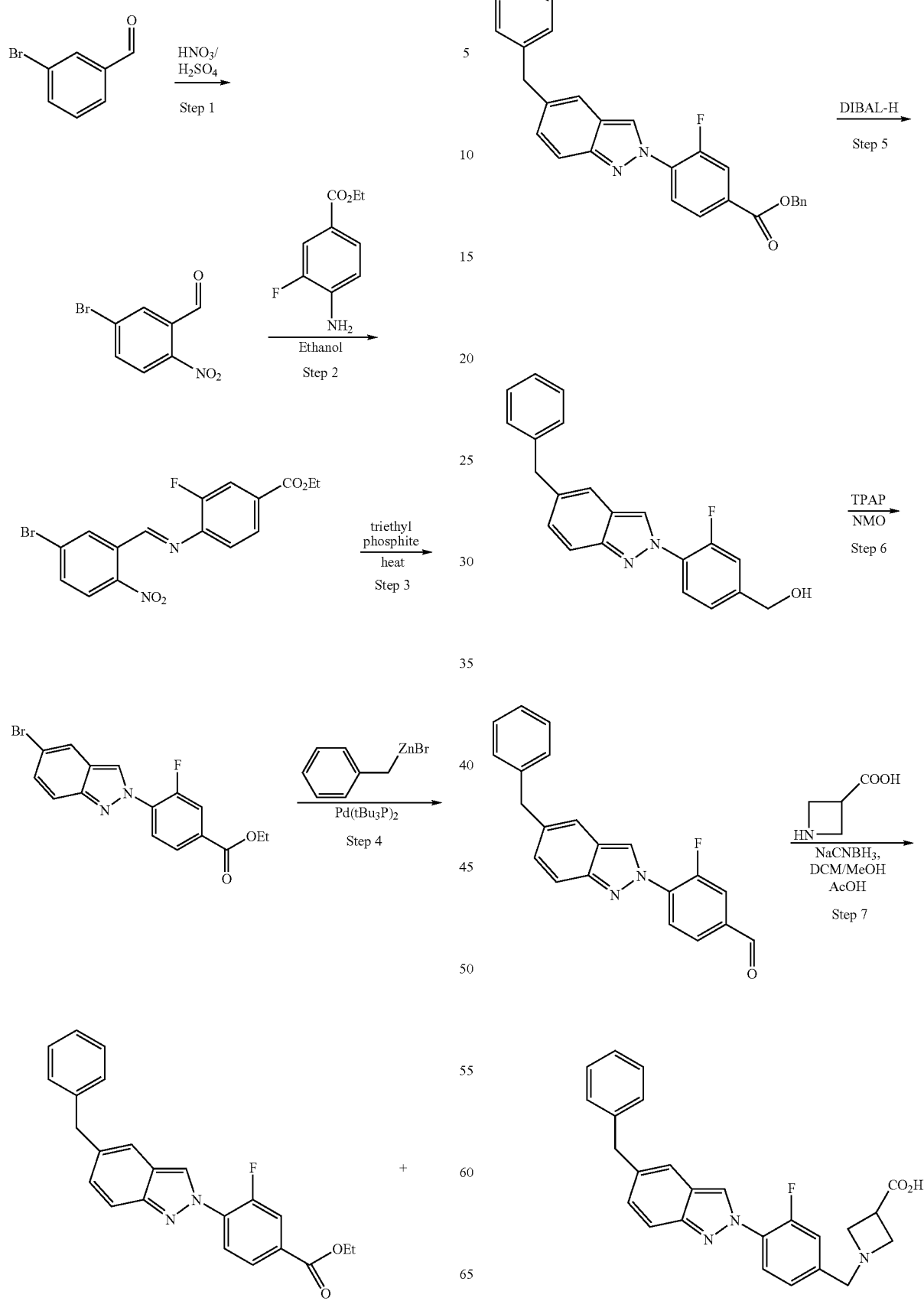

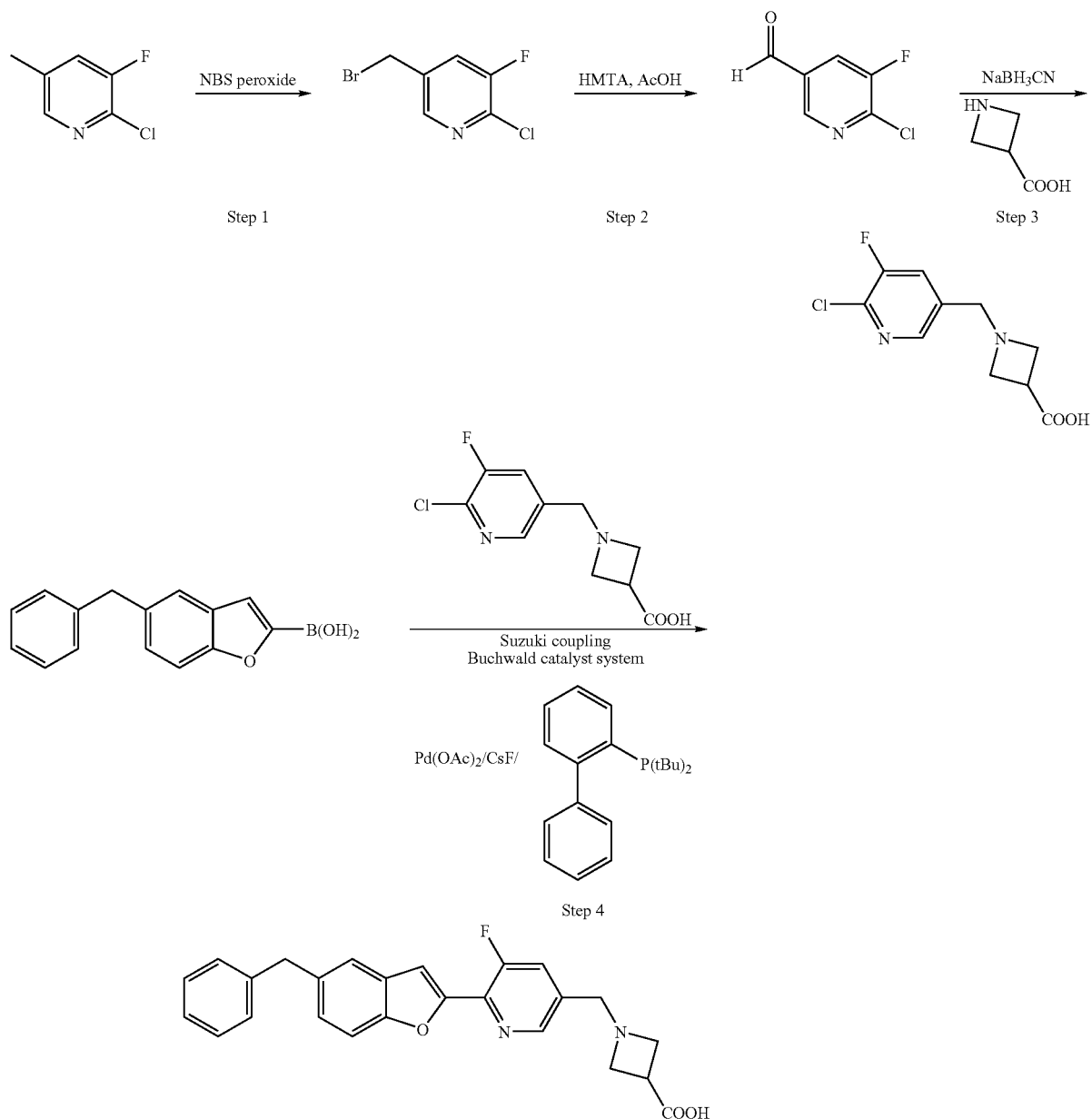
Scheme A-11
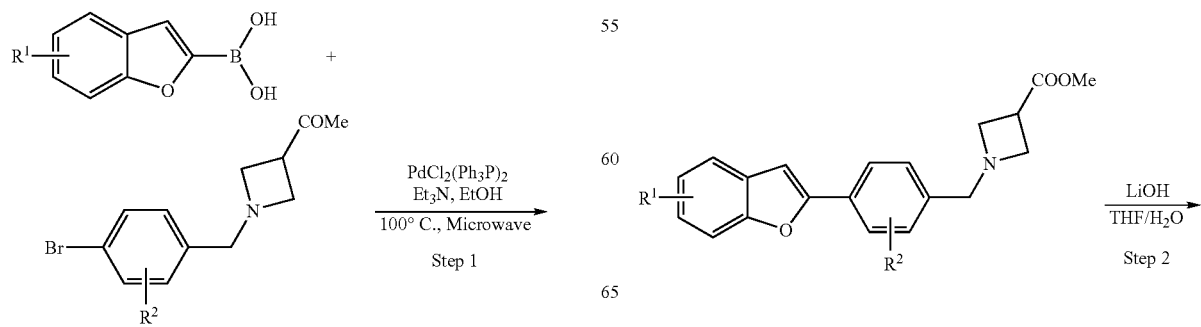
Scheme A-12

-continued

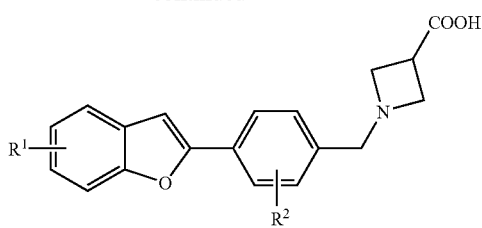

Scheme A-13

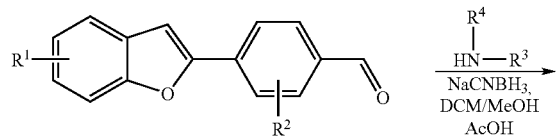

Step 1

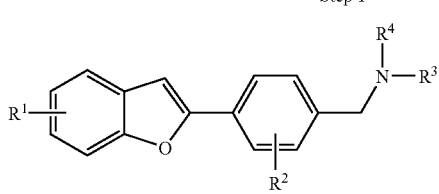

Compounds were prepared using the general procedures as described below:

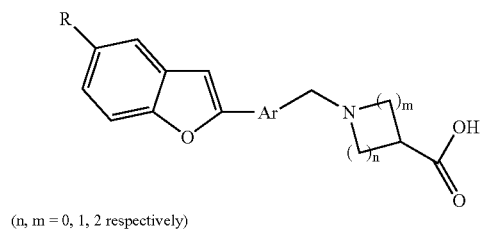

(n, m = 0, 1, 2 respectively)

Compound 62

(3R)-1-((4-(5-Benzylbenzofuran-2-yl)-3-fluorophenyl)methyl)piperidine-3-carboxylic acid

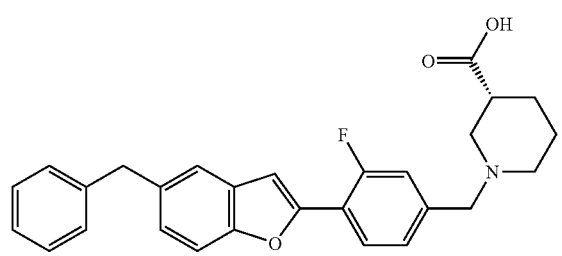

Synthesized according to Scheme 1 and general procedure E to give (3R)-1-((4-(5-benzylbenzofuran-2-yl)-3-fluorophenyl)methyl)piperidine-3-carboxylic acid [hS1P1 $EC_{50}$=5451 nM]. MS (ESI) m/z: Calculated: 443.2; Observed: 444.1 ($M^+$+1).

Compound 63

(3S)-1-((4-(5-Benzylbenzofuran-2-yl)-3-fluorophenyl)methyl)piperidine-3-carboxylic acid

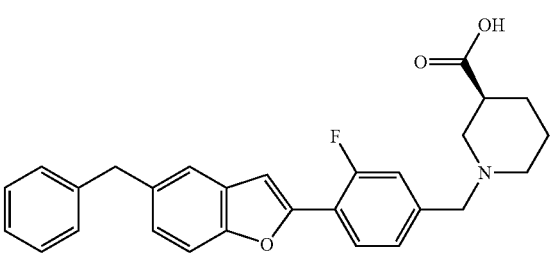

Synthesized according to Scheme 1 and general procedure E to give (3S)-1-((4-(5-benzylbenzofuran-2-yl)-3-fluorophenyl)methyl)piperidine-3-carboxylic acid [hS1P1 $EC_{50}$=3340 nM]. MS (ESI) m/z: Calculated: 443.2; Observed: 444.1 ($M^+$+1).

Compound 64

1-(3-Fluoro-4-(5-phenylthio)benzofuran-2-yl)benzyl)azetidine-3-carboxylic acid (4-(2,2-Diethoxyethoxy)phenyl)(phenyl)sulfane (step 2 in Scheme A-4)

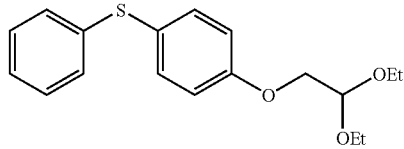

A mixture of 4-(phenylthio)phenol (4.7 g, 23 mmol), bromoacetaldehyde diethyl acetal (4.3 mL, 28 mmol) and $K_2CO_3$ (3.82 g, 28 mmol) in DMF (40 mL) was stirred at reflux for 6 h. The reaction mixture was allowed to cool down to room temperature and poured over ice and diluted to 100 mL with water. The solution was extracted with $Et_2O$ (20 mL×3); the combined extracts were washed with 1N NaOH solution, water and brine, dried, and concentrated under reduced pressure to yield a yellow oil that was used without further purification: $^1$H NMR (400 MHz, $CDCl_3$) δ 7.42 (d, 2H), 7.27-7.06 (m, 5H), 6.92 (d, 2H), 4.84 (t, 1H), 4.02 (d, 2H), 3.84-3.68 (m, 4H), 1.13 (m, 6H).

5-(Phenylthio)benzofuran (step 3 in Scheme A-4)

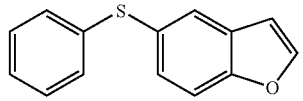

A mixture of (4-(2,2-Diethoxyethoxy)phenyl)(phenyl)sulfane (2.7 g, 8.5 mmol) and polyphosphoric acid (2.7 g, 27 mmol) in benzene (70 mL) was stirred at reflux for 2 h. The reaction mixture was cooled to room temperature, decanted from the PPA and filtered through a plug of silica gel, which was washed with hexanes. The filtrate and the wash were combined and concentrated under reduced pressure to yield 1.7 g (89%) of benzofuran: $^1$H NMR (400 MHz, CDCl$_3$) δ 7.74 (d, 1H), 7.64 (dd, 1H), 7.49-7.39 (m, 2H), 7.29-7.16 (m, 5H), 6.74 (dd, 1H).

5-(phenylthio)benzofuran-2-ylboronic acid (step 4 in Scheme A-4)

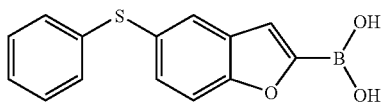

A solution of n-BuLi (1.5 mL, 2.5M solution in hexanes) was added dropwise to a solution of 5-(phenylthio)benzofuran (0.7 g, 3.1 mmol) in anhydrous THF (20 mL) at −78° C. The resulting mixture was stirred at −78° C. for 20 minute, and treated with B($^i$PrO)$_3$ (1.1 mL, 4.64 mmol). The reaction mixture was allowed to warm up slowly to room temperature and stirred for 1 hour. The reaction was quenched with 2N HCl and extracted with Et$_2$O. The combined extracts were washed with brine, dried and concentrated under reduced pressure to yield 0.81 g of crude boronic acid, that was used without further purification: $^1$H NMR (400 MHz, CDCl$_3$) δ 7.82 (dd, 1H), 7.58-7.42 (m, 2H), 7.38-7.17 (m, 6H).

3-Fluoro-4-(5-(phenylthio)benzofuran-2-yl)benzaldehyde (step 5 in Scheme A-4)

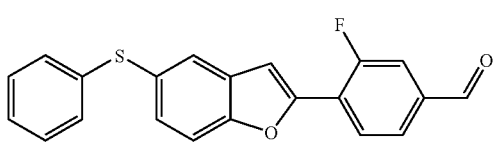

A solution of 5-(phenylthio)benzofuran-2-ylboronic acid (610 mg, 2.26 mmol), 4-bromobenzaldehyde (38 mg, 1.87 mmol), palladiumdichlorobis(triphenylphosphine) (66 mg, 0.094 mmol) and triethylamine (5 mL, 68 mmol) in EtOH (5 mL) was irradiated in the microwave at 110° C. for 1200 seconds. The crude reaction mixture was purified via chromatography (9/1 Hexane//Ethyl acetate) to yield the desired benzaldehyde. $^1$H NMR (400 MHz, CDCl$_3$) δ 10.05 (s, 1H), 8.21 (t, 1H), 7.75 (d, 1H), 7.72 (s, 1H), 7.68 (d, 1H), 7.52-7.16 (m, 8H). MS (ESI) m/z: Calculated: 348.06; Observed: 349.1 (M$^+$+1).

1-(3-Fluoro-4-(5-phenylthio)benzofuran-2-yl)benzyl)azetidine-3-carboxylic acid (step 6 in Scheme A-4)

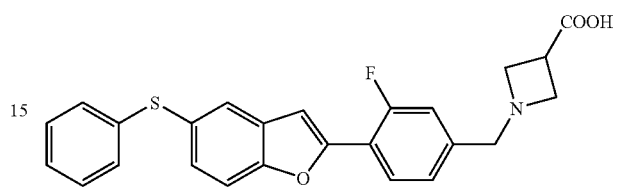

A mixture of 3-Fluoro-4-(5-(phenylthio)benzofuran-2-yl) benzaldehyde (350 mg, 1.04 mmol), azetidine-3-carboxylic acid (120 mg, 0.28 mmol) and acetic acid (0.12 mL, 2.0 mmol) in CH$_2$Cl$_2$ (10 mL) was stirred at room temperature for 1 hour. Sodium triacetoxyborohydride (340 mg, 1.6 mmol) was added in two portions and the reaction mixture was stirred for 16 h. Concentration of the solvent under reduced pressure yielded a yellow solid that was dissolved in DMSO (3 mL) and filtered to give a yellow solution that was purified by HPLC to yield the desired product [hS1P1 EC$_{50}$=142 nM]. $^1$H NMR (400 MHz, CD$_3$OD) δ 8.17 (t, 1H), 7.78 (s, 1H), 7.59 (d, 1H), 7.47-7.39 (m, 3H), 7.36-7.17 (m, 6H), 4.46 (s, 2H), 4.39 (m, 4H), 3.74 (m, 1H). MS (ESI) m/z: Calculated: 433.11; Observed: 433.9 (M$^+$+1).

Compound 65

1-(3-Fluoro-4-(5-phenylsulfinyl)benzofuran-2-yl) benzyl)azetidine-3-carboxylic acid (step 7 in Scheme A-4)

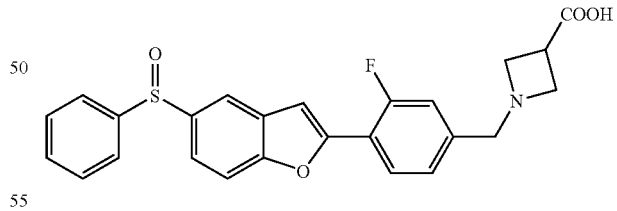

A mixture of 1-(3-Fluoro-4-(5-(phenylthio)benzofuran-2-yl)benzyl)azetidine-3-carboxylic acid (50 mg, 0.12 mmol) and m-chloroperbenzoic acid (35 mg, 0.12 mmol) in Chloroform (9 mL) and MeOH (1 mL) was stirred at −20° C. for 1 hour. Concentration of the solvent under reduced pressure yielded a white solid that was dissolved in DMSO (3 mL) and filtered to give a yellow solution that was purified by HPLC to yield the desired product [hS1P1 EC$_{50}$=67 nM]. $^1$H NMR (400 MHz, CD$_3$OD) δ 8.17 (t, 1H), 7.96 (s, 1H), 7.94 (d, 1H), 7.75-7.43 (m, 9H), 4.45 (s, 2H), 4.39 (m, 4H), 3.74 (m, 1H). MS (ESI) m/z: Calculated: 449.11; Observed: 449.9 (M++1).

Compound 66

1-(4-(5-(Cyclopropylmethoxymethyl)benzofuran-2-yl)-3-fluoro-benzyl)azetidine-3-carboxylic acid 5-((Cyclopropylmethoxy)methyl)benzofuran (step 1 in Scheme A-3-a)

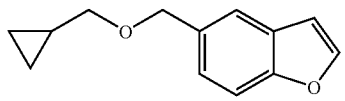

A mixture of benzofuran-5-ylmethanol (1.0 g, 6.8 mmol), and sodium hydride (0.25 g, 10.0 mmol) in DMF (20 mL) was stirred at 0° C. for 30 minutes. Cyclopropylmethyl bromide (0.97 g, 7.0 mmol) was the added and resultant reaction mixture was slowly warmed to room temperature and left stirring over night. Reaction mixture was diluted to 100 mL with water. The solution was extracted with Et$_2$O (20 mL×3); the combined extracts were washed with 1N NaOH solution, water and brine, dried, and concentrated under reduced pressure to yield the desired product after purification on silica (4/1 hexane/ethyl acetate). $^1$H NMR (400 MHz, CDCl$_3$) δ 7.61 (d, 2H), 7.44 (d, 1H), 7.27 (d, 1H), 6.76 (s, 1H), 4.62 (s, 2H) 3.37 (d, 2H), 1.41 (m, 1H), 0.58 (m, 2H), 0.21 (m, 2H).

5-((Cyclopropylmethoxy)methyl)benzofuran-2-ylboronic acid (step 2 in Scheme A-3-a)

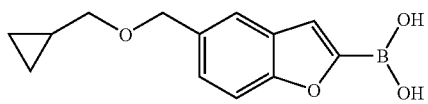

The title compound was prepared as Example Compound A (step 3) in the general method described above and used without further purification for the next step: $^1$H NMR (400 MHz, CDCl$_3$) δ 7.72 (m, 1H), 7.52 (m, 1H), 7.32 (m, 1H), 7.21 (m, 1H), 4.62 (s, 2H) 3.37 (d, 2H), 1.41 (m, 1H), 0.58 (m, 2H), 0.21 (m, 2H).

4-(5-(Cyclopropylmethoxy)methyl)benzofuran-2-yl)-3-fluorobenzaldehyde (step 3 in Scheme A-3-a)

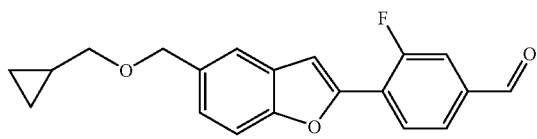

The title compound was prepared as Example Compound A (step 4) in the general method described above. $^1$H NMR (400 MHz, CDCl$_3$): δ 10.02 (s, 1H), 8.24 (t, 1H), 7.78 (d, 1H), 7.69 (d, 1H), 7.63 (s, 1H), 7.54 (d, 1H), 7.36 (m, 2H), 4.62 (s, 2H) 3.38 (d, 2H), 1.41 (m, 1H), 0.58 (m, 2H), 0.21 (m, 2H).

1-(4-(5-(Cyclopropylmethoxy)methyl)benzofuran-2-yl)-3-fluorobenzyl)azetidine-3-carboxylic acid (step 4 in Scheme A-3-a)

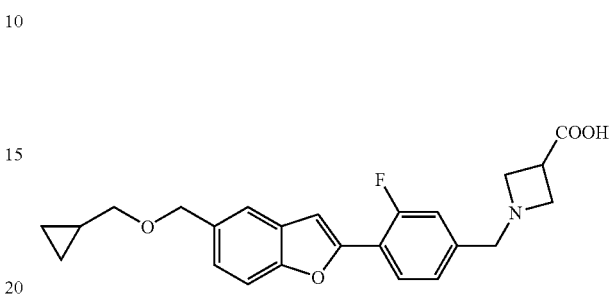

The title compound was prepared as Example Compound A (step 5) in the general method described above. Compound was isolated as free base via triturating [hS1P1 EC$_{50}$=75 nM]. $^1$H NMR (400 MHz, DMSO-d$_6$): 7.79 (t, 1H), 7.43 (m, 2H), 7.18 (m, 4H), 4.41 (s, 2H), 3.35 (m, 4H), 3.14 (d, 2H), 3.13 (m, 1H), 0.93 (m, 1H), 0.38 (m, 2H), 0.05 (m, 2H). MS (ESI) m/z: Calculated: 409.17; Observed: 409.9 (M++1).

Compound 67

1-(4-(5-(Cyclobutoxymethyl)benzofuran-2-yl)-3-fluoro-benzyl)azetidine-3-carboxylic acid 5-(Cyclobutoxymethyl)benzofuran (step 1 in Scheme A-3-b)

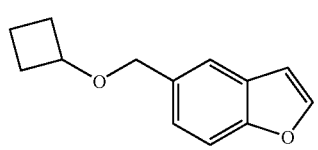

A mixture of cyclobutanol (1.0 mL, 14.0 mmol) and sodium hydride (0.5 g, 14.0 mmol) in DMF (20 mL) was stirred at 0° C. for 30 minutes. 5-(Bromomethyl)benzofuran (2.9 g, 14.0 mmol) was the added and resultant reaction mixture was slowly warmed to room temperature and left stirring over night. Reaction mixture was diluted to 100 mL with water. The solution was extracted with Et$_2$O (20 mL×3); the combined extracts were washed with 1N NaOH solution, water and brine, dried, and concentrated under reduced pressure to yield the desired product after purification on silica (4/1 hexane/ethyl acetate). $^1$H NMR (400 MHz, CDCl$_3$) δ

7.58 (d, 2H), 7.42 (d, 1H), 7.27 (d, 1H), 6.78 (s, 1H), 4.54 (s, 2H) 4.03 (m, 1H), 2.21 (m, 2H), 1.94 (m, 2H), 1.76 (m, 1H), 1.52 (m, 1H).

5-(Cyclobutoxymethyl)benzofuran-2-ylboronic acid (step 2 in Scheme A-3-b)

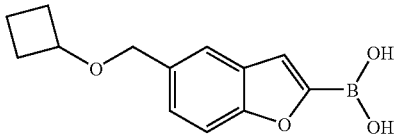

The title compound was prepared as Example Compound A (step 3) in the general method C described above and used without purification for the next step: $^1$H NMR (400 MHz, CDCl$_3$) δ 7.62 (m, 1H), 7.42 (m, 1H), 7.32 (m, 1H), 7.21 (m, 1H), 4.48 (s, 2H), 4.03 (m, 1H), 2.24 (m, 2H), 2.02 (m, 2H), 1.76 (m, 1H), 1.56 (m, 1H).

4-(5-(Cyclobutoxymethyl)benzofuran-2-yl)-3-fluorobenzaldehyde (step 3 in Scheme A-3-b)

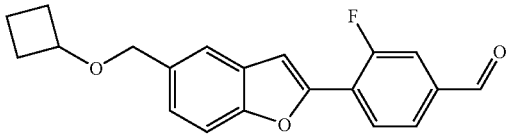

The title compound was prepared as Example Compound A (step 4) in the general method D described above (67% yield in two steps): $^1$H NMR (400 MHz, CDCl$_3$): δ 10.01 (s, 1H), 8.21 (t, 1H), 7.76 (d, 1H), 7.63 (d, 1H), 7.61 (s, 1H), 7.46 (d, 1H), 7.39 (m, 2H), 4.51 (s, 2H) 4.04 (m, 1H), 2.22 (m, 2H), 2.01 (m, 2H), 1.74 (m, 1H), 1.53 (m, 1H).

1-(4-(5-(Cyclobutoxymethyl)benzofuran-2-yl)-3-fluoro-benzyl)azetidine-3-carboxylic acid (step 4 in Scheme A-3-b)

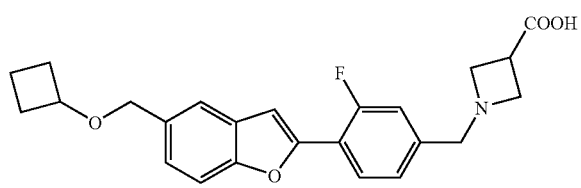

The title compound was prepared as Example Compound A (step 5) in the general method E described above [hS1P1 EC$_{50}$=25 nM]. The product was isolated as free base via triturating: $^1$H NMR (400 MHz, DMSO-d$_6$): 7.91 (t, 1H), 7.61 (m, 2H), 7.23 (m, 4H), 4.42 (s, 2H), 3.94 (m, 1H), 3.61 (s, 2H), 3.37 (m, 1H), 3.35 (m, 4H), 2.18 (m, 2H), 1.82 (m, 2H), 1.61 (m, 1H), 1.45 (m, 1H). MS (ESI) m/z: Calculated: 409.17; Observed: 410.0 (M$^+$+1).

Compound 68

1-(4-(benzofuran-2-yl)-3-fluoro-benzyl)azetidine-3-carboxylic acid 4-(benzofuran-2-yl)-3-fluorobenzaldehyde (step 4 in Scheme A-1)

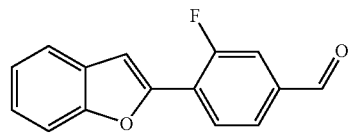

The title compound was prepared as Example Compound A (step 4) in the general method D described above (42% yield): $^1$H NMR (400 MHz, CDCl$_3$): δ 10.01 (s, 1H), 8.22 (t, 1H), 7.79-7.17 (m, 7H).

1-(4-(benzofuran-2-yl)-3-fluoro-benzyl)azetidine-3-carboxylic acid (step 5 in Scheme A-1)

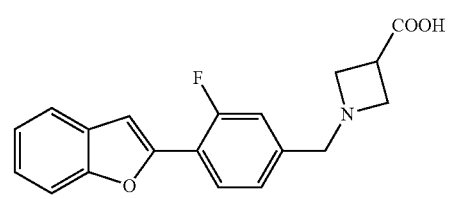

The title compound was prepared as Example Compound A (step 5) in the general method E described above. The product [hS1P1 EC$_{50}$=706 nM] was isolated as free base via triturating: $^1$H NMR (400 MHz, DMSO-d$_6$): δ 7.96 (t, 1H), 7.74 (d, 1H), 7.62 (d, 1H), 7.39-7.28 (m, 5H), 4.34 (s, 2H), 4.16 (m, 4H), 3.49 (m, 1H). MS (ESI) m/z: Calculated: 325.11; Observed: 326.0 (M$^+$+1).

Compound 69

1-(3-Fluoro-4-(5-(phenoxymethyl)benzofuran-2-yl)benzyl)azetidine-3-carboxylic acid 5-(Phenoxymethyl)benzofuran (step 1 in Scheme A-3-b)

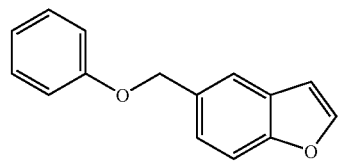

The title compound was prepared as Example Compound 5 (step 1): ¹H NMR (400 MHz, CDCl₃) δ 7.63 (d, 2H), 7.47 (d, 1H), 7.29 (d, 1H), 7.27 (m, 2H), 6.99 (m, 3H), 6.79 (s, 1H), 5.18 (s, 2H).

5-(Phenoxymethyl)benzofuran-2-ylboronic acid (step 2 in Scheme A-3-b)

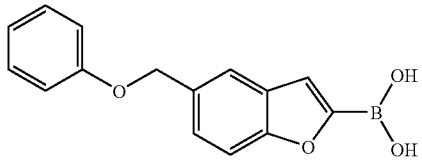

The title compound was prepared as Example Compound A (step 3) in the general method C described above and used without further purification for the next step: ¹H NMR (400 MHz, CDCl₃) δ 7.73 (m, 2H), 7.64 (m, 1H), 7.49 (m, 3H), 6.99 (m, 3H), 5.16 (s, 2H).

3-Fluoro-4-(5-(phenoxymethyl)benzofuran-2-yl)benzaldehyde (step 3 in Scheme A-3-b)

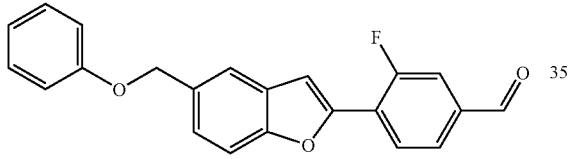

The title compound was prepared as Example Compound A (step 4) in the general method D described above. ¹H NMR (400 MHz, CDCl₃) δ 10.01 (s, 1H), 8.22 (t, 1H), 7.78 (d, 1H), 7.75 (s, 1H), 7.69 (d, 1H), 7.58 (d, 1H), 7.42-7.27 (m, 2H), 7.02 (m, 5H), 5.18 (s, 2H).

1-(3-Fluoro-4-(5-(phenoxymethyl)benzofuran-2-yl)benzyl)azetidine-3-carboxylic acid (step 4 in Scheme A-3-b)

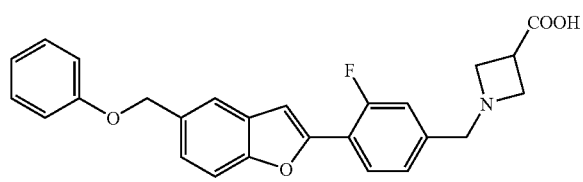

The title compound was prepared as Example Compound A (step 5) in the general method described above. Compound [hS1P1 EC₅₀=87 nM] was isolated as free base via triturating: ¹H NMR (400 MHz, DMSO-d₆) δ 7.87 (t, 1H), 7.78 (s, 1H), 7.63 (d, 1H), 7.43 (d, 1H), 7.39-7.26 (m, 5H), 7.06 (m, 2H), 6.97 (t, 1H), 5.18 (s, 2H), 4.46 (s, 2H), 4.39 (m, 4H), 3.74 (m, 1H). MS (ESI) m/z: Calculated: 431.15; Observed: 431.9 (M⁺+1).

Compound 70

1-(4-(5-(Cyclohexyloxymethyl)benzofuran-2-yl)-3-fluoro-benzyl)azetidine-3-carboxylic acid 5-(Cyclohexyloxymethyl)benzofuran (step 1 in Scheme A-3-b)

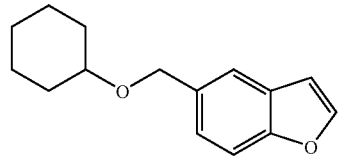

The title compound was prepared as Example Compound 5 (step 1): ¹H NMR (400 MHz, CDCl₃) δ 7.61 (d, 2H), 7.48 (d, 1H), 7.35 (d, 1H), 6.78 (s, 1H), 4.62 (s, 2H) 3.41 (m, 1H), 1.99 (m, 2H), 1.78 (m, 2H), 1.58 (m, 1H), 1.41 (m, 2H), 1.23 (m, 3H).

5-(Cyclohexyloxymethyl)benzofuran-2-ylboronic acid (step 2 in Scheme A-3-b)

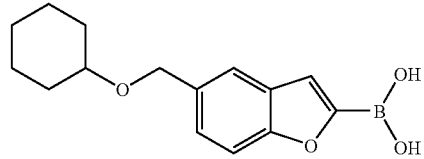

The title compound was prepared as Example Compound A (step 3) in the general method C described above and used as crude for the next step: ¹H NMR (400 MHz, CDCl₃) δ 7.71 (m, 2H), 7.58 (m, 1H), 7.47 (m, 1H), 4.63 (s, 2H) 3.42 (m, 1H), 1.99 (m, 2H), 1.78 (m, 2H), 1.58 (m, 1H), 1.41 (m, 3H), 0.95 (m, 3H).

4-(5-(Cyclohexyloxymethyl)benzofuran-2-yl)-3-fluorobenzaldehyde (step 3 in Scheme A-3-b)

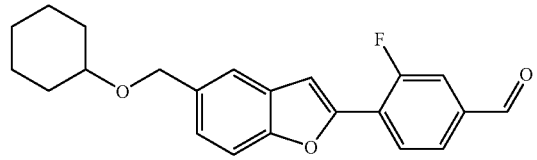

The title compound was prepared as Example Compound A (step 4) in the general method D described above. ¹H NMR (400 MHz, CDCl₃): δ 10.01 (s, 1H), 8.21 (t, 1H), 7.78 (d, 1H), 7.64 (d, 1H), 7.61 (s, 1H), 7.54 (d, 1H), 7.39 (m, 2H), 4.63 (s, 2H) 3.39 (m, 1H), 1.98 (m, 2H), 1.78 (m, 2H), 1.34 (m, 2H), 1.21 (m, 4H).

1-(4-(5-(Cyclohexyloxymethyl)benzofuran-2-yl)-3-fluoro-benzyl)azetidine-3-carboxylic acid (step 4 in Scheme A-3-b)

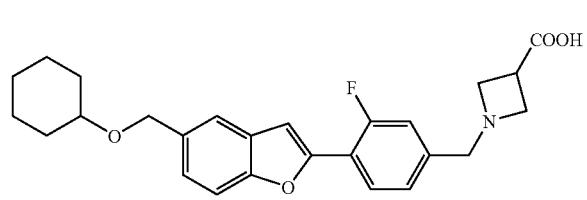

The title compound was prepared as Example Compound A (step 5) in the general method E described above. The product [hS1P1 EC$_{50}$=91 nM] was isolated as free base via triturating: $^1$H NMR (400 MHz, DMSO-d$_6$): 7.84 (t, 1H), 7.62 (s, 1H), 7.58 (d, 1H), 7.24 (m, 4H), 4.58 (s, 2H), 3.63 (m, 1H), 3.61 (s, 2H), 3.37 (m, 1H), 3.35 (m, 4H), 1.78 (m, 2H), 1.61 (m, 2H) 1.41 (m, 1H), 1.18 (m, 5H). MS (ESI) m/z: Calculated: 437.20; Observed: 437.9 (M$^+$+1).

Compound 71

1-(4-(5-(Cylopentyloxymethyl)benzofuran-2-yl)-3-fluoro-benzyl)azetidine-3-carboxylic acid 5-(Cyclopentyloxymethyl)benzofuran (step 1 in Scheme A-3-b)

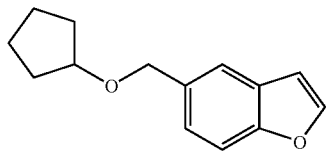

The title compound was prepared as Example Compound 5 (step 1). $^1$H NMR (400 MHz, CDCl$_3$) δ 7.57 (d, 2H), 7.45 (d, 1H), 7.27 (d, 1H), 6.77 (s, 1H), 4.53 (s, 2H), 4.01 (m, 1H), 1.76 (m, 4H), 1.57 (m, 2H), 1.24 (m, 1H), 0.94 (m, 1H).

5-(Cyclopentyloxymethyl)benzofuran-2-ylboronic acid (step 2 in Scheme B-3-b)

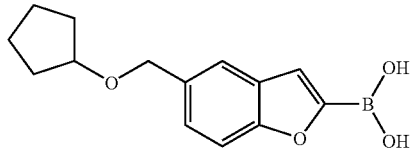

The title compound was prepared as Example Compound A (step 3) in the general method C described above and used without further purification for the next step: $^1$H NMR (400 MHz, CDCl$_3$) δ 7.72 (m, 1H), 7.48 (m, 1H), 7.38 (m, 1H), 7.21 (m, 1H), 4.58 (s, 2H), 4.03 (m, 1H), 1.78 (m, 4H), 1.56 (m, 2H), 1.24 (m, 1H), 0.96 (m, 1H).

4-(5-(Cyclopentyloxymethyl)benzofuran-2-yl)-3-fluorobenzaldehyde (step 3 in Scheme A-3-b)

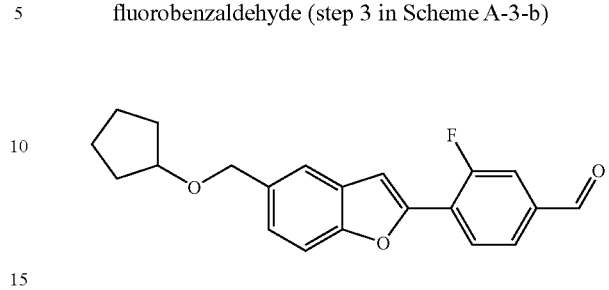

The title compound was prepared as Example Compound A (step 4) in the general method D described above. $^1$H NMR (400 MHz, CDCl$_3$): δ 10.01 (s, 1H), 8.23 (t, 1H), 7.86 (d, 1H), 7.66 (d, 1H), 7.61 (s, 1H), 7.52 (d, 1H), 7.39 (m, 2H), 4.73 (s, 2H) 4.03 (m, 1H), 1.78 (m, 4H), 1.61 (m, 2H), 1.21 (m, 1H), 0.95 (m, 1H).

1-(4-(5-(Cyclopentyloxymethyl)benzofuran-2-yl)-3-fluoro-benzyl)azetidine-3-carboxylic acid (step 4 in Scheme A-3)

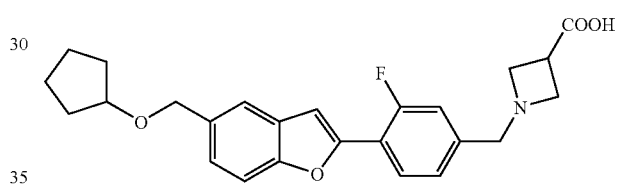

The title compound was prepared as Example Compound A (step 5) in the general method E described above. $^1$H NMR (400 MHz, CD$_3$OD): 8.14 (t, 1H), 7.48 (s, 1H), 7.52 (d, 1H), 7.41 (d, 2H), 7.37 (m, 2H), 4.58 (s, 2H), 4.43 (s, 2H), 4.39 (m, 4H), 4.04 (m, 1H), 3.63 (m, 1H), 1.78 (m, 4H), 1.58 (m, 2H) 1.21 (m, 2H). MS (ESI) m/z: Calculated: 423.18; Observed: 424.0 (M$^+$+1).

Compound 72

1-(3-Fluoro-4-(5-phenylsulfonyl)benzofuran-2-yl) benzyl)azetidine-3-carboxylic acid (3-Fluoro-4-(5-phenylsulfonyl)benzofuran-2-yl)phenyl)methanol (step 1 in Scheme A-5)

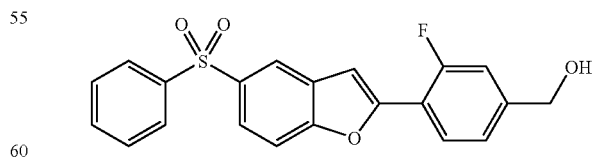

A mixture of 1-(3-Fluoro-4-(5-phenylthio)benzofuran-2-yl)benzyl)azetidine-3-carboxylic acid (50 mg, 0.12 mmol) and m-chloroperbenzoic acid (100 mg, 0.36 mmol) in chloroform (10 mL) and MeOH (1 mL) was stirred at −20° C. for 1 h and slowly warmed to room temperature overnight. Concentration of the solvent under reduced pressure yielded a white solid that was purified by chromatography (1/9 ethyl acetate/hexanes) to yield the desired product: $^1$H NMR (400 MHz, CDCl$_3$) δ 8.22 (s, 1H), 8.03 (dd, 2H), 7.71 (d, 1H), 7.61 (d, 1H), 7.58-7.43 (m, 3H), 7.22 (m, 4H), 4.77 (s, 2H). MS (ESI) m/z: Calculated: 382.07; Observed: 383.0 (M$^+$+1).

3-Fluoro-4-(5-phenylsulfonyl)benzofuran-2-yl)benzaldehyde (step 2 in Scheme A-5)

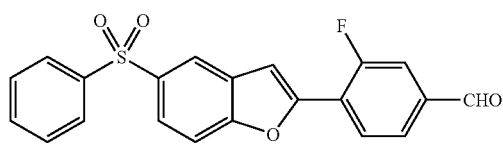

A suspension of (3-Fluoro-4-(5-phenylsulfonyl)benzofuran-2-yl)phenyl)methanol (46 mg, 0.12 mmol), Molecular sieves 4A (0.25 g), TPAP (0.0021 mg, 0.06 mmol) and N-morpholino oxide (0.029 g, 0.24 mmol) in acetonitrile was stirred for 1 hour and then filtered through celite to yield the title compound: $^1$H NMR (400 MHz, CDCl$_3$) δ 10.02 (s, 1H), 8.36 (s, 1H), 8.20 (t, 1H), 8.01 (dd, 2H), 7.79 (d, 1H), 7.71 (d, 1H), 7.62 (d, 1H), 7.56 (m, 5H), 4.77 (s, 2H).

1-(3-Fluoro-4-(5-phenylsulfonyl)benzofuran-2-yl)benzyl)azetidine-3-carboxylic acid (step 3 in Scheme A-5)

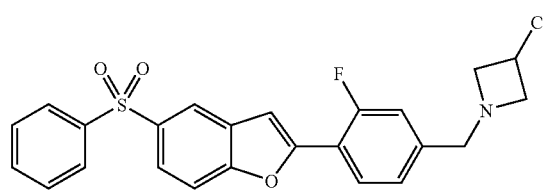

A mixture of 3-Fluoro-4-(5-(phenylthio)benzofuran-2-yl)benzaldehyde (49 mg, 0.14 mmol) and azetidine-3-carboxylic acid (30 mg, 0.28 mmol) in MeOH (1 mL) was stirred at room temperature for 1 hour. Sodium cyanoborohydride (60 mg, 0.28 mmol) was added in two portions and the reaction mixture was stirred for 16 h. Concentration of the solvent under reduced pressure yielded a yellow solid that was dissolved in DMSO (3 mL) and filtered to give a yellow solution that was purified by HPLC to yield 11.5 mg (22%) of the desired product: $^1$H NMR (400 MHz, CD$_3$OD) δ 8.39 (s, 1H), 8.16 (t, 1H), 8.01 (d, 2H), 7.96 (d, 1H), 7.76 (d, 1H), 7.62-7.41 (m, 6H), 4.46 (s, 2H), 4.38 (m, 4H), 3.64 (m, 1H). MS (ESI) m/z: Calculated: 465.10; Observed: 465.9 (M$^+$+1).

Compound 73

1-(3-fluoro-4-(5-(4-fluorobenzyl)benzofuran-2-yl)benzyl)azetidine-3-carboxylic acid 5-(4-fluorobenzyl)benzofuran

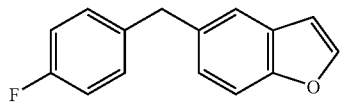

The title compound was prepared as Compound B (step 1 in Scheme A-2) in the general method A described above (85% yield): $^1$H NMR (400 MHz, CDCl$_3$) δ 7.59 (d, J=2.3, 1H), 7.42 (d, J=8.5, 1H), 7.37 (br s, 1H), 7.17-7.05 (m, 3H), 7.00-6.93 (m, 2H), 6.70 (dd, J=2.2, 0.7, 1H), 4.04 (s, 2H).

5-(4-fluorobenzyl)benzofuran-2-ylboronic acid

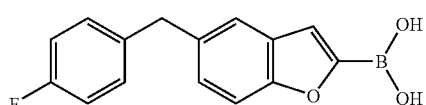

The title compound was prepared as Compound B (step 2 in Scheme A-2) in the general method C described above (64% yield): $^1$H NMR (400 MHz, CDCl$_3$) δ 7.43-7.41 (m, 2H), 7.30 (br s, 1H), 7.18-7.13 (m, 3H), 6.99-6.95 (m, 2H), 4.04 (s, 2H).

3-fluoro-4-(5-(4-fluorobenzyl)benzofuran-2-yl)benzaldehyde

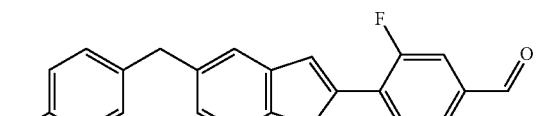

The title compound was prepared as Compound B (step 3 in Scheme A-2) in the general method D described above. $^1$H NMR (400 MHz, CDCl$_3$) δ 10.00 (d, J=1.8, 1H), 8.20 (t, J=7.7, 1H), 7.77 (dd, J=8.0, 1.5, 1H), 7.67 (dd, J=11.4, 1.5, 1H), 7.48-7.43 (m, 2H), 7.36 (dd, J=3.6, 0.8, 1H), 7.19-7.15 (m, 3H), 7.00-6.96 (m, 2H), 4.06 (s, 2H).

1-(4-(5-Benzylbenzofuran-2-yl)-3-chlorobenzyl) azetidine-3-carboxylic acid

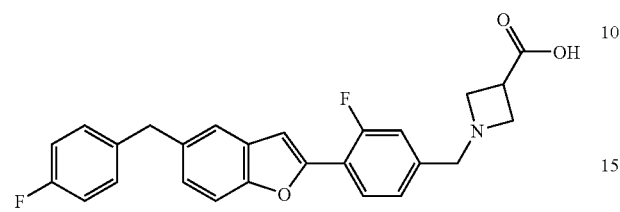

The title compound was prepared as Compound B (step 4 in Scheme A-2) in the general method E described above [hS1P1 EC$_{50}$=53 nM]. $^1$H NMR (400 MHz, DMSO-d$_6$) δ 8.12 (d, J=8.0, 1H), 7.49-7.40 (m, 4H), 7.29-7.20 (m, 4H), 7.02-6.97 (m, 2H), 4.47 (br s, 2H), 4.41-4.33 (m, 4H), 4.06 (s, 2H), 3.75-3.66 (m, 1H). MS (ESI) m/z: Calculated: 433.15; Observed: 434.0 (M$^+$+1).

Compound 74

1-(4-(5-(Cyclohexylmethyl)benzofuran-2-yl)-3-fluorobenzyl)azetidine-3-carboxylic acid 5-(Cyclohexylmethyl)benzofuran

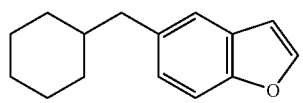

The title compound was prepared as Compound B (step 1 in Scheme A-2) in the general method A described above. $^1$H NMR (400 MHz, CDCl$_3$) δ 7.58 (d, J=2.2, 1H), 7.39 (d, J=8.4, 1H), 7.34 (br s, 1H), 7.07 (dd, J=8.2, 1.5, 1H), 6.70 (dd, J=2.2, 0.8, 1H), 2.57 (d, J=7.3, 2H), 1.70-1.60 (m, 5H), 1.58-1.48 (m, 1H), 1.22-1.15 (m, 3H), 1.00-0.94 (m, 2H).

5-(4-Fluorobenzyl)benzofuran-2-ylboronic acid

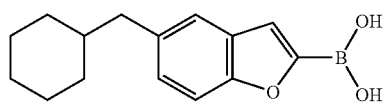

The title compound was prepared as Compound B (step 2 in Scheme A-2) in the general method C described above. $^1$H NMR (400 MHz, CDCl$_3$) δ 7.41-7.39 (m, 2H), 7.31 (s, 1H), 7.14 (dd, J=8.1, 1.5, 1H), 2.57 (d, J=7.9, 2H), 1.70-1.52 (m, 6H), 1.25-0.94 (m, 5H)

3-Fluoro-4-(5-(4-fluorobenzyl)benzofuran-2-yl)benzaldehyde

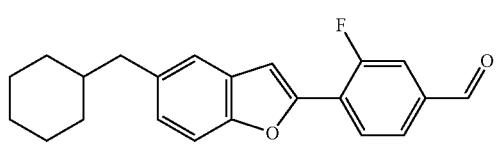

The title compound was prepared as Compound B (step 3 in Scheme A-2) in the general method D described above. $^1$H NMR (400 MHz, CDCl$_3$) δ 10.00 (d, J=1.8, 1H), 8.20 (t, J=7.3, 1H), 7.77 (dd, J=8.0, 1.4, 1H), 7.67 (dd, J=11.2, 1.6, 1H), 7.45-7.37 (m, 3H), 7.15 (dd, J=8.4, 1.5, 1H), 2.58 (d, J=6.9, 2H), 1.71-1.50 (m, 6H), 1.26-0.94 (m, 5H).

1-(4-(5-Benzylbenzofuran-2-yl)-3-chlorobenzyl) azetidine-3-carboxylic acid

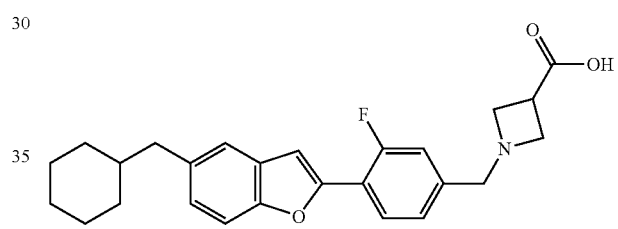

The title compound was prepared as Compound B (step 4 in Scheme A-2) in the general method E described above [hS1P1 EC$_{50}$=400 nM]. $^1$H NMR (400 MHz, DMSO-d$_6$) δ 8.12 (d, J=8.0, 1H), 7.46-7.40 (m, 4H), 7.27 (d, J=3.5, 1H), 7.16 (br d, J=10.2, 1H), 4.46 (br s, 2H), 4.36-4.34 (m, 4H), 3.71-3.63 (m, 1H), 2.58 (d, J=7.1, 2H), 1.76-1.55 (m, 6), 1.30-1.06 (m, 5H). MS (ESI) m/z: Calculated: 421.21; Observed: 422.0 (M$^+$+1).

Compound 75

1-(3-Fluoro-4-(5-(2-fluorobenzyl)benzofuran-2-yl) benzyl)azetidine-3-carboxylic acid 5-(2-Fluorobenzyl)benzofuran

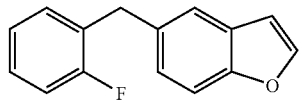

The title compound was prepared as Example Compound B (step 1 in Scheme A-2) in the general method A described above. $^1$H NMR (400 MHz, CD$_3$OD) δ 7.68 (s, 1H), 7.40 (d, J=10.4 Hz, 1H), 7.38 (d, J=8.0 Hz, 1H), 6.97-7.22 (m, 5H), 6.74 (S, 1H), 4.06 (s, 2H).

5-(2-Fluorobenzyl)benzofuran-2-ylboronic acid

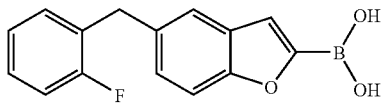

The title compound was prepared as Example Compound B (step 2 in Scheme A-2) in the general method C described above. The compound was used for the next step without further purification.

3-Fluoro-4-(5-(2-fluorobenzyl)benzofuran-2-yl)benzaldehyde

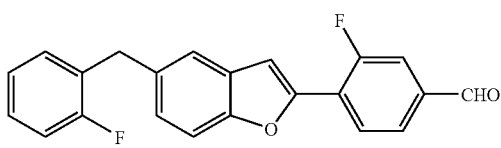

The title compound was prepared as Example Compound B (step 3 in Scheme A-2) in the general method D described above. $^1$H NMR (400 MHz, CDCl$_3$) δ 9.99 (s, 1H), 8.19 (t, J=7.2 Hz, 1H), 7.76 (d, J=8.0 Hz, 1H), 7.67 (d, J=11.2 Hz, 1H), 7.47 (d, J=9.2 Hz, 2H), 7.35 (d, J=3.6 Hz, 1H), 7.25 (m, 3H), 7.26 (m, 2H), 4.10 (s, 2H).

1-(3-Fluoro-4-(5-(2-fluorobenzyl)benzofuran-2-yl)benzyl)azetidine-3-carboxylic acid

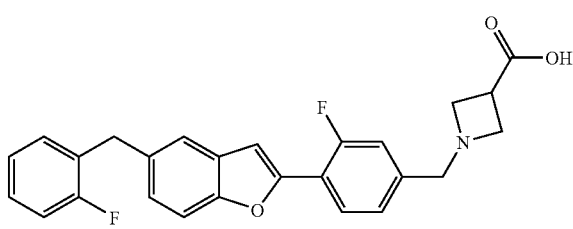

The title compound was prepared as Example Compound B (step 4 in Scheme A-2) in the general method E described above [hS1P1 EC$_{50}$=129 nM]. $^1$H NMR (400 MHz, CD$_3$OD) δ 8.12 (dd, J=7.6, 8.4 Hz, 1H), 7.49 (m, 2H), 7.43 (m, 2H), 7.24 (m, 4H), 7.07 (m, 2H), 4.47 (s, 2H), 4.37 (m, 4H), 4.10 (s, 2H), 3.71 (m, 1H). $^{19}$F NMR (376 MHz, CD$_3$OD) 6-77.6 (TFA), −113.1, −120.6. MS (ESI) m/z: Calculated: 433.15; Observed: 433.9 (M$^+$+1).

Compound 76

1-(3-Fluoro-4-(5-(3-fluorobenzyl)benzofuran-2-yl)benzyl)azetidine-3-carboxylic acid 5-(3-Fluorobenzyl)benzofuran

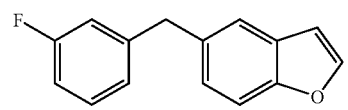

The title compound was prepared as Example Compound B (step 1 in Scheme A-2) in the general method A described above. $^1$H NMR (400 MHz, CD$_3$OD) δ 7.68 (s, 1H), 7.41 (d, J=6.8 Hz, 1H), 7.40 (d, J=8.4 Hz, 1H), 7.26 (m, 1H), 7.13 (d, J=8.0 Hz, 1H), 7.02 (d, J=8.0 Hz, 1H), 6.89 (m, 2H), 6.76 (m, 1H), 4.04 (s, 2H).

5-(3-Fluorobenzyl)benzofuran-2-ylboronic acid

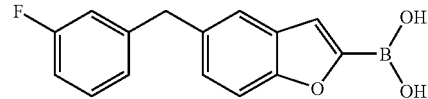

The title compound was prepared as Example Compound B (step 2 in Scheme A-2) in the general method C described above. $^1$H NMR (400 MHz, DMSO-d$_6$) δ 7.53 (s, 1H), 7.48 (d, J=8.4 Hz, 1H), 7.38 (s, 1H), 7.31 (m, 1H), 7.21 (d, J=5.2 Hz, 1H), 7.20 (m, 2H), 6.98 (m, 1H), 4.04 (s, 2H).

3-Fluoro-4-(5-(3-fluorobenzyl)benzofuran-2-yl)benzaldehyde

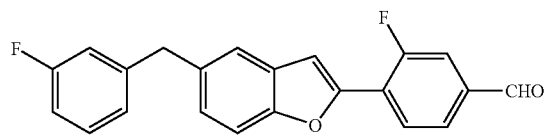

The title compound was prepared as Example Compound B (step 3 in Scheme A-2) in the general method D described above. $^1$H NMR (400 MHz, CDCl$_3$) δ 10.03 (s, 1H), 8.20 (t, J=7.6 Hz, 1H), 7.79 (dd, J=8.4, 1.2 Hz, 1H), 7.69 (dd, J=11.6, 1.2 Hz, 1H), 7.49 (d, J=8.4 Hz, 1H), 7.47 (d, J=6.0 Hz, 1H), 7.37 (d, J=3.6 Hz, 1H), 7.26 (m, 1H), 7.21 (dd, J=8.8, 1.2 Hz, 1H), 7.01 (d, J=8.4 Hz, 1H), 6.92 (m, 2H), 4.08 (s, 2H).

1-(3-Fluoro-4-(5-(3-fluorobenzyl)benzofuran-2-yl) benzyl)azetidine-3-carboxylic acid

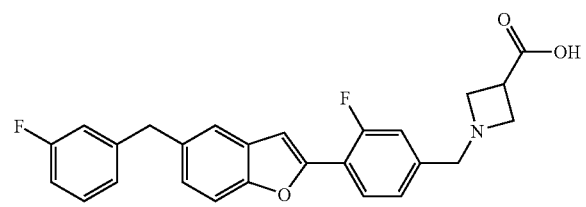

The title compound was prepared as Example Compound B (step 4 in Scheme A-2) in the general method E described above [hS1P1 EC$_{50}$=169 nM]. $^1$H NMR (400 MHz, CD$_3$OD) δ 8.10 (t, J=8.0 Hz, 1H), 7.49 (dd, J=9.6, 9.6 Hz, 2H), 7.43 (dd, J=8.0, 11.2 Hz, 1H), 7.40 (dd, J=3.2, 10.8 Hz, 1H), 7.28 (m, 3H), 7.06 (d, J=7.6 Hz, 1H), 6.92 (m, 2H), 4.45 (s, 2H), 4.34 (m, 4H), 4.08 (s, 2H), 3.68 (m, 1H). $^{19}$F NMR (376 MHz, CD$_3$OD) δ −77.4 (TFA), −113.1, −116.2. MS (ESI) m/z: Calculated: 433.15; Observed: 433.9 (M$^+$+1).

Compound 77

1-(3-Fluoro-4-(5-phenoxybenzofuran-2-yl)benzyl) azetidine-3-carboxylic acid methyl 1-(3-fluoro-4-(5-phenoxybenzofuran-2-yl)benzyl)azetidine-3-carboxylate

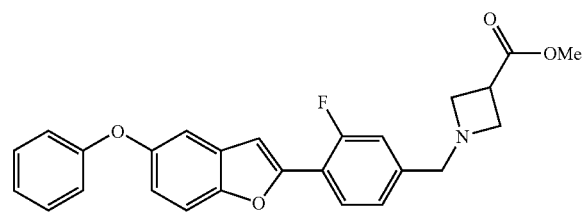

The title compound was prepared as Example Compound A (step 5 in Scheme A-1) in the general method D described above except using methyl 1-(4-bromo-3-fluorobenzyl)azetidine-3-carboxylate (54% yield). The product was isolated as a free base via triturating: MS (ESI) m/z: Calculated: 431.15; Observed: 432.00 (M$^+$+1).

1-(3-Fluoro-4-(5-phenoxybenzofuran-2-yl)benzyl) azetidine-3-carboxylic acid

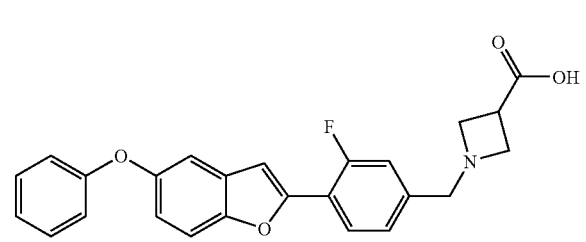

To a solution of ester (110 mg, 0.25 mmol) in 2 mL THF was added lithium hydroxide hydrate (30 mg, 1.25 mmol) in 1 mL water. The mixture was stirred until completion. The solvents were removed, and the solid was suspended in 2 mL water. 3 equivalents 2N HCl was then added to neutralize the base, and the mixture was sonicated. 4 mL 1 M pH 6 phosphate buffer was added and the reaction was sonicated. The slurry was filtered and the solid rinsed with water and EtOH and dried in vacuo to give the desired product as the white solid [hS1P1 EC$_{50}$=13 nM] $^1$H NMR (400 MHz, DMSO-d$_6$) δ 7.89 (s, 1H), 7.65 (s, 1H), 7.30 (m, 6H), 6.97 (m, 4H), 3.58 (m, 3H), 3.40 (m, 4H). $^{19}$F NMR (376 MHz, DMSO-d$_6$) δ −113.7. MS (ESI) m/z: Calculated: 417.14; Observed: 417.90 (M$^+$+1).

Compound 78

5-(1-(4-(5-Benzylbenzofuran-2-yl)-3-fluorobenzyl) azetidin-3-yl)-2H-tetrazole 5-(1-Benzhydrylazetidin-3-yl)-2H-tetrazole (step 1 in Scheme A-8)

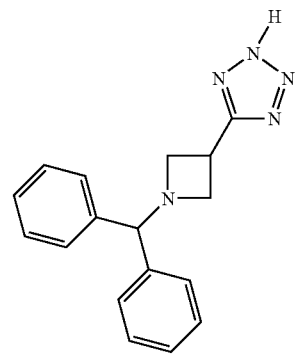

1-Benzhydrylazetidine-3-carbonitrile (2.48 g, 10 mmol), trimethylsilyl azide (2.30 g, 20 mmol) and dibutyltin oxide (498 mg, 2.0 mmol) were dissolved in toluene (20 mL) and heated to reflux for 32 h. The reaction mixture was then cooled to room temperature and applied directly to ISCO system with 10% methanol in dichloromethane to give the product. $^1$H NMR (400 MHz, CDCl$_3$) δ 7.54 (m, 4H), 7.31 (m, 6H), 5.11 (s, 1H), 4.47 (m, 1H), 4.05 (t, J=7.2 Hz, 2H), 3.91 (t, J=7.2 Hz, 2H). MS (ESI) m/z: Calculated: 291.15; Observed: 291.90 (M$^+$+1).

5-(Azetidin-3-yl)-2H-tetrazole hydrochloride (step 2 in Scheme A-8)

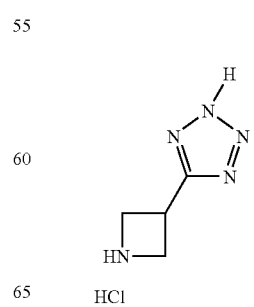

To a solution of (500 mg, 1.72 mmol) in MeOH (5 mL) and EtOAc (5 mL) was added 1N HCl in Et$_2$O (0.5 mL) and 10% palladium on carbon (500 mg). The mixture was stirred under hydrogen atmosphere for 72 h. The catalyst was removed by filtration and the solvent was removed under reduced pressure to give the crude compound which was used for the next step without further purification. MS (ESI) m/z: Calculated: 125.13; Observed: 126.2 (M$^+$+1).

5-(1-(4-(5-Benzylbenzofuran-2-yl)-3-fluorobenzyl)azetidin-3-yl)-2H-tetrazole

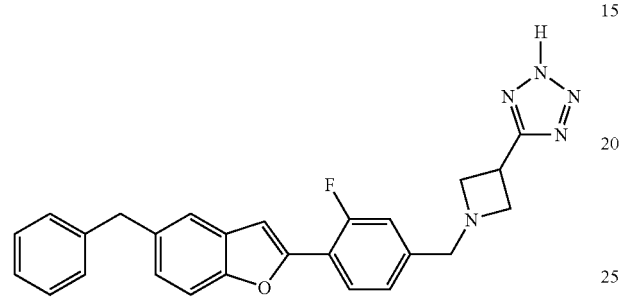

The title compound was prepared as Example Compound A (step 5 in Scheme A-1) in the general method E described above except using 5-(azetidin-3-yl)-2H-tetrazole hydrochloride [hS1P1 EC$_{50}$=2090 nM]. $^1$H NMR (400 MHz, CD$_3$OD) δ 8.13 (t, J=8.8 Hz, 1H), 7.48 (m, 4H), 7.25 (m, 7H), 4.63 (m, 4H), 4.51 (m, 3H), 4.07 (s, 2H). $^{19}$F NMR (376 MHz, CD$_3$OD) δ −77.4 (TFA), −113.1. MS (ESI) m/z: Calculated: 439.18; Observed: 440.00 (M$^+$+1).

Compound 80

1-(4-(2-Benzylbenzofuran-5-yl)-3-fluorobenzyl)azetidine-3-carboxylic acid (5-Bromobenzofuran-2-yl)(phenyl)methanone (step 1 in Scheme A-6)

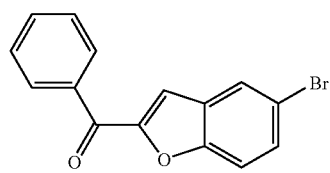

5-Bromosalicylaldehyde (2.01 g, 10 mmole), cesium carbonate (3.26 g, 10 mmole) and acetonitrile (100 mL) were combined and heated to reflux for 30 minutes. The mixture was cooled to 0° C. and a solution of 2-bromo-1-phenylethanone (1.99 g, 10 mmole) in acetonitrile (20 mL) was added. The cooling bath was removed, the mixture stirred at room temperature for 5 h and the precipitate collected the desired product as a white solid: $^1$H NMR (400 MHz, DMSO-d$_6$) δ 8.07 (d, J=2.0 Hz, 1H), 7.98 (d, J=7.6 Hz, 2H), 7.68-7.78 (m, 4H), 7.60 (dd, J=7.6, 8.0 Hz, 2H).

2-Benzyl-5-bromobenzofuran (step 2 in Scheme A-6)

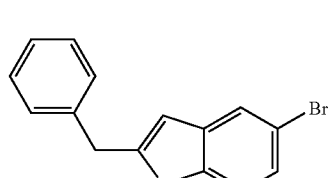

(5-bromobenzofuran-2-yl)(phenyl)methanone (2.0 g, 6.6 mmol), sodium cyanoborohydride (3.2 g, 51 mmol), zinc iodide (2.6 g, 13.2 mmol) and 1,2-dichloroethane (50 mL) were combined and heated to reflux for overnight. The mixture was cooled, quenched with saturated ammonium chloride, acidified with concentrated HCl and stirred for 30 minutes. The layers were separated, the aqueous layer was extracted with dichloromethane (2×100 mL) and the combined organic layers were washed with water (50 mL) and brine (50 mL), dried over sodium sulfate and concentrated. The residue was purified by silica gel column chromatography (ISCO system, 20% dichloromethane in hexanes) to give the product as a white solid: $^1$H NMR (400 MHz, CDCl$_3$) δ7.59 (s, 1H), 7.27-7.34 (m, 7H), 6.32 (s, 1H), 4.10 (s, 2H).

4-(2-Benzylbenzofuran-5-yl)-3-fluorobenzaldehyde (step 3 in Scheme A-6)

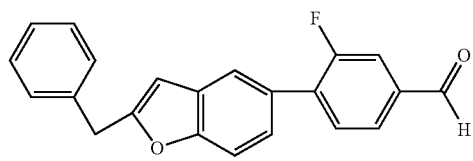

A solution of 2-fluoro-4-formylphenylboronic acid (58 mg, 0.348 mmol), 2-benzyl-5-bromobenzofuran (50 mg, 0.174 mmol), tetrakis(triphenylphosphine) palladium(0) (20 mg, 0.0174 mmol) and sodium carbonate (106 mg, 1.0 mmol) in 1,4-dioxane (4 mL) and water (1 mL) was heated at 100° C. for 12 h. The mixture was partitioned between brine (20 mL) and EtOAc (20 mL). The organic layer was dried. Removal of solvents gave the residue which was purified by silica gel column chromatography (ISCO system, 30% dichloromethane in hexanes) to give the product as a off white solid:

¹H NMR (400 MHz, CDCl₃) δ 10.0 (s, 1H), 7.61-7.75 (m, 5H), 7.27-7.51 (m, 7H), 6.45 (s, 1H), 4.14 (s, 2H).

1-(4-(2-Benzylbenzofuran-5-yl)-3-fluorobenzyl)azetidine-3-carboxylic acid

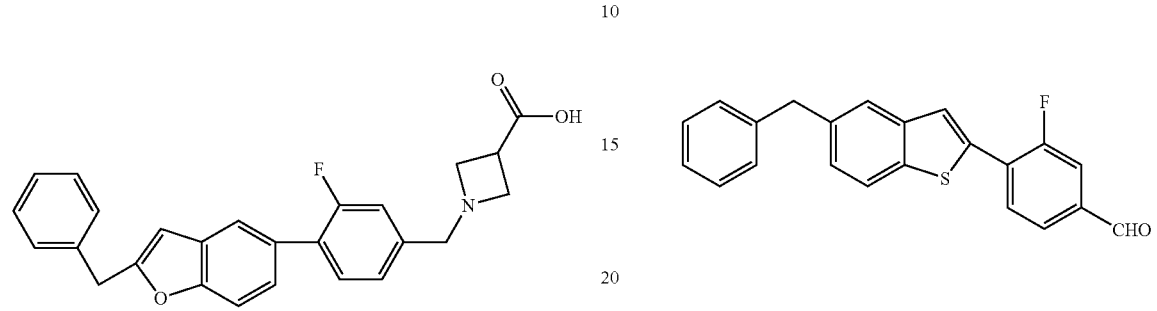

The title compound was prepared as Example Compound A (step 5 in Scheme A-2) in the general method E described above as a white TFA salt [hS1P1 EC₅₀=59 nM]. ¹H NMR (400 MHz, CD₃OD) δ 7.66 (s, 1H), 7.61 (t, J=8.8 Hz, 1H), 7.48 (d, J=8.4 Hz, 1H), 7.29-7.39 (m, 7H), 7.25 (m, 1H), 6.50 (s, 1H), 4.45 (s, 2H), 4.35 (m, 4H), 4.13 (s, 2H), 3.71 (m, 1H). ¹⁹F NMR (376 MHz, CD₃OD) δ −77.4 (TFA), −118.3. MS (ESI) m/z: Calculated: 415.16; Observed: 416.00 (M⁺+1).

Compound 81

1-(4-(5-Benzylbenzo[b]thiophen-2-yl)-3-fluorobenzyl)azetidine-3-carboxylic acid

5-Benzylbenzothiophene (step 1 in Scheme A-7)

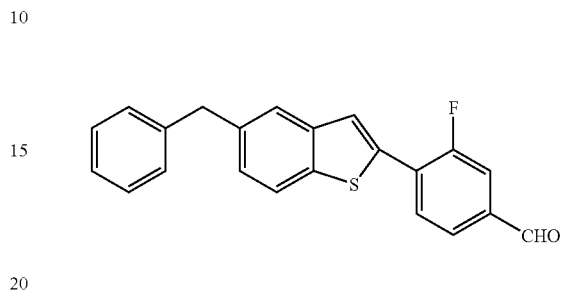

5-Bromobenzothiophene (2.13 g, 10 mmol) was dissolved in a THF solution of benzyl zinc(II) bromide (0.5M, 10 mL, 20 mmol) in a microwave reaction tube. Pd(P^tBu₃)₂ (255 mg, 0.5 mmol) was added to this solution. The mixture was purged with N₂ gas for 3-5 minutes and heated at 100° C. for 30 minutes under microwave irradiation. Upon completion of the reaction, the reaction mixture was diluted with ethyl acetate (150 mL), washed with 1N HCl aqueous solution, brine, filtered through Celite. The filtrate was dried over Na₂SO₄ and concentrated. The residue was purified by silica gel column chromatography (ISCO system, 5% EtOAc in hexanes) to give the desired product (65% yield): ¹H NMR (400 MHz, CDCl₃) δ 7.79 (d, J=8.4 Hz, 1H), 7.63 (s, 1H), 7.40 (d, J=5.6 Hz, 1H), 7.18-7.30 (m, 7H), 4.10 (s, 2H).

4-(5-Benzylbenzo[b]thiophen-2-yl)-3-fluorobenzaldehyde (step 2 in Scheme A-7)

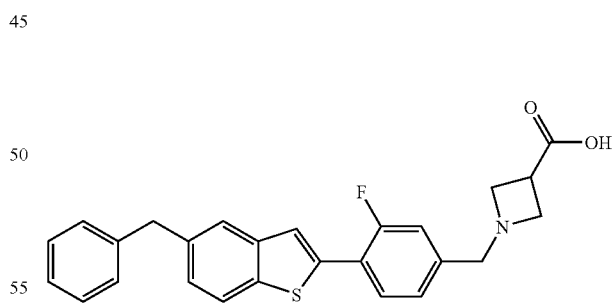

A mixture of 4-bromo-3-fluorobenzaldehyde (40 mg, 0.198 mmol), 5-benzylbenzothiophene (44 mg, 0.198 mmol), potassium acetate (5 mg, 0.05 mmol), tetrakis(triphenylphosphine) palladium(0) (11 mg, 0.010 mmol) and N,N-dimethylacetamide (5 mL) was heated at 150° C. for 12 h. The solvent was evaporated in vacuo and the residue was triturated with water (50 mL) and extracted with dichloromethane (2×100 mL). The organic phase was dried over sodium sulfate, filtered and concentrated. The residue was purified by silica gel column chromatography (ISCO system, 5% EtOAc in hexanes) to give the desired product. ¹H NMR (400 MHz, CDCl₃) δ 9.90 (s, 1H), 7.64-7.85 (m, 6H), 7.22-7.33 (m, 6H), 4.11 (s, 2H).

1-(4-(5-Benzylbenzo[b]thiophen-2-yl)-3-fluorobenzyl)azetidine-3-carboxylic acid

The title compound was prepared as Example Compound A (step 5 in Scheme A-2) in the general method E described above [hS1P1 EC₅₀=11 nM]. ¹H NMR (400 MHz, CD₃OD) δ 7.79 (t, J=8.4 Hz, 1H), 7.69 (m, 2H), 7.59 (s, 1H), 7.30 (m, 2H), 7.06-7.20 (m, 6H), 4.35 (s, 2H), 4.27 (m, 4H), 3.99 (s,

Compound 82

3-(4-(5-Benzylbenzofuran-2-yl)-3-fluorobenzylamino)-2-methylpropanoic acid 3-(4-(5-Benzylbenzofuran-2-yl)-3-fluorobenzylamino)-2-methylpropanoic acid (Step 1 of Scheme A-13)

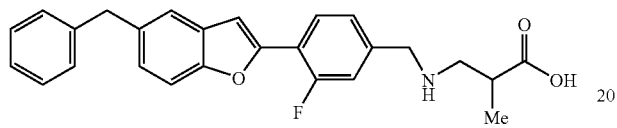

In a similar manner as described in general procedure E, 3-(4-(5-benzylbenzofuran-2-yl)-3-fluorobenzylamino)-2-methylpropanoic acid (white solid [hS1P1 $EC_{50}$=1300 nM]) was obtained as a TFA salt by using 4-(5-phenylbenzofuran-2-yl)-3-fluorobenzaldehyde (80 mg, 0.24 mmol), DL-3-aminoisoburic acid (49.9 mg, 0.48 mmol), sodium cyanoborohydride (30.4 mg, 0.48 mmol), acetic acid (30 μL), methanol (3.5 mL) and dichloromethane (2.5 mL). $^1$H NMR (400 MHz, CD$_3$OD) δ 8.11 (t, J=8.0 Hz, 1H), 7.49-7.43 (m, 4H), 7.29-7.14 (m, 7H), 4.31 (s, 2H), 4.07 (s, 2H), 3.32-3.28 (m, 1H), 3.10 (dd, J=4.6, 12.2 Hz, 1H), 2.88 (m, 1H), 1.29 (d, J=7.2 Hz, 3H); $^{19}$F NMR (376 MHz, CD$_3$OD) δ −77.5 (TFA), −113.5. MS (ESI) m/z: Calculated (without TFA): 417.47; Observed: 417.9 (M$^+$+1).

Compound 83

4-Amino-2-(4-(5-benzylbenzofuran-2-yl)-3-fluorobenzylamino)-4-oxobutanoic acid

4-Amino-2-(4-(5-benzylbenzofuran-2-yl)-3-fluorobenzylamino)-4-oxobutanoic acid (Step 1 of Scheme A-13)

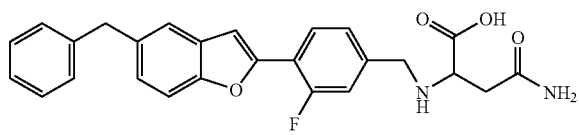

In a similar manner as described in general procedure E, 4-amino-2-(4-(5-benzylbenzofuran-2-yl)-3-fluorobenzylamino)-4-oxobutanoic acid (white solid [hS1P1 $EC_{50}$=2300 nM]) was obtained as a TFA salt by using 4-(5-phenylbenzofuran-2-yl)-3-fluorobenzaldehyde (83.9 mg, 0.25 mmol), DL-asparagine monohydrate (76.3 mg, 0.51 mmol), acetic acid (30 μL), sodium cyanoborohydride (32 mg, 0.51 mmol), methanol (3.5 mL) and dichloromethane (2.5 mL). $^1$H NMR (400 MHz, CD$_3$OD) δ 8.10 (t, J=8.0 Hz, 1H), 7.48-7.44 (m, 4H), 7.29-7.15 (m, 7H), 4.39 (q, J=12.8 Hz, 2H), 4.26 (b, 1H), 4.07 (s, 1H), 3.60 (q, J=6.8 Hz, 1H), 3.13-2.88 (m, 2H); $^{19}$F NMR (376 MHz, CD$_3$OD) δ −77.5 (TFA), −113.5. MS (ESI) m/z: Calculated (without TFA): 446.47; Observed: 446.9 (M$^+$+1).

Compound 84

1-((6-(5-Benzylbenzofuran-2-yl)-5-fluoropyridin-3-yl)methyl)azetidine-3-carboxylic acid 5-(Bromomethyl)-2-chloro-3-fluoropyridine (Step 1 of Scheme A-11)

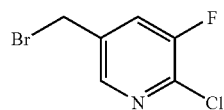

Benzoyl peroxide (100 mg, 41 mmol) was added to a refluxing mixture of 2-chloro-3-fluoro-5-methylpyridine (5.0 g, 34.35 mmol) and NBS (6.73 g, 37.79 mmol) in CCl$_4$ (180 mL). After stirring the mixture for 15 minutes, an additional amount of benzoyl peroxide (400 mg, 1.65 mmol) was added in four portions over a period of 1 hour and the stirring was continued for 1 hour. The reaction mixture was cooled to room temperature, filtered and the solid was washed with dichloromethane. The combined filtrates was washed with water, dried over anhydrous sodium sulfate and concentrated on a rotary evaporator. The crude product was purified by silica gel column chromatography (hexane/ethyl acetate) to afford 5-(bromomethyl)-2-chloro-3-fluoropyridine: $^1$H NMR (400 MHz, CDCl$_3$) δ 8.23 (d, J=2.0 Hz, 1H), 7.55 (dd, J=2.0, 8.8 Hz, 1H), 4.45 (s, 2H).

6-Chloro-5-fluoronicotinaldehyde (Step 2 of Scheme A-11)

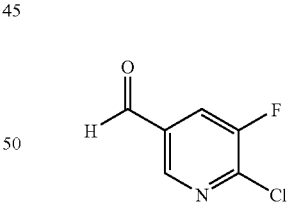

A mixture of 5-(bromomethyl)-2-chloro-3-fluoropyridine (2.0 g, 8.91 mmol) and hexamethylenetetramine (2.75 g, 19.6 mmol) in 50% aqueous acetic acid (53 ml) was heated to reflux. After 1 hour, the mixture was cooled to room temperature, neutralized carefully with solid NaHCO$_3$ (73.7 g), diluted with water (400 mL) and extracted with dichloromethane (2×100 mL). The combined organic extracts were dried over anhydrous sodium sulfate, concentrated on a rotary evaporator and purified by silica gel column chromatography (hexane/ethyl acetate) to afford 6-chloro-5-fluoronicotinaldehyde as pale-yellow solid: $^1$H NMR (400 MHz, CDCl$_3$) δ

10.12 (d, J=2.4 Hz, 1H), 8.72 (d, J=1.6 Hz, 1H), 7.94 (dd, J=2.0, 8.0 Hz, 1H); $^{19}$F NMR (376 MHz, CDCl$_3$) δ −116.3.

1-((6-Chloro-5-fluoropyridin-3-yl)methyl)azetidine-3-carboxylic acid (Step 3 of Scheme A-11)

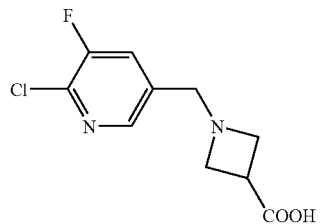

In a similar manner as described in general procedure E, 1-((6-chloro-5-fluoropyridin-3-yl)methyl)azetidine-3-carboxylic acid (203 mg, 0.83 mmol, white solid) was prepared by using 6-chloro-5-fluoronicotinaldehyde (284 mg, 1.78 mmol), azetidine-3-carboxylic acid (184 mg, 1.82 mmol), sodium cyanoborohydride (112 mg, 1.78 mmol), acetic acid (0.155 mL), methanol (6 mL) and dichloromethane (6 mL). MS (ESI) m/z: Calculated (without TFA): 244.65; Observed: 245.1 (M$^+$+1).

1-((6-(5-Benzylbenzofuran-2-yl)-5-fluoropyridin-3-yl)methyl)azetidine-3-carboxylic acid (Step 4 of Scheme A-11)

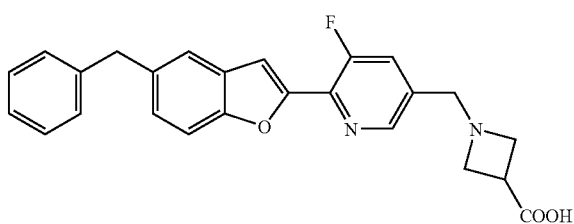

In a similar manner as described in general procedure D, 1-((6-(5-benzylbenzofuran-2-yl)-5-fluoropyridin-3-yl)methyl)azetidine-3-carboxylic acid was obtained as TFA salt (pale-yellow solid [hS1P1 EC$_{50}$=470 nM]) by using 5-benzylbenzofuran-2-ylboronic acid (272 mg, 1.08 mmol), 1-((6-chloro-5-fluoropyridin-3-yl)methyl)azetidine-3-carboxylic acid (203 mg, 0.83 mmol), palladium acetate (9.3 mg, 41.5 µmol), 2-(di-t-butylphosphino)biphenyl (24.8 mg, 83 µmol) and THF (15 mL). $^1$H NMR (400 MHz, CD$_3$OD) δ 8.59 (s, 1H), 7.91 (d, J=11.7 Hz, 1H), 7.56-7.51 (m, 3H), 7.30-7.12 (m, 6H), 4.55 (s, 2H), 4.40 (m, 4H), 4.08 (s, 2H), 3.72 (m, 1H); $^{19}$F NMR (376 MHz, CD$_3$OD) δ −77.5 (TFA), −120.8. MS (ESI) m/z: Calculated (without TFA): 416.44; Observed: 416.9 (M$^+$+1).

Compound 85

4-Amino-3-(4-(5-benzylbenzofuran-2-yl)-3-fluorobenzylamino)-4-oxobutanoic acid

4-Amino-3-(4-(5-benzylbenzofuran-2-yl)-3-fluorobenzylamino)-4-oxobutanoic acid (Step 1 of Scheme A-13)

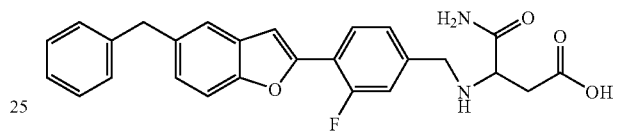

In a similar manner as described in general procedure E, 4-amino-3-(4-(5-benzylbenzofuran-2-yl)-3-fluorobenzylamino)-4-oxobutanoic acid (white solid [hS1P1 EC$_{50}$=1880 nM]) was obtained as a TFA salt by using 4-(5-phenylbenzofuran-2-yl)-3-fluorobenzaldehyde (80 mg, 0.24 mmol), DL-3,4-diamino-4-oxobutanoic acid (32 mg, 0.48 mmol), acetic acid (30 µL), sodium cyanoborohydride (30.4 mg, 0.48 mmol), methanol (3.5 mL) and dichloromethane (2.5 mL). $^1$H NMR (400 MHz, DMSO-d$_6$) δ 7.91 (t, J=8.0 Hz, 1H), 7.62 (s, 1H), 7.54-7.52 (m, 2H), 7.43 (d, J=12.8 Hz, 1H), 7.34 (d, J=7.6 Hz, 1H), 7.29-7.14 (m, 6H), 4.02 (s, 2H), 3.95-3.75 (m, 2H), 3.54 (b, 1H), 2.65-2.40 (m, 2H); $^{19}$F NMR (376 MHz, DMSO-d6) δ −77.5 (TFA), −117.4. MS (ESI) m/z: Calculated (without TFA): 446.47; Observed: 446.9 (M$^+$+1).

Compound 86

1-(3-Fluoro-4-(5-(4-methylbenzyl)benzofuran-2-yl)benzyl)azetidine-3-carboxylic acid

5-(4-Methylbenzyl)benzofuran (Step 1 of Scheme A-2)

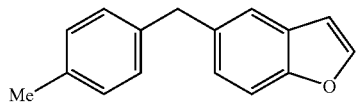

In a similar manner as described in general procedure A, 5-(4-methylbenzyl)benzofuran was obtained as colorless oil by using (4-methylbenzyl)zinc(II) chloride (14.7 mL of 0.5 M solution in THF, 7.35 mmol), 5-bromobenzofuran (500 mg, 2.53 mmol) and Pd(tBu$_3$)$_2$ (64.8 mg, 0.127 mmol). $^1$H NMR (400 MHz, CDCl$_3$) δ 7.55 (d, J=2.0 Hz, 1H), 7.40-7.37 (m, 2H), 7.12-7.06 (m, 5H), 6.66 (m, 1H), 4.02 (s, 2H), 2.30 (s, 3H).

5-(4-Methylbenzyl)benzofuran-2-ylboronic acid (Step 2 of Scheme A-2)

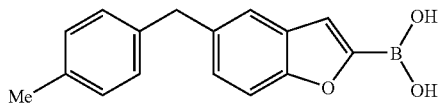

In a similar manner as described in general procedure C, 5-(4-methylbenzyl)benzofuran (253 mg, 1.138 mmol) was converted to 5-(4-methylbenzyl)benzofuran-2-ylboronic acid as white solid: $^1$H NMR (400 MHz, CDCl$_3$) δ 7.44-7.38 (m, 2H), 7.30 (s, 1H), 7.19 (d, J=8.4 Hz, 1H), 7.10 (s, 4H), 5.04 (b, 2H), 4.04 (s, 2H), 2.32 (s, 3H).

Methyl 1-(3-fluoro-4-(5-(4-methylbenzyl)benzofuran-2-yl)benzyl)azetidine-3-carboxylate (Step 1 of Scheme B-12)

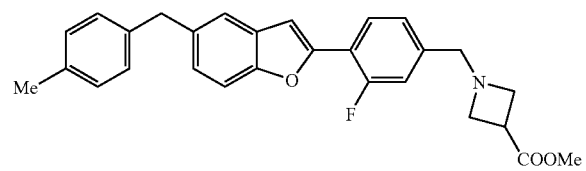

In a similar manner as described in general procedure D, 5-(4-methylbenzyl)-benzofuran-2-ylboronic acid (150 mg, 0.56 mmol) was reacted with methyl 1-(4-bromo-3-fluorobenzyl)azetidine-3-carboxylate (155 mg, 0.51 mmol) to give methyl 1-(3-fluoro-4-(5-(4-methylbenzyl)benzofuran-2-yl)benzyl)azetidine-3-carboxylate as white solid: MS (ESI) m/z: Calculated: 443.51; Observed: 444.0 (M$^+$+1).

1-(3-Fluoro-4-(5-(4-methylbenzyl)benzofuran-2-yl)benzyl)azetidine-3-carboxylic acid (Step 2 of Scheme B-12)

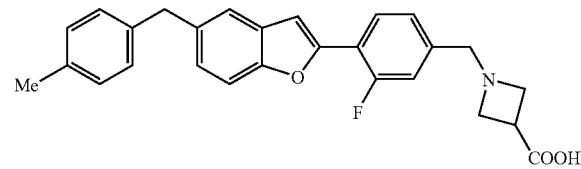

In a similar manner as described in general procedure H, methyl 1-(3-fluoro-4-(5-(4-methylbenzyl)benzofuran-2-yl)benzyl)azetidine-3-carboxylate (100 mg, 0.225 mmol) was hydrolyzed to give 1-(3-Fluoro-4-(5-(4-methylbenzyl)benzofuran-2-yl)benzyl)azetidine-3-carboxylic acid [hS1P1 EC$_{50}$=12 nM] as white foam: $^1$H NMR (400 MHz, DMSO-d$_6$) δ 7.87 (t, J=8.0 Hz, 1H), 7.52 (d, J=8 Hz, 1H), 7.48 (d, J=1.2 Hz, 1H), 7.25 (d, J=6.8 Hz, 1H), 7.23 (s, 1H), 7.21 (d, J=3.2 Hz, 1H), 7.17 (dd, J=1.2, 8.8 Hz, 1H), 7.11 (d, J=7.6 Hz, 2H), 7.07 (d, J=8.0 Hz, 2H). 3.96 (s, 2H), 3.58 (s, 2H), 3.39 (m, 2H), 3.18 (m, 3H), 2.22 (s, 3H); $^{19}$F NMR (376 MHz, DMSO-D6) δ −113.7. MS (ESI) m/z: Calculated: 429.48; Observed: 429.9 (M$^+$+1).

Compound 87

1-(4-(5-Benzyl-2H-indazol-2-yl)-3-fluorobenzyl)azetidine-3-carboxylic acid

5-Bromo-2-nitrobenzaldehyde (Step 1 of Scheme A-10)

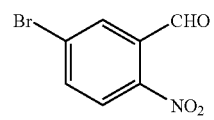

To concentrate nitric acid (10 mL) in concentrated sulfuric acid (120 mL) at 5° C. was added 5-bromo-2-nitrobenzaldehyde (11.71 mL, 100 mmol) dropwise. The reaction mixture was allowed to warm to room temperature and stirred overnight. The reaction mixture was poured onto ice and the resulting precipitates removed by filtration, dissolved in dichloromethane, dried over anhydrous sodium sulfate and concentrated at reduced pressure. The residue was purified by silica gel column chromatography (hexane/ethyl acetate) to give 5-bromo-2-nitrobenzaldehyde: $^1$H NMR (400 MHz, CDCl$_3$) δ 10.42 (s, 1H), 8.07 (d, J=2.0 Hz, 1H), 8.03 (d, J=8.6 Hz, 1H), 7.88 (dd, J=2.0, 8.6 Hz, 1H).

(E)-Ethyl 4-(5-bromo-2-nitrobenzylideneamino)-3-fluorobenzoate (Step 2 of Scheme A-10)

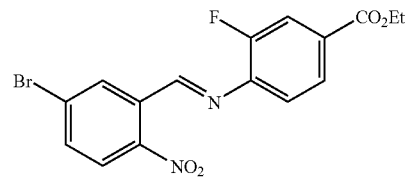

A mixture of 5-bromo-2-nitrobenzaldehyde (2.79 g, 12.13 mmol) and ethyl 4-amino-3-fluorobenzoate (2.22 g, 12.12 mmol) in ethanol (60 mL) was stirred at reflux for 2 h. After the solvent was removed under reduced pressure, the reaction mixture was purified by silica gel column chromatography to give (E)-ethyl 4-(5-bromo-2-nitrobenzylideneamino)-3-fluorobenzoate as pale yellow solid: $^1$H NMR (400 MHz, CDCl$_3$) δ 9.01 (s, 1H), 8.47 (d, J=2.0 Hz, 1H), 8.02 (d, J=8.6 Hz, 1H), 7.91 (dd, J=1.6, 2.3, 9.0 Hz, 1H), 7.85 (dd, J=1.6, 11.0 Hz, 1H), 7.80 (dd, J=2.3, 8.6 Hz, 1H), 7.24 (t, J=8.0 Hz, 1H), 4.40 (q, J=7.0 Hz, 2H), 1.42 (t, J=7.0 Hz, 3H); $^{19}$F NMR (376 MHz, CDCl$_3$) δ −125.6.

Ethyl 4-(5-bromo-2H-indazol-2-yl)-3-fluorobenzoate (Step 3 of Scheme A-10)

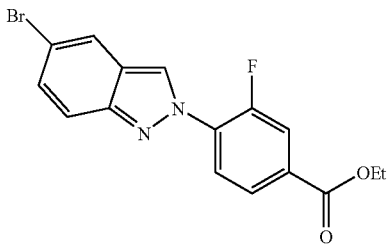

A mixture of (E)-ethyl 4-(5-bromo-2-nitrobenzylideneamino)-3-fluorobenzoate (432 mg, 1.09 mmol) and triethyl phosphate (1.5 mL, 9.0 mmol) was irradiated in a microwave instrument at 150° C. for 1.5 h. The cooled reaction mixture was purified by silica gel column chromatography (hexane/ethyl acetate) to give ethyl 4-(5-bromo-2H-indazol-2-yl)-3-fluorobenzoate as pale yellow solid. $^1$H NMR (400 MHz, CDCl$_3$) δ 8.56 (d, J=2.0 Hz, 1H), 8.25 (t, J=7.8 Hz, 1H), 8.02-7.90 (m, 2H), 7.89 (d, J=0.8 Hz, 1H), 7.66 (d, J=9.2 Hz, 1H), 7.40 (dd, J=1.6, 9.2 Hz, 1H), 4.43 (q, J=7.2 Hz, 2H), 1.44 (t, J=7.2 Hz, 3H); $^{19}$F NMR (376 MHz, CDCl$_3$) δ −123.4. MS (ESI) m/z: Calculated: 363.18; Observed: 363.2 (M$^+$+1).

Ethyl 4-(5-benzyl-2H-indazol-2-yl)-3-fluorobenzoate and benzyl 4-(5-benzyl-2H-indazol-2-yl)-3-fluorobenzoate (Step 4 of Scheme A-10)

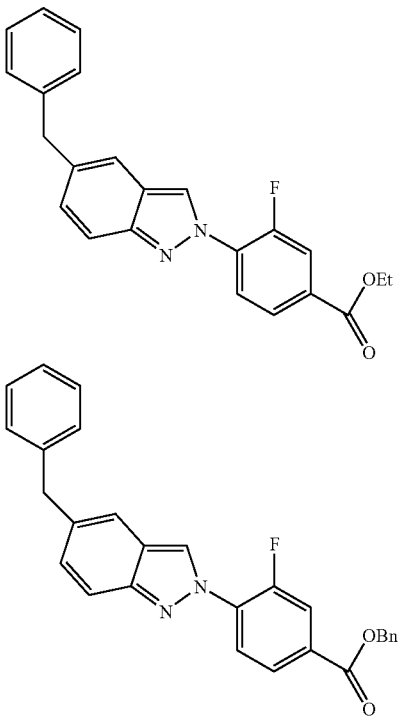

In a similar manner as described in general procedure A, a mixture (171 mg) of ethyl 4-(5-benzyl-2H-indazol-2-yl)-3-fluorobenzoate and benzyl 4-(5-benzyl-2H-indazol-2-yl)-3-fluorobenzoate was obtained by using ethyl 4-(5-bromo-2H-indazol-2-yl)-3-fluorobenzoate (135 mg, 0.372 mmol), 0.5 M solution of benzylzinc(II) bromide in THF (2.16 mL, 1.08 mmol) and Pd(tBu$_3$P)$_2$ (9.5 mg, 19 μmol). Ethyl 4-(5-benzyl-2H-indazol-2-yl)-3-fluorobenzoate: MS (ESI) m/z: Calculated: 374.41; Observed: 375.3 (M$^+$+1).

Benzyl 4-(5-benzyl-2H-indazol-2-yl)-3-fluorobenzoate: MS (ESI) m/z: Calculated: 436.48; Observed: 437.3 (M$^+$+1).

(4-(5-Benzyl-2H-indazol-2-yl)-3-fluorophenyl)methanol (step 5 of Scheme A-10)

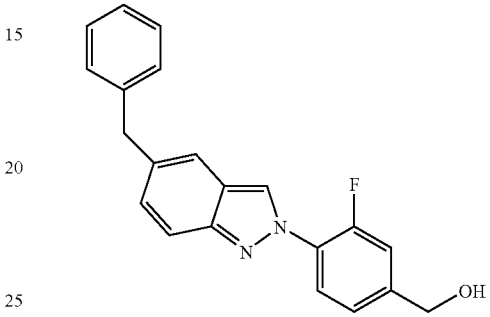

To a mixture (171 mg) of ethyl 4-(5-benzyl-2H-indazol-2-yl)-3-fluorobenzoate and benzyl 4-(5-benzyl-2H-indazol-2-yl)-3-fluorobenzoate in dichloromethane (10 mL) was added 1.0 M solution of DIBAL-H (1.37 mL, 1.37 mmol) in dichloromethane slowly at −78° C. The mixture stirred for 1 hour at −78° C. followed by quenching at −78° C. with 0.5 mL of a saturated solution of ammonium chloride. Hydrochloric acid (2N, 0.6 mL) was added, the cooling bath removed, and the mixture stirred for 1 hour. The mixture was subsequently extracted with dichloromethane and the extracts were dried over anhydrous sodium sulfate. The solvent was removed under reduced pressure to give (4-(5-benzyl-2H-indazol-2-yl)-3-fluorophenyl)methanol. MS (ESI) m/z: Calculated: 332.37; Observed: 333.3 (M$^+$+1).

4-(5-Benzyl-2H-indazol-2-yl)-3-fluorobenzaldehyde (Step 6 of Scheme A-10)

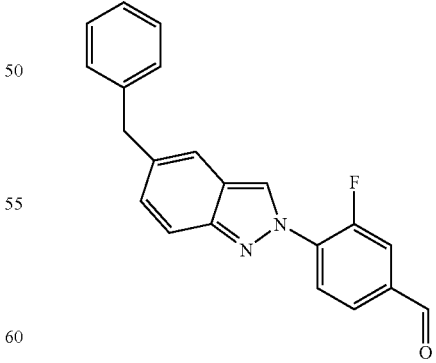

To a mixture of (4-(5-benzyl-2H-indazol-2-yl)-3-fluorophenyl)methanol (100 mg, 0.30 mmol), 4-methylmorpholine N-oxide (43 mg, 0.36 mmol) and activated molecular sieves (200 mg) in dichloromethane (10 mL) was added TPAP (10.6 mg, 0.03 mmol) at room temperature. After stirred overnight, the reaction mixture was filtered, concentrated and purified by silica gel column chromatography (hexane/ethyl acetate) to give 4-(5-benzyl-2H-indazol-2-yl)-3-fluorobenzaldehyde as white solid: $^1$H NMR (400 MHz, CD$_3$OD) δ 10.0 (d, J=1.6 Hz, 1H), 8.55 (m, 1H), 8.41 (t, J=7.4 Hz, 1H), 7.84 (m, 2H), 7.68 (d, J=9.0 Hz, 1H), 7.46 (s, 1H), 7.34-7.30 (m, 2H), 7.27-7.19 (m, 4H), 4.06 (s, 2H); $^{19}$F NMR (376 MHz, CD$_3$OD) δ −122.3. MS (ESI) m/z: Calculated: 330.36; Observed: 331.2 (M$^+$+1).

1-(4-(5-Benzyl-2H-indazol-2-yl)-3-fluorobenzyl)azetidine-3-carboxylic acid (Step 7 of Scheme A-10)

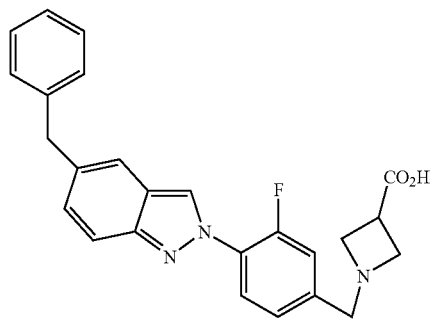

In a similar manner as described in general procedure E, 1-(4-(5-benzyl-2H-indazol-2-yl)-3-fluorobenzyl)azetidine-3-carboxylic acid (white foam [hS1P1 EC$_{50}$=94 nM]) was obtained as TFA salt by using 4-(5-benzyl-2H-indazol-2-yl)-3-fluorobenzaldehyde (108 mg, 0.328 mmol), azetidine-3-carboxylic acid (66 mg, 0.657 mmol), acetic acid (45 μL), sodium cyanoborohydride (41 mg, 0.66 mmol), methanol (7.5 mL) and dichloromethane (4.5 mL). $^1$H NMR (400 MHz, CD$_3$OD) δ 8.61 (d, J=2.0 Hz, 1H), 8.09 (t, J=8.2 Hz, 1H), 7.61-7.49 (m, 4H), 7.30-7.18 (m, 6H), 4.52 (s, 2H), 4.43-4.35 (m, 4H), 4.05 (s, 2H), 3.76-3.67 (m, 1H); $^{19}$F NMR (376 MHz, CD$_3$OD) δ −77.5 (TFA), −124.3. MS (ESI) m/z: Calculated (without TFA): 415.46; Observed: 416.2 (M$^+$+1).

Scheme B1

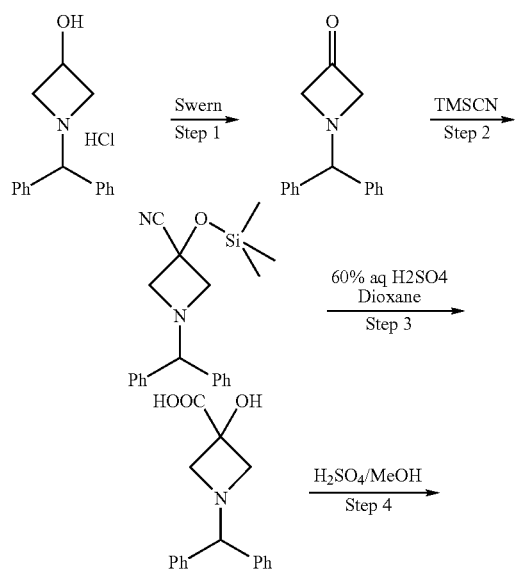

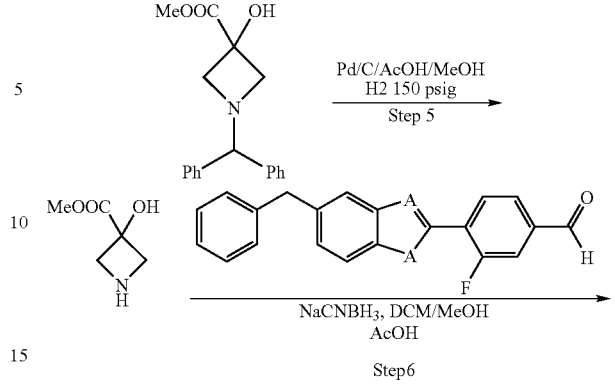

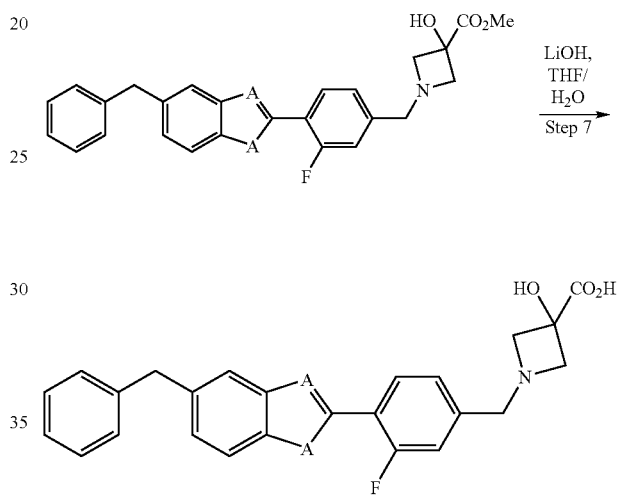

Scheme B1a

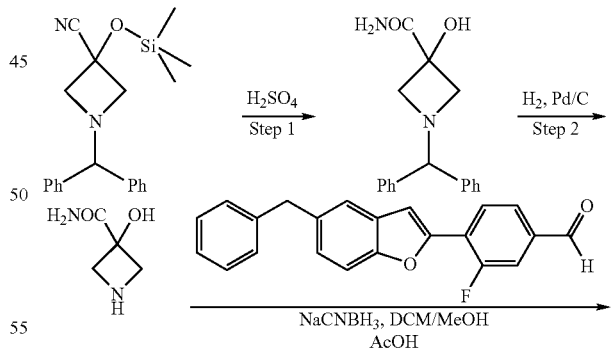

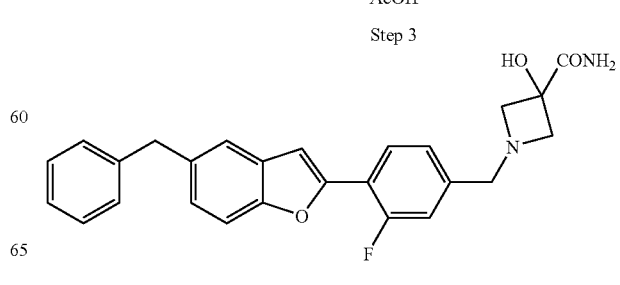

Scheme B2
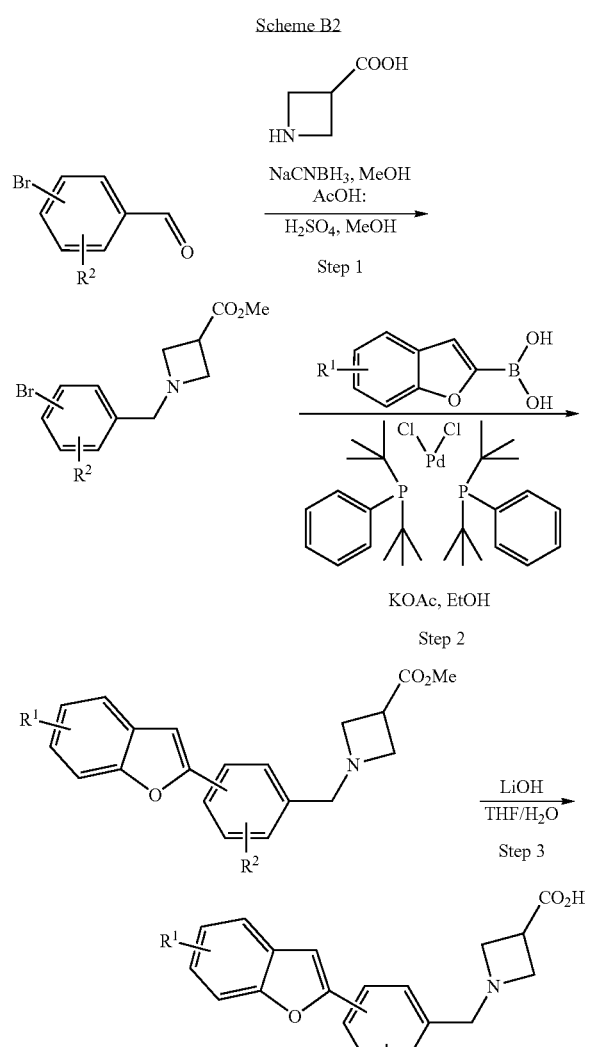
Scheme B3
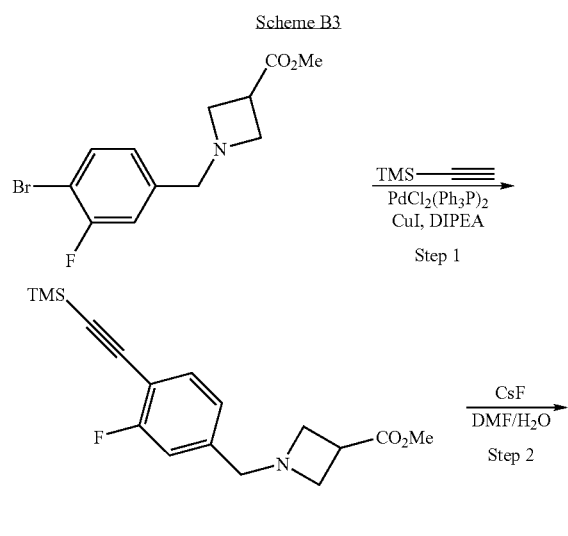
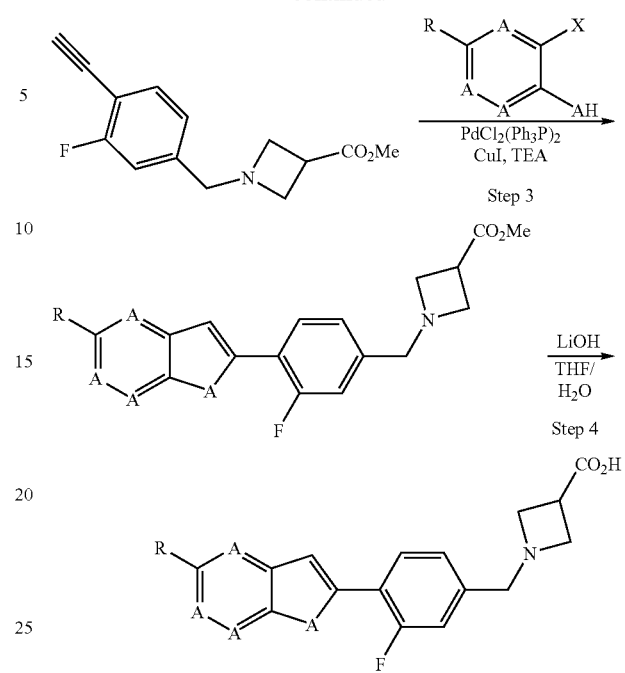
Scheme B4
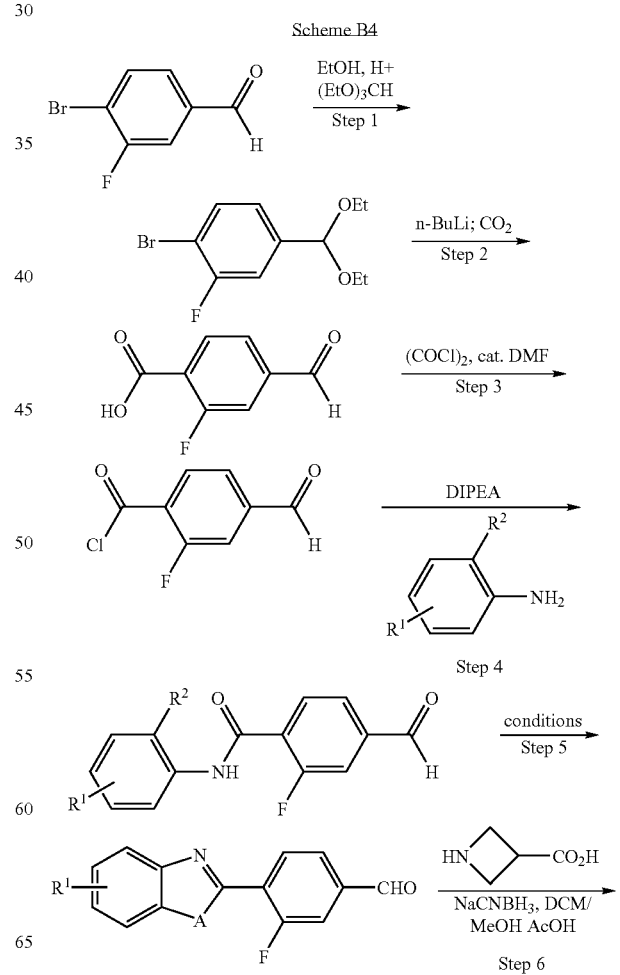

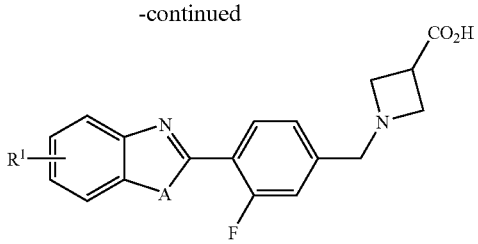

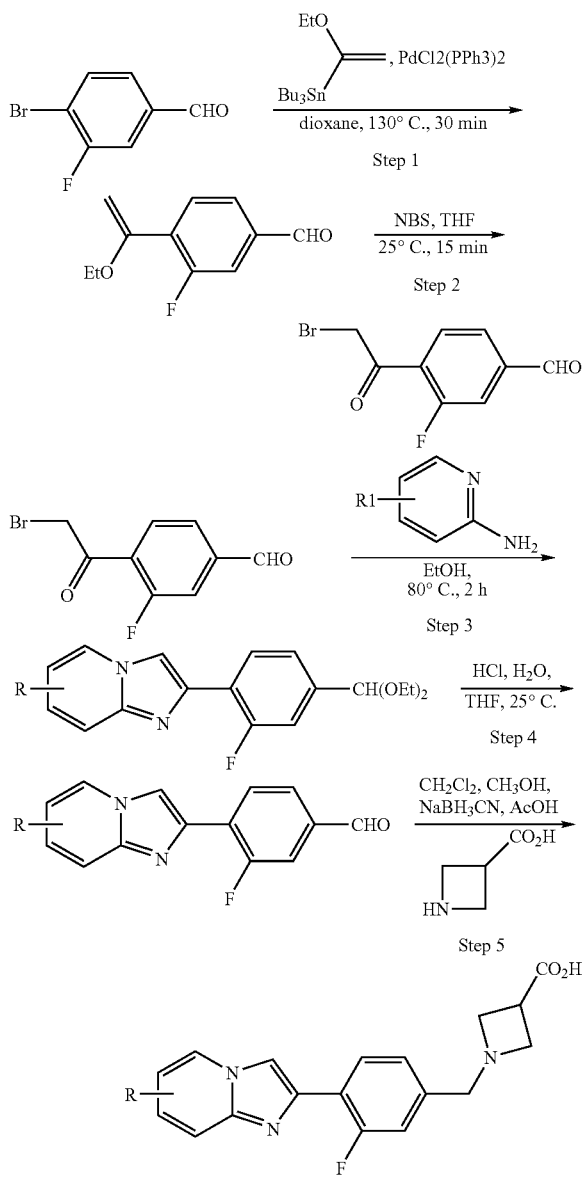

F: General Procedure of Coupling Boronic Acids with Aryl Halides

Bis(di-tert-Butyl(phenyl)phosphine)palladium dichloride (0.0285 mmol), methyl or ethyl 1-(4-bromo-3-fluorobenzyl)azetidine-3-carboxylate (0.474 mmol), boronic acid (0.617 mmol), potassium acetate (0.949 mmol) were combined in a sealable tube and diluted with EtOH. The mixture was flushed with nitrogen and heated to 80° C. for several hours. The reaction was cooled and partitioned between EtOAc and 1N NaOH. The organic layer was washed with brine, dried over sodium sulfate, filtered, and concentrated. The residue was purified by silica gel chromatography to give the desired product.

G: General Procedure for Alkyne Cyclization

PdCl$_2$(PPh$_3$)$_2$ (0.129 mmol), copper(I) iodide (0.129 mmol), 2-halophenol or 2-haloaniline (1.29 mmol), and methyl 1-(4-ethynyl-3-fluorobenzyl)azetidine-3-carboxylate (1.54 mmol) were combined in a sealable tube and 3 mL DMF and 3 mL TEA was added. Argon was bubbled through the solvent for 3 min, and the homogeneous brown reaction was sealed and heated to 100° C. After completion of the reaction, the reaction was concentrated in vacuo and adsorbed onto 5 g silica gel and purified by silica gel chromatography to give the desired product.

H: General Procedure for Ester Hydrolysis

To a solution of ester (0.428 mmol) in 2 mL THF was added lithium hydroxide hydrate (1.29 mmol) in 1 mL water. The lt. yellow reaction was stirred until completion. The THF was removed, and the solid was suspended in 2 mL water. HCl (3 equiv, 2N) was added to neutralize the base, and the mixture was sonicated. Phosphate buffer (4 mL, 1M, pH 6) was added and the reaction was sonicated. The slurry was filtered and the solid rinsed with water and EtOH and dried in vacuo to give the desired product.

I: General Procedure of Reductive Amination

A mixture of aldehyde (1.0 mmol), acetic acid (1.5-2 mmol) and azetidine-3-carboxylic acid or piperidine-4-carboxylic acid (1-3 mmol) in DCM/MeOH (1:1, 10 mL) was stirred at room temperature for 1 h. Sodium cyanoborohydride (0.5-1.0 mmol) was added and the reaction mixture was stirred for 2-3 h at room temperature. The reaction mixture was filtered, and the resulting residue was rinsed with DCM. The solid was suspended in 0.5-1.0M pH 6 phosphate buffer with sonication, filtered, and rinsed with water followed by EtOH to give the desired product.

Common Intermediates

Intermediate 1

Methyl 3-hydroxyazetidine-3-carboxylate

1-Benzhydrylazetidin-3-ol

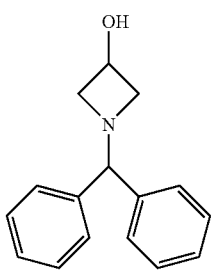

NaOH (5N aqueous, 26.1 mL, 131 mmol) was added to a mixture of 1-benzhydrylazetidin-3-ol hydrochloride (30.00 g, 109 mmol) in water (150 mL). The mixture was allowed to stir for 15 min, extracted with AcOEt, dried over MgSO$_4$ to give 1-benzhydrylazetidin-3-ol. 1H NMR (300 MHz, CDCl$_3$) δ ppm 7.35-7.44 (m, 4H), 7.22-7.32 (m, 4H), 7.13-7.22 (m, 2H), 4.40-4.52 (m, 1H), 4.35 (s, 1H), 3.47-3.60 (m, 2H), 2.80-2.97 (m, 2H). MS (ESI) m/z: Calculated; 239.1 Observed: 340.1 (M⁺+1).

1-Benzhydrylazetidin-3-one

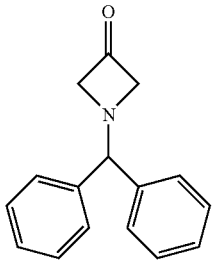

A three-neck flask was charged with oxalyl dichloride (10.6 mL, 119 mmol) and DCM (100.00 ml, 306 mmol), and the solution was cooled to −78° C. To the stirred solution was added, via dropping funnel, dimethylsulfoxide (16.9 mL, 238 mmol) in DCM (50 mL) over 30 min. The reaction was stirred at −78° C. for an additional 5 min, and then 1-benzhydrylazetidin-3-ol (25.90 g, 108 mmol) in DCM (50 mL) and DMSO (10 mL) was added dropwise over 5 min (T was maintained <−60° C.). The solution was stirred at −78° C. for an additional 20 min, and Et₃N (75.3 mL, 541 mmol) was added slowly. The reaction was allowed to reach room temperature over 30 min and water (200 mL) was added. The mixture was extracted with EtOAc, washed with brine, dried over MgSO₄ and evaporated. Purification by flash chromatography using 2% Et₃N/hexanes gave 1-benzhydrylazetidin-3-one. 1H NMR (300 MHz, CDCl₃) δ ppm 7.41-7.52 (m, 4H), 7.26-7.35 (m, 4H), 7.16-7.26 (m, 2H), 4.59 (s, 1H), 3.90-4.07 (m, 4H).

1-Benzhydryl-3-(trimethylsilyloxy)azetidine-3-carbonitrile

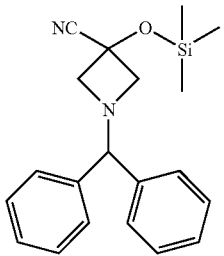

Trimethylsilyl cyanide (4.5 mL, 34 mmol) was added to a solution of 1-benzhydrylazetidin-3-one (4.00 g, 17 mmol) in DCM (85 mL) followed by addition of a solution of tetrabutylammonium cyanide (0.45 g, 1.7 mmol) in DCM (85 mL). The solution was allowed to stir at room temperature for 1 h, treated with water, extracted with DCM, dried over MgSO₄, and evaporated to give 1-benzhydryl-3-(trimethylsilyloxy) azetidine-3-carbonitrile. 1H NMR (300 MHz, CDCl₃) δ ppm 7.15-7.28 (m, 4H), 7.03-7.14 (m, 4H), 6.92-7.03 (m, 2H), 4.15 (s, 1H), 3.34-3.62 (m, 2H), 2.72-2.94 (m, 2H), 0.00 (s, 9H). MS (ESI) m/z: Calculated; 336.2 Observed: 337.1 (M⁺+1).

1-Benzhydryl-3-hydroxyazetidine-3-carboxylic acid

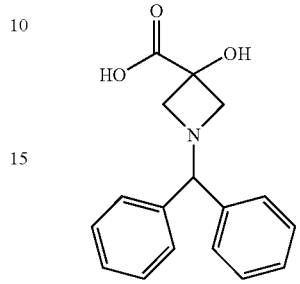

1-Benzhydryl-3-(trimethylsilyloxy)azetidine-3-carbonitrile (2.85 g, 8.47 mmol) was taken up in a 1:1 mixture of 1,4-dioxane (30 mL) and 60% aqueous sulfuric acid (30 mL). The mixture was heated to 95° C. for 1 h. The solvent was removed and the residue was taken to pH 7 using 5N NaOH. The solid was isolated by filtration, rinsed with Et₂O to give 1-benzhydryl-3-hydroxyazetidine-3-carboxylic acid. 1H NMR (300 MHz, DMSO-d₆) δ ppm 7.36-7.47 (m, 4H), 7.22-7.33 (m, 4H), 7.13-7.23 (m, 2H), 4.52 (s, 1H), 3.46 (d, J=8.3 Hz, 2H), 3.02 (d, J=8.2 Hz, 2H). MS (ESI) m/z: Calculated; 283.1 Observed: 284.1 (M⁺+1).

Methyl 1-benzhydryl-3-hydroxyazetidine-3-carboxylate

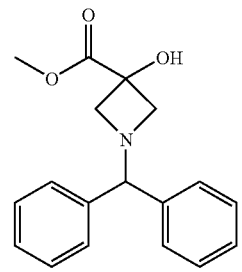

Sulfuric acid (4.00 mL, 47.3 mmol) was added to a mixture of 1-benzhydryl-3-hydroxyazetidine-3-carboxylic acid (2.13 g, 7.50 mmol) in MeOH (20 mL). The mixture was heated to 80° C. for 18 h, diluted with EtOAc, extracted with water, 1N NaOH, dried over MgSO₄, and evaporated. The solid was rinsed with Et₂O to give methyl 1-benzhydryl-3-hydroxyazetidine-3-carboxylate. 1H NMR (300 MHz, CDCl₃) δ ppm 7.43-7.49 (m, 4H), 7.24-7.31 (m, 4H), 7.15-7.23 (m, 2H), 4.54 (s, 1H), 3.90 (s, 3H), 3.59-3.72 (m, 2H), 3.24-3.39 (m, 2H). MS (ESI) m/z: Calculated; 297.14 Observed: 298.1 ($M^++1$).

Methyl 3-hydroxyazetidine-3-carboxylate

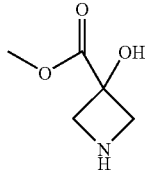

A reactor was charged with methyl 1-benzhydryl-3-hydroxyazetidine-3-carboxylate (1.6 g, 5.4 mmol), 10% Pd/C (0.300 g, 2.8 mmol), and glacial acetic acid (0.300 mL, 5.2 mmol) in MeOH (30 mL). The mixture was allowed to stir for 3 h under 50 psig of $H_2$. The crude was filtered through Celite and rinsed with MeOH. After evaporation, the solid was rinsed with $Et_2O$ to give methyl 3-hydroxyazetidine-3-carboxylate as the acetic acid salt. 1H NMR (300 MHz, DMSO-$d_6$) δ ppm 3.74 (d, J=9.1 Hz, 2H), 3.69 (s, 3H), 3.44 (d, J=8.9 Hz, 2H), 1.88 (s, 3H).

Intermediate 2

Methyl 1-(4-bromo-3-fluorobenzyl)azetidine-3-carboxylate

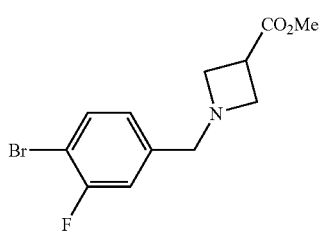

Azetidine-3-carboxylic acid (43 g, 421 mmol), 4-bromo-3-fluorobenzaldehyde (81.4 g, 401 mmol), methyl orthoformate (219 mL, 2005 mmol), and AcOH (34 mL, 601 mmol), was added to DCM (700 mL) at rt under $N_2$ atm. The mixture was stirred for 15 min, at which point sodium triacetoxyborohydride (127 g, 601 mmol) was added portionwise (exothermic). After 2 h, solvent swap with MeOH (257 g, 8019 mmol), and sulfuric acid (79 g, 802 mmol) was added slowly (exothermic). The mixture was heated at reflux for 18 h. Solvent was removed and the mixture was extracted using DCM and water. The organic layer was purified using Biotage column (isopropanol/heptane) affording methyl 1-(4-bromo-3-fluorobenzyl)azetidine-3-carboxylate as a clear oil. MS (ESI) m/z: Calculated: 301.0; Observed: 302.0 ($M^++1$).

Intermediate 3

Ethyl 1-(4-bromo-3-fluorobenzyl)azetidine-3-carboxylate

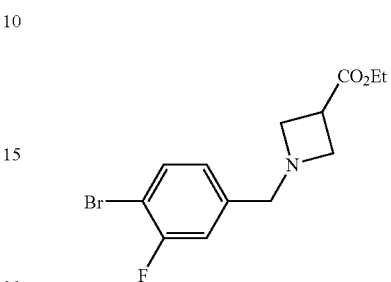

Synthesized in an analogous fashion as methyl 1-(4-bromo-3-fluorobenzyl)azetidine-3-carboxylate, but MeOH from step 1 was removed and EtOH was used for step 2. MS (ESI) m/z: Calculated: 315.0; Observed: 316.0 ($M^++1$).

Intermediate 4

Methyl 1-(4-ethynyl-3-fluorobenzyl)azetidine-3-carboxylate

Methyl 1-(3-fluoro-4-(2-(trimethylsilyl)ethynyl)benzyl)azetidine-3-carboxylate

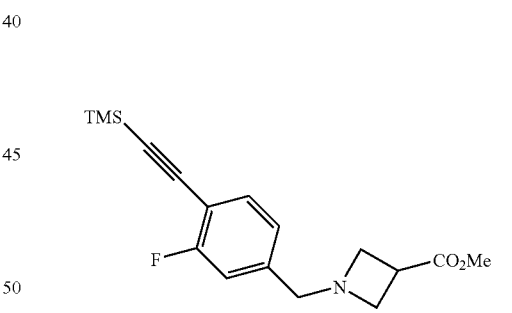

Methyl 1-(4-bromo-3-fluorobenzyl)azetidine-3-carboxylate (25.00 g, 82.7 mmol), copper (1) iodide (3.14 g, 16.5 mmol), (trimethylsilyl)acetylene (81.9 mL, 579 mmol), bis(triphenylphosphine)palladium(ii) chloride (5.81 g, 8.27 mmol), and Hunig's base (115 mL, 662 mmol) was added in a sealable tube along with 100 mL THF. The reaction is sealed and heated to 80° C. under vigorous stirring for 24 h. The mixture was cooled to room temperature, filtered and evaporated. The resulting oil was purified using Biotage (75 L, 0-50% EtOAc/hexanes) affording methyl 1-(3-fluoro-4-(2-

(trimethylsilyl)ethynyl)benzyl)azetidine-3-carboxylate as a transparent brown oil. MS (ESI) m/z: Calculated: 319.1; Observed: 320.1 (M++1).

Methyl 1-(4-ethynyl-3-fluorobenzyl)azetidine-3-carboxylate

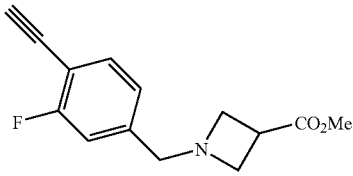

Methyl 1-(3-fluoro-4-(2-(trimethylsilyl)ethynyl)benzyl) azetidine-3-carboxylate (20.9 g, 65 mmol), and cesium fluoride (11 g, 72 mmol), was added to DMF (50 mL). MeOH (100 mL) was added. After 2 h, MeOH was removed and the mixture was extracted with DCM and water. The organic layer is washed with brine and dried over magnesium sulfate. The solvent was removed and the material purified using Biotage (75 L, 7-100% EtOAc/hexanes) affording methyl 1-(4-ethynyl-3-fluorobenzyl)azetidine-3-carboxylate as light yellow oil. MS (ESI) m/z: Calculated: 247.1; Observed: 248.0 (M++1).

Intermediate 5

2-Fluoro-4-formylbenzoyl chloride

1-Bromo-4-(diethoxymethyl)-2-fluorobenzene

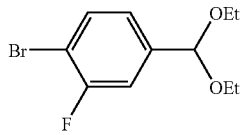

To a solution of 3-fluoro-4-bromobenzaldehyde (20.0 g, 98.5 mmol) in dry EtOH (120 mL) was added acetyl chloride (2.04 mL, 29.6 mmol) followed by the addition of triethyl orthoformate (6.55 mL, 39.4 mmol) and the contents were heated to 70° C. for 3 h. The contents were cooled to room temperature and shifted to a rotary evaporator and subjected to reduced pressure (280 mm Hg) with bath temperature 65° C. for 45 min. The pressure was further lowered to remove all the solvent. To this mixture, fresh Ethanol (60 mL), acetyl chloride (1.5 mL), triethyl orthoformate (5.0 mL) and heated to 70° C. for 2 h. The solvent was removed under the reduced pressure and diluted with EtOAc (200 mL), washed with saturated sodium bicarbonate (3×100 mL), brine and dried over anhydrous sodium sulfate. The solvent was evaporated and the residue purified by silica gel column (basified with 5% Et$_3$N, eluent: EtOAc/hexanes, 1/20) to afford 1-bromo-4-(diethoxymethyl)-2-fluorobenzene as a colorless oil. 1H NMR (400 MHz, CDCl$_3$) δ ppm 8.03 (t, J=8.1 Hz, 1H), 7.36-7.33 (m, 2H), 5.54 (s, 1H), 3.63-3.52 (m, 4H), 1.25 (m, 6H).

2-Fluoro-4-formylbenzoic acid

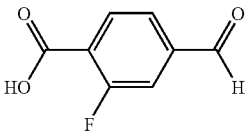

To a solution of 1-bromo-4-(diethoxymethyl)-2-fluorobenzene (10.12 g, 36.53 mmol) in dry THF (90 mL) cooled to −78° C. was added n-butyllithium (2.5 M in hexanes, 16.5 mL, 43.83 mmol) was added dropwise over a period of 10 min. The contents were further stirred for 30 min and CO$_2$ was bubbled through the mixture for 0.5 h. (exothermic). The cooling bath was removed and the contents warmed to room temperature. The mixture was treated with aqueous NaOH (1N, 100 mL) and washed with EtOAc. The aqueous layer was acidified to pH 2 with HCl (5N) and the free acid was extracted with EtOAc (3×75 mL). The combined organic layers were washed with water and brine, dried over MgSO$_4$ and evaporated. The residue was dissolved in ether (30 mL), TFA (1.5 mL) and water (2.0 mL) and stirred overnight. The volatiles were removed under reduced pressure and co-evaporated with toluene. The residue was then treated with diethyl ether (75 mL) and filtered. The filter cake was dried under vacuum without further purification to give 2-fluoro-4-formylbenzoic acid as a white solid. 1H NMR (400 MHz, DMSO-d6) δ ppm 13.48 (s, 1H), 10.06 (s, 1H), 8.06 (t, J=7.4 Hz, 1H), 7.84-7.79 (m, 2H). MS (ESI) m/z: Calculated: 168.0; Observed: 167.0 (M−−1).

2-Fluoro-4-formylbenzoyl chloride

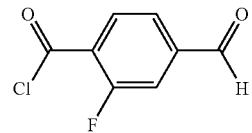

To a slurry of 2-fluoro-4-formylbenzoic acid (0.531 g, 3.16 mmol) 10 mL DCM was added oxalyl chloride (0.168 mL, 1.89 mmol) and catalytic DMF (2 drops). The reaction was allowed to stir under a positive pressure of argon with a needle outlet to air. After 2 h, a quenched aliquot of the reaction (MeOH) was determined to contain no acid. The reaction was concentrated in vacuo and dried on a hood pump for 10 min to give a yellow solid, which was used without further purification.

Intermediate 6

4-(2-Bromoacetyl)-3-fluorobenzaldehyde

1-Bromo-4-(diethoxymethyl)-2-fluorobenzene

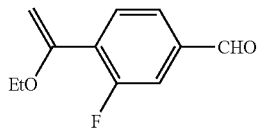

To a solution of 4-bromo-3-fluorobenzaldehyde (1.00 g, 4.9 mmol) in dioxane (10.0 mL) was added tributyl(1-ethoxyvinyl)stannane (1.7 mL, 5.2 mmol) and Pd(PPh$_3$)$_2$Cl$_2$ (0.069 g, 0.099 mmol). The resulting solution was purged with argon for 2 min and then heated (microwave) in a sealed tube at 130° C. for 30 min. The cooled reaction solution was filtered through a plug of silica gel (eluting with 80 mL EtOAc), and the filtrate was concentrated in vacuo. Chromatographic purification of the residue (ISCO, 40 g, 0-30% EtOAc/Hex) afforded 1-bromo-4-(diethoxymethyl)-2-fluorobenzene as a light yellow oil. 1H NMR (400 MHz, CHLOROFORM-d) δ ppm 9.98 (s, 1H), 7.81 (t, J=7.5 Hz, 1H), 7.65 (d, J=7.5 Hz, 1H), 7.57 (d, J=11.0 Hz, 1H), 4.90 (d, J=2.0 Hz, 1H), 4.58 (s, 1H), 3.94 (q, J=7.0 Hz, 2H), 1.42 (t, J=6.8 Hz, 3H).

4-(2-Bromoacetyl)-3-fluorobenzaldehyde

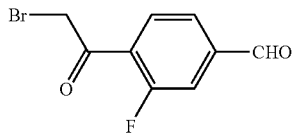

N-Bromosuccinimide (505 mg, 2837 μmol) was added in one portion to a solution of 1-bromo-4-(diethoxymethyl)-2-fluorobenzene (551 mg, 2837 μmol) in 3:1 THF-H$_2$O (6.0 mL) at 25° C., and the resulting solution was stirred at 25° C. for 10 min. The solution was partitioned between EtOAc (50 mL) and brine (8 mL). The organic layer was separated, dried over sodium sulfate, and concentrated in vacuo. Chromatographic purification of the residue (ISCO, 4 g, 0-100% EtOAc/hexanes) furnished 4-(2-bromoacetyl)-3-fluorobenzaldehyde as a white solid. 1H NMR (400 MHz, CDCl$_3$) δ ppm 10.08 (d, J=1.8 Hz, 1H), 8.06-8.12 (m, 1H), 7.79 (dd, J=8.0, 1.4 Hz, 1H), 7.69 (dd, J=10.6, 1.4 Hz, 1H), 4.52 (d, J=2.3 Hz, 2H).

Compound 88

1-((4-(5-Benzylbenzofuran-2-yl)-3-fluorophenyl)methyl)-3-hydroxyazetidine-3-carboxylic acid Methyl 1-((4-(5-benzylbenzofuran-2-yl)-3-fluorophenyl)methyl)-3-hydroxyazetidine-3-carboxylate

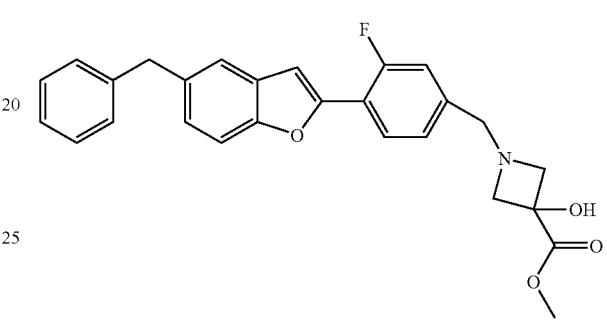

Synthesized according to Scheme B1 and general procedure I from 4-(5-benzylbenzofuran-2-yl)-3-fluorobenzaldehyde (0.100 g, 0.30 mmol) and methyl 3-hydroxyazetidine-3-carboxylate (0.058 g, 0.30 mmol) to give methyl 1-((4-(5-benzylbenzofuran-2-yl)-3-fluorophenyl)methyl)-3-hydroxyazetidine-3-carboxylate. 1H NMR (300 MHz, DMSO-d$_6$) δ ppm 7.91 (t, J=7.9 Hz, 1H), 7.40-7.61 (m, 2H), 7.15-7.36 (m, 8H), 6.26 (s, 1H), 4.04-4.10 (m, 1H), 4.04 (s, 2H), 3.70 (s, 3H), 3.68-3.69 (m, 1H), 3.63 (d, J=7.9 Hz, 1H), 3.12-3.18 (m, 4H). MS (ESI) m/z: Calculated: 445.2 Observed: 446.1 (M$^+$+1).

1-((4-(5-Benzylbenzofuran-2-yl)-3-fluorophenyl)methyl)-3-hydroxyazetidine-3-carboxylic acid

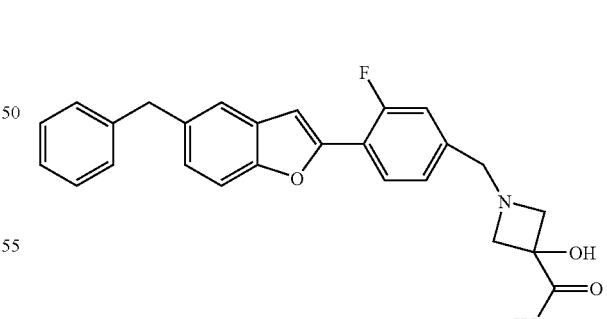

Synthesized according to general procedure H from methyl 1-(4-(5-benzylbenzofuran-2-yl)-3-fluorobenzyl)-3-hydroxyazetidine-3-carboxylate (0.078 g, 0.18 mmol) to give 1-((4-(5-benzylbenzofuran-2-yl)-3-fluorophenyl)methyl)-3-hydroxyazetidine-3-carboxylic acid [hS1P1 EC$_{50}$=105 nM]. 1H NMR (400 MHz, DMSO-d$_6$) δ ppm 8.05 (t, J=7.5 Hz, 1H), 7.54-7.65 (m, 3H), 7.44-7.54 (m, 1H), 7.36 (s, 1H), 7.23-7.33 (m, 5H), 7.13-7.23 (m, 1H), 4.43-4.58 (m, 4H), 3.64-4.23 (m, 4H). MS (ESI) m/z: Calculated: 431.2 Observed: 432.1 (M+ +1).

Compound 89

1-((4-(5-Benzylbenzo[d]thiazol-2-yl)-3-fluorophenyl)methyl)-3-hydroxyazetidine-3-carboxylic acid Methyl 1-((4-(5-benzylbenzo[d]thiazol-2-yl)-3-fluorophenyl)methyl)-3-hydroxyazetidine-3-carboxylate

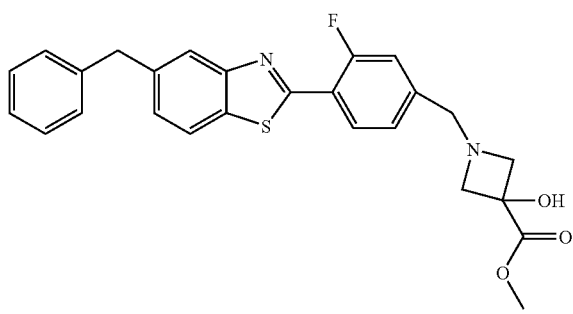

Synthesized according to Scheme B1 and general procedure I from 4-(5-benzylbenzo[d]thiazol-2-yl)-3-fluorobenzaldehyde (0.057 g, 0.16 mmol) and methyl 3-hydroxyazetidine-3-carboxylate (0.031 g, 0.16 mmol) to give methyl 1-((4-(5-benzylbenzo[d]thiazol-2-yl)-3-fluorophenyl)methyl)-3-hydroxyazetidine-3-carboxylate. 1H NMR (300 MHz, CDCl$_3$) δ ppm 8.37 (t, J=7.7 Hz, 1H), 7.93 (s, 1H), 7.84 (d, J=8.2 Hz, 1H), 7.21-7.35 (m, 8H), 4.15 (s, 2H), 3.93-4.07 (m, 7H), 3.52-3.67 (m, 2H). MS (ESI) m/z: Calculated: 462.1 Observed: 463.1 (M+ +1).

1-((4-(5-Benzylbenzo[d]thiazol-2-yl)-3-fluorophenyl)methyl)-3-hydroxyazetidine-3-carboxylic acid

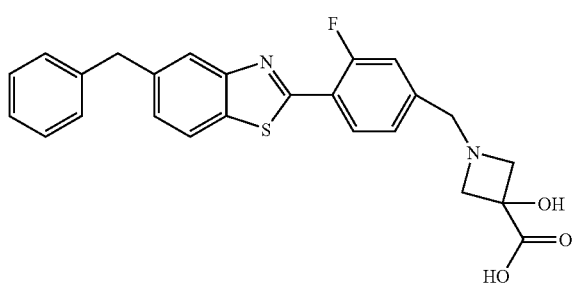

Synthesized according to general procedure H from methyl 1-(4-(5-benzylbenzo[d]thiazol-2-yl)-3-fluorobenzyl)-3-hydroxyazetidine-3-carboxylate (0.035 g, 0.076 mmol) to give 1-((4-(5-Benzylbenzo[d]thiazol-2-yl)-3-fluorophenyl)methyl)-3-hydroxyazetidine-3-carboxylic acid [hS1P1 EC$_{50}$=27 nM]. 1H NMR (400 MHz, DMSO-d$_6$) δ ppm 7.23 (br. t, J=8.0 Hz, 1H), 6.61-6.66 (br. s, 2H), 6.21-6.34 (m, 2H), 5.85-6.06 (m, 6), 3.29-3.20 (m, 4H), 2.92-2.97 (br. m, 2H), 2.86 (br. s, 2H). MS (ESI) m/z: Calculated: 448.1 Observed: 449.2 (M+ +1).

Compound 90

1-((3-Fluoro-4-(5-(1-phenylethyl)benzofuran-2-yl)phenyl)methyl)azetidine-3-carboxylic acid Benzofuran-5-yl(phenyl)methanol

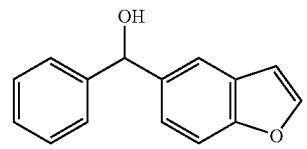

To a solution of 1-benzofuran-5-carbaldehyde (2.70 g, 18.5 mmol) in 50 mL THF under N$_2$ was added phenylmagnesium bromide 3.0M solution in diethyl ether (7.39 mL, 22.2 mmol). The reaction was allowed to stir for 1 h, then was quenched with NH$_4$Cl sat'd aq., extracted with diethyl ether, washed with brine, dried over anhyd. sodium sulfate, filtered, and concentrated in vacuo to a solid to give benzofuran-5-yl(phenyl)methanol which was used without further purification. 1H NMR (400 MHz, DMSO-d$_6$) δ ppm 7.94 (d, J=2.0 Hz, 1H), δ 7.64 (s, 1H), 7.49 (d, J=8.5 Hz, 1H), 7.36-7.42 (m, 2H), 7.26-7.33 (m, 3H), 7.19 (t, J=7.3 Hz, 1H), 6.92 (d, J=1.5 Hz, 1H), 5.88 (d, J=4.0 Hz, 1H), 5.77-5.83 (m, 1H).

Benzofuran-5-yl(phenyl)methanone

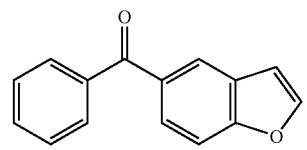

To a solution of benzofuran-5-yl(phenyl)methanol (4.0 g, 18 mmol) and triethylamine (7.3 mL, 54 mmol) in 30 mL 1:1 DCM/DMSO under nitrogen at 0° C. was added a solution of SO$_3$*py (8.5 g, 54 mmol) in 20 mL DMSO dropwise via addition funnel. The reaction was allowed to stir 5 h at 0° C. and was quenched by addition of water and 250 mL Et$_2$O. The organic layer was washed with water, 1N HCl, 1N NaOH, brine, and was dried over sodium sulfate, filtered, and concentrated. The resulting solid benzofuran-5-yl(phenyl)methanone was used without further purification. MS (ESI) m/z: Calculated: 222.1; Observed: 223.0 (M+ +1).

1-(Benzofuran-5-yl)-1-phenylethanol

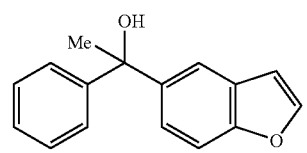

To a solution of benzofuran-5-yl(phenyl)methanone (1.0 g, 4.5 mmol) in 20 mL THF under nitrogen at 0° C. was added methylmagnesium bromide 3.0M in diethyl ether (2.2 mL, 6.7 mmol) dropwise via syringe. The reaction was allowed to warm to ambient temperature slowly. The reaction was quenched with sat'd aq. NH$_4$Cl and DCM. The aqueous layer was extracted 2×DCM, and the combined organics were dried over anhyd sodium sulfate, filtered, and concentrated in vacuo to give 1-(benzofuran-5-yl)-1-phenylethanol as an oil, which was used without further purification. MS (ESI) m/z: Calculated: 238.1; Observed: 238.8 (M$^+$+1).

5-(1-Phenylethyl)benzofuran

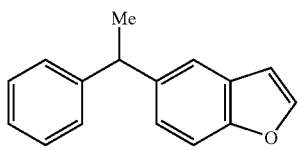

To a solution of 1-(benzofuran-5-yl)-1-phenylethanol (1.1 g, 4.6 mmol) in 20 mL DCM at 0° C. under nitrogen was added triethylsilane (0.88 mL, 5.5 mmol) followed by trifluoroacetic acid (0.39 mL, 5.1 mmol) dropwise from a syringe. Each drop of TFA resulted in a yellow color which persisted slightly upon complete addition. After 1.5 h at 0° C., and was quenched by sat. aq. NaHCO$_3$. The aqueous layer was extracted 2×DCM, and the combined organics were dried over anhyd. sodium sulfate, filtered, and concentrated in vacuo to give an oil. The material was further purified by silica gel chromatography, ISCO, 40 g, 0-10% EtOAc/hexanes to give 0.94 g of a mixture of 5-(1-phenylethyl)benzofuran and 5-(1-phenylvinyl)benzofuran. This material was taken up in 1 mL DCM at 0° C. and triethylsilane (0.629 mL, 3.94 mmol) was added followed by trifluoroacetic acid (1.52 mL, 19.7 mmol) dropwise via syringe. The reaction became yellow upon complete addition. After 15 min, the reaction was quenched at 0° C. by addition of 1 N NaOH and diluted with DCM. The aq. layer was extracted 1×DCM, and the combined organics were dried over anhyd sodium sulfate, filtered, and concentrated in vacuo. The resulting oil was purified by silica gel chromatography, ISCO, 80 g, 0-15% EtOAc/hexanes. The product-containing fractions were concentrated in vacuo to give 5-(1-phenylethyl)benzofuran as a clear and colorless oil. 1H NMR (400 MHz, DMSO-d$_6$) δ ppm 7.94 (d, J=2.0 Hz, 1H), 7.53 (s, 1H), 7.48 (d, J=8.5 Hz, 1H), 7.24-7.34 (m, 4H), 7.12-7.22 (m, 2H), 6.89 (d, J=2.0 Hz, 1H), 4.26 (q, J=7.5 Hz, 1H), 1.62 (d, J=7.0 Hz, 3H).

5-(1-Phenylethyl)benzofuran-2-ylboronic acid

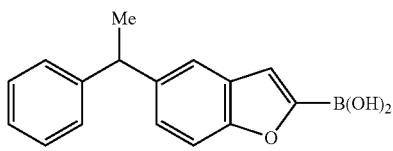

To a solution of 5-(1-phenylethyl)benzofuran (0.713 g, 3.21 mmol) in 32 mL THF at −78° C. was added 1-butyllithium (1.54 mL, 3.85 mmol) slowly dropwise. The reaction was allowed to stir for 25 min, at which point triisopropyl borate (1.08 mL, 4.72 mmol) was added slowly dropwise. After 0.5 h, the bath was removed and the reaction was allowed to warm to ambient temperature. After 0.5 h, 50 mL 2N HCl was added. The mixture was extracted 2×MTBE, and the combined organics were washed with brine, dried over anhyd. sodium sulfate, filtered, and concentrated in vacuo to give an oil. Treatment with 30 mL hexanes and sonication for 5 min resulted in a white solid which was collected by filtration and dried in vacuo to give 5-(1-phenylethyl)benzofuran-2-ylboronic acid. 1H NMR (400 MHz, DMSO-d$_6$) δ ppm 8.49-8.57 (m, 2H), 7.58 (s, 1H), 7.46 (d, J=8.5 Hz, 1H), 7.40 (s, 1H), 7.12-7.32 (m, 6H), 4.26 (q, J=7.5 Hz, 1H), 1.62 (d, J=7.0 Hz, 3H).

1-((3-Fluoro-4-(5-(1-phenylethyl)benzofuran-2-yl)phenyl)methyl)azetidine-3-carboxylic acid

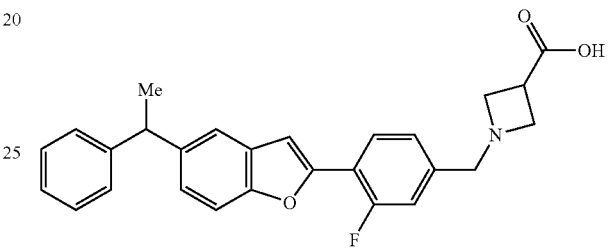

According to Scheme B2 and general procedure F, methyl 1-(4-bromo-3-fluorobenzyl)azetidine-3-carboxylate (0.241 g, 0.797 mmol) and 5-(1-phenylethyl)benzofuran-2-ylboronic acid (0.212 g, 0.797 mmol) were employed to give methyl 1-((3-fluoro-4-(5-(1-phenylethyl)benzofuran-2-yl)phenyl)methyl)azetidine-3-carboxylate. According to Scheme B2 and general procedure H, methyl 1-((3-fluoro-4-(5-(1-phenylethyl)benzofuran-2-yl)phenyl)-methyl)azetidine-3-carboxylate (0.275 g, 0.620 mmol) provided 1-((3-fluoro-4-(5-(1-phenylethyl)benzofuran-2-yl)phenyl)methyl)azetidine-3-carboxylic acid as a white solid [hS1P1 EC$_{50}$=99 nM]. 1H NMR (400 MHz, DMSO-d$_6$) δ ppm 7.89 (t, J=8.0 Hz, 1H), 7.59 (s, 1H), 7.53 (d, J=8.5 Hz, 1H), 7.20-7.35 (m, 8H), 7.12-7.20 (m, 1H), 4.28 (q, J=7.0 Hz, 1H), 3.60 (s, 2H), 3.18-3.46 (m, 5H), 1.64 (d, J=7.5 Hz, 3H). MS (ESI) m/z: Calculated: 429.2; Observed: 430.2 (M$^+$+1).

Compound 91

1-((4-(5-(Difluoro(phenyl)methyl)benzofuran-2-yl)-3-fluorophenyl)methyl)azetidine-3-carboxylic acid 5-(2-Phenyl-1,3-dithiolan-2-yl)benzofuran

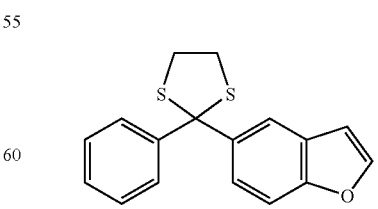

To a solution of benzofuran-5-yl(phenyl)methanone (2.45 g, 11.0 mmol), glacial acetic acid (1.27 mL, 22.0 mmol) and 1,2-ethanedithiol (1.39 mL, 16.5 mmol) in 30 mL DCM at ambient temperature was added boron trifluoride diethyletherate (1.38 mL, 11.0 mmol). The reaction was allowed to stir overnight, and was quenched by the addition of 1N NaOH. The aq. layer was extracted 1×DCM, and the combined organics were dried over sodium sulfate, filtered, and concentrated. Purification by silica gel chromatography, ISCO, 0-20% EtOAc/hexanes provided 5-(2-phenyl-1,3-dithiolan-2-yl)benzofuran as a clear/colorless oil. 1H NMR (400 MHz, DMSO-$d_6$) δ ppm 7.99 (d, J=2.0 Hz, 1H), 7.84 (d, J=2.0 Hz, 1H), 7.48-7.57 (m, 3H), 7.38-7.45 (m, 1H), 7.29-7.36 (m, 2H), 7.24 (t, J=7.3 Hz, 1H), 6.96 (d, J=2.0 Hz, 1H) 3.43 (s, 4H).

5-(Difluoro(phenyl)methyl)benzofuran

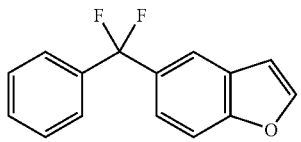

To a solution of selectfluor(tm) fluorinating reagent (3.70 g, 10.5 mmol) in 30 mL HF*py at 0° C. in a nalgene bottle was added a solution of 5-(2-phenyl-1,3-dithiolan-2-yl)benzofuran (1.56 g, 5.23 mmol) in 15 mL DCM (5 mL rinse) slowly via pipette. The dark red reaction was allowed to stir for 15 min, at which point it was quenched with ice and basified with 1N and 10N NaOH. Et$_2$O (250 mL) was added and the organic layer was washed 2×1N HCl, 1× brine, dried over sodium sulfate, filtered, and concentrated in vacuo. The resulting material was purified by silica gel chromatography, ISCO, 0-20% EtOAc/hexanes to give 5-(difluoro(phenyl)methyl)benzofuran. 1H NMR (400 MHz, DMSO-$d_6$) δ ppm 8.10 (d, J=2.0 Hz, 1H), 7.83 (s, 1H), 7.71 (d, J=9.0 Hz, 1H), 7.48-7.58 (m, 5H), 7.45 (d, J=8.5 Hz, 1H), 7.04 (s, 1H).

Ethyl 1-((4-(5-(difluoro(phenyl)methyl)benzofuran-2-yl)-3-fluorophenyl)methyl)azetidine-3-carboxylate

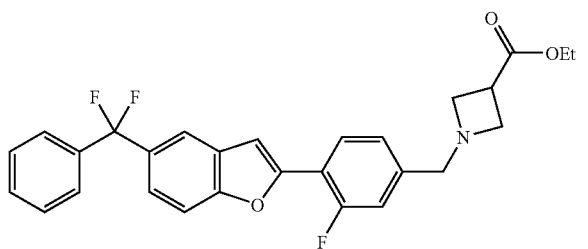

To a solution of 5-(difluoro(phenyl)methyl)benzofuran (0.684 g, 2.8 mmol) in 28 mL THF at −78° C. under nitrogen was added butyllithium, 2.5M solution in hexanes (1.3 mL, 3.4 mmol) dropwise. The clear solution was allowed to stir for 30 min, at which point triisopropyl borate (0.97 mL, 4.2 mmol) was added. After 30 min, the bath was removed and the reaction allowed reaching ambient temperature. After 30 min, 28 mL 2N HCl was added, and the reaction was diluted with MTBE. The organic layer was washed with brine and dried with anhyd sodium sulfate, filtered, and concentrated to a ] clear oil. Hexanes was added to give a white solid, which was collected by filtration. A portion of the unpurified material was carried forward as follows: ethyl 1-(4-bromo-3-fluorobenzyl)azetidine-3-carboxylate (0.150 g, 0.474 mmol) and 5-(difluoro(phenyl)methyl)benzofuran-2-ylboronic acid (0.273 g, 0.949 mmol) were reacted according to Scheme B2 and general procedure F to give ethyl 1-((4-(5-(difluoro(phenyl)methyl)benzofuran-2-yl)-3-fluorophenyl)methyl)azetidine-3-carboxylate. 1H NMR (400 MHz, DMSO-$d_6$) δ ppm 7.94 (t, J=8.0 Hz, 1H), 7.89 (s, 1H), 7.76 (d, J=8.5 Hz, 1H), 7.45-7.60 (m, 6H), 7.38 (d, J=3.0 Hz, 1H), 7.26-7.33 (m, 2H), 4.10 (q, J=7.0 Hz, 2H), 3.63 (s, 2H), 3.43-3.51 (m, 2H), 3.20-3.38 (m, 3H), 1.19 (t, J=7.0 Hz, 3H).

1-((4-(5-(Difluoro(phenyl)methyl)benzofuran-2-yl)-3-fluorophenyl)methyl)azetidine-3-carboxylic acid

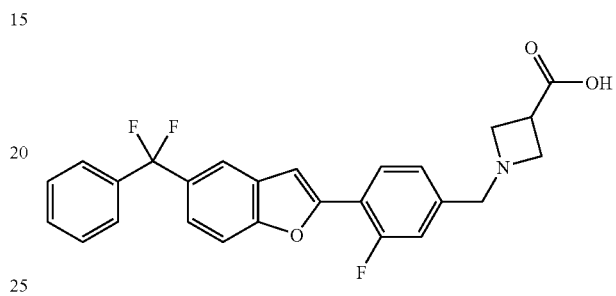

Synthesized according to Scheme B2 and general procedure H using ethyl 1-((4-(5-(difluoro(phenyl)methyl)benzofuran-2-yl)-3-fluorophenyl)methyl)azetidine-3-carboxylate (0.181 g, 0.377 mmol) to give 1-((4-(5-(difluoro(phenyl)methyl)benzofuran-2-yl)-3-fluorophenyl)methyl)azetidine-3-carboxylic acid as a white solid [hS1P1 $EC_{50}$=13 nM]. 1H NMR (400 MHz, DMSO-$d_6$) δ ppm 7.93 (t, J=8.0 Hz, 1H), 7.89 (s, 1H), 7.76 (d, J=8.5 Hz, 1H), 7.45-7.61 (m, 6H), 7.38 (d, J=3.0 Hz, 1H), 7.26-7.33 (m, 2H), 3.62 (s, 2H), 3.39-3.48 (m, 2H), 3.17-3.32 (m, 3H). MS (ESI) m/z: Calculated: 451.1; Observed: 452.2 (M$^+$+1).

Compound 92

1-((4-(6-Benzylbenzofuran-2-yl)-3-fluorophenyl)methyl)azetidine-3-carboxylic acid 6-Benzylbenzofuran-2-ylboronic acid

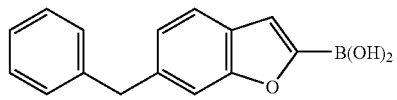

To a purple mixture of benzofuran-6-ol (1.85 g, 13.8 mmol) and N,N-diisopropylethylamine 99% (7.21 mL, 41.4 mmol) in 50 mL DCM was added 1,1,1-trifluoro-n-phenyl-n-((trifluoromethyl)sulfonyl)methanesulfonamide (4.93 g, 13.8 mmol). The reaction became light blue. After 2 h, the reaction was light yellow. The reaction was quenched with saturated aq. sodium bicarbonate, and the aqueous layer was extracted with DCM. The combined organics were dried over anhyd sodium sulfate, filtered, and concentrated in vacuo. The resulting material was purified by silica gel chromatography, 0-15% EtOAc/hexanes, to give benzofuran-6-yl trifluoromethanesulfonate as a semi-solid. A portion of the unpurified material was carried on as follows. A mixture of 9-benzyl-9-bora-bicyclo[3.3.1]nonane 0.5M in THF (23 mL, 11 mmol), benzofuran-6-yl trifluoromethanesulfonate (1.50 g, 5.6 mmol), potassium phosphate (3.6 g, 17 mmol), benzofuran-6-yl trifluoromethanesulfonate (1.50 g, 5.6 mmol), S-Phos (0.19 g, 0.45 mmol), Pd(OAc)$_2$ (0.051 g, 0.23 mmol)

was flushed with argon, sealed, and heated to 60° C. overnight. The green/gray reaction was cooled and filtered through celite rinsing with Et₂O. The filtrate was concentrated and adsorbed onto 15 g silica gel and dried. The material was purified by silica gel chromatography, ISCO, 80 g, 0-10% EtOAc/hexanes to give 6-benzylbenzofuran. A portion of this material was processed as follows. To a solution of 6-benzylbenzofuran (0.663 g, 3.18 mmol) in 30 mL THF at −78° C. was added 1-butyllithium 2.5 M in hexanes (1.53 mL, 3.82 mmol) slowly dropwise. The reaction was allowed to stir for 25 min, at which point triisopropyl borate (1.08 mL, 4.68 mmol) was added slowly dropwise. After 0.5 h, the bath was removed and the reaction was allowed to warm to ambient temperature. After 10 min, 50 mL 2N HCl was added. The mixture was diluted with MTBE, and the organics were washed with brine, dried over anhyd. MgSO₄, filtered, and concentrated in vacuo to give an oil. The oil was treated with hexanes to give a solid, and the material was filtered and rinsed with hexanes and dried in vacuo to give 6-benzylbenzofuran-2-ylboronic acid as a white solid. 1H NMR (400 MHz, DMSO-d₆) δ ppm 8.47 (s, 2H), 7.57 (d, J=8.0 Hz, 1H), 7.42 (s, 1H), 7.39 (s, 1H), 7.24-7.33 (m, 4H), 7.15-7.22 (m, 1H), 7.10 (d, J=8.0 Hz, 1H), 4.06 (s, 2H).

Ethyl 1-((4-(6-benzylbenzofuran-2-yl)-3-fluorophenyl)methyl)azetidine-3-carboxylate

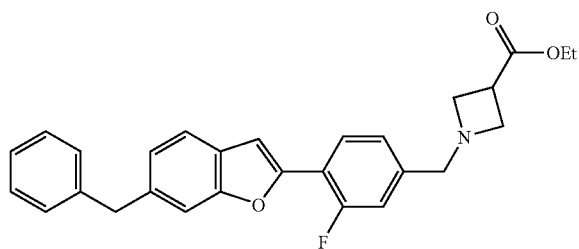

Synthesized according to Scheme B2 and general procedure F using ethyl 1-(4-bromo-3-fluorobenzyl)azetidine-3-carboxylate (0.150 g, 0.474 mmol) and 6-benzylbenzofuran-2-ylboronic acid (0.155 g, 0.617 mmol) to give ethyl 1-((4-(6-benzylbenzofuran-2-yl)-3-fluorophenyl)methyl)azetidine-3-carboxylate. MS (ESI) m/z: Calculated: 443.2; Observed: 444.1 (M⁺+1).

1-((4-(6-Benzylbenzofuran-2-yl)-3-fluorophenyl)methyl)azetidine-3-carboxylic acid

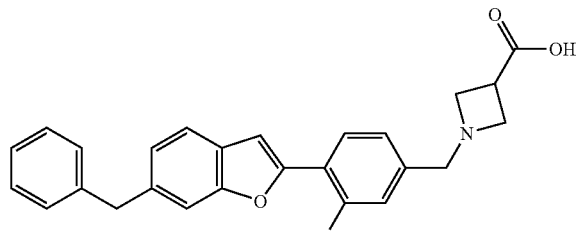

Synthesized according to Scheme B2 and general procedure H using ethyl 1-((4-(6-benzylbenzofuran-2-yl)-3-fluorophenyl)methyl)azetidine-3-carboxylate (0.190 g, 0.428 mmol) to give 1-((4-(6-benzylbenzofuran-2-yl)-3-fluorophenyl)methyl)azetidine-3-carboxylic acid as a white solid [hS1P1 EC₅₀=7 nM]. 1H NMR (400 MHz, DMSO-d₆) δ ppm 7.89 (t, J=8.0 Hz, 1H), 7.60 (d, J=8.0 Hz, 1H), 7.50 (s, 1H), 7.21-7.34 (m, 7H), 7.15-7.21 (m, 2H), 4.07 (s, 2H), 3.60 (s, 2H), 3.37-3.49 (m, 2H), 3.15-3.30 (m, 3H). MS (ESI) m/z: Calculated: 415.2; Observed: 416.1 (M⁺+1).

Compound 93

1-((3-Fluoro-4-(5-(pyridin-2-ylmethyl)benzofuran-2-yl)phenyl)methyl)azetidine-3-carboxylic acid Benzofuran-5-yl(pyridin-2-yl)methanol

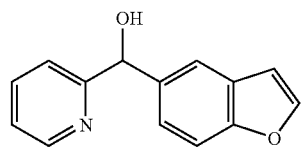

Under argon at −78° C., a mixture of 2-bromopyridine (1.11 g, 7.05 mmol) in THF (30 mL) was dropwise treated with n-BuLi (1.05 equiv. 2.7 mL of 2.5M BuLi in hexanes) over a period of 10 min, and stirred for 10 min. The resulting brown solution was treated dropwise with a solution of benzofuran-5-carbaldehyde (0.937 g, 6.41 mmol) in THF (10 mL) and continued to stir for 15 min at −78° C. The mixture was treated with MeOH (3 mL), followed by H₂O (20 mL) and warmed to 4° C. The mixture was treated with EtOAc, the layers separated, and the aqueous layer extracted 1× with EtOAc. The combined organic layers were dried over MgSO₄ and evaporated, which resulted in a dark yellow oil which was used without further purification.

2-(Benzofuran-5-ylmethyl)pyridine

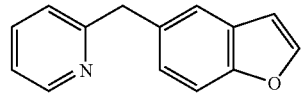

A solution of benzofuran-5-yl(pyridin-2-yl)methanol (500 mg, 2220 μmol) in DCM (10 mL) at 0° C. was treated with tribromophosphine (314 μL, 3330 μmol) and stirred for 1.5 h. The mixture was diluted with CHCl₃, washed with sat. aqueous KHCO₃, dried over MgSO₄, and evaporated. A suspension of the crude material and 10% Pd—C (50 mg) in EtOAc (5 mL) and MeOH (3 mL) was stirred under 1 atm H₂ at 24° C. for 1 h. The solids were filtered off (Celite) and washed with EtOAc. The filtrate was evaporated and purified by flash chromatography (hexanes to EtOAc to 5% MeOH in DCM) to give 2-(benzofuran-5-ylmethyl)pyridine as a yellow foam. 1H NMR (400 MHz, CD₃OD) δ ppm 8.71 (br. s, 1H), 8.17 (t, J=7.6 Hz, 1H), 7.70-7.64 (m, 3H), 7.50-7.48 (m, 2H), 7.29 (d, J=8.1 Hz, 1H), 6.76 (s, 1H), 4.71 (s, 2H). MS (ESI) m/z: Calculated: 209.1; Observed: 210.0 (M⁺+1).

5-(Pyridin-2-ylmethyl)benzofuran-2-ylboronic acid

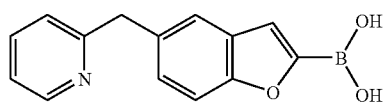

A solution of 2-(benzofuran-5-ylmethyl)pyridine (66 mg, 315 mmol) in THF (2 mL) was cooled to −78° C. (under argon), treated with 2.5 M n-BuLi (in hexanes, 2.5 equiv, 0.315 mL) and stirred for 2 min, warmed to 0° C. for 30 min, cooled to −78° C., and treated with triisopropyl borate (178 µL, 946 µmol). After 5 min, cooling was removed, the mixture slowly warmed to room temperature and stirred for 2 h. The mixture was diluted with EtOAc, washed with 1× with brine, dried over MgSO₄ and evaporated yielding yellow solids used without further purification. MS (ESI) m/z: Calculated: 253.1; Observed: 254.1 (M⁺+1).

Ethyl 1-((3-fluoro-4-(5-(pyridin-2-ylmethyl)benzofuran-2-yl)phenyl)methyl)azetidine-3-carboxylate

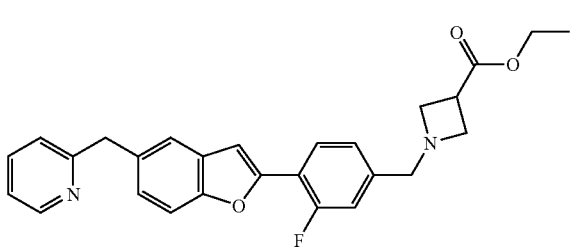

In a sealed flask, a mixture of 5-(pyridin-2-ylmethyl)benzofuran-2-ylboronic acid (214 mg, 846 µmol) and potassium acetate (166 mg, 1691 µmol) was set under argon, treated with bis{di(ᵗbutyl)phenyl}palladium(II) dichloride (32 mg, 51 µmol), followed by a solution of ethyl 1-(4-bromo-3-fluorobenzyl)azetidine-3-carboxylate (267 mg, 846 µmol) in EtOH (5 mL). The resulting suspension was degassed again and heated to 80° C. for 2.5 h. The mixture was cooled to ~10° C. and dropwise treated with H₂O (15 mL). The mixture was extracted 2× with EtOAc. The combined organic layers were dried over MgSO₄ and evaporated. Purification by flash chromatography (DCM to DCM/MeOH=4:1) gave ethyl 1-((3-fluoro-4-(5-(pyridin-2-ylmethyl)benzofuran-2-yl)phenyl)methyl)azetidine-3-carboxylate as a yellow foam.

1-((3-Fluoro-4-(5-(pyridin-2-ylmethyl)benzofuran-2-yl)phenyl)methyl)azetidine-3-carboxylic acid

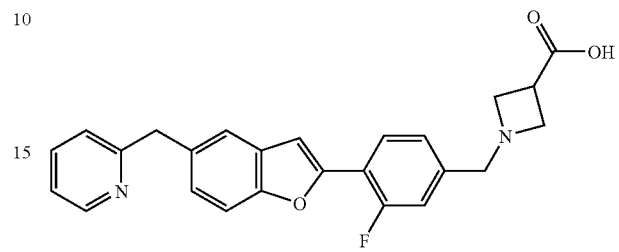

A mixture of ethyl 1-(3-fluoro-4-(5-(pyridin-2-ylmethyl)benzofuran-2-yl)benzyl)azetidine-3-carboxylate (31 mg, 70 µmol) in THF (2 mL) was treated with 1M LiOH in H₂O (0.4 mL) and stirred at 24° C. for 3 h, neutralized with 0.1M aqueous HCl, and evaporated. Purification by SFC (super-critical flash chromatography) resulted in title compound as its diethylammonium salt [hS1P1 EC₅₀=31 nM]. 1H NMR (400 MHz, CD₃OD) δ ppm 8.48 (d, J=0.8 Hz, 1H), 8.02 (t, J=7.9 Hz, 1H), 7.78 (t, J=5.9 Hz, 1H), 7.54 (s, 1H), 7.48 (d, J=10.0 Hz, 1H), 7.33-7.22 (m, 6H), 4.25 (s, 2H), 3.95 (s, 2H), 3.82 (t, J=8.6 Hz, 2H), 3.68 (t, J=8.5 Hz, 2H), 3.36-3.34 (m, 1H, partially overlapping with CD₃OH signal), 3.05 (q, J=7.4 Hz, 2H), 1.31 (t, J=7.2 Hz, 3H). MS (ESI) m/z: Calculated: 416.2; Observed: 417.2 (M⁺+1).

Compound 94

1-((3-Fluoro-4-(5-(thiazol-2-ylmethyl)benzofuran-2-yl)phenyl)methyl)azetidine-3-carboxylic acid Benzofuran-5-yl(thiazol-2-yl)methanol

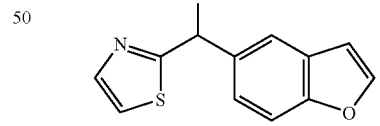

Under argon at −78° C., a mixture of thiazole (1.13 g, 13.2 mmol) in THF (50 mL) was dropwise treated with 2.5M n-BuLi (1.05 equiv., 5.04 mL, in hexanes) over a period of 10 min and stirred for 45 min. The resulting yellow mixture was treated dropwise with a solution of benzofuran-5-carbaldehyde (1.76 g, 12.0 mmol) in THF (10 mL). Cooling was removed after addition. When the mixture reached room temperature, it was treated with EtOAc, washed with 1M aqueous HCl and brine, dried over MgSO₄, and evaporated, to give benzofuran-5-yl(thiazol-2-yl)methanol as a yellow oil. 1H NMR (400 MHz, CDCl₃) δ ppm 7.71-7.75 (m, 2H), 7.64 (d, J=2.2 Hz, 1H), 7.50 (d, J=8.6 Hz, 1H), 7.39 (dd, J=8.6, 1.7 Hz, 1H), 7.29 (d, J=3.1 Hz, 1H), 6.76-6.75 (m, 1H), 6.17 (s, 1H).

2-(Benzofuran-5-ylmethyl)thiazole

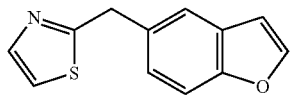

Under argon at 24° C., crude benzofuran-5-yl(thiazol-2-yl)methanol (2.50 g, 10.8 mmol) was dissolved in 1,2-dichloroethane (40 mL), treated with triethylsilane (3.14 g, 27.0 mmol) and trifluoroacetic acid (1.25 mL, 16.2 mmol), and heated to reflux for 20 h. The mixture was diluted with EtOAc and ice, washed 1× with saturated aqueous NaHCO$_3$, brine, dried over MgSO$_4$, and evaporated. Purification by flash chromatography (hexanes to hexanes/EtOAc=3:2) gave 2-(benzofuran-5-ylmethyl)thiazole as a yellow oil. 1H NMR (400 MHz, CDCl$_3$) δ ppm 7.71 (d, J=3.3 Hz, 1H), 7.61 (d, J=2.3 Hz, 1H), 7.55 (br. s, 1H), 7.47 (d, J=8.4 Hz, 1H), 7.27-7.24 (m, 1H), 7.19 (d, J=3.3 Hz, 1H), 6.74-6.73 (m, 1H), 4.44 (s, 2H). MS (ESI) m/z: Calculated: 215.0; Observed: 216.1 (M$^+$+1).

5-(Thiazol-2-ylmethyl)benzofuran-2-ylboronic acid

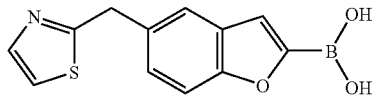

A solution of 2-(benzofuran-5-ylmethyl)thiazole (0.68 g, 3 mmol) in THF (20 mL) was cooled to −78° C. (under argon), treated with 2.5 M n-BuLi (3.0 equiv, 3.6 mL, in hexanes), and stirred for 2 min, warmed to 0° C. for 30 min, cooled to −78° C., and treated with triisopropyl borate (1 mL, 6 mmol). After 5 min, cooling was removed and the mixture slowly warmed to room temperature and stirred for 2 h. The mixture was diluted with EtOAc, washed 1× with brine, dried over MgSO$_4$ and evaporated to give 5-(thiazol-2-ylmethyl)benzofuran-2-ylboronic acid as a yellow solid. MS (ESI) m/z: Calculated: 259.1; Observed: 260.4 (M$^+$+1).

Ethyl 1-((3-fluoro-4-(5-(thiazol-2-ylmethyl)benzofuran-2-yl)phenyl)methylazetidine-3-carboxylate

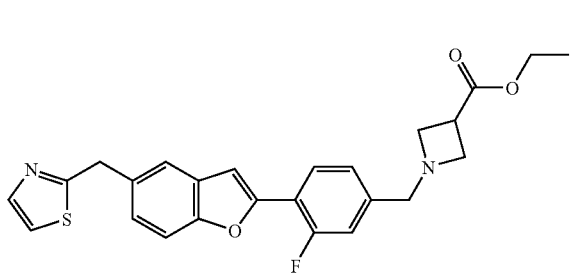

In a sealed flask, a mixture of 5-(thiazol-2-ylmethyl)benzofuran-2-ylboronic acid (373 mg, 1440 μmol) and potassium acetate (283 mg, 2879 μmol) was set under argon, treated with bis{di($^t$butyl)phenyl}palladium(II) dichloride (53.7 mg, 86.4 mmol), followed by a solution of ethyl 1-(4-bromo-3-fluorobenzyl)azetidine-3-carboxylate (455 mg, 1440 μmol) in EtOH (10 mL). The resulting suspension was degassed again and heated to 80° C. for 2.5 h. The mixture was cooled to 24° C., treated with H$_2$O (15 mL) and extracted 2× with EtOAc. The combined organic layers were washed with brine, dried over MgSO$_4$ and evaporated. Purification by flash chromatography (DCM to DCM/MeOH=19:1) gave ethyl 1-((3-fluoro-4-(5-(thiazol-2-ylmethyl)benzofuran-2-yl)phenyl)methylazetidine-3-carboxylate as a yellow foam. MS (ESI) m/z: Calculated: 450.5; Observed: 451.2 (M$^+$+1).

1-((3-Fluoro-4-(5-(thiazol-2-ylmethyl)benzofuran-2-yl)phenyl)methyl)azetidine-3-carboxylic acid

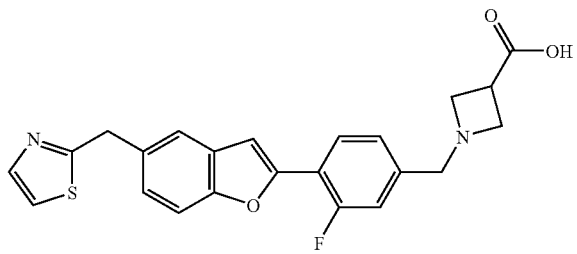

A mixture of ethyl 1-((3-fluoro-4-(5-(thiazol-2-ylmethyl)benzofuran-2-yl)phenyl)methyl)azetidine-3-carboxylate (290 mg, 644 μmol) in THF (5 mL) was treated with a solution of LiOH (27 mg) in H$_2$O (2 mL) and stirred at 24° C., neutralized with 0.1M aqueous HCl, and concentrated. The resulting solids were collected by filtration and purified by RP-HPLC to give 1-((3-fluoro-4-(5-(thiazol-2-ylmethyl)benzofuran-2-yl)phenyl)methyl)azetidine-3-carboxylic acid as a white solid [hS1P1 EC$_{50}$=76 nM]. $^1$H NMR (400 MHz, DMSO-d6) δ ppm 7.93-7.91 (m, 1H), 7.73 (s, 1H), 7.66-7.58 (m, 3H), 7.32-7.28 (m, 4H), 4.44 (s, 2H), 3.65 (br. s, 2H), 3.46 (br. s, 2H), 3.30-3.26 (m, 3H). MS (ESI) m/z: Calculated: 422.1; Observed: 423.2 (M$^+$+1).

Compound 95

1-((3-Fluoro-4-(5-(1-phenylpropyl)benzofuran-2-yl)phenyl)methyl)azetidine-3-carboxylic acid 1-(Benzofuran-5-yl)-1-phenylpropan-1-ol

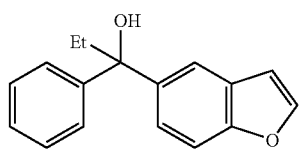

To a solution of ethylmagnesium chloride (2M in tetrahydrofuran, 10.63 mL, 21.26 mmol) under nitrogen at room temperature was added zinc chloride (0.5M in tetrahydrofuran, 5.67 mL, 2.84 mmol) via syringe. The mixture was stirred at room temperature for 1 h. The reaction mixture was brought to 0° C. and benzofuran-5-yl(phenyl)methanone (3.15 g, 14.17 mmol) in tetrahydrofuran (10 mL) was added via syringe. The reaction mixture was stirred at 0° C. for 2.5 h. The reaction mixture was cooled to room temperature and quenched with saturated aqueous NH₄Cl. EtOAc was added, and the aqueous layer was separated and extracted with EtOAc (2×). The combined organic layers were washed with brine, dried (MgSO₄), and concentrated to give a crude oil. The crude product was purified by silica flash chromatography (0-100% DCM/hexanes) to give 1-(benzofuran-5-yl)-1-phenylpropan-1-ol as an off-white oil. 1H NMR (400 MHz, Chloroform-d) δ ppm 7.69 (1H, d, J=1.6 Hz), 7.60 (1H, d, J=2.2 Hz), 7.39-7.45 (3H, m), 7.28-7.34 (3H, m), 7.22 (1H, tt, J=7.2, 1.4 Hz), 6.73 (1H, dd, J=2.2, 1.0 Hz), 2.38 (2H, q, J=7.3 Hz), 2.09 (1H, s), 0.90 (3H, t, J=7.3 Hz).

5-(1-Phenylpropyl)benzofuran

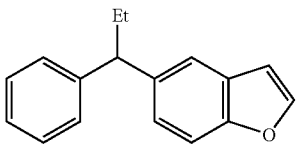

To a stirred solution of 1-(benzofuran-5-yl)-1-phenylpropan-1-ol (3.14 g, 12.4 mmol) and triethylsilane (2.39 mL, 14.9 mmol) in DCM (10 mL) under nitrogen at 0° C. was added trifluoroacetic acid (4.62 mL, 62.2 mmol) dropwise via syringe. The reaction mixture was stirred at 0° C. for 3 h. Additional triethylsilane (2.39 mL, 14.9 mmol) followed by trifluoroacetic acid (4.62 mL, 62.2 mmol) were added via syringe, and the reaction was brought to room temperature and stirred for 2 h. The reaction mixture was quenched with 1M aqueous NaOH. DCM was added, and the aqueous layer was separated and extracted again with DCM. The combined organic layers were dried (MgSO₄) and concentrated to give a crude oil. The crude product was purified by silica flash chromatography to give 5-(1-phenylpropyl)-benzofuran as a transparent oil. MS (ESI) m/z: Calculated: 236.1; Observed: 237.2 (M⁺+1).

5-(1-Phenylpropyl)benzofuran-2-ylboronic acid

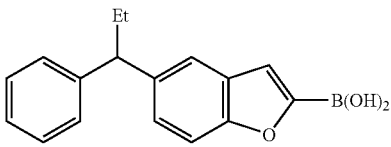

Synthesized according to Scheme 1 and general procedure C using 5-(1-phenylpropyl)benzofuran (2.30 g, 9.73 mmol) to give 5-(1-phenylpropyl)benzofuran-2-ylboronic acid. 1H NMR (400 MHz, DMSO-d₆) δ ppm 8.50 (2H, s), 7.60 (1H, s), 7.45 (1H, d, J=8.6 Hz), 7.39 (1H, s), 7.23-7.34 (5H, m), 7.14 (1H, t, J=7.1 Hz), 3.91 (1H, t, J=7.7 Hz), 2.08 (2H, dq, J=7.7, 7.2 Hz), 0.83 (3H, t, J=7.2 Hz).

Methyl 1-((3-fluoro-4-(5-(1-phenylpropyl)benzofuran-2-yl)phenyl)methyl)azetidine-3-carboxylate

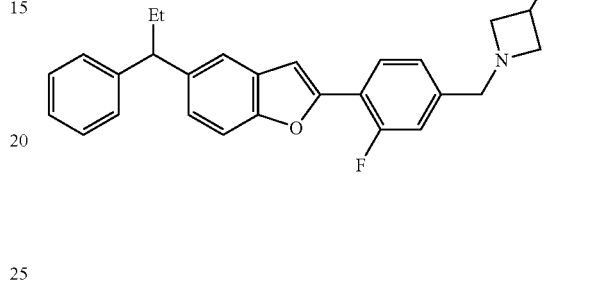

Synthesized according to Scheme B2 and general procedure F using methyl 1-(4-bromo-3-fluorobenzyl)azetidine-3-carboxylate (1.76 g, 5.81 mmol) and 5-(1-phenylpropyl)-benzofuran-2-ylboronic acid (1.63 g, 5.81 mmol) to give methyl 1-((3-fluoro-4-(5-(1-phenylpropyl)benzofuran-2-yl)phenyl)methyl)azetidine-3-carboxylate. MS (ESI) m/z: Calculated: 457.2; Observed: 458.3 (M⁺+1).

1-((3-Fluoro-4-(5-(1-phenylpropyl)benzofuran-2-yl)phenyl)methyl)azetidine-3-carboxylic acid

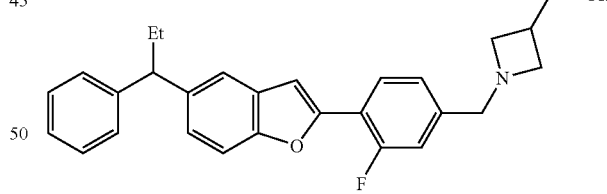

Synthesized according to Scheme B2 and general procedure H using methyl 1-((3-fluoro-4-(5-(1-phenylpropyl)benzofuran-2-yl)phenyl)methyl)azetidine-3-carboxylate (151 mg, 330 μmol) to give 1-((3-fluoro-4-(5-(1-phenylpropyl) benzofuran-2-yl)phenyl)methyl)azetidine-3-carboxylic acid as a white solid. 1H NMR (400 MHz, DMSO-d₆) δ ppm 7.89 (1H, dd, J=8.0, 8.0 Hz), 7.62 (1H, s), 7.53 (1H, d, J=8.6 Hz), 7.22-7.35 (8H, m), 7.15 (1H, t, J=7.1 Hz), 3.93 (1H, t, J=7.7 Hz), 3.60 (2H, s), 3.37-3.45 (2H, m), 3.16-3.24 (3H, m), 2.09

(2H, dq, J=7.7, 7.1 Hz), 0.84 (3H, t, J=7.1 Hz). MS (ESI) m/z: Calculated: 443.2; Observed: 444.2 (M⁺+1).

Compound 96

1-(3-(5-Benzylbenzofuran-2-yl)benzyl)azetidine-3-carboxylic acid

Methyl 1-(3-bromobenzyl)azetidine-3-carboxylate

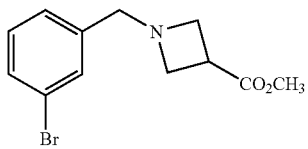

Synthesized according to Scheme B2, Step 1 from 3-bromobenzaldehyde and azetidine-3-carboxylic acid to give methyl 1-(3-bromobenzyl)azetidine-3-carboxylate as a clear oil. MS (ESI) m/z: Calculated: 283.0; Observed: 284 (M⁺+1).

Methyl 1-(3-(5-benzylbenzofuran-2-yl)benzyl)azetidine-3-carboxylate

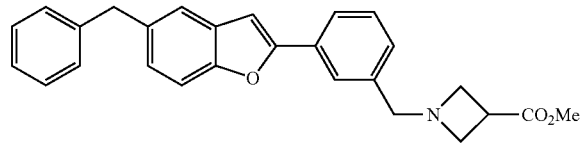

Synthesized according to Scheme B2, Step 2 and general procedure F from 5-benzylbenzofuran-2-ylboronic acid and methyl 1-(3-bromobenzyl)azetidine-3-carboxylate to give methyl 1-(3-(5-benzylbenzofuran-2-yl)benzyl)azetidine-3-carboxylate as a light yellow oil. MS (ESI) m/z: Calculated: 411.2; Observed: 412 (M⁺+1).

1-(3-(5-Benzylbenzofuran-2-yl)benzyl)azetidine-3-carboxylic acid

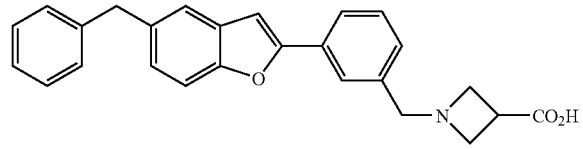

Synthesized according to Scheme B2, Step 3 and general procedure H from methyl 1-(3-(5-benzylbenzofuran-2-yl)benzyl)azetidine-3-carboxylate to give 1-(3-(5-benzylbenzofuran-2-yl)benzyl)azetidine-3-carboxylic acid as a white solid [hS1P1 $EC_{50}$=4834 nM]. 1H NMR (400 MHz, DMSO-d₆) δ ppm 7.76-7.85 (m, 2H), 7.54 (d, J=8.4 Hz, 1H), 7.49 (s, 1H), 7.45 (t, J=7.6 Hz, 1H), 7.38 (s, 1H), 7.30-7.35 (m, 1H), 7.25-7.30 (m, 4H), 7.16-7.21 (m, 2H), 4.04 (s, 2H), 3.74 (s, 2H), 3.54 (s, 2H), 3.31 (s, 4H). MS (ESI) m/z: Calculated: 397.2; Observed: 398 (M⁺+1).

Compound 97

1-((3-Fluoro-4-(5-(2-phenylpropan-2-yl)benzofuran-2-yl)phenyl)methyl)azetidine-3-carboxylic acid 1-(2,2-Diethoxyethoxy)-4-(2-phenylpropan-2-yl)benzene

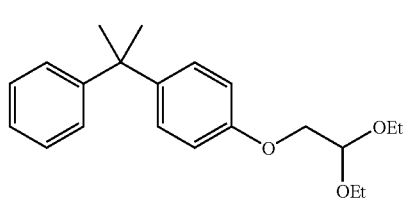

Synthesized according to Scheme 1, Step 1 from (4-(2-phenylisopropyl)phenol) and 2-bromo-1,1-diethoxyethane to give 1-(2,2-diethoxyethoxy)-4-(2-phenylpropan-2-yl)benzene as a yellow-orange oil. 1H NMR (400 MHz, CHLOROFORM-d) δ ppm 7.19-7.29 (m, 4H), 7.14-7.19 (m, 1H), 7.13 (d, J=9.0 Hz, 2H), 6.82 (d, J=8.5 Hz, 2H), 4.82 (t, J=5.3 Hz, 1H), 3.98 (d, J=5.0 Hz, 2H), 3.70-3.81 (m, 2H), 3.57-3.68 (m, 2H), 1.65 (s, 6H), 1.24 (t, J=7.0 Hz, 6H).

5-(2-Phenylpropan-2-yl)benzofuran

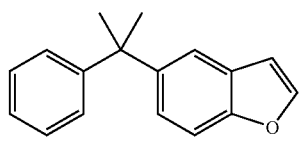

Synthesized according to Scheme 1, Step 2 from 1-(2,2-diethoxyethoxy)-4-(2-phenylpropan-2-yl)benzene to give 5-(2-phenylpropan-2-yl)benzofuran as a light yellow oil. 1H NMR (400 MHz, CHLOROFORM-d) δ ppm 7.58 (d, J=2.0 Hz, 1H), 7.52 (s, 1H), 7.36 (d, J=8.5 Hz, 1H), 7.22-7.30 (m, 4H), 7.14-7.20 (m, 1H), 7.11 (d, J=8.5 Hz, 1H), 6.71 (s, 1H), 1.74 (s, 6H).

5-(2-Phenylpropan-2-yl)benzofuran-2-ylboronic acid

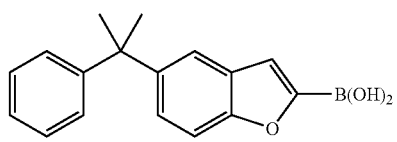

Synthesized according to Scheme 1, Step 3 from 5-(2-phenylpropan-2-yl)benzofuran to give 5-(2-phenylpropan-2-yl)benzofuran-2-ylboronic acid as a white solid. 1H NMR (400 MHz, DMSO-d₆) δ ppm 8.50 (s, 2H), 7.59 (d, J=1.8 Hz, 1H), 7.39-7.44 (m, 2H), 7.20-7.30 (m, 4H), 7.15 (m, J=6.7 Hz, 1H), 7.09 (dd, J=8.6, 2.0 Hz, 1H), 3.31 (s, 6H).

Ethyl 1-(3-fluoro-4-(5-(2-phenylpropan-2-yl)benzofuran-2-yl)benzyl)azetidine-3-carboxylate

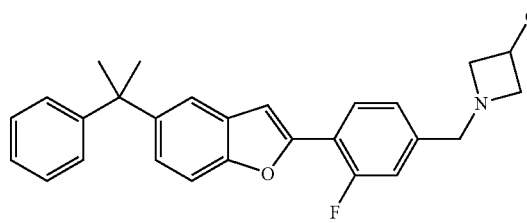

Synthesized according to Scheme B2, Step 2 and general procedure F from 5-(2-phenylpropan-2-yl)benzofuran-2-yl-boronic acid and ethyl 1-(4-bromo-3-fluorobenzyl)azetidine-3-carboxylate to give ethyl 1-(3-fluoro-4-(5-(2-phenylpropan-2-yl)benzofuran-2-yl)benzyl)azetidine-3-carboxylate as a yellow foam. MS (ESI) m/z: Calculated: 471.2; Observed: 472 (M⁺+1).

1-((3-Fluoro-4-(5-(2-phenylpropan-2-yl)benzofuran-2-yl)phenyl)methyl)azetidine-3-carboxylic acid

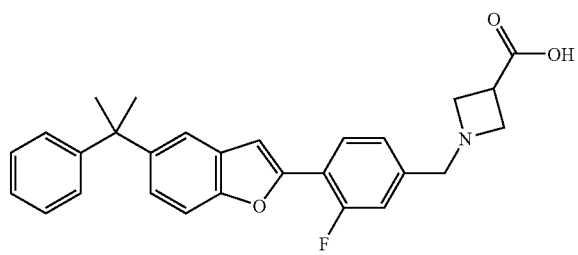

Synthesized according to Scheme B2, Step 3 and general procedure H from ethyl 1-(3-fluoro-4-(5-(2-phenylpropan-2-yl)benzofuran-2-yl)benzyl)azetidine-3-carboxylate to give 1-((3-fluoro-4-(5-(2-phenylpropan-2-yl)benzofuran-2-yl)phenyl)methyl)azetidine-3-carboxylic acid as a white solid [hS1P1 EC$_{50}$=365 nM]. 1H NMR (400 MHz, DMSO-d$_6$) δ ppm 7.89 (t, J=8.2 Hz, 1H), 7.61 (d, J=1.8 Hz, 1H), 7.51 (d, J=8.8 Hz, 1H), 7.22-7.31 (m, 7H), 7.15-7.19 (m, 1H), 7.12 (dd, J=8.8, 2.0 Hz, 1H), 3.60 (s, 2H), 3.42 (s, 1H), 3.32 (s, 4H), 3.21 (s, 1H), 1.70 (s, 6H). MS (ESI) m/z: Calculated: 443.2; Observed: 444 (M⁺+1).

Scheme B3

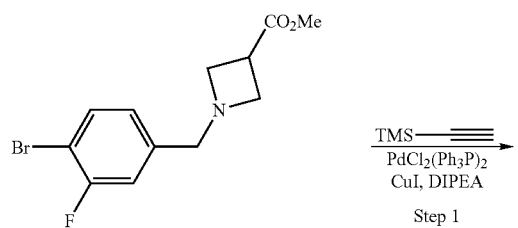

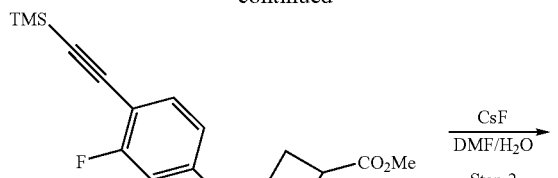

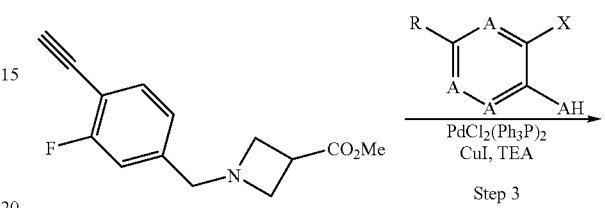

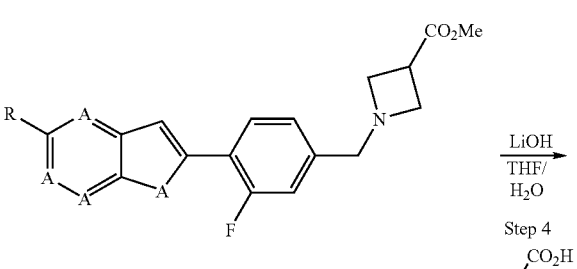

Compound 98

1-((3-Fluoro-4-(5-(phenylmethyl)furo[2,3-b]pyridin-2-yl)phenyl)methyl)-3-azetidinecarboxylic acid 5-Benzyl-2-methoxypyridine

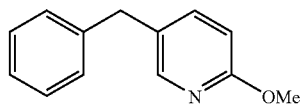

A sealable tube was charged with S-phos (0.22 g, 0.53 mmol), palladium acetate (0.060 g, 0.27 mmol), potassium phosphate (8.5 g, 40 mmol) and 5-bromo-2-methoxypyridine (1.8 mL, 13 mmol) under argon. 9-Benzyl-9-bora-bicyclo [3.3.1]nonane 0.5M in THF (53 mL, 27 mmol) was added, the vessel was sealed and heated to 60° C. overnight. The mixture was diluted with diethyl ether and was filtered through a pad of celite. Evaporation of the filtrate and purification by flash chromatography (0-40% EtOAc/hexanes) gave 5-benzyl-2-methoxypyridine. MS (ESI) m/z: Calculated: 199.1; Observed: 200.1 (M$^+$+1).

5-Benzyl-pyridin-2-ol

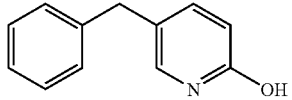

5-Benzyl-2-methoxypyridine (2.6 g, 13 mmol) in 15 mL AcOH was added 15 mL 48% HBr. The mixture was heated to 140° C. for 3 h, cooled and poured onto ice. The mixture was basified to pH 6-7 and the resulting solid was collected by filtration, rinsed with water, and dried in vacuo to give 5-benzylpyridin-2-ol as an off-white solid. MS (ESI) m/z: Calculated: 185.1; Observed: 186.0 (M$^+$+1).

5-Benzyl-3-iodopyridin-2-ol

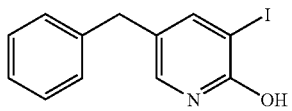

To a yellow solution of 5-benzylpyridin-2-ol (1.10 g, 5.94 mmol) in 22 mL AcOH under Ar was added 1.5 mL TFA, followed by N-iodosuccinimide (1.34 g, 5.94 mmol). The red homogeneous solution was allowed to stir overnight, poured onto ice and neutralized with conc. NH$_4$OH. The solids were collected by filtration, rinsed with water, treated with MeOH/DCM, dried over sodium sulfate, and evaporated. The resulting brown solid was purified by silica gel chromatography (ISCO, 80 g, 0-70% 90/10 DCM/MeOH in DCM) to give 5-benzyl-3-iodopyridin-2-ol as a yellow/brown solid. MS (ESI) m/z: Calculated: 311.0; Observed: 311.9 (M$^+$+1).

Methyl 1-((3-fluoro-4-(5-(phenylmethyl)furo[2,3-b]pyridin-2-yl)phenyl)methyl)-3-azetidinecarboxylate

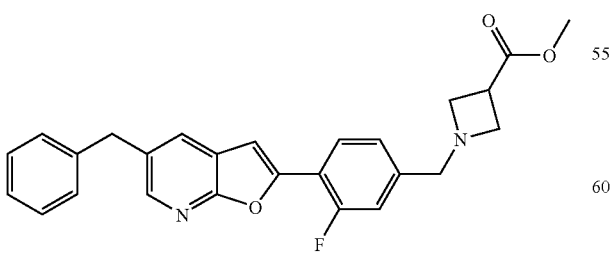

Synthesized according to Scheme B3 and general procedure G from 5-benzyl-3-iodopyridin-2-ol (0.400 g, 1.29 mmol) and methyl 1-(4-ethynyl-3-fluorobenzyl)azetidine-3-carboxylate (0.381 g, 1.54 mmol): light yellow solid. MS (ESI) m/z: Calculated: 430.2; Observed: 431.1 (M$^+$+1).

1-((3-Fluoro-4-(5-(phenylmethyl)furo[2,3-b]pyridin-2-yl)phenyl)methyl)-3-azetidinecarboxylic acid

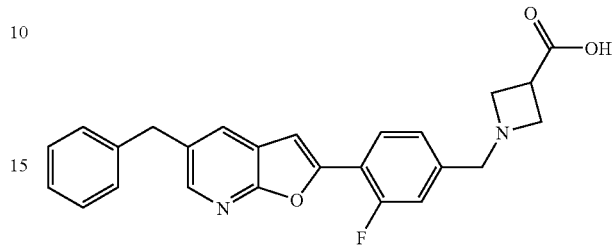

Synthesized according to Scheme B3 and general procedure H from methyl 1-(4-(5-benzylfuro[2,3-b]pyridin-2-yl)-3-fluorobenzyl)azetidine-3-carboxylate (0.146 g, 0.339 mmol): white solid [hS1P1 EC$_{50}$=27 nM]. 1H NMR (400 MHz, DMSO-d$_6$) δ ppm 8.26 (d, J=1.5 Hz, 1H), 7.97 (d, J=2.0 Hz, 1H), 7.92 (t, J=8.0 Hz, 1H), 7.25-7.35 (m, 7H), 7.16-7.25 (m, 1H), 4.09 (s, 2H), 3.62 (s, 2H), 3.37-3.48 (m, 2H), 3.26-3.36 (m, 1H), 3.16-3.25 (m, 2H). MS (ESI) m/z: Calculated: 416.2; Observed: 417.2 (M$^+$+1).

Compound 99

1-((3-Fluoro-4-(5-(phenylmethyl)-1H-indol-2-yl)phenyl)methyl)-3-azetidinecarboxylic acid Methyl 1-(4-(5-benzyl-1H-indol-2-yl)-3-fluorobenzyl)azetidine-3-carboxylate

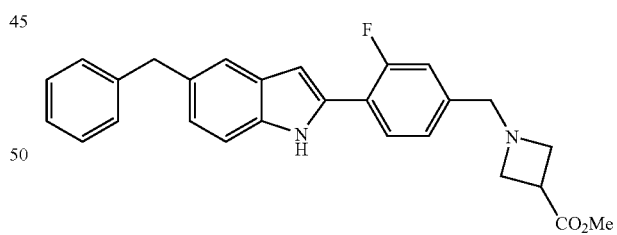

To a sealed flask was added 4-benzyl-2-iodobenzenamine (0.20 g, 0.65 mmol) and methyl 1-(4-ethynyl-3-fluorobenzyl)azetidine-3-carboxylate (0.32 g, 1.3 mmol) in THF (15 mL). To this solution was added PdCl$_2$(PPh$_3$)$_2$ (0.045 g, 0.065 mmol), CuI (0.025 g, 0.13 mmol), and ethyldiisopropylamine (0.90 mL, 5.2 mmol). The flask was flushed with Ar, sealed and placed in a preheated oil bath at 100° C. for 3 h. The mixture was concentrated under reduced pressure to afford a dark oil which was adsorbed onto silica and purified (30%

EtOAc/hexanes to 100% EtOAc) to afford title compound as a yellow oil. MS (ESI) m/z: Calculated: 428.1; Observed: 429.1 (M⁺+1).

1-((3-Fluoro-4-(5-(phenylmethyl)-1H-indol-2-yl)phenyl)methyl)-3-azetidinecarboxylic acid

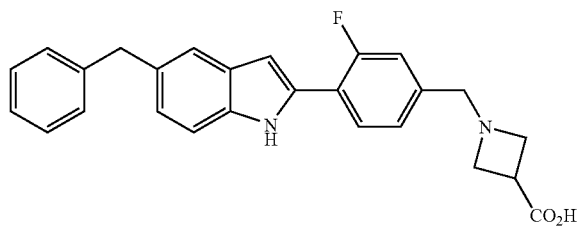

To a solution of methyl 1-(4-(5-benzyl-1H-indol-2-yl)-3-fluorobenzyl)azetidine-3-carboxylate (0.090 g, 0.21 mmol) in THF (1.0 mL) and water (1.0 mL) was added lithium hydroxide (0.025 g, 1.1 mmol). The solution was stirred at rt for 1 h, or until starting material was no longer observed by LCMS. The solvent was removed under reduced pressure, and 0.5M phosphate buffer (3.0 mL, pH 6.0) was added (pH was ca. 9-10). The mixture was acidified with 1N HCl to pH 6.0 and sonicated for 5 min. The aqueous solution was extracted with EtOAc (3×15 mL), and the separated organic extracts were dried over MgSO₄, filtered and concentrated to afford a brown oil. The oil was dissolved in AcOH (3.0 mL), and the excess AcOH was removed under reduced pressure. Ether (15 mL) was added, and the resulting precipitate was collected by filtration. The brown solids were washed with water (10 mL) and chloroform (15 mL) to afford title compound as a yellow solid [hS1P1 EC₅₀=1336 nM]. MS (ESI) m/z: Calculated: 414.1; Observed: 415.1 (M⁺+1).

Compound 100

1-((3-Fluoro-4-(5-(pyrimidin-2-ylmethyl)benzofuran-2-yl)phenyl)methyl)azetidine-3-carboxylic acid (4-(Bromomethyl)phenoxy)(tert-butyl)dimethylsilane

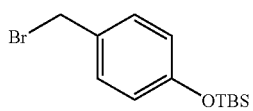

4-Hydroxybenzaldehyde (8.86 mL, 81.9 mmol) was added as a solution in THF (50 mL) to a suspension of sodium hydride (2.36 g, 98.3 mmol) in THF (100 mL) via syringe. The mixture was stirred until gas evolution stopped and chloro-tert-butyldimethylsilane (18.5 g, 123 mmol) was added as a solution in THF (50 mL). The reaction was stirred for 1.5 h and quenched with 1N NaOH. The mixture was extracted with EtOAc twice and the extracts were washed with water once, brine once, dried over MgSO₄ and concentrated in vacuo to give an oil.

The oil was dissolved in EtOH (200 mL) and cooled to 0° C. Sodium borohydride (3.41 g, 90.1 mmol) was added and the mixture was stirred at 0° C. for 30 min. The reaction was quenched with satd. NH₄Cl and extracted with Et₂O twice. The organic extracts were dried over MgSO₄ and concentrated to give an oil, which was purified by column chromatography to an oil.

Methanesulfonyl chloride (0.56 mL, 7.06 mmol) was added dropwise to a solution of triethylamine (1.79 mL, 12.8 mmol) and the above oil (1.53 g, 6.42 mmol) in DCM (25 mL) at 0° C. The mixture was stirred for 1 h at 0° C., Et₂O was added and the mixture was washed with water once, 1N HCl once, satd. NaHCO₃ once, dried over MgSO₄ and concentrated in vacuo to give an oil. This oil was dissolved in acetone (50 mL) and lithium bromide (2.79 g, 32.1 mmol) was added. The mixture was stirred at reflux for 15 min, cooled to room temperature, diluted with Et₂O, and washed with water twice, sodium thiosulfate once, dried over MgSO₄, and concentrated to give (4-(bromomethyl)phenoxy)(tertbutyl)dimethylsilane as a light-yellow oil. 1H NMR (400 MHz, CHLOROFORM-d) δ ppm 7.26 (2H, d, J=8.5 Hz), 6.79 (2H, d, J=8.0 Hz), 4.48 (2H, s), 0.98 (9H, s), 0.19 (6H, m).

2-(4-(tert-Butyldimethylsilyloxy)benzyl)pyrimidine

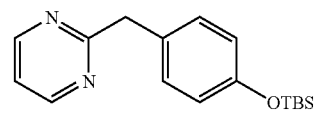

Zinc (0.33 g, 4.97 mmol) and iodine (0.008 g, 0.033 mmol) were added to an oven-dried flask (25 mL). The mixture was heated under vacuum with a heat gun for 10 min, cooled to RT, placed under argon atmosphere, suspended in 3 mL DMF (dry, degassed by bubbling nitrogen through it for 10 min), and cooled to 0° C. (4-(Bromomethyl)phenoxy)(tertbutyl)dimethylsilane (1.00 g, 3.31 mmol) was added as a solution in 3 mL DMF, the mixture was stirred at 0° C. for 30 min, then room temperature for 30 min. Next, 2-bromopyrimidine (526 mg, 3.31 mmol), Pd₂dba₃ (0.091 mg, 0.099 mmol), and S-Phos (0.163 g, 0.40 mmol) were added. The flask was purged with argon and heated for 1 h at 60° C., cooled to RT, filtered through Celite, and concentrated in vacuo. The resulting solid was purified by flash chromatography to give title compound as a light yellow oil. MS (ESI) m/z: Calculated: 300.2; Observed: 301.5 (M⁺+1).

4-(Pyrimidin-2-ylmethyl)phenol

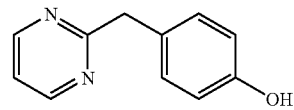

Tetrabutylammonium fluoride (1.68 mL, 1.68 mmol, 1M in THF) was added to a solution of 2-(4-(tert-butyldimethylsilyloxy)benzyl)pyrimidine (0.50 g, 1.68 mmol) in THF (5 mL) at 0° C. The mixture was stirred for 30 min, diluted with water, and extracted with DCM three times. The combined organic extracts were dried over MgSO₄, concentrated in vacuo, and purified by column chromatography to give 4-(pyrimidin-2-ylmethyl)phenol as an oil. MS (ESI) m/z: Calculated: 186.1; Observed: 187.3 (M⁺+1).

2-Iodo-4-(pyrimidin-2-ylmethyl)phenol

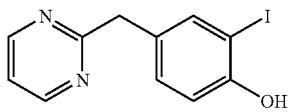

Bis(pyridine)iodonium tetrafluoroborate (379 mg, 1.02 mmol) was added to a solution of 4-(pyrimidin-2-ylmethyl)phenol (200 mg, 1.07 mmol) in 9:1 DCM:TFA (6 mL) at 0° C. The mixture was stirred for 1 h, partitioned between EtOAc and water, the layers were separated, and the organic layer was washed with satd. sodium thiosulfate. The organic layer was dried over MgSO₄, concentrated in vacuo, and purified by column chromatography to give 2-iodo-4-(pyrimidin-2-ylmethyl)phenol. MS (ESI) m/z: Calculated: 312.0; Observed: 313.0 (M⁺+1).

Methyl 1-((3-fluoro-4-(5-(pyrimidin-2-ylmethyl)benzofuran-2-yl)phenyl)methyl)azetidine-3-carboxylate

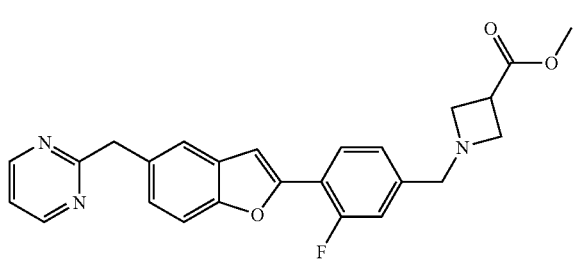

Synthesized according to Scheme B3 and general procedure G from 2-iodo-4-(pyrimidin-2-ylmethyl)phenol (0.230 g, 0.74 mmol) and methyl 1-(4-ethynyl-3-fluorobenzyl)azetidine-3-carboxylate (0.220 g, 0.89 mmol). MS (ESI) m/z: Calculated: 431.2; Observed: 432.5 (M⁺+1).

1-((3-Fluoro-4-(5-(pyrimidin-2-ylmethyl)benzofuran-2-yl)phenyl)methyl)azetidine-3-carboxylic acid

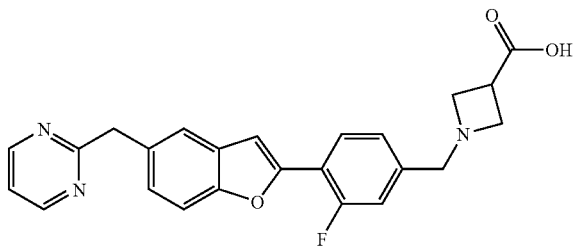

Synthesized according to Scheme B3 and general procedure H from methyl 1-((3-fluoro-4-(5-(pyrimidin-2-ylmethyl)benzofuran-2-yl)phenyl)methyl)azetidine-3-carboxylate (0.180 g, 0.42 mmol): white solid [hS1P1 EC₅₀=87 nM]. 1H NMR (400 MHz, DMSO-d₆) δ ppm 8.74 (d, J=4.9 Hz, 2H), 7.90 (t, J=8.0 Hz, 1H), 7.61 (s, 1H), 7.55 (d, J=8.4 Hz, 1H), 7.35 (t, J=4.9 Hz, 1H), 7.21-7.32 (m, 4H), 4.30 (s, 2H), 3.61 (s, 2H), 3.38-3.46 (m, 2H), 3.19-3.26 (m, 3H). MS (ESI) m/z: Calculated: 417.2; Observed: 418.5 (M⁺+1).

Compound 101

1-((3-fluoro-4-(5-(pyridin-3-ylmethyl)benzofuran-2-yl)phenyl)methyl)azetidine-3-carboxylic acid 3-(4-Methoxybenzyl)pyridine

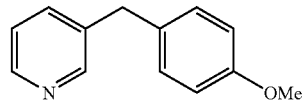

Zinc (0.976 g, 14.9 mmol) and iodine (0.025 g, 0.100 mmol) were added to a flame-dried flask (25 mL) and heated with a heat gun under vacuum for 10 min. The flask was cooled to 0° C. and DMF (5 mL) was added. 1-(Bromomethyl)-4-methoxybenzene (1.43 mL, 9.95 mmol) was added as a solution in DMF (5 mL) and the mixture was stirred for 20 min at 0° C., then RT for 20 min. S-Phos (0.490 g, 1.19 mmol), Pd₂ dba₃ (0.273 g, 0.299 mmol), and 3-bromopyridine (0.976 mL, 9.95 mmol) were added and the mixture was heated 60° C. for 1 h. The mixture was cooled to RT, filtered through celite, concentrated in vacuo, and purified by column chromatography to give 3-(4-methoxybenzyl)pyridine as a light-yellow oil. MS (ESI) m/z: Calculated: 199.1; Observed: 200.3 (M⁺+1).

3-(3-Iodo-4-methoxybenzyl)pyridine

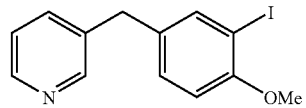

Bis(pyridine)iodonium tetrafluoroborate (1.35 g, 3.64 mmol) was added to a solution of 3-(4-methoxybenzyl)pyridine (720 mg, 3.64 mmol) in 9:1 TFA:DCM (20 mL) and the mixture was stirred for 1 h at 0° C. The ice bath was removed and the reaction was stirred for 2 h. EtOAc was added and the mixture was washed with water twice, satd. sodium thiosulfate twice, dried over MgSO₄, concentrated in vacuo, and purified by column chromatography to give 3-(3-iodo-4-methoxybenzyl)pyridine as a yellow oil. MS (ESI) m/z: Calculated: 325.0; Observed: 326.3 (M⁺+1).

2-Iodo-4-(pyridin-3-ylmethyl)phenol

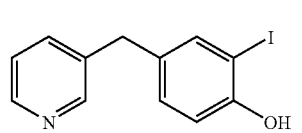

Boron tribromide (11.1 mL, 11.1 mmol, 1M in DCM) was added to a solution of 3-(3-iodo-4-methoxybenzyl)pyridine (720 mg, 2.21 mmol) in DCM (3 mL) at 0° C., and the mixture was stirred for 1 h. The mixture was quenched by the careful addition of water, the layers were separated, and the organic layer was washed with water three times. The combined organic extracts were dried over MgSO₄, concentrated in vacuo, and purified by column chromatography to give 2-iodo-4-(pyridin-3-ylmethyl)phenol as a yellow oil. MS (ESI) m/z: Calculated: 311.0; Observed: 312.3 (M⁺+1).

Methyl-1-((3-fluoro-4-(5-(pyridin-3-ylmethyl)benzofuran-2-yl)phenyl)methyl)azetidine-3-carboxylate

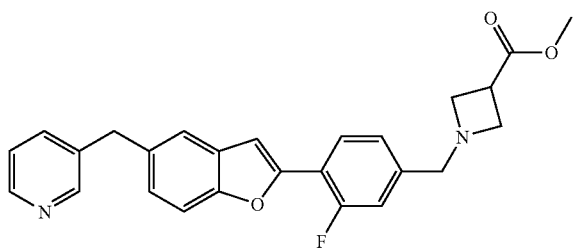

Synthesized according to Scheme B3 and general procedure G from 2-iodo-4-(pyridin-3-ylmethyl)phenol (0.305 g, 0.98 mmol) and methyl 1-(4-ethynyl-3-fluorobenzyl)azetidine-3-carboxylate (0.220 g, 0.89 mmol): yellow solid. MS (ESI) m/z: Calculated: 430.2; Observed: 431.5 (M$^+$+1).

1-((3-Fluoro-4-(5-(pyridin-3-ylmethyl)benzofuran-2-yl)phenyl)methyl)azetidine-3-carboxylic acid

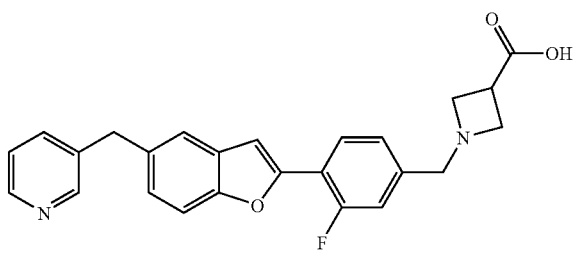

Synthesized according to Scheme B3 and general procedure H from methyl 1-((3-fluoro-4-(5-(pyridin-3-ylmethyl)benzofuran-2-yl)phenyl)methyl)azetidine-3-carboxylate (0.068 g, 0.16 mmol): white solid. 1H NMR (400 MHz, MeOH) δ ppm 8.47 (s, 1H), 8.39 (d, J=4.5 Hz, 1H), 8.11 (dd, J=8.2, 7.6 Hz, 1H), 7.73 (d, 6.4 Hz, 1H), 7.50-7.55 (m, 2H), 7.43 (s, 1H), 7.35-7.42 (m, 2H), 7.29 (d, J=2.9 Hz, 1H), 7.25 (d, J=8.6 Hz, 1H), 4.40 (s, 2H), 4.20-4.31 (m, 4H), 4.15 (s, 2H), 3.53 (dt, J=8.8, 7.8 Hz, 1H). MS (ESI) m/z: Calculated: 416.2; Observed: 417.5 (M$^+$+1).

Compound 102

1-((4-(5-Benzoylbenzofuran-2-yl)-3-fluorophenyl)methyl)azetidine-3-carboxylic acid (4-Hydroxy-3-iodophenyl)(phenyl)methanone

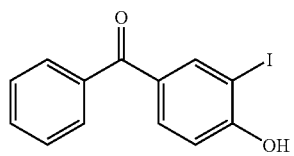

A solution of (4-hydroxyphenyl)(phenyl)methanone (2.0 g, 10 mmol) in saturated aqueous ammonium hydroxide (130 mL) was stirred at 25° C. for 15 min, and then treated with a solution of potassium iodide (8.2 g, 49 mmol) and iodine (2.6 g, 10 mmol) in water (260 mL). After 30 min, the mixture was adjusted to pH 2 with concentrated aqueous HCl and extracted with EtOAc (500 mL). The organic extract was sequentially washed with sat. aqueous sodium thiosulfate (100 mL) and brine (100 mL), dried over sodium sulfate, filtered, and concentrated in vacuo. Chromatographic purification of the residue (ISCO, 40 g, 0->80% EtOAc/hexanes) gave (4-hydroxy-3-iodophenyl)(phenyl)methanone as a white solid. MS (ESI) m/z: Calculated: 324.0; Observed: 325 (M$^+$+1).

Methyl 1-(4-(5-benzoylbenzofuran-2-yl)-3-fluorobenzyl)azetidine-3-carboxylate

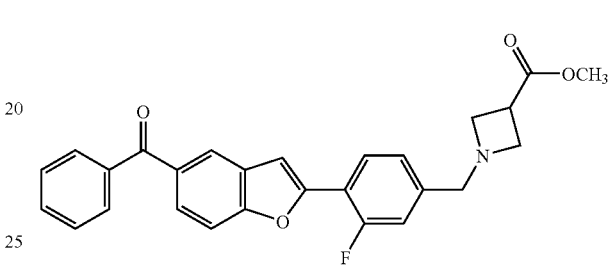

Synthesized according to Scheme B3, Step 3 and general procedure G from (4-hydroxy-3-iodophenyl)(phenyl)methanone and methyl 1-(4-ethynyl-3-fluorobenzyl)azetidine-3-carboxylate: yellow-orange solid. MS (ESI) m/z: Calculated: 443.2; Observed: 444 (M$^+$+1).

1-((4-(5-Benzoylbenzofuran-2-yl)-3-fluorophenyl)methyl)azetidine-3-carboxylic acid

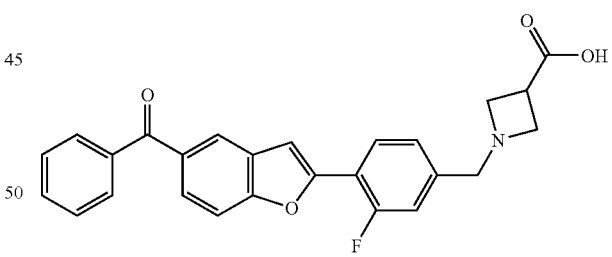

Synthesized according to Scheme B3, Step 4 and general procedure H from methyl 1-(4-(5-benzoylbenzofuran-2-yl)-3-fluorobenzyl)azetidine-3-carboxylate: off-white solid [hS1P1 EC$_{50}$=80 nM]. 1H NMR (400 MHz, DMSO-d$_6$) δ ppm 8.13 (s, 1H), 7.97 (t, J=8.0 Hz, 1H), 7.80-7.85 (m, 2H), 7.75-7.80 (m, 2H), 7.70 (t, J=7.4 Hz, 1H), 7.59 (t, J=7.5 Hz, 2H), 7.45 (d, J=3.1 Hz, 1H), 7.32 (d, J=4.1 Hz, 1H), 7.30 (s, 1H), 3.63 (s, 2H), 3.40-3.48 (m, 2H), 3.32 (s, 2H), 3.19-3.27 (m, 2H). MS (ESI) m/z: Calculated: 429.1; Observed: 430 (M$^+$+1).

Compound 103

(E/Z)-1-((3-Fluoro-4-(5-((hydroxyimino)(phenyl)methyl)benzofuran-2-yl)phenyl)methyl)azetidine-3-carboxylic acid

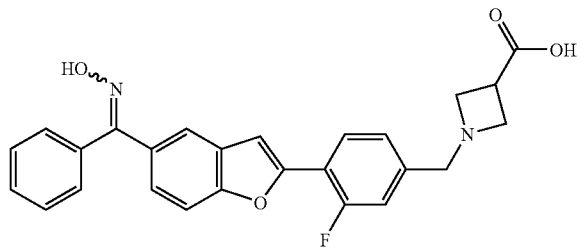

Hydroxylamine, 50 wt. %, solution in water (146 μL, 2375 μmol) was added to a solution of 1-((4-(5-benzoylbenzofuran-2-yl)-3-fluorophenyl)methyl)azetidine-3-carboxylic acid (34.0 mg, 79 μmol) in acetic acid (0.560 mL), and the resulting yellow solution was stirred at 60° C. for 15 h. 1 M pH 6 phosphate buffer (6.0 mL) was added to the resulting solution, and the mixture was sonicated for 1 min. The resulting white slurry was filtered, and the collected solid was washed with water (12 mL) and EtOH (10 mL) to afford title compound as a light yellow solid [hS1P1 $EC_{50}$=16 nM]. 1H NMR (400 MHz, DMSO-$d_6$) δ ppm 11.34 (s, 0.5H), 11.25 (s, 0.5H), 7.87-8.00 (m, 1H), 7.72 (d, J=8.5 Hz, 1H), 7.61-7.68 (m, 1H), 7.59 (s, 1H), 7.44-7.52 (m, 2H), 7.42 (dd, J=7.3, 3.3 Hz, 1H), 7.30-7.39 (m, 3H), 7.24-7.30 (m, 2H), 3.62 (d, J=5.5 Hz, 2H), 3.39-3.48 (m, 3H), 3.23 (d, J=4.5 Hz, 2H). MS (ESI) m/z: Calculated: 444.2; Observed: 445 ($M^+$+1).

Compound 104

(E/Z)-1-((3-Fluoro-4-(5-((methoxyimino)(phenyl)methyl)benzofuran-2-yl)phenyl)methyl)azetidine-3-carboxylic acid, trifluoroacetic acid salt

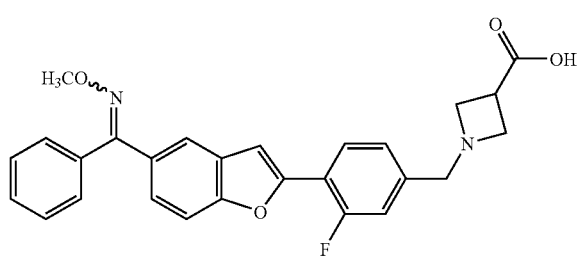

O-Methyl hydroxylamine hydrochloride, 25% in water (257 μL, 848 μmol) was added to a solution of 1-((4-(5-benzoylbenzofuran-2-yl)-3-fluorophenyl)methyl)azetidine-3-carboxylic acid (36.4 mg, 85 μmol) and sodium acetate (70 mg, 848 μmol) in acetic acid (700 μL; 0.13M), and the resulting yellow solution was stirred at 70° C. for 17 h. The solution was filtered through a cotton plug and concentrated in vacuo. The residue was taken up in MeOH, filtered through a cotton plug, and purified by HPLC (Phenomenex C18, 5-100% $CH_3CN/H_2O$+0.1% TFA) to provide (E/Z)-1-((3-fluoro-4-(5-((methoxyimino)(phenyl)methyl)benzofuran-2-yl)phenyl)methyl)azetidine-3-carboxylic acid, trifluoroacetic acid salt as a white solid. 1H NMR (400 MHz, MeOH-$d_4$) δ ppm 8.18-8.23 (m, 0.5H), 8.16 (t, J=7.0 Hz, 0.5H), 7.68 (d, J=1.6 Hz, 0.5H), 7.64-7.67 (m, 0.5H), 7.59-7.62 (m, 0.5H), 7.55-7.59 (m, 0.5H), 7.44-7.51 (m, 4H), 7.40-7.44 (m, 2H), 7.37-7.40 (m, 1H), 7.30-7.37 (m, 2H), 4.51 (s, 1H), 4.50 (s, 1H), 4.34-4.44 (m, 4H), 3.96 (s, 1.5H), 3.96 (s, 1.5H), 3.67-3.79 (m, 1H). MS (ESI) m/z: Calculated: 458.2; Observed: 459 ($M^+$+1).

Compound 105

(E/Z)-1-((3-Fluoro-4-(5-((ethoxyimino)(phenyl)methyl)benzofuran-2-yl)phenyl)methyl)azetidine-3-carboxylic acid, trifluoroacetic acid salt

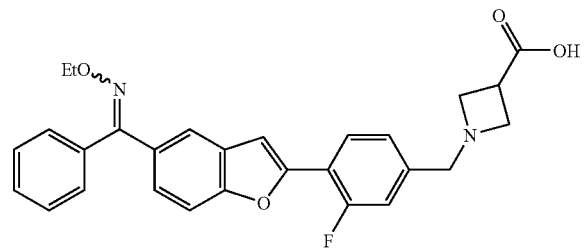

O-Ethyl hydroxylamine hydrochloride (86 mg, 885 μmol) was added to a solution of 1-((4-(5-benzoylbenzofuran-2-yl)-3-fluorophenyl)methyl)azetidine-3-carboxylic acid (38.0 mg, 88 μmol) and sodium acetate (73 mg, 885 μmol) in acetic acid (700 μL; 0.13M) and water (200 μL) and the resulting yellow solution was stirred at 70° C. for 17 h. The solution was concentrated in vacuo, and the residue was taken up in MeOH, filtered through a cotton plug, and purified by HPLC (Phenomenex C18, 5-100% $CH_3CN/H_2O$+0.1% TFA) to provide (E/Z)-1-((4-(5-((ethoxyimino)(phenyl)methyl)benzofuran-2-yl)-3-fluorophenyl)methyl)azetidine-3-carboxylic acid, trifluoroacetic acid salt as a white solid. 1H NMR (400 MHz, MeOD-$d_4$) δ ppm 8.18-8.23 (m, 0.5H), 8.14-8.18 (m, 0.5H), 7.66-7.69 (m, 0.5H), 7.66 (d, J=3.7 Hz, 0.5H), 7.58-7.62 (m, 0.5H), 7.55-7.58 (m, 0.5H), 7.44-7.51 (m, 4H), 7.40-7.44 (m, 1H), 7.31-7.40 (m, 4H), 4.51 (s, 1H), 4.50 (s, 1H), 4.34-4.44 (m, 4H), 4.24-4.27 (m, 1H), 4.20-4.24 (m, 1H), 3.68-3.77 (m, 1H), 1.30 (t, J=7.0 Hz, 3H). MS (ESI) m/z: Calculated: 472.2; Observed: 473 ($M^+$+1).

Compound 106

(±)-1-((3-Fluoro-4-(5-(hydroxy(phenyl)methyl)benzofuran-2-yl)phenyl)methyl)azetidine-3-carboxylic acid, trifluoroacetic acid salt (±)-Methyl 1-((3-fluoro-4-(5-(hydroxy(phenyl)methyl)benzofuran-2-yl)phenyl)methyl)-azetidine-3-carboxylate To solution of methyl 1-((4-(5-benzoylbenzofuran-2-yl)-3-fluorophenyl)methyl)-azetidine-3-carboxylate (190 mg, 428 µmol) in MeOH (5.0 mL; 0.14M) and THF (1.0 mL) was added sodium borohydride (130 mg, 3438 µmol) at 0° C., and the resulting mixture was stirred at 0° C. for 10 min, then at 25° C. for 30 min. Saturated aqueous ammonium chloride (10 mL) was added, and the resulting mixture was extracted twice with EtOAc (30 mL). The combined extracts were washed with brine, dried over sodium sulfate, filtered, and concentrated in vacuo. Chromatographic purification of the residue (ISCO, 4 g, 0-100% EtOAc/hexanes) furnished (±)-methyl 1-((3-fluoro-4-(5-(hydroxy(phenyl)methyl)benzofuran-2-yl)phenyl)methyl)azetidine-3-carboxylate as a clear oil. MS (ESI) m/z: Calculated: 445.2; Observed: 446 (M$^+$+1).

(±)-1-((3-Fluoro-4-(5-(hydroxy(phenyl)methyl)benzofuran-2-yl)phenyl)methyl)azetidine-3-carboxylic acid, trifluoroacetic acid salt

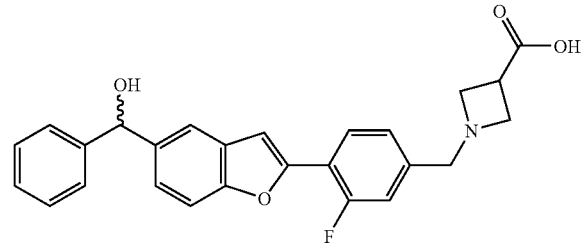

Lithium hydroxide monohydrate (17.6 mg, 420 µmol) in water (2.0 mL) was added to a solution of (±)-methyl 1-((3-fluoro-4-(5-(hydroxy(phenyl)methyl)benzofuran-2-yl)phenyl)methyl)azetidine-3-carboxylate (62.3 mg, 140 µmol) in THF (3.0 mL) at 25° C., and the resulting solution was stirred for 1.5 h. 2N HCl (0.210 mL) was added, and the resulting solution was concentrated in vacuo. The residue was taken up in DMSO (3.0 mL), filtered through cotton plug, and purified by HPLC (Phenomenex C18, 5-50-100% CH$_3$CN/H$_2$O+ 0.1% TFA) to furnish 1-((3-fluoro-4-(5-(hydroxy(phenyl) methyl)benzofuran-2-yl)phenyl)-methyl)azetidine-3-carboxylic acid, trifluoroacetic acid salt as a white solid. 1H NMR (400 MHz, MeOH-d$_4$) δ ppm 8.13 (t, J=8.0 Hz, 1H), 7.70 (d, J=1.8 Hz, 1H), 7.51 (d, J=8.6 Hz, 1H), 7.40-7.46 (m, 4H), 7.38 (dd, J=8.6, 1.8 Hz, 1H), 7.30-7.36 (m, 3H), 7.21-7.27 (m, 1H), 5.91 (s, 1H), 4.47 (s, 2H), 4.38 (d, J=3.1 Hz, 2H), 4.36 (d, J=1.2 Hz, 2H), 3.65-3.75 (m, 1H). MS (ESI) m/z: Calculated: 431.2; Observed: 432 (M$^+$+1).

Compound 107

1-((4-(5-Benzyl-7-chlorofuro[2,3-c]pyridin-2-yl)-3-fluorophenyl)methyl)azetidine-3-carboxylic acid 2-Chloro-6-iodopyridin-3-ol

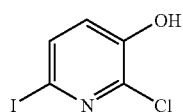

Iodine (2.38 mL, 46.3 mmol) was added to a solution of 2-chloro-3-pyridinol (5.00 g, 38.6 mmol) in water (60 mL) containing potassium carbonate (18.7 g, 135 mmol). The resulting solution was allowed to stir for 2 h at room temperature. The mixture was treated with sodium thiosulfate, acidified to pH 2 using 12M aqueous HCl, and extracted with EtOAc. The organic phase was dried over MgSO$_4$ and evaporated. Purification by flash chromatography using EtOAc/hexanes gave 2-chloro-6-iodopyridin-3-ol. 1H NMR (300 MHz, CDCl$_3$) δ ppm 7.56 (d, J=8.2 Hz, 1H), 7.02 (d, J=8.3 Hz, 1H). MS (ESI) m/z: Calculated; 254.9 Observed: 255.8 (M$^+$+1).

6-Benzyl-2-chloropyridin-3-ol

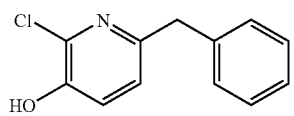

A mixture of K$_3$PO$_4$ (12 g, 55 mmol), S-Phos (0.45 g, 1.1 mmol), and palladium acetate (0.21 g, 0.91 mmol) in THF (55 mL) was prepared in a sealed tube. The mixture was treated with 2-chloro-6-iodopyridin-3-ol (4.67 g, 18 mmol) and β-benzyl-9-BBN (0.5M solution in THF, 73 mL, 37 mmol) and heated to 80° C. for 2 h. The crude mixture was diluted with EtOAc, washed with 2M aqueous NaOH, brine, dried over MgSO$_4$, and evaporated. Purification by flash chromatography (EtOAc/hexanes) gave 6-benzyl-2-chloropyridin-3-ol. 1H NMR (300 MHz, CDCl$_3$) δ ppm 7.11-7.41 (m, 6H), 6.94 (d, J=8.2 Hz, 1H), 5.49 (br. s, 1H), 4.06 (s, 2H). MS (ESI) m/z: Calculated; 219.1 Observed: 220.0 (M$^+$+1).

6-Benzyl-2-chloro-4-iodopyridin-3-ol

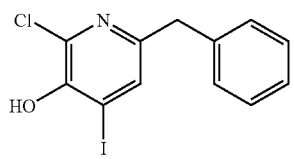

Iodine (5.87 g, 23.1 mmol) was added to a solution of 6-benzyl-2-chloropyridin-3-ol (2.54 g, 11.6 mmol) in water (45 mL) containing potassium carbonate (3.20 g, 23.1 mmol). The mixture was allowed to stir for 3 h at room temperature, treated with sodium thiosulfate, and acidified to pH 2 using 12M aqueous HCl. The mixture was extracted with EtOAc. The organic phase was dried over MgSO$_4$ and evaporated. Purification by flash chromatography using EtOAc/hexanes gave 6-benzyl-2-chloro-4-iodopyridin-3-ol. 1H NMR (300 MHz, DMSO-d$_6$) δ ppm 10.36 (br. s, 1H), 7.68 (s, 1H), 7.15-7.35 (m, 5H), 3.93 (s, 2H). MS (ESI) m/z: Calculated; 345.0; Observed: 345.9 (M⁺+1).

Methyl 1-((4-(5-benzyl-7-chlorofurofluorophenyl)methyl)azetidine-3-carboxylate

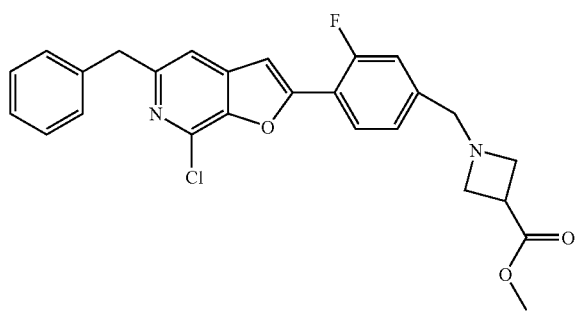

Synthesized according to Scheme B3 and general procedure G from 6-benzyl-2-chloro-4-iodopyridin-3-ol (1.00 g, 2.89 mmol) and 1-(4-ethynyl-3-fluorobenzyl)azetidine-3-carboxylate (0.859 g, 3.47 mmol). 1H NMR (300 MHz, CDCl$_3$) δ ppm 8.03 (t, J=7.8 Hz, 1H), 6.98-7.40 (m, 9H), 4.22 (s, 2H), 3.72 (s, 3H), 3.66 (s, 2H), 3.52-3.61 (m, 2H), 3.26-3.40 (m, 3H). MS (ESI) m/z: calculated; 464.1 Observed: 465.0 (M⁺+1).

1-((4-(5-Benzyl-7-chlorofuro[2,3-c]pyridin-2-yl)-3-fluorophenyl)methyl)azetidine-3-carboxylic acid

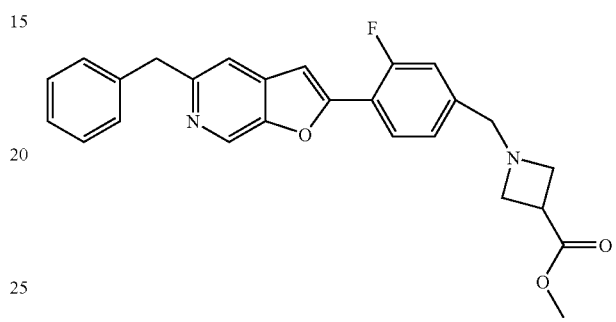

Synthesized according to Scheme B3 and general procedure H from methyl 1-((4-(5-benzyl-7-chlorofurofluorophenyl)methyl)azetidine-3-carboxylate [hS1P1 EC$_{50}$=2583 nM]. 1H NMR (400 MHz, DMSO-d$_6$) δ ppm 7.95 (br. t, J=8.0 Hz, 1H), 7.59 (br. s, 1H), 7.16-7.45 (m, 8H), 4.15 (br. s, 2H), 3.63 (br. s, 2H), 3.42 (br. s, 2H), 3.17-3.26 (m, 3H). MS (ESI) m/z: Calculated; 450.1 Observed: 451.0 (M⁺+1).

Compound 108

1-((4-(5-Benzylfuro[2,3-c]pyridin-2-yl)-3-fluorophenyl)methyl)azetidine-3-carboxylic acid

Methyl 1-((4-(5-benzylfuro[2,3-c]pyridin-2-yl)-3-fluorophenyl)methyl)azetidine-3-carboxylate

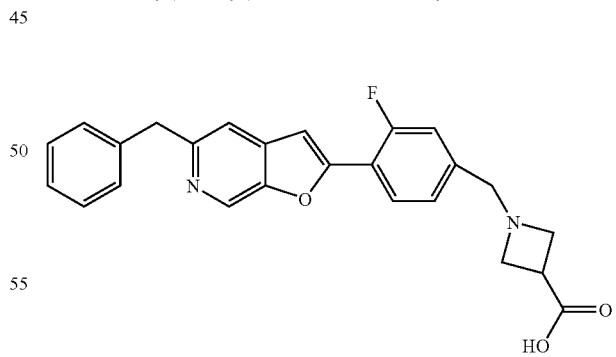

A mixture of methyl 1-(4-(5-benzyl-7-chlorofuro[2,3-c]pyridin-2-yl)-3-fluorobenzyl)azetidine-3-carboxylate (0.320 g, 0.69 mmol), cyclohexene (1.00 mL, 9.9 mmol), palladium (10 wt. % on activated carbon, 0.320 g, 3.0 mmol) in EtOH (6.0 mL) was prepared in a sealed tube and heated under N$_2$ to 85° C. for 4 h. The mixture was filtered through Celite, and the filtrate evaporated purified by flash chromatography using EtOAc/hexanes to give title compound. 1H NMR (300 MHz, CDCl$_3$) δ ppm 8.82 (s, 1H), 7.96 (t, J=7.7 Hz, 1H), 6.99-7.38 (m, 9H), 4.25 (s, 2H), 3.72 (s, 3H), 3.65 (s, 2H), 3.48-3.59 (m, 2H), 3.33-3.39 (m, 3H). MS (ESI) m/z: Calculated; 430.2 Observed: 431.2 (M⁺+1).

1-((4-(5-Benzylfuro[2,3-c]pyridin-2-yl)-3-fluorophenyl)methyl)azetidine-3-carboxylic acid Synthesized according to Scheme B3 and general procedure H from methyl 1-((4-(5-benzylfuro[2,3-c]pyridin-2-yl)-3-fluorophenyl)methyl)azetidine-3-carboxylate [hS1P1 EC$_{50}$=409 nM]. 1H NMR (400 MHz, DMSO-d$_6$) δ ppm 8.88 (br. s, 1H), 7.96 (br. t, J=8.0 Hz, 1H), 7.57 (s, 1H), 7.16-7.34 (m, 8H), 4.17 (br. s, 2H), 3.62 (br. s, 2H), 3.40-3.45 (m, 2H), 3.20-3.25 (m, 3H). MS (ESI) m/z: Calculated; 416.2 Observed: 417.1 (M⁺+1).

Compound 109

1-((4-(5-Benzylfuro[3,2-b]pyridin-2-yl)-3-fluorophenyl)methyl)azetidine-3-carboxylic acid 6-Benzylpyridin-3-ol

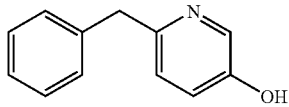

In a sealed tube, a mixture of K$_3$PO$_4$ (16 g, 78 mmol), S-Phos (0.64 g, 1.6 mmol), and palladium acetate (0.29 g, 1.3 mmol) in THF (70 mL) was treated with 6-bromopyridin-3-ol (4.50 g, 26 mmol) and β-benzyl-9-BBN (0.5M solution in THF, 103 mL, 52 mmol). The mixture was heated to 80° C. for 18 h and diluted with EtOAc. The organic phase was washed with 2M aqueous NaOH, brine, dried over MgSO$_4$, and concentrated. Purification by flash chromatography using EtOAc/hexanes gave 6-benzylpyridin-3-ol. 1H NMR (300 MHz, DMSO-d$_6$) δ ppm 9.66 (br. s, 1H), 8.03 (t, J=1.8 Hz, 1H), 7.13-7.30 (m, 4H), 7.07 (d, J=1.9 Hz, 2H), 3.95 (s, 2H). MS (ESI) m/z: Calculated; 185.1 Observed: 186.1 (M$^+$+1).

6-Benzyl-2-iodopyridin-3-ol

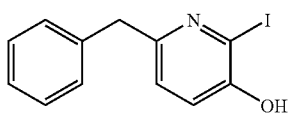

Iodine (3.21 g, 12.6 mmol) was added to a solution of 6-benzylpyridin-3-ol (2.34 g, 12.6 mmol) and sodium carbonate anhydrous (1.06 mL, 25.3 mmol) in water (60 mL) and THF (60 mL). The mixture was allowed to stir for 1 h at room temperature, treated with sodium thiosulfate, and acidified pH 3 using 5M aqueous HCl. Extractive workup and flash chromatography using EtOAc/hexanes gave 6-benzyl-2-iodopyridin-3-ol. 1H NMR (300 MHz, DMSO-d$_6$) δ ppm 10.62 (s, 1H), 7.13-7.34 (m, 5H), 6.99-7.11 (m, 2H), 3.95 (s, 2H). MS (ESI) m/z: Calculated; 311.0 Observed: 311.9 (M$^+$+1).

Methyl 1-((4-(5-benzylfuro[3,2-b]pyridin-2-yl)-3-fluorophenyl)methyl)azetidine-3-carboxylate

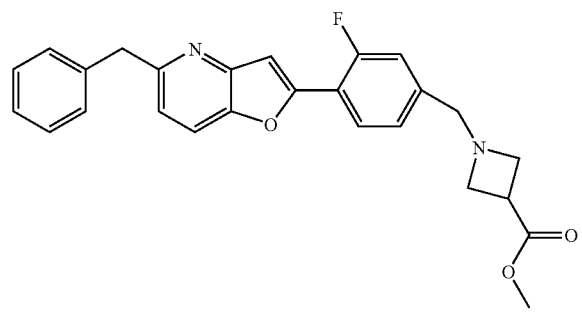

Synthesized according to Scheme B3 and general procedure G from 6-benzyl-2-iodopyridin-3-ol (0.500 g, 1.61 mmol) and methyl 1-(4-ethynyl-3-fluorobenzyl)azetidine-3-carboxylate (0.477 g, 1.93 mmol). 1H NMR (300 MHz, CDCl$_3$) δ ppm 7.93 (t, J=7.9 Hz, 1H), 7.65 (d, J=8.5 Hz, 1H), 7.37 (d, J=3.1 Hz, 1H), 7.10-7.33 (m, 7H), 7.04 (d, J=8.5 Hz, 1H), 4.27 (s, 2H), 3.72 (s, 3H), 3.65 (s, 2H), 3.48-3.60 (m, 2H), 3.30-3.40 (m, 3H). MS (ESI) m/z: Calculated; 430.2 Observed: 431.1 (M$^+$+1).

1-((4-(5-Benzylfuro[3,2-b]pyridin-2-yl)-3-fluorophenyl)methyl)azetidine-3-carboxylic acid

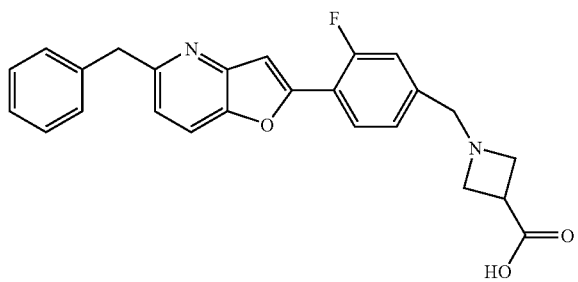

Synthesized according to Scheme B3 and general procedure H from methyl 1-(4-(5-benzylfuro[3,2-b]pyridin-2-yl)-3-fluorobenzyl)azetidine-3-carboxylate [hS1P1 EC$_{50}$=409 nM]. 1H NMR (400 MHz, DMSO-d$_6$) δ ppm 7.82-8.07 (m, 2H), 7.20-7.42 (m, 8H), 7.14-7.23 (m, 1H), 4.19 (s, 2H), 3.62 (s, 2H), 3.37-3.49 (m, 2H), 3.14-3.29 (m, 3H). MS (ESI) m/z: Calculated: 416.2 Observed: 417.1 (M$^+$+1).

Compound 110

1-((4-(6-Benzyl-5-chlorofuro[3,2-b]pyridin-2-yl)-3-fluorophenyl)methyl)azetidine-3-carboxylic acid

5-Benzyl-6-chloropyridin-3-ol

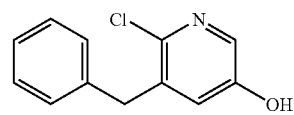

Starting material (5-bromo-6-chloropyridin-3-ol) is available from a published 3-step procedure: *Synthesis*, 1990, 499-501. To an oven-dried flask was added zinc (2.45 g, 37.4 mmol) and a crystal of iodine. The mixture was heated with a heat gun for 10 min under vacuum and then allowed to cool under Ar atmosphere. After charging the flask with degassed DMF (10 mL), the mixture was cooled to 0° C., and benzyl bromide (2.96 mL, 24.9 mmol) was added. After stirring the resulting mixture at 0° C. for 30 min, a mixture of Pd$_2$(dba)$_3$ (0.571 g, 0.624 mmol), S-Phos (1.02 g, 2.49 mmol) and 5-bromo-6-chloropyridin-3-ol (2.60 g, 12.5 mmol) was added to the flask quickly, and then the reaction was flushed with Ar and placed in an oil bath at 60° C. for 4 h or until starting material was gone by LCMS. The reaction was cooled to rt and filtered through a fine fritted funnel. The filtrate was concentrated to afford a yellow oil that was adsorbed onto silica and purified by flash chromatography (25% EtOAc/Hex, ramped to 100% EtOAc). The product was further purified after the column by recrystallization from hexane and minimal cold chloroform to afford a white solid. MS (ESI) m/z: Calculated: 219.1; Observed: 220.0 (M⁺+1).

5-Benzyl-6-chloro-2-iodopyridin-3-ol

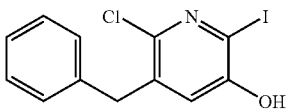

To a solution of K₂CO₃ (1.6 g, 12 mmol) in water (25.0 mL) was added 5-benzyl-6-chloropyridin-3-ol (0.73 g, 3.3 mmol) and I₂ (0.21 mL, 4.0 mmol). The mixture became homogeneous and yellow after stirring for 16 h. The mixture was washed with sodium thiosulfate (100 mL), and then treated cautiously with conc. HCl until the pH was 2 by pH paper. The solution was extracted with EtOAc (3×50 mL), and the combined organic extracts were dried over MgSO₄, filtered and concentrated to afford a pale yellow solid. The solid was purified by triturating with minimal DCM and ether to give a beige solid. ¹H NMR (300 MHz, DMSO-d₆) δ ppm 10.90-11.09 (1H, br s), 7.30-7.37 (2H, m), 7.17-7.28 (3H, m), 6.99 (1H, s), 3.95 (2H, s); MS (ESI) m/z: Calculated: 344.9; Observed: 345.9 (M⁺+1).

Methyl 1-((4-(6-benzyl-5-chlorofuro[3,2-b]pyridin-2-yl)-3-fluorophenyl)methyl)azetidine-3-carboxylate

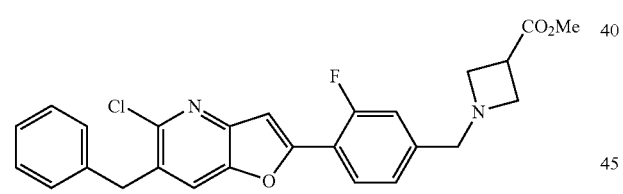

In a sealed flask was combined 5-benzyl-6-chloro-2-iodopyridin-3-ol (1.50 g, 4.3 mmol), PdCl₂(PPh₃)₂ (0.30 g, 0.43 mmol), copper(I) iodide (0.17 g, 0.87 mmol), N-ethyl-N-isopropylpropan-2-amine (6.1 mL, 35 mmol), methyl 1-(4-ethynyl-3-fluorobenzyl)azetidine-3-carboxylate (1.2 g, 4.8 mmol) and DMF (10 mL, 129 mmol). The flask was flushed with argon, sealed and placed in an oil bath for 16 h at 80° C. The reaction was concentrated to remove solvent, and the resulting black mixture was adsorbed onto silica. Flash chromatography (100% EtOAc) afforded a yellow oil that was further purified on a Varian HF Mega Bond Elut SCX column (eluted with 2M ammonia in MeOH). Trituration with of the resulting solids with ether afforded an off-white solid. ¹H NMR (300 MHz, CHLOROFORM-d) δ ppm 7.83-7.90 (1H, m), 7.49 (1H, s), 7.27-7.40 (5H, m), 7.22-7.24 (1H, m), 7.12-7.19 (2H, m), 4.20 (2H, s), 3.72 (3H, s), 3.65 (2H, s), 3.52-3.59 (2H, m), 3.32-3.38 (3H, m); MS (ESI) m/z: Calculated: 464.1; Observed: 465.1 (M⁺+1).

1-((4-(6-benzyl-5-chlorofuro[3,2-b]pyridin-2-yl)-3-fluorophenyl)methyl)azetidine-3-carboxylic acid

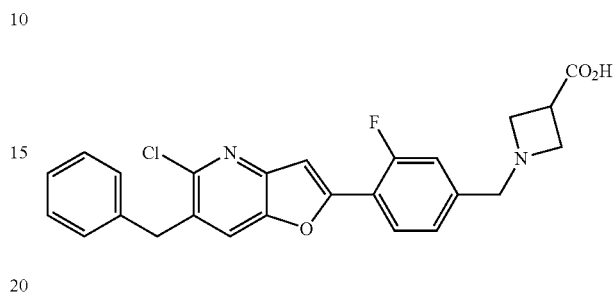

To a solution of LiOH (0.022 g, 0.90 mmol) in water (3.0 mL) was added methyl 1-((4-(6-benzyl-5-chlorofuro[3,2-b]pyridin-2-yl)-3-fluorophenyl)methyl)azetidine-3-carboxylate (0.084 g, 0.18 mmol) in THF (2.0 mL). The solution was stirred for 30 min and then the solvent was removed under reduced pressure to afford a white suspension. To the mixture was added 0.5M phosphate buffer, pH 6.0 (3 mL), and then 1 N HCl was added until the pH was 6.0 as indicated by pH paper. The resulting suspension was filtered, and the off white solid was collected and dried under vacuum at 50° C. ¹H NMR (400 MHz, DMSO-d₆ with 1 drop of TFA-d) δ ppm 8.04-8.21 (2H, m), 7.44-7.70 (3H, m), 7.18-7.40 (5H, m), 4.45-4.60 (2H, m), 4.13-4.40 (6H, m), 3.60-3.76 (1H, m); MS (ESI) m/z: Calculated: 450.1; Observed: 451.1 (M⁺+1).

Compound 111

1-((4-(6-Benzylbenzo[d]oxazol-2-yl)-3-fluorophenyl)methyl)azetidine-3-carboxylic acid 4-Benzyl-2-iodobenzenamine

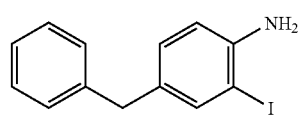

To a solution of 4-benzylbenzenamine (3.00 g, 16.4 mmol) in 16 mL MeOH was added iodine (2.49 g, 9.82 mmol) followed by hydrogen peroxide, 30% in water (1.67 mL, 16.4 mmol). The dark solution was allowed to stir overnight. The reaction was partitioned between water/brine and EtOAc. The organic layer was washed 1× brine, dried over MgSO₄, filtered, and concentrated. The resulting oil was purified by ISCO (120 g, 0-10% EtOAc/hexanes) to give 4-benzyl-2- iodobenzenamine as a red oil which slowly solidified to a red solid. MS (ESI) m/z: Calculated: 309.0; Observed: 310.0 (M$^+$+1).

N-(4-Benzyl-2-iodophenyl)-2-fluoro-4-formylbenzamide

To a slurry of 2-fluoro-4-formylbenzoyl chloride (1.5 mmol) in 5 mL THF was added N-ethyl-N-isopropylpropan-2-amine (0.39 mL, 2.2 mmol) and 4-benzyl-2-iodobenzenamine (0.41 g, 1.3 mmol). After 30 min, the reaction was treated with 1N HCl and Et$_2$O. The organic layer was washed 1×1N HCl, 2×sat'd aq. NaHCO$_3$, and 1× brine. The org. layer was dried over MgSO$_4$, filtered, and concentrated in vacuo. The resulting material was purified by ISCO, 40 g, 0-20% EtOAc/hexanes to give N-(4-benzyl-2-iodophenyl)-2-fluoro-4-formylbenzamide as a white solid. MS (ESI) m/z: Calculated: 459.0; Observed: 457.9 (M$^-$−1).

4-(6-Benzylbenzo[d]oxazol-2-yl)-3-fluorobenzaldehyde

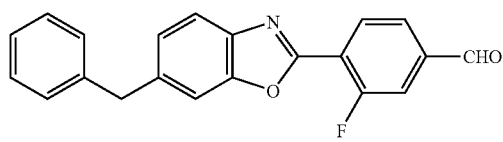

1,10-Phenanthroline (0.016 g, 0.087 mmol), cuprous iodide (0.008 g, 0.044 mmol), cesium carbonate (0.21 g, 0.65 mmol), and N-(4-benzyl-2-iodophenyl)-2-fluoro-4-formylbenzamide (0.200 g, 0.44 mmol) were combined under argon. Dioxane (2 mL) was added and the reaction was sealed and heated to 90° C. for 24 h. The reaction was cooled and partitioned between EtOAc and water. The organics were washed with brine, dried over sodium sulfate, filtered, and concentrated. The residue was purified by ISCO, 40 g, 0-30% EtOAc/hexanes to give 4-(6-benzylbenzo[d]oxazol-2-yl)-3-fluorobenzaldehyde as a white solid. MS (ESI) m/z: Calculated: 331.1; Observed: 332.1 (M$^+$+1).

1-((4-(6-Benzylbenzo[d]oxazol-2-yl)-3-fluorophenyl)methyl)azetidine-3-carboxylic acid

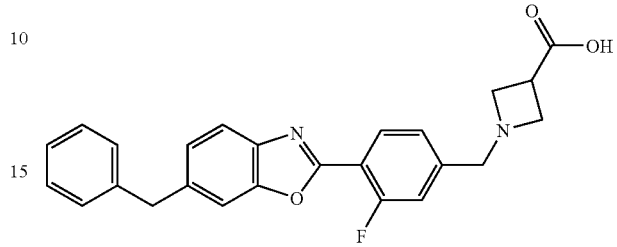

Synthesized according to Scheme B4 and general procedure I using 4-(6-benzylbenzo[d]oxazol-2-yl)-3-fluorobenzaldehyde as a white solid [hS1P1 EC$_{50}$=8 nM]. 1H NMR (400 MHz, DMSO-d$_6$) δ ppm 8.12 (t, J=7.8 Hz, 1H), 7.73 (d, J=8.0 Hz, 1H), 7.69 (s, 1H), 7.26-7.38 (m, 7H), 7.16-7.25 (m, 1H), 4.11 (s, 2H), 3.65 (s, 2H), 3.19-3.48 (m, 5H). MS (ESI) m/z: Calculated: 416.2; Observed: 417.2 (M$^+$+1).

Compound 112

1-((4-(5-Benzylbenzo[d]oxazol-2-yl)-3-fluorophenyl)methyl)azetidine-3-carboxylic acid 4-Benzyl-2-nitrophenol

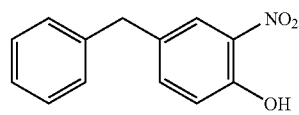

To a solution of 4-benzylphenol (10.0 g, 54.3 mmol) in 300 mL AcOH at ambient temperature was added slowly dropwise a solution of nitric acid, red fuming (2.28 mL, 54.3 mmol) in 100 mL AcOH over 1-2 h. The reaction was allowed to stir for 3 h, poured onto ice, and the resulting solid was collected by filtration, rinsing with water to give 4-benzyl-2-nitrophenol as a yellow solid. MS (ESI) m/z: Calculated: 229.1; Observed: 227.8 (M$^+$+1).

2-Amino-4-benzylphenol

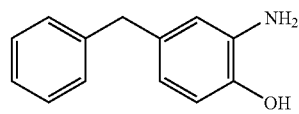

10% Palladium on carbon, Pearlman, (50% wet) (2.3 g, 2.2 mmol) and 4-benzyl-2-nitrophenol (5.00 g, 22 mmol) were combined under nitrogen and diluted with 80 mL MeOH delivered via syringe. The vessel was pressurized to 40 psi and shaken in a Parr shaker for ~24 h. The resulting material was flushed with nitrogen and filtered through Celite, rinsing with MeOH. The filtrate was concentrated in vacuo to give 2-amino-4-benzylphenol as a brown solid. MS (ESI) m/z: Calculated: 199.1; Observed: 200.0 (M⁺+1).

N-(5-Benzyl-2-hydroxyphenyl)-2-fluoro-4-formylbenzamide

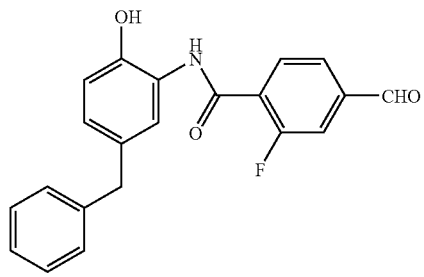

To a mixture of 2-fluoro-4-formylbenzoic acid (0.600 g, 3.57 mmol) in 15 mL DCM was added oxalyl dichloride (0.374 mL, 4.28 mmol) and N,N-dimethylformamide (0.00261 g, 0.0357 mmol) (a few drops). The mixture was allowed to stir for several h, treated with additional (COCl)₂ (0.100 mL), stirred further for 1 h, concentrated in vacuo, and the semi-solid was suspended in 15 mL THF. N,N-diisopropylethylamine (0.808 mL, 4.64 mmol) was added followed by 2-amino-4-benzylphenol (0.711 g, 3.57 mmol). After 4 h, the reaction was treated with EtOAc, water, and 1N HCl. The organic layer was washed 1× brine, dried over sodium sulfate, filtered, and concentrated. The material was purified by silica gel chromatography to give title compound as a solid. MS (ESI) m/z: Calculated: 349.1; Observed: 347.7 (M⁻−1).

5-Benzyl-2-(4-(dimethoxymethyl)-2-fluorophenyl)benzo[d]oxazole

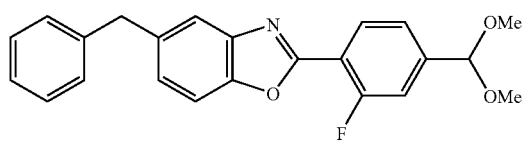

A mixture of N-(5-benzyl-2-hydroxyphenyl)-2-fluoro-4-formylbenzamide (0.500 g, 1.43 mmol), p-toluenesulfonic acid monohydrate (0.817 g, 4.29 mmol) in 14 mL toluene in a flask fitted with a water-cooled reflux condensor under nitrogen was heated to 115° C. After 3 h the reaction was cooled, and diluted with DCM and MeOH to give a solution and 15 g Si-carbonate (derivitized silica gel, silicycle) was added and the mixture dried. The material was purified by silica gel chromatography, 0-50% EtOAc/hexanes to give title compound as an off-white solid. MS (ESI) m/z: Calculated: 377.1; Observed: 378.1 (M⁺+1).

5-Benzyl-2-(4-(dimethoxymethyl)-2-fluorophenyl)benzo[d]oxazole

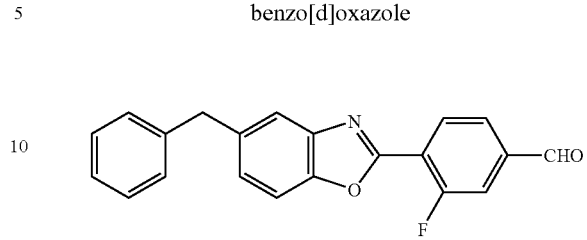

5-Benzyl-2-(4-(dimethoxymethyl)-2-fluorophenyl)benzo[d]oxazole (0.160 g, 0.424 mmol) was dissolved in 2 mL THF and 1 mL 5N HCl was added. The mixture was stirred for 1 h, diluted with DCM, and quenched with 10N NaOH until basic. The aqueous was extracted 2×DCM. Combined organics were dried over sodium sulfate, filtered, and concentrated to give 4-(5-benzylbenzo[d]oxazol-2-yl)-3-fluorobenzaldehyde as an orange solid. 1H NMR (400 MHz, DMSO-d₆) δ ppm 10.09 (s, 1H), 8.43 (t, J=7.3 Hz, 1H), 7.90-8.04 (m, 2H), 7.72-7.83 (m, 2H), 7.38 (d, J=8.5 Hz, 1H), 7.26-7.33 (m, 4H), 7.17-7.24 (m, 1H), 4.11 (s, 2H).

1-((4-(5-Benzylbenzo[d]oxazol-2-yl)-3-fluorophenyl)methyl)azetidine-3-carboxylic acid

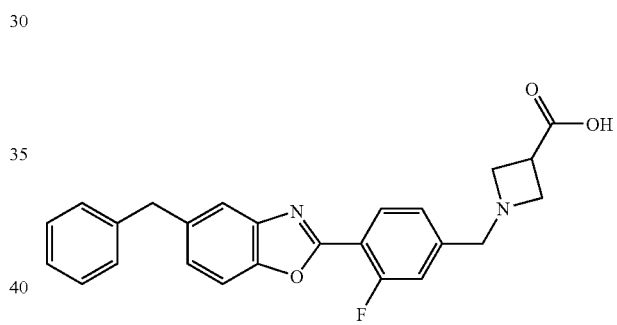

Synthesized according to Scheme B4 and general procedure I using 4-(5-benzylbenzo[d]oxazol-2-yl)-3-fluorobenzaldehyde [hS1P1 EC₅₀ =19 nM] as a white solid. ¹H NMR (400 MHz, DMSO-d₆) δ ppm 8.13 (t, J=8.0 Hz, 1H), 7.67-7.74 (m, 2H), 7.26-7.39 (m, 7H), 7.16-7.24 (m, 1H), 4.09 (s, 2H), 3.66 (s, 2H), 3.39-3.51 (m, 2H), 3.20-3.36 (m, 3H). MS (ESI) m/z: Calculated: 416.2; Observed: 417.0 (M⁺+1).

Compound 113

1-((4-(5-Benzylbenzo[d]oxazol-2-yl)phenyl)methyl)azetidine-3-carboxylic acid

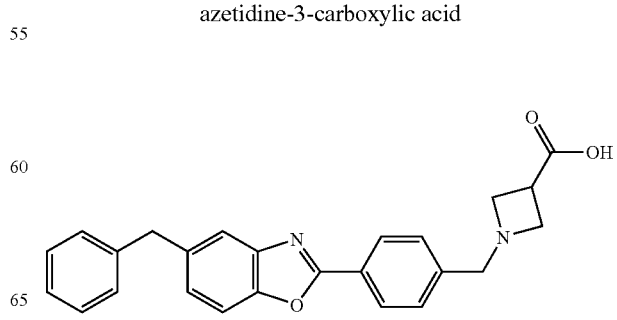

Synthesized in a manner analogous to 1-((4-(5-benzyl-benzo[d]oxazol-2-yl)-3-fluorophenyl)methyl)azetidine-3-carboxylic acid, except employing 4-formylbenzoyl chloride. white solid [hS1P1 EC$_{50}$=364 nM]. 1H NMR (400 MHz, DMSO-d$_6$) δ ppm 8.12 (d, J=8.0 Hz, 2H), 7.61-7.72 (m, 2H), 7.49 (d, J=8.0 Hz, 2H), 7.25-7.35 (m, 5H), 7.15-7.24 (m, 1H), 4.08 (s, 2H), 3.64 (s, 2H), 3.19-3.48 (m, 5H). MS (ESI) m/z: Calculated: 398.2; Observed: 399.2 (M$^+$+1).

Compound 114

1-((4-(6-Benzylbenzo[d]thiazol-2-yl)-3-fluorophenyl)methyl)azetidine-3-carboxylic acid S-4-Benzyl-2-nitrophenyl dimethylcarbamothioate

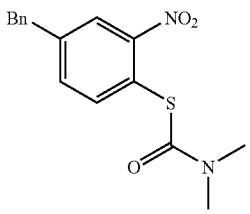

To a yellow solution of 4-benzyl-2-nitrophenol (2.0 g, 8.7 mmol) in 20 mL DMF at 0° C. was added sodium hydride (0.38 g, 9.6 mmol). The reaction became deep orange, and after 30 min dimethylthiocarbamoyl chloride (1.2 g, 9.6 mmol) was added. The reaction was stirred over the weekend at room temperature. Water was added, and the mixture was extracted with DCM 3 times. The combined extracts were washed with 0.5M NaHCO$_3$, dried over anhydrous sodium sulfate, filtered, and concentrated in vacuo to give a brown oil. The oil was heated to 160° C. for a total of 2 h. The reaction was cooled, and the resulting oil was loaded directly onto a 120 g ISCO column and eluted with 0-30-50% EtOAc/hexanes, to give S-4-benzyl-2-nitrophenyl dimethylcarbamothioate. MS (ESI) m/z: Calculated: 316.1; Observed: 317.1 (M$^+$+1).

S-2-Amino-4-benzylphenyl dimethylcarbamothioate

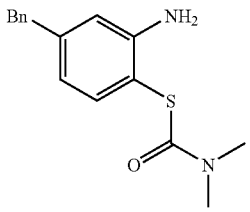

To a solution of S-4-benzyl-2-nitrophenyl dimethylcarbamothioate (1.58 g, 4.99 mmol) in 25 mL 5:1 acetone/water under nitrogen was added zinc, nanosize activated powder (1.63 g, 25.0 mmol) and ammonium chloride (2.67 g, 49.9 mmol). The reaction became hot and was cooled with an ice bath. The heterogeneous reaction was allowed to stir for ~4 h. The reaction was allowed to stand overnight and was partitioned between 200 mL EtOAc and water. The organic layer was washed with brine, and dried over sodium sulfate, filtered, and concentrated to give S-2-amino-4-benzylphenyl dimethylcarbamothioate which was used without further purification. MS (ESI) m/z: Calculated: 286.1; Observed: 287.0 (M$^+$+1).

2-(2-(2-Amino-4-benzylphenyl)disulfanyl)-5-benzyl-benzenamine

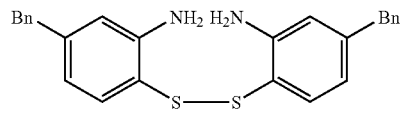

To a slurry of S-2-amino-4-benzylphenyl dimethylcarbamothioate (1.43 g, 4.99 mmol) in 15 mL ethylene glycol was added potassium hydroxide (0.840 g, 15.0 mmol) (solid, finely crushed). The reaction was heated to 60° C. under nitrogen. 10 mL 2-BuOH was added as cosolvent and the resulting solution was heated for 2 h. The reaction was fitted with a water-cooled reflux condenser and heated to 90° C. for 3 h. The reaction was cooled, and concentrated in vacuo. The material was partitioned between Et$_2$O and water. The organic layer was dried over sodium sulfate, filtered, and concentrated in vacuo to give an oil, which was purified by silica gel chromatography, ISCO, 0-30% EtOAc/hexanes to give 2-(2-(2-amino-4-benzylphenyl)disulfanyl)-5-benzyl-benzenamine as a brown oil. MS (ESI) m/z: Calculated: 428.1; Observed: 429.0 (M$^+$+1).

4-(5-Benzylbenzo[d]thiazol-2-yl)-3-fluorobenzaldehyde

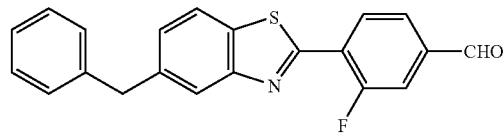

2-Fluoro-4-formylbenzoyl chloride (3.16 mmol) was dissolved in 5 mL THF, and a solution of N,N-diisopropylethylamine (0.879 mL, 5.05 mmol) and 2-(2-(2-amino-4-benzylphenyl)disulfanyl)-5-benzylbenzenamine (0.541 g, 1.26 mmol) in 5 mL THF was added dropwise via syringe, 1 mL THF rinse. The mixture became brown and then a precipitate formed. The mixture was allowed to stir overnight. The reaction was diluted with EtOAc and 1N NaOH. The orgn. layer was washed 1× brine, dried over anhyd. sodium sulfate, filtered, and concentrated in vacuo to give a brown oil. The resulting brown oil was treated with 16 mL EtOH, 2 mL water, and 8 mL conc. HCl followed by tin II chloride dihydrate. (1.71 g, 7.57 mmol). The heterogeneous reaction was fitted with a water cooled reflux condensor and was heated to reflux overnight. The reaction was cooled to 0° C. and basified with 10N NaOH. The reaction was partitioned between water and DCM. The aqueous layer was extracted with DCM 3 times, and the combined organics were dried over anhydrous sodium sulfate, filtered, and concentrated in vacuo. The material was treated with 10% MeOH in DCM and adsorbed onto 5 g silica gel and passed through a Redi-Sep® pre-packed silica gel column (80 g) using 0-15% EtOAc/hexane. The product-containing fractions were concentrated to afford title compound as a pale yellow solid. MS (ESI) m/z: Calculated: 347.1; Observed: 348.0 (M⁺+1).

1-((4-(5-Benzylbenzo[d]thiazol-2-yl)-3-fluorophenyl)methyl)azetidine-3-carboxylic acid

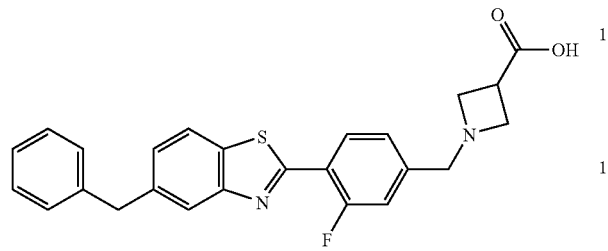

Synthesized according to Scheme B4 and general procedure I using 4-(5-benzylbenzo[d]thiazol-2-yl)-3-fluorobenzaldehyde: light yellow solid [hS1P1 $EC_{50}$=29 nM]. 1H NMR (400 MHz, DMSO-$d_6$) δ ppm 8.27 (t, J=8.0 Hz, 1H), 8.07 (d, J=8.5 Hz, 1H), 7.95 (s, 1H), 7.27-7.44 (m, 7H), 7.16-7.25 (m, 1H), 4.13 (s, 2H), 3.65 (s, 2H), 3.40-3.50 (m, 2H), 3.20-3.30 (m, 3H). MS (ESI) m/z: Calculated: 432.1; Observed: 433.0 (M⁺+1).

Compound 115

1-((4-(5-Benzyl-1H-benzo[d]imidazol-2-yl)-3-fluorophenyl)methyl)azetidine-3-carboxylic acid 4-Benzyl-2-nitrobenzenamine

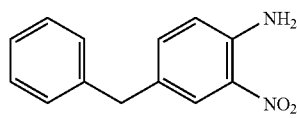

4-Aminodiphenylmethane (5.00 g, 27 mmol) was added in portions to acetic anhydride (26 mL, 273 mmol) with rapid stirring. A solid mass formed which was liberated by the addition of 15 mL additional acetic anhydride. The reaction was allowed to cool to ambient temp, and nitric acid (2.0 mL, 41 mmol) was added slowly dropwise via addition funnel over 30 min. The homogeneous red mixture was allowed to stir overnight and poured into a rapidly stirring solution of 30 mL water, 7 mL conc. HCl, and 24 mL EtOH (exothermic!). The reaction was allowed to cool and was then heated to reflux for ~4 h, cooled and poured onto ice and neutralized with 10N NaOH to pH 8-9. The aqueous layer was extracted 3×DCM and dried over sodium sulfate, filtered, and concentrated. The resulting dark red oil was purified by silica gel chromatography, ISCO 120 g, 0-20% EtOAc/hexanes, to give 4-benzyl-2-nitrobenzenamine as a red oil. MS (ESI) m/z: Calculated: 228.1; Observed: 229.0 (M⁺+1).

N-(4-Benzyl-2-nitrophenyl)-4-(dimethoxymethyl)-2-fluorobenzamide

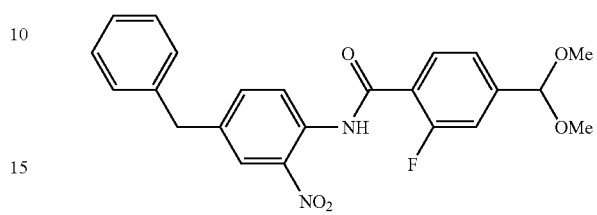

2-Fluoro-4-formylbenzoic acid (0.300 g, 1.78 mmol) was slurried in 10 mL DCM and catalytic DMF was added, followed by oxalyl chloride (0.317 mL, 3.57 mmol). The reaction was allowed to stir several h. Upon consumption of the acid, the reaction was concentrated in vacuo and diluted with 7 mL THF. 4-Benzyl-2-nitrobenzenamine (0.611 g, 2.68 mmol) and diisopropylethylamine (0.622 mL, 3.57 mmol) was added as a solution in 5 mL THF. The reaction was allowed to stir overnight and worked up with EtOAc/saturated sodium bicarbonate, dried over sodium sulfate, filtered, and concentrated. The residue was treated with p-toluenesulfonic acid monohydrate (0.170 g, 0.892 mmol) and MeOH. After 1 h, the mixture was concentrated and adsorbed onto silica gel and purified by chromatography to give N-(4-benzyl-2-nitrophenyl)-4-(dimethoxymethyl)-2-fluorobenzamide. MS (ESI) m/z: Calculated: 424.1; Observed: 425.2 (M⁺+1).

(4-(5-Benzyl-1H-benzo[d]imidazol-2-yl)-3-fluorophenyl)methanol

To a yellow-orange solution of N-(4-benzyl-2-nitrophenyl)-4-(dimethoxymethyl)-2-fluorobenzamide (0.466 g, 1.1 mmol) in 5 mL 3:2 AcOH/EtOH was added iron powder—325 mesh (0.078 mL, 11 mmol). The reaction was fitted with a reflux condensor and was stirred rapidly at 120° C. bath. The reaction became a nearly solid mass after 10 min, and 3 mL 2:1 AcOH/EtOH was added to promote stirring. After 3 h, the mixture was bright yellow. The reaction was diluted with water, EtOAc, and brine, and the layers were separated. The aqueous layer was extracted 2× EtOAc, and the combined organics were washed 2×1N NaOH and 1× brine, dried over sodium sulfate, filtered, and concentrated to an orange oil. The material was purified by silica gel chromatography, ISCO, 40 g, 0-40% 90/10 DCM/MeOH in DCM to give title compound. MS (ESI) m/z: Calculated: 332.1; Observed: 333.1 (M$^+$+1).

4-(5-Benzyl-1H-benzo[d]imidazol-2-yl)-3-fluorobenzaldehyde

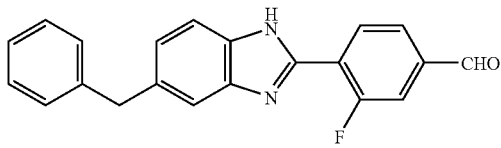

To a solution of (4-(5-benzyl-1H-benzo[d]imidazol-2-yl)-3-fluorophenyl)methanol (0.055 g, 0.17 mmol) and triethylamine (0.12 mL, 0.83 mmol) in 1.5 mL 1:1 DCM/DMSO under nitrogen at 0° C. was added a solution of SO$_3$*py (0.13 g, 0.83 mmol) in 0.75 mL DMSO. The reaction was allowed to stir for 2 h and was then diluted with EtOAc and water. The organic layer was washed 1× water, 1× brine, dried over anhydrous sodium sulfate, filtered, and concentrated. The residue was purified by ISCO, 12 g, 0-40% EtOAc/hexanes, to give 4-(5-benzyl-1H-benzo[d]imidazol-2-yl)-3-fluorobenzaldehyde as a light yellow oil. MS (ESI) m/z: Calculated: 330.1; Observed: 331.0 (M$^+$+1).

1-((4-(5-Benzyl-1H-benzo[d]imidazol-2-yl)-3-fluorophenyl)methyl)azetidine-3-carboxylic acid

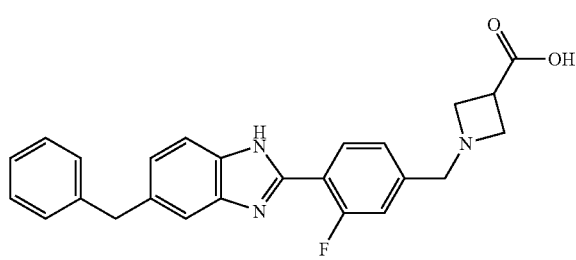

Synthesized according to Scheme B4 and general procedure I using 4-(5-benzyl-1H-benzo[d]imidazol-2-yl)-3-fluorobenzaldehyde to give 1-((4-(5-benzyl-1H-benzo[d]imidazol-2-yl)-3-fluorophenyl)methyl)azetidine-3-carboxylic acid as a white solid [hS1P1 EC$_{50}$=4954 nM]. MS (ESI) m/z: Calculated: 415.2; Observed: 416.2 (M$^+$+1).

Compound 116

1-((3-Fluoro-4-(5-phenoxybenzo[d]oxazol-2-yl)phenyl)methyl)azetidine-3-carboxylic acid 2-Nitro-4-phenoxyphenol

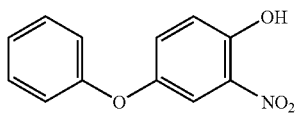

To a solution of 4-phenoxyphenol (10.0 g, 54 mmol) in 100 mL AcOH was added slowly dropwise nitric acid (69-70%, 3.2 mL, 54 mmol) over about 3 min from an addition funnel. The reaction became warm and was cooled with a water bath. After 1 h, the reaction was poured onto ice and allowed to warm to rt. A gummy solid resulted, which was partitioned between MTBE and water. The organic layer was washed 1× water, 1× brine, dried over sodium sulfate, filtered, and concentrated to a dark oil. This was adsorbed onto 36 g silica gel and dried, and purified in two parts by silica gel chromatography, ISCO, 0-10% EtOAC/hexanes. Product-containing fractions were combined and concentrated to give 2-nitro-4-phenoxyphenol as an orange oil. MS (ESI) m/z: Calculated: 231.1; Observed: 230.0 (M$^-$−1).

2-Amino-4-phenoxyphenol

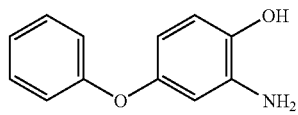

10% Palladium on carbon, 50% water wet (1.43 g, 1.34 mmol) and 2-nitro-4-phenoxyphenol (3.10 g, 13.4 mmol) were combined under nitrogen and 30 mL MeOH was added. The mixture was exposed to H$_2$ from a balloon and was stirred rapidly overnight. In the morning the reaction was flushed with nitrogen and filtered and concentrated in vacuo to give 2-amino-4-phenoxyphenol as a light brown solid. MS (ESI) m/z: Calculated: 201.1; Observed: 202.1 (M$^+$+1).

3-Fluoro-4-(5-phenoxybenzo[d]oxazol-2-yl)benzaldehyde

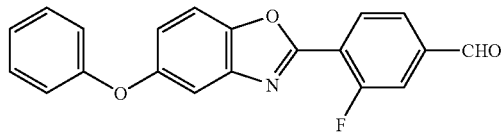

To a slurry of 2-fluoro-4-formylbenzoic acid (0.500 g, 3.0 mmol) in 8 mL DCM was added 2 drops N,N-dimethylformamide (0.011 g, 0.15 mmol), followed by oxalyl dichloride (0.39 mL, 4.5 mmol). After 30 min, the reaction became clear, light yellow, and homogeneous. The reaction was evaporated and dried in vacuo. The resulting solid was suspended in 10 mL THF, and 2-amino-4-phenoxyphenol (0.60 g, 3.0 mmol) was added as a solid followed by Hunig's base (0.67 mL, 3.9 mmol). The resulting brown solution became warm, and was allowed to stir for overnight. The reaction was diluted with DCM and 1N HCl. The aq. layer was extracted 1×DCM, and the organics were dried over sodium sulfate, filtered, and concentrated to give a brown solid. This was treated with 4-methylbenzenesulfonic acid hydrate (0.85 g, 4.5 mmol) and 10 mL toluene. The reaction was fitted with a water-cooled reflux condensor and drying tube, and placed in a 120° C. bath for ~4 h, cooled and partitioned between DCM and 1N NaOH with stirring. The reaction was filtered, and the aq. layer was extracted 1×DCM. The combined organics were dried over sodium sulfate, filtered, and concentrated to give an orange oil which was purified by ISCO, 0-30% EtOAc/hexanes to give title compound as an off-white solid. 1H NMR (400 MHz, DMSO-d$_6$) δ ppm 10.10 (s, 1H), 8.45 (t, J=7.5 Hz, 1H), 7.94-8.02 (m, 2H), 7.90 (d, J=9.0 Hz, 1H), 7.54 (d, J=2.0 Hz, 1H), 7.37-7.46 (m, 2H), 7.22 (dd, J=8.8, 2.3 Hz, 1H), 7.15 (t, J=7.3 Hz, 1H), 7.04 (d, J=8.5 Hz, 2H).

1-((3-Fluoro-4-(5-phenoxybenzo[d]oxazol-2-yl)phenyl)methyl)azetidine-3-carboxylic acid

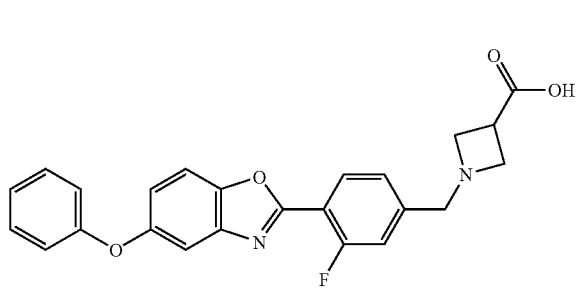

Synthesized according to Scheme B4 and general procedure I using 3-fluoro-4-(5-phenoxybenzo[d]oxazol-2-yl)benzaldehyde (0.035 g, 0.11 mmol) to give 1-(3-fluoro-4-(5-phenoxybenzo[d]oxazol-2-yl)benzyl)azetidine-3-carboxylic acid as a white solid [hS1P1 EC$_{50}$=12 nM]. 1H NMR (400 MHz, DMSO-d$_6$) δ ppm 8.15 (t, J=7.8 Hz, 1H), 7.84 (d, J=8.5 Hz, 1H), 7.48 (d, J=2.0 Hz, 1H), 7.31-7.44 (m, 4H), 7.10-7.20 (m, 2H), 7.03 (d, J=8.5 Hz, 2H), 3.67 (s, 2H), 3.40-3.51 (m, 2H), 3.21-3.35 (m, 3H). MS (ESI) m/z: Calculated: 418.1; Observed: 419.2 (M$^+$+1).

Compound 117

1-((3-Fluoro-4-(5-(phenylthio)benzo[d]oxazol-2-yl)phenyl)methyl)azetidine-3-carboxylic acid 5-(Phenylthio)benzo[d]oxazole

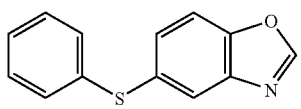

A 150 mL pressure bottle was charged with 5-bromobenzo[d]oxazole (2.43 g, 12.3 mmol), N,N-diisopropylethylamine (4.28 mL, 24.5 mmol), and 24 mL dioxane. N$_2$ was bubbled through the solution for 3 min, at which point tris(dibenzylidineacetone)palladium(0) (0.281 g, 0.307 mmol), 4,5-bis(diphenylphosphino)-9,9-dimethyl-9H-xanthene (0.355 g, 0.614 mmol), and benzenethiol (1.26 mL, 12.3 mmol) were added. The dark brown solution was sealed and heated to 100° C. overnight. The mixture was diluted with EtOAc and NaOH, and the organic layer was extracted 2×1N NaOH. The organic layer was dried over anhydrous sodium sulfate, filtered, and concentrated to give an orange oil, which was purified by ISCO, 0-100% 10% EtOAc/hexanes in hexanes to give 5-(phenylthio)benzo[d]oxazole as an orange oil. MS (ESI) m/z: Calculated: 227.0; Observed: 228.0 (M$^+$+1).

2-Amino-4-(phenylthio)phenol hydrochloride

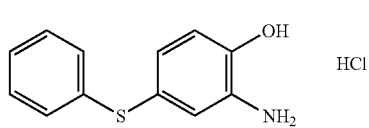

A solution of 5-(phenylthio)benzo[d]oxazole (1.04 g, 4.6 mmol) and conc. HCl (0.97 mL, 11 mmol) under nitrogen in 4.6 mL EtOH in a 50 mL rbf fitted with a water-cooled reflux condensor was placed in a 100° C. bath. After 2 h, the mixture was cooled, concentrated in vacuo and dried to give a yellow solid. The material was sonicated in 10 mL DCM, filtered, rinsing with DCM, and dried to give 2-amino-4-(phenylthio)phenol hydrochloride as an off-white solid. 1H NMR (400 MHz, DMSO-d$_6$) δ ppm 10.72 (s, 1H), 8.75 (br. s., 1H), 7.28-7.35 (m, 2H), 7.12-7.25 (m, 5H), 6.99 (d, J=8.0 Hz, 1H), 4.32 (br. s., 2H).

2-Fluoro-4-formyl-N-(2-hydroxy-5-(phenylthio)phenyl)benzamide

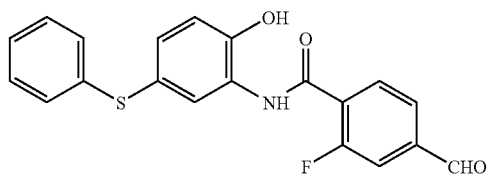

To a slurry of 2-fluoro-4-formylbenzoic acid (0.600 g, 3.57 mmol) in 10 mL anhydrous DCM under nitrogen was added 3 drops DMF, followed by oxalyl chloride (0.380 mL, 4.28 mmol). The reaction was allowed to stir under N$_2$. The reaction was allowed to stir for 4 h and concentrated in vacuo to a yellow oil. This material was dissolved in 10 mL THF and was added via pipette to a slurry of 2-amino-4-(phenylthio)phenol hydrochloride (0.906 g, 3.57 mmol) and diisopropylethylamine (1.55 mL, 8.92 mmol) in THF at 0° C. The bright yellow slurry was allowed to stir overnight. The mixture was treated with 1N HCl and DCM, and the organic layer was extracted 1×DCM. The organics were dried, filtered, and concentrated in vacuo. The orange oil was dissolved in 5 mL DCM, and a thick yellow precipitate resulted. This was collected by filtration, rinsing with DCM to give 2-fluoro-4- formyl-N-(2-hydroxy-5-(phenylthio)phenyl)benzamide as a bright yellow solid. MS (ESI) m/z: Calculated: 367.1; Observed: 366.0 (M$^-$−1).

3-Fluoro-4-(5-(phenylthio)benzo[d]oxazol-2-yl)benzaldehyde

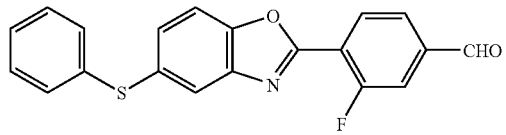

A mixture of 2-fluoro-4-formyl-N-(2-hydroxy-5-(phenylthio)phenyl)benzamide (0.180 g, 0.490 mmol) and pyridinium p-toluenesulfonate (0.123 g, 0.490 mmol) in 5.0 mL toluene was heated to 130° C. in a sealed tube for a total of 6 h. The reaction was cooled and was partitioned between 1N NaOH and EtOAc. The organic layer was washed 1× brine, dried over sodium sulfate, filtered, and concentrated in vacuo to give a solid that was purified by silica gel chromatography, 0-30-60% EtOAc/hexanes to give 3-fluoro-4-(5-(phenylthio)benzo[d]oxazol-2-yl)benzaldehyde as a yellow solid. MS (ESI) m/z: Calculated: 349.1; Observed: 350.0 (M$^+$+1).

1-((3-Fluoro-4-(5-(phenylthio)benzo[d]oxazol-2-yl)phenyl)methyl)azetidine-3-carboxylic acid

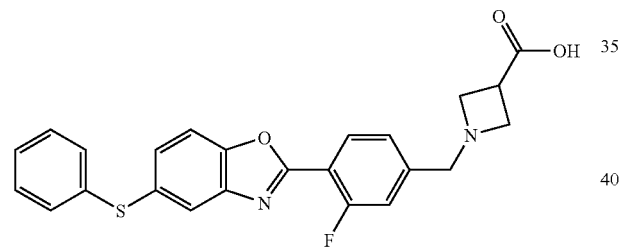

Synthesized according to Scheme B4 and general procedure I using 3-fluoro-4-(5-(phenylthio)benzo[d]oxazol-2-yl)benzaldehyde (0.116 g, 0.33 mmol): white solid [hS1P1 EC$_{50}$=3 nM]. 1H NMR (400 MHz, DMSO-d$_6$) δ ppm 8.15 (t, J=7.8 Hz, 1H), 7.82-7.91 (m, 2H), 7.48 (d, J=8.5 Hz, 1H), 7.25-7.42 (m, 7H), 3.67 (s, 2H), 3.40-3.50 (m, 2H), 3.18-3.38 (m, 3H). MS (ESI) m/z: Calculated: 434.1; Observed: 435.2 (M$^+$+1).

Compound 118

1-((4-(6-Benzylbenzo[d]thiazol-2-yl)-3-fluorophenyl)methyl)azetidine-3-carboxylic acid

6-Benzylbenzo[d]thiazol-2-amine

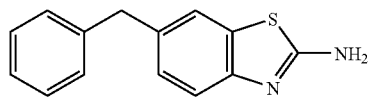

A mixture of 4-benzylbenzenamine (10.37 g, 56.6 mmol) and ammonium thiocyanate (3.30 mL, 56.6 mmol) in AcOH (100 mL) at 12-18° C. was treated dropwise with Br$_2$ (2.93 mL). During the addition, the temperature was kept below 18° C. After completion of the addition, the mixture was stirred at 24° C. for 2 h and the solvent was partially evaporated. The precipitates were collected by filtration, partially dissolved in 400 mL EtOAc at reflux temperature, and cooled to ~50° C. The solids were collected by filtration, washed with cold EtOAc, and dried in vacuo to give light yellow solids (16.17 g). This material was recrystallized from acetone to give 6-benzylbenzo[d]thiazol-2-amine as a beige solid. 1H NMR (400 MHz, DMSO-d6) δ ppm 8.89 (br. s, 2H), 7.67 (s, 1H), 7.35 (d, J=9.2 Hz, 1H), 7.29-7.20 (m, 6H), 3.98 (s, 2H). MS (ESI) m/z: Calculated: 240.3; Observed: 241.1 (M$^+$+1).

4-(6-Benzylbenzo[d]thiazol-2-yl)-3-fluorobenzaldehyde

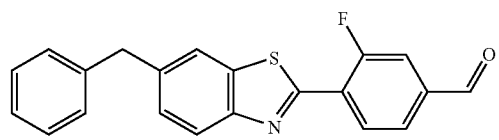

A solution of 12.3 g KOH in H$_2$O (15 mL) was mixed with ethylene glycol (8 mL). 6-benzylbenzo[d]thiazol-2-amine (3.00 g, 12.5 mmol) was added to the mixture under N$_2$ atmosphere. The mixture was stirred at 135° C. for 6 h, added to a 100 mL volume of ice and acidified to pH 6 using 5M aqueous HCl. The resulting suspension was extracted 2× with DCM. The organic layers were washed 1× with brine, dried over MgSO$_4$, and evaporated to give beige solids (1.81 g, used without further purification). A solution of the crude material (0.695 g, 3.23 mmol) in THF (5 mL) was added to a mixture of 2-fluoro-4-formylbenzoyl chloride (0.55 g) in THF (5 mL) and Hunig's base (0.844 mL, 4.84 mmol) and stirred for 17 h at 24° C. The mixture was diluted with EtOAc, washed 1× with saturated aqueous NaHCO$_3$, 1× with brine, dried over MgSO$_4$ and evaporated to give a red foam (0.916 g, used for the next step). The crude material was treated with EtOH (16 mL), water (2 mL), and concentrated aqueous HCl (8 mL) followed by SnCl$_2$ (1.67 g, 8798 μmol) and heated to reflux for 6 h (heterogeneous). The mixture was cooled to 0° C., basified with 10M aqueous NaOH, and partitioned between water and DCM. The aqueous layer was extracted with DCM (3×) and the combined organic layers were dried over MgSO$_4$ and evaporated. Purification by flash chromatography (hexanes/EtOAc=5:1) gave 4-(6-Benzylbenzo[d]thiazol-2-yl)-3-fluorobenzaldehyde as a yellow solid. 1H NMR (400 MHz, CDCl$_3$) δ ppm 10.06 (s, 1H), 8.67 (t, J=7.0 Hz, 1H), 8.09 (d, J=8.4 Hz, 1H), 7.83 (d, J=8.0 Hz, 1H), 7.76-7.73 (m, 2H), 7.43-7.40 (m, 1H), 7.33-7.31 (m, 2H), 7.26-7.23 (m, 3H), 4.16 (s, 2H). MS (ESI) m/z: Calculated: 347.4; Observed: 348.1 (M$^+$+1).

1-((4-(6-Benzylbenzo[d]thiazol-2-yl)-3-fluorophenyl)methyl)azetidine-3-carboxylic acid

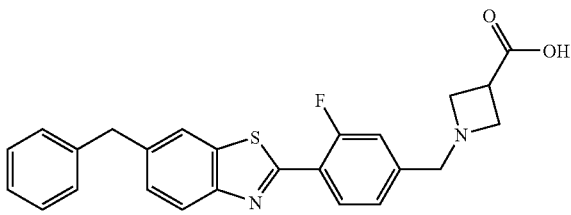

At 24° C., a mixture of 4-(6-benzylbenzo[d]thiazol-2-yl)-3-fluorobenzaldehyde (190 mg, 547 µmol), azetidine-3-carboxylic acid (166 mg, 1641 µmol), acetic acid (0.095 mL, 1641 µmol) in MeOH (2 mL) and DCM (2 mL) was stirred for 1 h. The light yellow solution was treated with sodium borocyanohydride (34 mg, 547 µmol). The mixture was stirred for 12 h. The solids were filtered off and washed 3× with DCM, suspended in 4 mL of an aqueous buffered solution (phosphate buffer pH 6) and sonicated for 10 min. The mixture was filtered and the solids washed with water and dried in vacuo to yield 1-((4-(6-Benzylbenzo[d]thiazol-2-yl)-3-fluorophenyl)methyl)azetidine-3-carboxylic acid as a white solid [hS1P1 EC$_{50}$=149 nM]. 1H NMR (400 MHz, DMSO-d6) δ ppm 8.27 (t, J=8.4 Hz, 1H), 8.04 (s, 1H), 8.01 (d, J=8.4 Hz, 1H), 7.44 (d, J=6.6 Hz, 1H), 7.34-7.29 (m, 6H), 7.21-7.20 (m, 1H), 4.11 (s, 2H), 3.83-3.82 (br. m, 1H), 3.63 (s, 2H), 3.41 (t, J=6.8 Hz, 2H), 3.21 (t, J=7.0 Hz, 2H). MS (ESI) m/z: Calculated: 432.5; Observed: 433.2 (M$^+$+1).

Compound 119

1-(4-(7-Benzyl-1H-imidazo[1,2-a]pyridin-2-yl)-3-fluorobenzyl)azetidine-3-carboxylic acid, trifluoroacetic acid salt 4-Benzylpyridin-2-amine

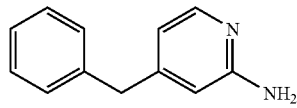

A mixture of 4-benzylpyridine (14.1 mL, 88.6 mmol), sodium amide (5.71 g, 146 mmol), and p-cymene (105 mL) was heated to 165° C. After 1 d, the mixture was allowed to cool; water (30 mL) and concentrated hydrochloric acid (30 mL) were sequentially added, the aqueous layer was separated, and the organic layer was extracted with 60 mL of 2N HCl (aq). The aqueous extracts were then combined, washed with ether (50 mL), and made strongly basic with solid potassium hydroxide, during which time a brown oil separated. The oil was extracted into DCM (2×150 mL). The combined extracts were then dried over sodium sulfate, filtered, and concentrated to give a brown oil. Column chromatography (ISCO, 80 g, 50->100% EtOAc/Hex) afforded 4-benzylpyridin-2-amine as a tan solid. MS (ESI) m/z: Calculated: 184.1; Observed: 185 (M$^+$+1).

4-(7-Benzyl-1H-imidazo[1,2-a]pyridin-2-yl)-3-fluorobenzaldehyde

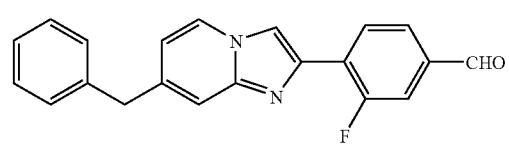

A solution of 4-benzylpyridin-2-amine (175 mg, 949 µmol) and 4-(2-bromoacetyl)-3-fluorobenzaldehyde (232.5 mg, 949 µmol) in EtOH (3.0 mL) was heated at reflux for 2 h, then cooled to 25° C. and concentrated in vacuo. The residue was taken up in THF (8.0 mL), concentrated aqueous hydrochloric acid (788 µL, 1576 µmol) was added, and the resulting mixture was stirred for 20 min. NaOH (1M, aq; 5.2 eq) was subsequently added to the reaction solution, which was then partitioned between EtOAc (20 mL) and brine (3 mL). The organic layer was dried over sodium sulfate and concentrated in vacuo. Chromatographic purification of the residue (ISCO, 4 g, 0-100% EtOAc/Hex+2% Et$_3$N) furnished 4-(7-Benzyl-1H-imidazo[1,2-a]pyridin-2-yl)-3-fluorobenzaldehyde as a white solid. MS (ESI) m/z: Calculated: 330.1; Observed: 331 (M$^+$+1).

1-(4-(7-Benzyl-1H-imidazo[1,2-a]pyridin-2-yl)-3-fluorobenzyl)azetidine-3-carboxylic acid, trifluoroacetic acid salt

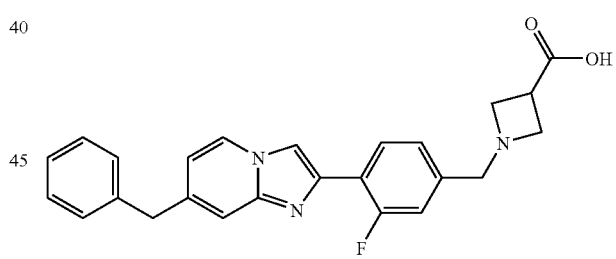

4-(7-Benzyl-1H-imidazo[1,2-a]pyridin-2-yl)-3-fluorobenzaldehyde (47.3 mg, 143 µmol) was dissolved in 1.0 mL DCM, and 1.0 mL MeOH was added to the resulting solution, followed by azetidine-3-carboxylic acid (43 mg, 430 µmol), and acetic acid (25 µL, 430 µmol). The mixture was stirred rapidly for 1 h, and sodium cyanoborohydride (9.0 mg, 143 µmol) was then added in one portion. After 15 h, the reaction solution was concentrated in vacuo and the residue was taken up in methanol (3.0 mL), filtered through a cotton plug, and purified by HPLC (Phenomenex C18, 1-100% CH3CN/H2O+0.1% TFA) to give 1-(4-(7-Benzyl-1H-imidazo[1,2-a]pyridin-2-yl)-3-fluorobenzyl)azetidine-3-carboxylic acid, trifluoroacetic acid salt as a clear oil [hS1P1 EC$_{50}$=54 nM]. 1H NMR (400 MHz, MeOH-d$_4$) δ ppm 8.71 (d, J=6.8 Hz, 1H), 8.59 (d, J=2.0 Hz, 1H), 8.05 (t, J=7.9 Hz, 1H), 7.69 (s, 1H), 7.52-7.64 (m, 1H), 7.38-7.43 (m, 2H), 7.36 (d, J=6.1 Hz, 3H), 7.33 (dd, J=6.1, 1.6 Hz, 1H), 7.28-7.32 (m, 1H), 4.55 (s, 2H), 4.36-4.47 (m, 4H), 4.28 (s, 2H), 3.76 (t, J=8.2 Hz, 1 H). MS (ESI) m/z: Calculated: 415.2; Observed: 416 (M++1).

Compound 120

1-(4-(6-Benzyl-1H-imidazo[1,2-a]pyridin-2-yl)-3-fluorobenzyl)azetidine-3-carboxylic acid, trifluoroacetic acid salt 5-Benzylpyridin-2-amine

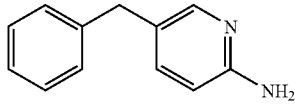

9-Benzyl-9-bora-bicyclo[3.3.1]nonane (0.5M solution in THF, 12727 µL, 6363 µmol) was added to a mixture of 5-iodopyridin-2-amine (700 mg, 3182 µmol), potassium phosphate (2026 mg, 9545 µmol), Pd$_2$dba$_3$ (58 mg, 64 µmol), and X-Phos (61 mg, 127 µmol) suspended in H$_2$O (1 mL) in a sealable reaction vial. The vial was flushed with argon gas and then sealed and heated (microwave) at 120° C. for 30 min. The crude mixture was diluted with EtOAc, and the resulting solution was sequentially washed with 1M NaOH and brine. The organic layer was dried over sodium sulfate and concentrated in vacuo. The residue was taken up in MeOH (5 mL), concentrated aqueous HCl (0.30 mL) was added, and the resulting solution was stirred 10 min. Solid NaOH (120 mg) was then added, and the resulting solution was concentrated onto silica gel. Chromatographic purification of the product (ISCO, 12 g, 0-10% MeOH/CH$_2$Cl$_2$) furnished 5-benzylpyridin-2-amine as a yellow solid. 1H NMR (400 MHz, CHLOROFORM-d) δ ppm 7.95 (s, 1H), 7.28 (t, J=7.5 Hz, 2H), 7.23 (d, J=11.0 Hz, 2H), 7.17 (t, J=8.5 Hz, 2H), 6.44 (d, J=8.5 Hz, 1H), 4.34 (s, 2H), 3.80-3.86 (m, 2H).

6-Benzyl-2-(4-(diethoxymethyl)-2-fluorophenyl)H-imidazo[1,2-a]pyridine

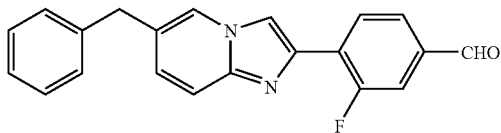

A solution of 5-benzylpyridin-2-amine (340.9 mg, 1850 µmol) and 4-(2-bromoacetyl)-3-fluorobenzaldehyde (453.4 mg, 1850 µmol) in ethanol (6.0 mL) was heated at reflux for 5 h. The solution was cooled to 25° C., triethylamine (260 µL) was added, and the resulting solution was concentrated onto silica gel and purified by column chromatography (ISCO, 4 g, 0->100% EtOAc/Hex, both +2% triethylamine) to furnish crude 6-benzyl-2-(4-(diethoxymethyl)-2-fluorophenyl)H-imidazo[1,2-a]pyridine as an orange oil. This oil was taken up in THF (10.0 mL), concentrated aqueous HCl (1.24 mL, 2487 µmol) was added, and the resulting mixture was stirred for 20 min at 25° C. NaOH (1M, aq; 5.2 eq) was then added to the reaction solution, and the resulting mixture was partitioned between EtOAc (40 mL) and brine (5 mL). The organic layer was dried over sodium sulfate and concentrated in vacuo. Chromatographic purification of the residue (ISCO, 4 g, 0-100% EtOAc/hexanes+2% Et$_3$N) provided 4-(6-Benzyl-1H-imidazo[1,2-a]pyridin-2-yl)-3-fluorobenzaldehyde as a yellow oil. MS (ESI) m/z: Calculated: 330.1; Observed: 331 (M++1).

1-(4-(6-Benzyl-1H-imidazo[1,2-a]pyridin-2-yl)-3-fluorobenzyl)azetidine-3-carboxylic acid, trifluoroacetic acid salt

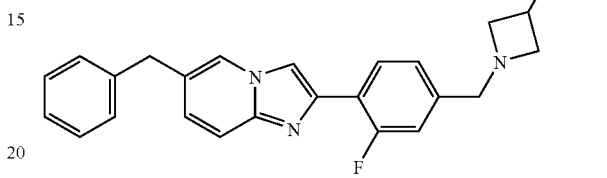

4-(6-Benzyl-1H-imidazo[1,2-a]pyridin-2-yl)-3-fluorobenzaldehyde (100.5 mg, 304 µmol) was dissolved in 2.0 mL DCM, and 2.0 mL MeOH was added, followed by azetidine-3-carboxylic acid (92.3 mg, 913 µmol), and acetic acid (52.7 µL, 913 µmol). The mixture was stirred rapidly for 1 h, at which point sodium cyanoborohydride (19.1 mg, 304 µmol) was added in one portion. After 2.5 d, the mixture was diluted with 2 mL DCM and the slurry was filtered, rinsing with DCM. The filtrate was concentrated in vacuo to afford a white foam, which was taken up in MeOH (3.0 mL), filtered through a cotton plug, and purified by HPLC (Phenomenex C18, 5-50-100% CH$_3$CN/H$_2$O+0.1% TFA) to afford 1-(4-(6-Benzyl-1H-imidazo[1,2-a]pyridin-2-yl)-3-fluorobenzyl) azetidine-3-carboxylic acid, trifluoroacetic acid salt as a clear oil. 1H NMR (400 MHz, MeOH) δ ppm 8.66 (s, 1H), 8.59 (s, 1H), 8.07 (t, J=7.8 Hz, 1H), 7.87 (s, 2H), 7.53-7.62 (m, 2H), 7.32-7.40 (m, 4H), 7.28 (t, J=6.8 Hz, 1H), 4.55 (s, 2H), 4.35-4.48 (m, 4H), 4.18 (s, 2H), 3.70-3.81 (m, 1H). MS (ESI) m/z: Calculated: 415.2; Observed: 416 (M++1).

Compound 121

1-((2-(5-Benzylbenzofuran-2-yl)pyrimidin-5-yl)methyl)azetidine-3-carboxylic acid 2-(5-Benzylbenzofuran-2-yl)pyrimidine-5-carbaldehyde

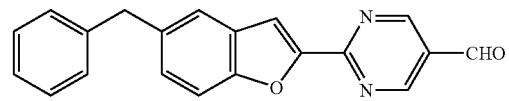

A 25 mm tube was charged with trifuran-2-ylphosphine (0.0737 g, 0.317 mmol), Pd$_2$dba$_3$ (0.0411 g, 0.0397 mmol), 5-benzylbenzofuran-2-ylboronic acid (0.500 g, 1.98 mmol), CuTC (0.492 g, 2.58 mmol), 2-(methylthio)pyrimidine-5-carbaldehyde (0.306 g, 1.98 mmol) under argon. The reactants were diluted in 8 mL THF, sealed, and heated to 50° C. overnight. The mixture was filtered through Celite rinsing with 200 mL EtOAc. The green solution was concentrated and adsorbed onto 5 g silica gel, and purified by ISCO, 0-20% EtOAc/hexanes to give 2-(5-benzylbenzofuran-2-yl)pyrimidine-5-carbaldehyde as a light yellow solid. MS (ESI) m/z: Calculated: 314.1; Observed: 315.1 (M++1).

1-((2-(5-Benzylbenzofuran-2-yl)pyrimidin-5-yl)methyl)azetidine-3-carboxylic acid

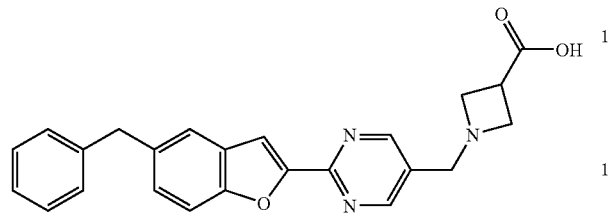

Synthesized according general procedure I from 2-(5-benzylbenzofuran-2-yl)pyrimidine-5-carbaldehyde (0.110 g, 0.35 mmol): white solid [hS1P1 EC$_{50}$=1323 nM]. 1H NMR (400 MHz, DMSO-d$_6$) δ ppm 8.79 (s, 2H), 7.70 (s, 1H), 7.57-7.65 (m, 2H), 7.25-7.37 (m, 5H), 7.14-7.23 (m, 1H), 4.06 (s, 2H), 3.62 (s, 2H), 3.40-3.51 (m, 2H), 3.17-3.30 (m, 3H). MS (ESI) m/z: Calculated: 399.2; Observed: 400.2 (M++1).

Compound 122

1-((6-(5-Benzylbenzofuran-2-yl)-2-methylpyridin-3-yl)methyl)azetidine-3-carboxylic acid

6-(5-Benzylbenzofuran-2-yl)-2-methylnicotinaldehyde

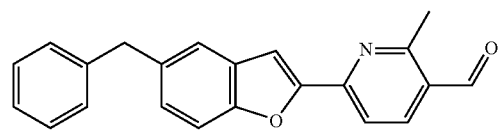

In a sealed flask, a mixture of 5-benzylbenzofuran-2-ylboronic acid (525 mg, 2.1 mmol) and potassium acetate (0.41 g, 4.2 mmol) was set under argon, treated with bis{di($^t$butyl)phenyl}palladium(II) dichloride (0.078 g, 0.12 mmol), followed by a solution of 6-chloro-2-methylnicotinaldehyde (0.29 g, 1.9 mmol) in EtOH (10 mL). The resulting suspension was degassed again and heated to 80° C. for 2 h. The mixture was cooled to 24° C., treated with EtOAc and washed with saturated aqueous NaHCO$_3$ and brine (each 1×). The combined organic layers were dried over MgSO$_4$ and evaporated. Purification by flash chromatography (hexanes to hexanes/EtOAc=9:1) gave 6-(5-Benzylbenzofuran-2-yl)-2-methylnicotinaldehyde as a pale yellow solid. 1H NMR (400 MHz, CDCl$_3$) δ ppm 10.33 (s, 1H), 8.27 (d, J=8.0 Hz, 1H), 7.97-7.95 (m, 2H), 7.51-7.49 (m, 2H), 7.31-7.29 (m, 2H), 7.24-7.21 (m, 3H), 4.10 (s, 2H), 3.07 (s, 3H). MS (ESI) m/z: Calculated: 327.4; Observed: 328.1 (M++1).

1-((6-(5-Benzylbenzofuran-2-yl)-2-methylpyridin-3-yl)methyl)azetidine-3-carboxylic acid

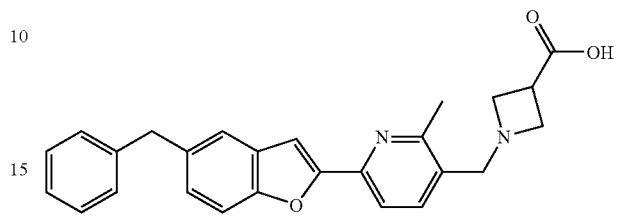

A suspension of 6-(5-benzylbenzofuran-2-yl)-2-methylnicotinaldehyde (160 mg, 489 μmol) and 3-azetidinecarboxylic acid (49.4 mg, 489 μmol) in MeOH (8 mL) and glacial acetic acid (44.0 mg, 733 μmol) was stirred at 24° C. for 1 h, treated with sodium borocyanohydride (15.4 mg, 244 μmol), and stirred for 2 h. The mixture was diluted with 30 mL of 1M HCl in Et$_2$O and evaporated. Purification of the residue by RP-HPLC to give title compound as an off-white solid [hS1P1 EC$_{50}$=420 nM]. 1H NMR (400 MHz, DMSO-d$_6$) δ ppm 7.72 (s, 2H), 7.55-7.53 (m, 2H), 7.43 (s, 1H), 7.28-7.18 (m, 6H), 4.04 (s, 2H), 3.59 (s, 2H), 3.45-3.23 (m, 8H). MS (ESI) m/z: Calculated: 412.5; Observed: 413.3 (M++1).

Compound 123

1-(1-(4-(5-benzylbenzofuran-2-yl)-3-fluorophenyl)ethyl)azetidine-3-carboxylic acid

1-(4-(5-Benzylbenzofuran-2-yl)-3-fluorophenyl)ethanol

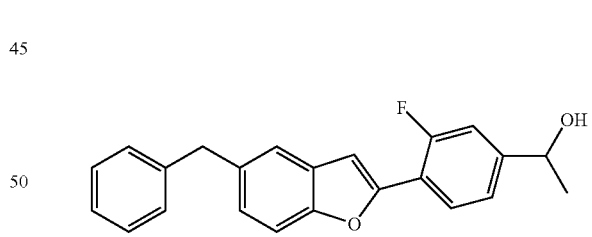

To a mixture of 4-(5-benzylbenzofuran-2-yl)-3-fluorobenzaldehyde (0.559 g, 2 mmol) in THF at 0° C. was added methyl-magnesium bromide (1.4M solution in toluene/THF=3:1, 2.40 mL, 3 mmol) dropwise over 5 min. The mixture was allowed to stir for 20 min at 0° C., treated with NH$_4$Cl, extracted with EtOAc, dried over MgSO$_4$, and evaporated. The crude product was purified by flash chromatography (EtOAc/hexanes) to give 1-(4-(5-benzylbenzofuran-2-yl)-3-fluorophenyl)ethanol. 1H NMR (300 MHz, CDCl$_3$) δ ppm 7.98 (t, J=8.0 Hz, 1H), 7.38-7.46 (m, 2H), 7.10-7.34 (m, 9H), 4.77-5.04 (m, 1H), 4.08 (s, 2H), 1.85 (d, J=3.8 Hz, 1H), 1.46-1.60 (m, 3H). MS (ESI) m/z: Calculated; 346.1 Observed: 347.1 (M$^+$+1).

1-(4-(5-benzylbenzofuran-2-yl)-3-fluorophenyl)ethanone

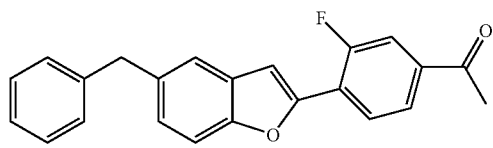

Dess-Martin reagent (0.411 g, 0.970 mmol) was added to a solution of 1-(4-(5-benzylbenzofuran-2-yl)-3-fluorophenyl) ethanol (0.280 g, 0.808 mmol) in DCM (25 mL) and stirred at room temperature for 1 h. The mixture was treated with saturated aqueous NaHCO$_3$, stirred for 5 min, and extracted with DCM. The combined organic layers were dried over MgSO$_4$ and evaporated. Purification by flash chromatography using EtOAc/hexanes gave 1-(4-(5-benzylbenzofuran-2-yl)-3-fluorophenyl)ethanone. 1H NMR (300 MHz, CDCl$_3$) δ ppm 8.11 (t, J=7.7 Hz, 1H), 7.68-7.88 (m, 2H), 7.41-7.48 (m, 2H), 7.12-7.35 (m, 7H), 4.09 (s, 2H), 2.63 (s, 3H). MS (ESI) m/z: Calculated; 344.4 Observed: 345.0 (M$^+$+1).

1-(1-(4-(5-benzylbenzofuran-2-yl)-3-fluorophenyl) ethyl)azetidine-3-carboxylic acid

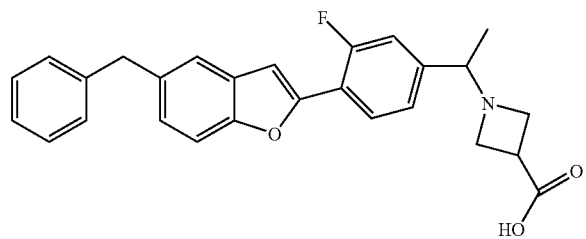

A mixture of azetidine-3-carboxylic acid (0.015 g, 0.15 mmol), 1-(4-(5-benzylbenzofuran-2-yl)-3-fluorophenyl) ethanone (0.050 g, 0.15 mmol), acetic acid (0.013 mL, 0.22 mmol) in methanol (3.0 mL) was stirred at room temperature for 1 h. Sodium triacetoxyborohydride (0.037 g, 0.17 mmol) was added and the mixture was stirred for 1 h at room temperature. Evaporation and purification by flash chromatography (5% AcOH in CHCl$_3$ and MeOH). The resulting solid was suspended in in an aqueous buffered solution (pH 6, phosphate buffer) and sonicated. The solids were collected by filtration, washed with water and Et$_2$O to give title compound [hS1P1 EC$_{50}$=313 nM]. 1H NMR (400 MHz, DMSO-d$_6$) δ ppm 7.89 (t, J=7.9 Hz, 1H), 7.51-7.59 (m, 2H), 7.14-7.34 (m, 9H), 4.04 (s, 2H), 2.92-3.50 (m, 6H partially overlapping with HDO signal), 1.11 (d, J=6.3 Hz, 3H). MS (ESI) m/z: Calculated; 429.2 Observed: 430.2 (M$^+$+1).

Activity of Compounds of the Invention

The compounds of the invention made according to the synthesis noted above were assayed for their ability to modulate the S1P-1 receptor. Compounds were evaluated for the ability to induce S1P1-specific receptor internalization using standard in-vitro receptor internalization assays and their utility as immunoregulatory agents was demonstrated by their activity as agonists of the S1P1 receptor measured in the receptor internalization assay (>50% of S1P control at 10 nM or 300 nM). The compounds accordingly are expected to be useful as S1P-1 receptor modulators, e.g., in the treatment of a variety of S1P-1 receptor-mediated clinical conditions. Such conditions include transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

To further demonstrate the suitability of compounds of the invention as S1P-1 receptor modulators for treating conditions such as transplant rejection; cancer; autoimmune/inflammatory diseases; rheumatoid arthritis; lupus; diabetes; multiple sclerosis; psoriasis; ulcerative colitis; inflammatory bowel disease; Crohn's disease; acute and chronic lymphocytic leukemias and lymphomas where immunosuppression is central (of which reduction of lymphopenia is therefore a well-established indicator), compounds of the invention were evaluated in laboratory animals as described below.

Protocol

Mice

C57BL/6J mice (B6, Jackson Laboratories, Bar Harbor, Me.) were maintained in a specific pathogen-free environment under a microisolator containment system. Both adult male and female age-matched mice were used for all experiments, which were reviewed and approved by the Animal Care and Use Committee at the University of Virginia. Whenever the protocol stated Mice were anesthetized via intraperitoneal injections of ketamine hydrochloride (125 mg/kg; Sanofi Winthrop Pharmaceuticals, New York, N.Y.), xylazine (12.5 mg/kg TranquiVed; Phoenix Scientific, St. Joseph, Mo.), and atropine sulfate (0.025 mg/kg; Fujisawa USA, Deerfield, Ill.).

Flow Cytometry Preparation and Analysis

Blood was harvested from at least six mice for each time point of 0, 4, 8, 24, 48, 72 h following one day, 3 days or 7 days daily dosing with the test compound. Following terminal bleeds brain and certain other tissues were harvested from all animals undergoing treatment. Cell counts were determined from whole blood, yielding cell counts in thousands of cells per microliter (K/IL).

To identify and quantify lymphocyte subsets, cell suspensions were analyzed by flow cytometry. Following red blood cell lysis, cells were stained with anti-mouse monoclonal antibodies against CD3, CD4, CD8, CD19, and NK1.1 (BD Biosciences, San Jose, Calif.). Cells were analyzed via four-color flow cytometry on a FACSCalibur (BD Biosciences) in the University of Virginia Cancer Center Core Facility. Lymphocyte subsets, including B cells, total T cells, CD4 T cells, CD8 T cells, double-positive thymocytes, double-negative thymocytes, NK cells, and NK/T cells, were analyzed. The size of each cell population was calculated as the product of the total lymphocyte count recorded by the Hemavet or hemocytometer and the percentage of positive lymphocytes recorded by the flow cytometer. All data were analyzed with BD Biosciences Cell Quest analysis software.

Statistical Analysis
Statistical significance was determined using Student's t-test to compare all time points to −24 hour group.
The compounds tested:
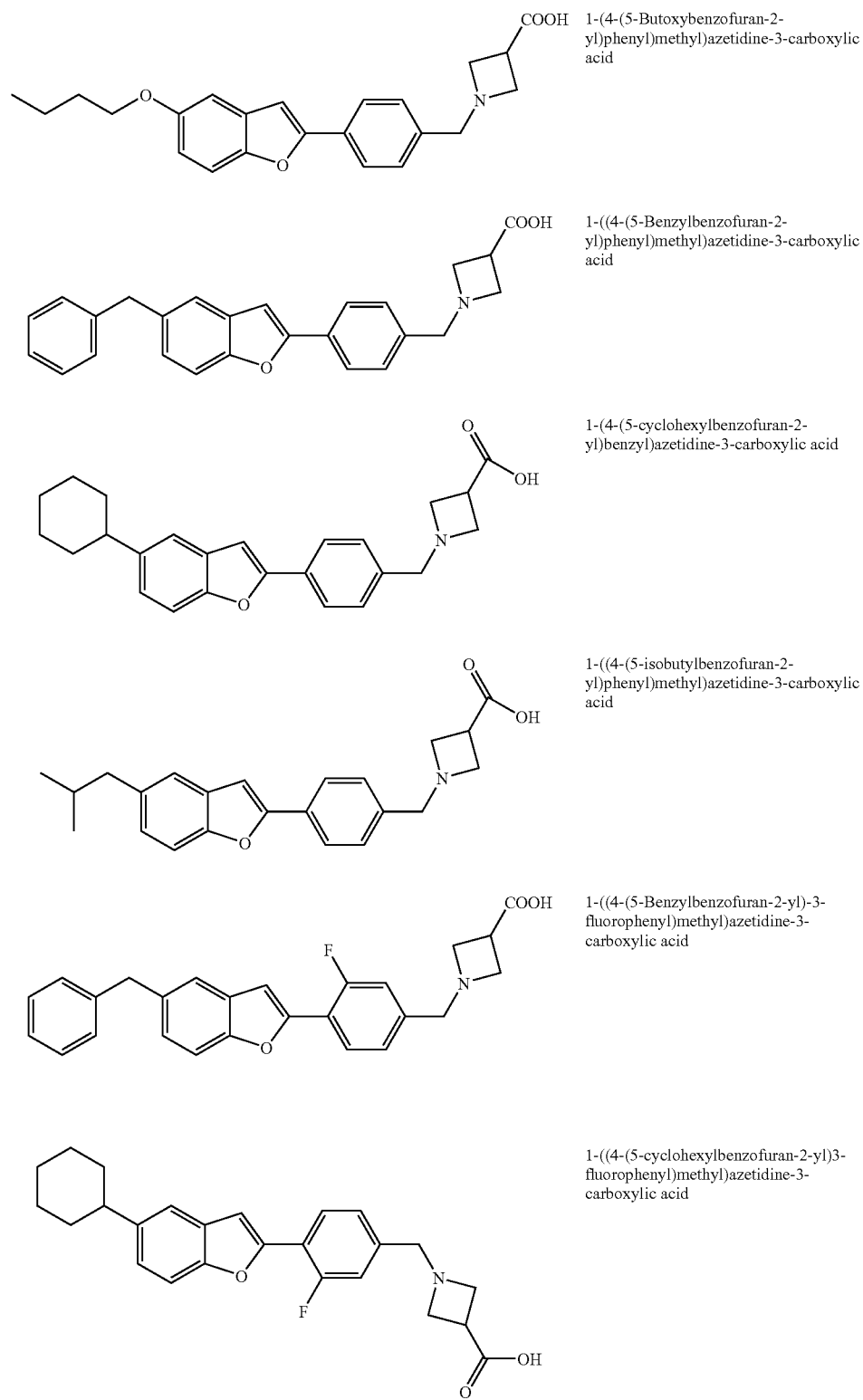

-continued

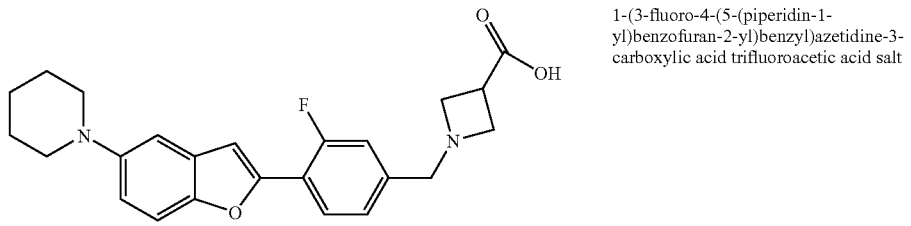

1-(3-fluoro-4-(5-(piperidin-1-yl)benzofuran-2-yl)benzyl)azetidine-3-carboxylic acid trifluoroacetic acid salt

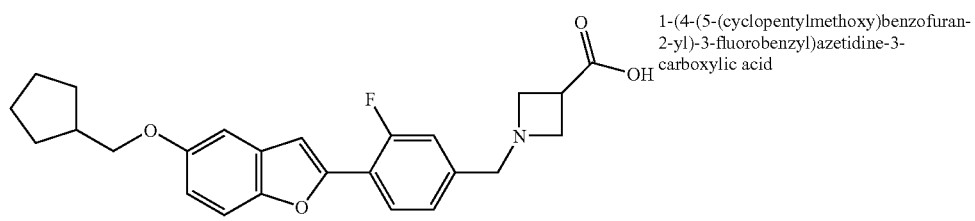

1-(4-(5-(cyclopentylmethoxy)benzofuran-2-yl)-3-fluorobenzyl)azetidine-3-carboxylic acid

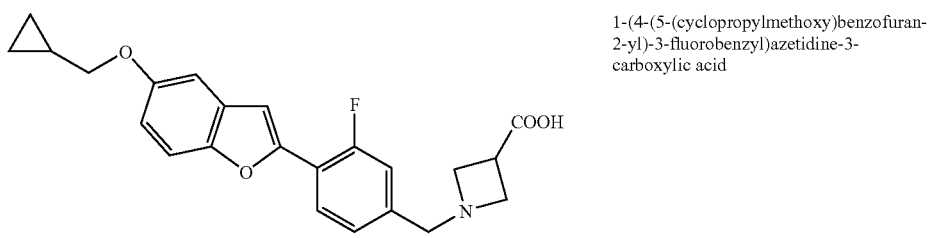

1-(4-(5-(cyclopropylmethoxy)benzofuran-2-yl)-3-fluorobenzyl)azetidine-3-carboxylic acid

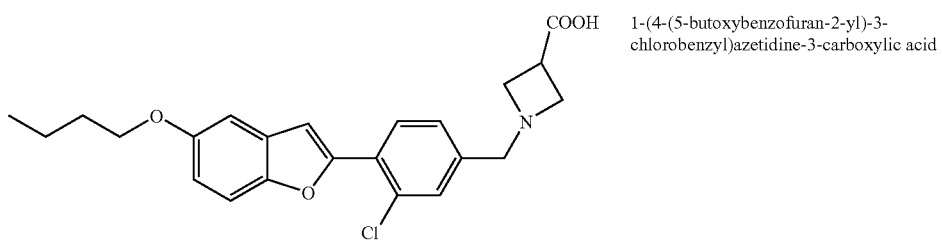

1-(4-(5-butoxybenzofuran-2-yl)-3-chlorobenzyl)azetidine-3-carboxylic acid

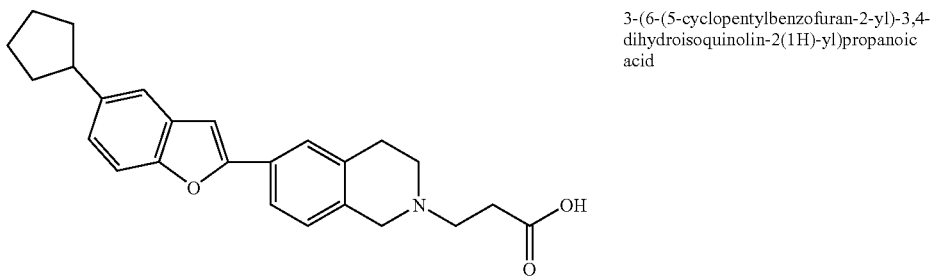

3-(6-(5-cyclopentylbenzofuran-2-yl)-3,4-dihydroisoquinolin-2(1H)-yl)propanoic acid

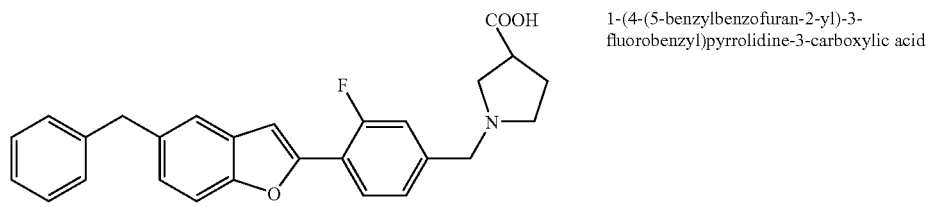

1-(4-(5-benzylbenzofuran-2-yl)-3-fluorobenzyl)pyrrolidine-3-carboxylic acid showed a reduction in lymphopenia ranging from 35% to 90% compared to baseline at dosages of 0.3 to 10 mg/kg. The final two compounds in the above table did not show lymphopenia reduction under the conditions tested. As such, the compounds of the invention are expected to be useful drugs for treating conditions such as transplant rejection; cancer; autoimmune/inflammatory diseases; rheumatoid arthritis; lupus; diabetes; multiple sclerosis; psoriasis; ulcerative colitis; inflammatory bowel disease; Crohn's disease; acute and chronic lymphocytic leukemias and lymphomas where immunosuppression is central.

Rat Lymphopenia Study Protocol

Animals:

Female Lewis rats (150-175 gms, 6-8 wks) are received from Charles River Laboratories and allowed to acclimatize for at least one week before being placed on study.

Procedure:

1) Rats (n=4/group) are administered compound or vehicle (12.5% captisol in water) orally (PO, 10 mL/kg) at time 0.

2) At various time points following dosing (1, 4, 8, or 24 hrs), animals are sacrificed by CO2 inhalation.

3) Using a 20 G needle and 1 cc syringe, blood is collected by cardiac puncture.

4) Approximately 500 uL of blood is placed in a microtainer tube containing EDTA (BD #365973), and the sample is mixed thoroughly.

5) Differential cell counts are performed using an Advia 120 hematology system by Bayer.

The following compounds exhibited hS1P1:hS1P3 $EC_{50}$ selectivity ratios of better than 1:100:

1-((4-(5-Benzylbenzofuran-2-yl)-3-fluorophenyl)methyl) azetidine-3-carboxylic acid;
1-(4-(5-phenoxybenzofuran-2-yl)benzyl)azetidine-3-carboxylic acid;
1-(((6-(5-Butoxybenzofuran-2-yl)pyridin-3-yl)methyl)azetidine-3-carboxylic acid;
1-((4-(5-benzylbenzofuran-2-yl)-3-methoxyphenyl)methyl) azetidine-3-carboxylic acid;
1-(3-fluoro-4-(5-(tetrahydro-2H-pyran-4-yl)benzofuran-2-yl)phenyl)methyl)azetidine-3-carboxylic acid;
(E/Z)-1-((3-Fluoro-4-(5-((hydroxyimino)(phenyl)methyl) benzofuran-2-yl)phenyl)methyl)azetidine-3-carboxylic acid;
1-((3-Fluoro-4-(5-(phenylmethyl)furo[2,3-b]pyridin-2-yl) phenyl)methyl)-3-azetidinecarboxylic acid;
1-((3-Fluoro-4-(5-(phenylthio)benzo[d]oxazol-2-yl)phenyl) methyl)azetidine-3-carboxylic acid;
1-((3-Fluoro-4-(5-(pyridin-2-ylmethyl)benzofuran-2-yl) phenyl)methyl)azetidine-3-carboxylic acid;
1-((3-Fluoro-4-(5-(pyrimidin-2-ylmethyl)benzofuran-2-yl) phenyl)methyl)azetidine-3-carboxylic acid;
1-((3-Fluoro-4-(5-(thiazol-2-ylmethyl)benzofuran-2-yl)phenyl)methyl)azetidine-3-carboxylic acid;
1-((4-(5-(Difluoro(phenyl)methyl)benzofuran-2-yl)-3-fluorophenyl)methyl)azetidine-3-carboxylic acid;
1-((4-(5-Benzylbenzo[d]thiazol-2-yl)-3-fluorophenyl)methyl)azetidine-3-carboxylic acid;
1-((4-(6-Benzylbenzofuran-2-yl)-3-fluorophenyl)methyl) azetidine-3-carboxylic acid;
1-(3-Fluoro-4-(5-(4-methylbenzyl)benzofuran-2-yl)benzyl) azetidine-3-carboxylic acid;
1-(3-Fluoro-4-(5-(phenoxymethyl)benzofuran-2-yl)benzyl) azetidine-3-carboxylic acid;
1-(3-Fluoro-4-(5-phenoxybenzofuran-2-yl)benzyl)azetidine-3-carboxylic acid;
1-(3-Fluoro-4-(5-phenylsulfinyl)benzofuran-2-yl)benzyl) azetidine-3-carboxylic acid;
1-(3-Fluoro-4-(5-phenylthio)benzofuran-2-yl)benzyl)azetidine-3-carboxylic acid;
1-(4-(5-(Cyclobutoxymethyl)benzofuran-2-yl)-3-fluorobenzyl)azetidine-3-carboxylic acid;
1-(4-(5-Benzylbenzo[b]thiophen-2-yl)-3-fluorobenzyl)azetidine-3-carboxylic acid; and
1-(4-(7-Benzyl-1H-imidazo[1,2-a]pyridin-2-yl)-3-fluorobenzyl)azetidine-3-carboxylic acid, trifluoroacetic acid salt.

EQUIVALENTS

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A compound having the formula

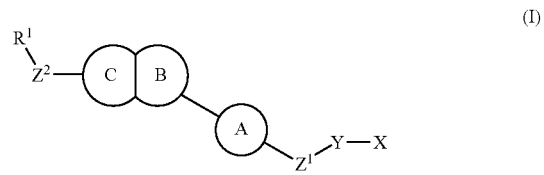

(I)

wherein

A is phenyl optionally substituted with one, two or three substituents selected from the group consisting of halogen, hydroxyl, $SR^2$, $S(O)_2R^2$, $S(O)_2NR^2$, $NHS(O)_2R^2$, $COR^2$, $CO_2R^2$, cyano, amino, $C_{1-5}$ alkylamino, arylamino, heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy;

$R^2$ is selected from the group consisting of hydrogen, hydroxyl, amino, alkylamino, arylamino, $C_{1-6}$ alkyl, $C_{1-5}$ alkoxy, $C_{1-5}$ alkylthio, halogen-substituted $C_{1-6}$ alkyl, halogen-substituted $C_{1-5}$ alkoxy, aryl, and heteroaryl;

B and C are selected from the group consisting of

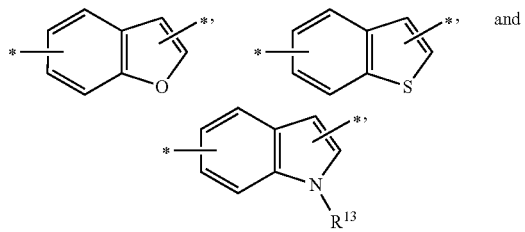

optionally substituted with 1 to 5 substituents selected from the group consisting of $C_{1-6}$ alkyl, $C_{1-5}$ alkylthio, $C_{1-5}$ alkoxy, halogen, hydroxyl, cyano, halogen-substituted $C_{1-6}$ alkyl and halogen-substituted $C_{1-5}$ alkoxy;

$R^{13}$ is selected from the group consisting of H, $C_{1-6}$alkyl, $C_{1-6}$alkylthio, $C_{1-5}$alkoxy, halogen, hydroxyl, cyano, halogen-substituted $C_{1-6}$alkyl, and halogen-substituted $C_{1-5}$alkoxy;

X is selected from the group consisting of $WC(O)OR^{6a}$, $WP(O)R^{6b}R^{6c}$, $WS(O)_2OH$, $WCONHSO_3H$ and 1H-tetrazol-5-yl;

W is a direct bond, oxygen or $C_{1-4}$ alkyl having one or more substituents independently selected from the group consisting of halogen, hydroxyl, cyano, amino, alkylamino, arylamino, heteroarylamino groups, $C_{1-4}$ alkoxy and $CO_2H$;

$R^{6a}$ is hydrogen or $C_{1-4}$ alkyl;

$R^{6b}$ and $R^{6c}$ are independently hydrogen, hydroxyl, $C_{1-4}$ alkyl or halogen substituted $C_{1-4}$ alkyl;

Y is formula (a) where the left and right asterisks indicate the point of attachment

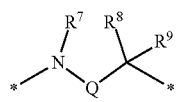

(a)

wherein

Q is selected from the group consisting of a direct bond, $C=O$, $C=S$, $SO_2$, $C=ONR$ and $(CR^{10}R^{11})_m$;

m is 0, 1, 2 or 3;

$R^7$ and $R^8$ are independently selected from the group consisting of hydrogen, halogen, amino, $C_{1-5}$ alkylamino, hydroxyl, cyano, $C_{1-6}$ alkyl, $C_{1-6}$ hydroxyalkyl (e.g., hydroxy-terminated alkyl), $C_{1-5}$ alkylthio, $C_{1-5}$ alkoxy, halogen-substituted $C_{1-6}$ alkyl and halogen-substituted $C_{1-5}$ alkoxy;

$R^9$ is selected from the group consisting of hydrogen, halogen, hydroxyl, cyano, $C_{1-6}$ alkyl, $C_{1-5}$ alkylthio, $C_{1-5}$ alkoxy, halogen-substituted $C_{1-6}$ alkyl and halogen-substituted $C_{1-5}$ alkoxy;

$R^{10}$ and $R^{11}$ are independently selected from the group consisting of hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy;

$Z^1$ is independently selected from the group consisting of O, $NR^3$, S, $S(O)$, $S(O)_2NR^3$, $(CR^4R^5)_n$, $C=O$, $C=S$, $C=N-R^3$, and a direct bond;

$Z^2$ is independently selected from the group consisting of O, $NR^3$, S, $S(O)$, $S(O)_2$, $S(O)_2NR^3$, $(CR^4R^5)_n$, $C=O$, $C=S$, $C=N-R^3$, and a direct bond;

$R^3$ is selected from the group consisting of hydrogen, hydroxyl, $SO_2$, $C=O$, $C=S$, $C=NH$, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy, aryl and heteroaryl, or when $Z^2$ is a direct bond, $R^3$ is a $C_3$-$C_6$ ring optionally containing a heteroatom;

$R^4$ and $R^5$ are independently selected from the group consisting of hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy, aryl and heteroaryl, or together form $C=O$;

n is 0, 1, 2 or 3; and $R^1$ is selected from the group consisting of $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl, heteroaryl, and heterocycle, wherein the $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl, and heteroaryl groups are optionally substituted with a substituent selected from the group consisting of hydroxyl, halogen, cyano, amino, alkylamino, aryl amino, and heteroarylamino, wherein the aryl and heteroaryl groups are optionally substituted with 1 to 5 substituents selected from the group consisting of hydroxyl, halogen, cyano, $C_{1-6}$ alkyl, $C_{1-5}$ alkylthio, $C_{1-5}$ alkoxy, and $C_{3-6}$ cycloalkyl, and wherein the heterocyclic groups are optionally substituted with one or more substituents selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxy, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, azido, heterocyclyl, aryl, and heteroaryl;

or a pharmaceutically acceptable salt thereof.

2. The compound of claim 1, wherein A is substituted with one, two or three substituents selected from the group consisting of halogen, hydroxyl, $SR^2$, $S(O)_2R^2$, $S(O)_2NR^2$, NHS$(O)_2R^2$, $COR^2$, $CO_2R^2$, cyano, amino, $C_{1-5}$ alkylamino/arylamino/heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy.

3. The compound of claim 1, wherein the pharmaceutically acceptable salt is selected from the group consisting of hydrochloride, maleate, citrate, fumarate, succinate, tartarate, mesylate, sodium, potassium, magnesium, and calcium salts.

4. A compound having the formula

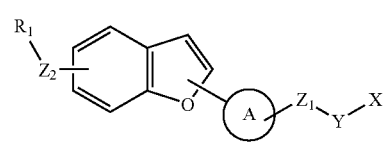

(II)

wherein the benzofuranyl ring is optionally substituted with 1 to 5 substituents selected from the group consisting of $C_{1-6}$ alkyl, $C_{1-5}$ alkylthio, $C_{1-5}$ alkoxy, halogen, hydroxyl, cyano, halogen-substituted $C_{1-6}$ alkyl and halogen-substituted $C_{1-5}$ alkoxy;

A is phenyl optionally substituted with one, two or three substituents selected from the group consisting of halogen, hydroxyl, $SR^2$, $S(O)_2R^2$, $S(O)_2NR^2$, $NHS(O)_2R^2$, $COR^2$, $CO_2R^2$, cyano, amino, $C_{1-5}$ alkylamino, arylamino, heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy;

$R^2$ is selected from the group consisting of hydrogen, hydroxyl, amino, alkylamino, arylamino, $C_{1-6}$ alkyl, $C_{1-5}$ alkoxy, $C_{1-5}$ alkylthio, halogen-substituted $C_{1-6}$ alkyl, halogen-substituted $C_{1-5}$ alkoxy, aryl and heteroaryl;

X is —C(O)OR$^{6a}$, where R$^{6a}$ is hydrogen or C$_{1-4}$ alkyl;
Y is a residue of formula (a)

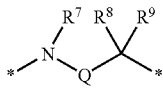

wherein
Q is (CR$^{10}$R$^{11}$)$_m$;
m is 0, 1, 2, 3 or 4;
R$^7$ and R$^8$ are independently hydrogen, hydroxyl, or lower alkyl;
R$^9$ is selected from the group consisting of hydrogen, halogen, hydroxyl, and cyano;
Z$^1$ and Z$^2$ are independently O or (CR$^4$R$^5$)$_n$;
R$^4$ and R$^5$ are independently hydrogen, halogen, hydroxyl, cyano, C$_{1-6}$ alkyl, or C$_{1-5}$ alkoxy;
n is 0, 1, 2 or 3;
R$^4$ is selected from the group consisting of C$_{1-6}$ alkyl, C$_{2-6}$ alkenyl, C$_{2-6}$ alkynyl, C$_{3-6}$ cycloalkyl, C$_{1-5}$ alkoxy, C$_{1-5}$ alkylamino, aryl heteroaryl, and heterocycle, wherein the C$_{1-6}$ alkyl, C$_{2-6}$ alkenyl, C$_{2-6}$ alkynyl, C$_{3-6}$ cycloalkyl, C$_{1-5}$ alkoxy, and C$_{1-5}$ alkylamino groups are optionally substituted with a substituent selected from the group consisting of hydroxyl, halogen, cyano, amino, alkylamino, arylamino, and heteroarylamino, wherein the aryl and heteroaryl groups are optionally substituted with one to five substituents selected from the group consisting of hydroxyl, halogen, cyano, C$_{1-6}$ alkyl, C$_{1-5}$ alkylthio, C$_{1-5}$ alkoxy, and C$_{3-6}$ cycloalkyl, and wherein the heterocyclic groups are optionally substituted with one or more substituents selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxy, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, azido, heterocyclyl, aryl, and heteroaryl;
or a pharmaceutically acceptable salt thereof.

5. The compound of claim 4, wherein A is substituted with one, two or three substituents selected from the group consisting of halogen, hydroxyl, SR$^2$, S(O)$_2$R$^2$, S(O)$_2$NR$^2$, NHS(O)$_2$R$^2$, COR$^2$, CO$_2$R$^2$, cyano, amino, C$_{1-5}$ alkylamino/arylamino/heteroarylamino, C$_{1-6}$ alkyl, C$_{1-5}$ alkylthio, C$_{1-5}$ alkoxy, halogen-substituted C$_{1-6}$ alkyl, and halogen-substituted C$_{1-5}$ alkoxy.

6. The compound of claim 4, wherein the pharmaceutically acceptable salt is selected from the group consisting of hydrochloride, maleate, citrate, fumarate, succinate, tartarate, mesylate, sodium, potassium, magnesium, and calcium salts.

7. A pharmaceutical composition comprising the compound of claim 1 in a therapeutically effective amount.

8. A compound or pharmaceutically acceptable salt or hydrate thereof, selected from the group consisting of:
   3-(4-(5-Benzylbenzofuran-2-yl)-3-fluorobenzylamino)-2-methylpropanoic acid;
   4-Amino-2-(4-(5-benzylbenzofuran-2-yl)-3-fluorobenzylamino)-4-oxobutanoic acid; and
   4-Amino-3-(4-(5-benzylbenzofuran-2-yl)-3-fluorobenzylamino)-4-oxobutanoic acid.

* * * * *

UNITED STATES PATENT AND TRADEMARK OFFICE
CERTIFICATE OF CORRECTION

| | | |
|---|---|---|
| PATENT NO. | : 7,919,519 B2 | Page 1 of 1 |
| APPLICATION NO. | : 11/726351 | |
| DATED | : April 5, 2011 | |
| INVENTOR(S) | : Burli et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this
Twenty-fourth Day of May, 2011

David J. Kappos
*Director of the United States Patent and Trademark Office*